(12) United States Patent
Krieg et al.

(10) Patent No.: US 10,837,014 B2
(45) Date of Patent: *Nov. 17, 2020

(54) COMPOSITIONS AND METHODS FOR MODULATING SMN GENE FAMILY EXPRESSION

(71) Applicants: Translate Bio MA, Inc., Cambridge, MA (US); The General Hospital Corporation, Boston, MA (US)

(72) Inventors: Arthur M. Krieg, Cambridge, MA (US); Romesh Subramanian, Framingham, MA (US); James McSwiggen, Arlington, MA (US); Jeannie T. Lee, Boston, MA (US)

(73) Assignee: Translate Bio MA, Inc., Lexington, MA (US)

( * ) Notice: Subject to any disclaimer, the term of this patent is extended or adjusted under 35 U.S.C. 154(b) by 215 days.

This patent is subject to a terminal disclaimer.

(21) Appl. No.: 15/872,684

(22) Filed: Jan. 16, 2018

(65) Prior Publication Data

US 2018/0298384 A1 Oct. 18, 2018
US 2020/0040333 A9 Feb. 6, 2020

Related U.S. Application Data

(63) Continuation-in-part of application No. 14/401,194, filed as application No. PCT/US2013/041440 on May 16, 2013, now Pat. No. 10,059,941, application No. 15/872,684, which is a continuation-in-part of application No. 14/401,196, filed as application No. PCT/US2013/041452 on May 16, 2013, now Pat. No. 10,058,623, application No. 15/872,684, which is a continuation-in-part of application No. 14/401,201, filed as application No. PCT/US2013/041382 on May 16, 2013, now Pat. No. 10,174,315, application No. 15/872,684, which is a continuation-in-part of application No. 14/401,214, filed as application No. PCT/US2013/041381 on May 16, 2013, now Pat. No. 10,074,323, application No. 15/872,684, which is a continuation-in-part of application No. 14/401,223, filed as application No. PCT/US2013/041455 on May 16, 2013, now abandoned, application No. 15/872,684, which is a continuation-in-part of application No. 14/401,227, filed as application No. PCT/US2013/041389 on May 16, 2013, now abandoned, application No. 15/872,684, which is a continuation-in-part of application No. 14/401,234, filed as application No. PCT/US2013/041385 on May 16, 2013, now abandoned, application No. 15/872,684, which is a continuation-in-part of application No. 15/787,876, filed on Oct. 19, 2017, (Continued)

(51) Int. Cl.
| | |
|---|---|
| C12N 15/113 | (2010.01) |
| C07H 21/00 | (2006.01) |
| C07H 21/02 | (2006.01) |
| C07H 21/04 | (2006.01) |
| A61K 31/7125 | (2006.01) |
| A61K 31/712 | (2006.01) |
| A61K 31/7115 | (2006.01) |
| A61K 47/64 | (2017.01) |
| A61K 47/61 | (2017.01) |

(52) U.S. Cl.
CPC .......... *C12N 15/113* (2013.01); *A61K 31/712* (2013.01); *A61K 31/7115* (2013.01); *A61K 31/7125* (2013.01); *A61K 47/61* (2017.08); *A61K 47/6455* (2017.08); *C07H 21/00* (2013.01); *C07H 21/02* (2013.01); *C07H 21/04* (2013.01); *C12N 2310/11* (2013.01); *C12N 2310/315* (2013.01); *C12N 2310/321* (2013.01); *C12N 2310/322* (2013.01); *C12N 2310/3231* (2013.01); *C12N 2310/3521* (2013.01)

(58) Field of Classification Search
None
See application file for complete search history.

(56) References Cited

U.S. PATENT DOCUMENTS

| | | |
|---|---|---|
| 4,725,677 A | 2/1988 | Köster et al. |
| 5,491,133 A | 2/1996 | Walder et al. |
| | (Continued) | |

FOREIGN PATENT DOCUMENTS

| | | |
|---|---|---|
| CA | 2805791 A1 | 1/2012 |
| EP | 0 999 270 A1 | 5/2000 |
| | (Continued) | |

OTHER PUBLICATIONS

[No Author Listed] Catalogue of Parent of Origin Effects, Imprinted Genes and Related Effects, Parental Origins of de novo Mutations, downloaded at http://igc.otago.ac.nz/home.html on May 22, 2015, 2 pgs.

(Continued)

*Primary Examiner* — Tracy Vivlemore
(74) *Attorney, Agent, or Firm* — Wolf, Greenfield & Sacks, P.C.

(57) ABSTRACT

Aspects of the invention provide single stranded oligonucleotides for activating or enhancing expression of SMN1 or SMN2. Further aspects provide compositions and kits comprising single stranded oligonucleotides for activating or enhancing expression of SMN1 or SMN2 that comprises exon 7. Methods for modulating expression of SMN1 or SMN2 using the single stranded oligonucleotides are also provided. Further aspects of the invention provide methods for selecting a candidate oligonucleotide for activating or enhancing expression of SMN1 or SMN2.

32 Claims, 12 Drawing Sheets

Specification includes a Sequence Listing.

Related U.S. Application Data now Pat. No. 10,655,128, which is a continuation of application No. 14/401,237, filed as application No. PCT/US2013/041394 on May 16, 2013, now abandoned, application No. 15/872,684, which is a continuation-in-part of application No. 14/401,240, filed as application No. PCT/US2013/041434 on May 16, 2013, now abandoned, said application No. 15/787,876 is a continuation-in-part of application No. 14/401,248, filed as application No. PCT/US2013/041437 on May 16, 2013, now abandoned, application No. 15/872,684, which is a continuation-in-part of application No. 14/691,361, filed on Apr. 20, 2015, now abandoned, which is a continuation of application No. 14/401,252, filed as application No. PCT/US2013/041461 on May 16, 2013, now abandoned.

(60) Provisional application No. 61/785,832, filed on Mar. 14, 2013, provisional application No. 61/786,232, filed on Mar. 14, 2013, provisional application No. 61/785,529, filed on Mar. 14, 2013, provisional application No. 61/785,885, filed on Mar. 14, 2013, provisional application No. 61/785,956, filed on Mar. 14, 2013, provisional application No. 61/785,529, filed on Mar. 14, 2013, provisional application No. 61/786,095, filed on Mar. 14, 2013, provisional application No. 61/785,778, filed on Mar. 14, 2013, provisional application No. 61/719,394, filed on Oct. 27, 2012, provisional application No. 61/648,041, filed on May 16, 2012, provisional application No. 61/648,058, filed on May 16, 2012, provisional application No. 61/648,051, filed on May 16, 2012, provisional application No. 61/648,016, filed on May 16, 2012, provisional application No. 61/647,858, filed on May 16, 2012, provisional application No. 61/647,915, filed on May 16, 2012, provisional application No. 61/647,938, filed on May 16, 2012, provisional application No. 61/647,901, filed on May 16, 2012, provisional application No. 61/648,069, filed on May 16, 2012, provisional application No. 61/648,052, filed on May 16, 2012, provisional application No. 61/647,886, filed on May 16, 2012, provisional application No. 61/647,949, filed on May 16, 2012, provisional application No. 61/648,077, filed on May 16, 2012, provisional application No. 61/647,925, filed on May 16, 2012, provisional application No. 61/648,045, filed on May 16, 2012, provisional application No. 61/648,021, filed on May 16, 2012, provisional application No. 61/648,030, filed on May 16, 2012.

(56) References Cited

U.S. PATENT DOCUMENTS

| | | |
|---|---|---|
| 5,576,208 A | 11/1996 | Monia et al. |
| 5,623,065 A | 4/1997 | Cook et al. |
| 5,652,355 A | 7/1997 | Metelev et al. |
| 5,661,134 A | 8/1997 | Cook et al. |
| 5,734,039 A | 3/1998 | Calabretta et al. |
| 5,766,903 A | 6/1998 | Sarnow et al. |
| 5,912,332 A | 6/1999 | Agrawal et al. |
| 5,914,396 A | 6/1999 | Cook et al. |
| 5,919,619 A | 7/1999 | Tullis |
| 5,965,722 A | 10/1999 | Ecker et al. |
| 5,976,879 A | 11/1999 | Kole et al. |
| 6,015,710 A | 1/2000 | Shay et al. |
| 6,040,142 A | 3/2000 | Melki et al. |
| 6,046,307 A | 4/2000 | Shay et al. |
| 6,063,400 A | 5/2000 | Geho et al. |
| 6,080,577 A | 6/2000 | Melki et al. |
| 6,107,094 A | 8/2000 | Crooke |
| 6,143,881 A | 11/2000 | Metelev et al. |
| 6,146,829 A | 11/2000 | Cook et al. |
| 6,187,545 B1 | 2/2001 | McKay et al. |
| 6,197,944 B1 | 3/2001 | Walder et al. |
| 6,210,892 B1 | 4/2001 | Bennett et al. |
| 6,284,458 B1 | 9/2001 | Anderson et al. |
| 6,294,650 B1 | 9/2001 | Shay et al. |
| 6,326,199 B1 | 12/2001 | Cook et al. |
| 6,346,614 B1 | 2/2002 | Metelev et al. |
| 6,359,124 B1 | 3/2002 | Ecker et al. |
| 6,395,492 B1 | 5/2002 | Manoharan et al. |
| 6,451,991 B1 | 9/2002 | Martin et al. |
| 6,503,754 B1 | 1/2003 | Zhang et al. |
| 6,531,584 B1 | 3/2003 | Cook et al. |
| 6,602,857 B1 | 8/2003 | Cowsert et al. |
| 6,608,035 B1 | 8/2003 | Agrawal et al. |
| 6,677,445 B1 | 1/2004 | Innis et al. |
| 6,727,355 B2 | 4/2004 | Matsuo et al. |
| 6,753,423 B1 | 6/2004 | Cook et al. |
| 6,794,499 B2 | 9/2004 | Wengel et al. |
| 6,831,166 B2 | 12/2004 | Manoharan et al. |
| 6,919,439 B2 | 7/2005 | Manoharan et al. |
| 7,015,315 B1 | 3/2006 | Cook et al. |
| 7,033,752 B1 | 4/2006 | Melki et al. |
| 7,041,816 B2 | 5/2006 | Ravikumar et al. |
| 7,045,609 B2 | 5/2006 | Metelev et al. |
| 7,226,785 B2 | 6/2007 | Kmiec et al. |
| 7,374,927 B2 | 5/2008 | Palma et al. |
| 7,449,297 B2 | 11/2008 | Freije et al. |
| 7,655,785 B1 | 2/2010 | Bentwich |
| 7,683,036 B2 | 3/2010 | Esau et al. |
| 7,687,616 B1 | 3/2010 | Bentwich et al. |
| 7,687,617 B2 | 3/2010 | Thrue et al. |
| 7,709,456 B2 | 5/2010 | Corey et al. |
| 7,838,657 B2 | 11/2010 | Singh et al. |
| 7,858,592 B2 | 12/2010 | Shames et al. |
| 7,879,992 B2 | 2/2011 | Vickers et al. |
| 7,888,012 B2 | 2/2011 | Iversen et al. |
| 7,960,541 B2 | 6/2011 | Wilton et al. |
| 8,067,569 B2 | 11/2011 | Iversen et al. |
| 8,092,992 B2 | 1/2012 | Kuwabara et al. |
| 8,110,560 B2 | 2/2012 | Singh et al. |
| 8,129,515 B2 | 3/2012 | Esau et al. |
| 8,153,365 B2 | 4/2012 | Wengel et al. |
| 8,153,602 B1 | 4/2012 | Bennett et al. |
| 8,153,606 B2 | 4/2012 | Collard et al. |
| 8,222,221 B2 | 7/2012 | Corey et al. |
| 8,232,384 B2 | 7/2012 | Wilton et al. |
| 8,288,354 B2 | 10/2012 | Wahlestedt |
| 8,288,356 B2 | 10/2012 | Obad et al. |
| 8,318,690 B2 | 11/2012 | Collard et al. |
| 8,361,977 B2 | 1/2013 | Baker et al. |
| 8,361,980 B2 | 1/2013 | Kauppinen et al. |
| 8,404,659 B2 | 3/2013 | Kauppinen et al. |
| 8,415,313 B2 | 4/2013 | Mourich et al. |
| 8,846,639 B2 | 9/2014 | Swayze et al. |
| 9,328,346 B2 | 5/2016 | Lee et al. |
| 9,567,581 B2 | 2/2017 | Lee et al. |
| 9,580,708 B2 | 2/2017 | Uhlmann et al. |
| 9,593,330 B2 | 3/2017 | Collard et al. |
| 10,059,941 B2 | 8/2018 | Krieg et al. |
| 2002/0160379 A1 | 10/2002 | Cook et al. |
| 2003/0198983 A1 | 10/2003 | Zhou |
| 2003/0208061 A1 | 11/2003 | Manoharan et al. |
| 2003/0219770 A1 | 11/2003 | Eshleman et al. |
| 2003/0228690 A1 | 12/2003 | Baker et al. |
| 2003/0235822 A1 | 12/2003 | Lokhov et al. |
| 2004/0002153 A1 | 1/2004 | Monia et al. |
| 2004/0038274 A1 | 2/2004 | Cook et al. |
| 2004/0096848 A1 | 5/2004 | Thrue et al. |
| 2004/0241651 A1 | 12/2004 | Olek et al. |
| 2004/0248840 A1 | 12/2004 | Hansen et al. |
| 2005/0003369 A1 | 1/2005 | Christians et al. |
| 2005/0026160 A1 | 2/2005 | Allerson et al. |
| 2005/0054836 A1 | 3/2005 | Krainer et al. |

(56) References Cited

U.S. PATENT DOCUMENTS

| | | |
|---|---|---|
| 2005/0100923 A1 | 5/2005 | Dreyfuss et al. |
| 2005/0108783 A1 | 5/2005 | Koike |
| 2005/0130924 A1 | 6/2005 | Monia et al. |
| 2005/0164209 A1 | 7/2005 | Bennett et al. |
| 2005/0176025 A1 | 8/2005 | McSwiggen et al. |
| 2005/0203042 A1 | 9/2005 | Frieden et al. |
| 2005/0226848 A1 | 10/2005 | Kuwabara et al. |
| 2005/0233455 A1 | 10/2005 | Damha et al. |
| 2005/0244851 A1 | 11/2005 | Blume et al. |
| 2005/0246794 A1 | 11/2005 | Khvorova et al. |
| 2005/0261218 A1 | 11/2005 | Esau et al. |
| 2005/0272080 A1 | 12/2005 | Palma et al. |
| 2006/0003322 A1 | 1/2006 | Bentwich |
| 2006/0046260 A1 | 3/2006 | Kriksunov et al. |
| 2006/0089490 A1 | 4/2006 | Melki et al. |
| 2006/0128646 A1 | 6/2006 | Christensen et al. |
| 2006/0135458 A1 | 6/2006 | Vaillant et al. |
| 2006/0270624 A1 | 11/2006 | Cook et al. |
| 2007/0032446 A1 | 2/2007 | Cook et al. |
| 2007/0042380 A1 | 2/2007 | Bentwich et al. |
| 2007/0111963 A1 | 5/2007 | Corey et al. |
| 2007/0123484 A1 | 5/2007 | Bhat et al. |
| 2007/0166737 A1 | 7/2007 | Melki et al. |
| 2007/0191294 A1 | 8/2007 | Elmen et al. |
| 2007/0219244 A1 | 9/2007 | Jenssen et al. |
| 2007/0269815 A1 | 11/2007 | Rivory et al. |
| 2007/0292408 A1 | 12/2007 | Singh et al. |
| 2008/0015162 A1 | 1/2008 | Bhanot et al. |
| 2008/0139472 A1 | 6/2008 | Lauterborn et al. |
| 2008/0176793 A1 | 7/2008 | Simons et al. |
| 2008/0194463 A1 | 8/2008 | Weller et al. |
| 2008/0242629 A1 | 10/2008 | Crooke et al. |
| 2008/0249039 A1 | 10/2008 | Elmen et al. |
| 2008/0293655 A1 | 11/2008 | Aygun et al. |
| 2008/0311039 A1 | 12/2008 | Bonavida et al. |
| 2008/0318895 A1 | 12/2008 | Lee et al. |
| 2009/0082297 A1 | 3/2009 | Lioy et al. |
| 2009/0092988 A1 | 4/2009 | Schwartz et al. |
| 2009/0099066 A1 | 4/2009 | Moulton et al. |
| 2009/0099109 A1 | 4/2009 | Shames et al. |
| 2009/0123467 A1 | 5/2009 | Bedi et al. |
| 2009/0143326 A1 | 6/2009 | Obad et al. |
| 2009/0155910 A1 | 6/2009 | McGonigle |
| 2009/0156538 A1 | 6/2009 | Dobie |
| 2009/0221685 A1 | 9/2009 | Esau et al. |
| 2009/0258925 A1 | 10/2009 | Wahlestedt |
| 2009/0324549 A1 | 12/2009 | Battaglia et al. |
| 2009/0325868 A1 | 12/2009 | Liu et al. |
| 2009/0326051 A1 | 12/2009 | Corey et al. |
| 2010/0004314 A1 | 1/2010 | Dondero et al. |
| 2010/0021914 A1 | 1/2010 | Moeller et al. |
| 2010/0087511 A1 | 4/2010 | Singh et al. |
| 2010/0105760 A1 | 4/2010 | Collard et al. |
| 2010/0111982 A1 | 5/2010 | Zang et al. |
| 2010/0112042 A1 | 5/2010 | Polisky et al. |
| 2010/0124547 A1 | 5/2010 | Bramlage et al. |
| 2010/0143359 A1 | 6/2010 | Ebert et al. |
| 2010/0197762 A1 | 8/2010 | Swayze et al. |
| 2010/0210707 A1 | 8/2010 | Li et al. |
| 2010/0210712 A1 | 8/2010 | Hansen et al. |
| 2010/0216238 A1 | 8/2010 | Baker et al. |
| 2010/0247543 A1 | 9/2010 | Maes et al. |
| 2010/0256223 A1 | 10/2010 | Moeller et al. |
| 2010/0280100 A1 | 11/2010 | Collard et al. |
| 2010/0286141 A1 | 11/2010 | Durden et al. |
| 2010/0286234 A1 | 11/2010 | Elmen et al. |
| 2010/0298410 A1 | 11/2010 | Obad et al. |
| 2010/0317606 A1 | 12/2010 | Chan et al. |
| 2011/0039910 A1 | 2/2011 | Crooke et al. |
| 2011/0077286 A1 | 3/2011 | Damha et al. |
| 2011/0086833 A1 | 4/2011 | Paushkin et al. |
| 2011/0150868 A1 | 6/2011 | Yu et al. |
| 2011/0159587 A1 | 6/2011 | Krainer et al. |
| 2011/0172292 A1 | 7/2011 | Hansen et al. |
| 2011/0191912 A1 | 8/2011 | Alexandrov |
| 2011/0207217 A1 | 8/2011 | Corey et al. |
| 2011/0224277 A1 | 9/2011 | Esau et al. |
| 2011/0237606 A1 | 9/2011 | Chai et al. |
| 2011/0237649 A1 | 9/2011 | Collard et al. |
| 2011/0237650 A1 | 9/2011 | Collard et al. |
| 2011/0237651 A1 | 9/2011 | Collard et al. |
| 2011/0251261 A1 | 10/2011 | Burnett et al. |
| 2011/0263687 A1 | 10/2011 | Mattick et al. |
| 2011/0294870 A1 | 12/2011 | Collard et al. |
| 2011/0319283 A1 | 12/2011 | Thompson |
| 2011/0319317 A1 | 12/2011 | Collard et al. |
| 2011/0319475 A1 | 12/2011 | Collard et al. |
| 2011/0319476 A1 | 12/2011 | Collard et al. |
| 2012/0004184 A1 | 1/2012 | Collard et al. |
| 2012/0004278 A1 | 1/2012 | Chang et al. |
| 2012/0010156 A1 | 1/2012 | Collard et al. |
| 2012/0046236 A1 | 2/2012 | Collard et al. |
| 2012/0046344 A1 | 2/2012 | Collard et al. |
| 2012/0046345 A1 | 2/2012 | Collard et al. |
| 2012/0064048 A1 | 3/2012 | Collard et al. |
| 2012/0071418 A1 | 3/2012 | Copeland et al. |
| 2012/0083596 A1 | 4/2012 | Elmen et al. |
| 2012/0088817 A1 | 4/2012 | Collard et al. |
| 2012/0094934 A1 | 4/2012 | Collard et al. |
| 2012/0095079 A1 | 4/2012 | Collard et al. |
| 2012/0095081 A1 | 4/2012 | Collard et al. |
| 2012/0129917 A1 | 5/2012 | Collard et al. |
| 2012/0135941 A1 | 5/2012 | Collard et al. |
| 2012/0142610 A1 | 6/2012 | Collard et al. |
| 2012/0142758 A1 | 6/2012 | Collard et al. |
| 2012/0149756 A1 | 6/2012 | Schumperli et al. |
| 2012/0149759 A1 | 6/2012 | Collard et al. |
| 2012/0157333 A1 | 6/2012 | Kauppinen et al. |
| 2012/0171170 A1 | 7/2012 | Collard et al. |
| 2012/0252869 A1 | 10/2012 | Collard et al. |
| 2012/0264812 A1 | 10/2012 | Collard et al. |
| 2012/0277290 A1 | 11/2012 | Collard et al. |
| 2012/0288869 A1 | 11/2012 | Schwartz et al. |
| 2012/0289581 A1 | 11/2012 | Chang et al. |
| 2012/0289583 A1 | 11/2012 | Collard et al. |
| 2012/0295952 A1 | 11/2012 | Collard et al. |
| 2012/0295953 A1 | 11/2012 | Colalrd et al. |
| 2012/0295954 A1 | 11/2012 | Collard et al. |
| 2012/0295959 A1 | 11/2012 | Collard et al. |
| 2012/0309814 A1 | 12/2012 | Collard et al. |
| 2012/0322851 A1 | 12/2012 | Hardee et al. |
| 2012/0322853 A1 | 12/2012 | Collard et al. |
| 2012/0329727 A1 | 12/2012 | Collard et al. |
| 2012/0329855 A1 | 12/2012 | Collar et al. |
| 2013/0035372 A1 | 2/2013 | Collard et al. |
| 2013/0035373 A1 | 2/2013 | Collard et al. |
| 2013/0053428 A1 | 2/2013 | Wahlestedt |
| 2013/0065947 A1 | 3/2013 | Collard et al. |
| 2013/0072421 A1 | 3/2013 | Collard et al. |
| 2013/0072546 A1 | 3/2013 | Collard et al. |
| 2013/0079505 A1 | 3/2013 | Moeller et al. |
| 2013/0085112 A1 | 4/2013 | Collard et al. |
| 2013/0096183 A1 | 4/2013 | Collard et al. |
| 2013/0116300 A1 | 5/2013 | Collard et al. |
| 2013/0137751 A1 | 5/2013 | Collard et al. |
| 2013/0143946 A1 | 6/2013 | Collard et al. |
| 2013/0164846 A1 | 6/2013 | Saestrom |
| 2013/0184325 A9 | 7/2013 | Collard et al. |
| 2013/0210893 A1 | 8/2013 | Collard et al. |
| 2013/0245095 A1 | 9/2013 | Collard et al. |
| 2013/0245099 A1 | 9/2013 | Collard et al. |
| 2013/0253036 A1 | 9/2013 | Collard et al. |
| 2013/0261065 A1 | 10/2013 | Collard et al. |
| 2013/0289092 A1 | 10/2013 | Rigo et al. |
| 2014/0142160 A1 | 5/2014 | Lee et al. |
| 2014/0187606 A1 | 7/2014 | Collard et al. |
| 2014/0356459 A1 | 12/2014 | Oncostamen |
| 2015/0099791 A1 | 4/2015 | Krieg et al. |
| 2015/0133362 A1 | 5/2015 | Krieg et al. |
| 2015/0133528 A1 | 5/2015 | Krieg et al. |
| 2015/0133529 A1 | 5/2015 | Krieg et al. |
| 2015/0141320 A1 | 5/2015 | Krieg et al. |
| 2015/0152410 A1 | 6/2015 | Krieg et al. |
| 2015/0159160 A1 | 6/2015 | Krieg et al. |

(56) References Cited

U.S. PATENT DOCUMENTS

| | | |
|---|---|---|
| 2015/0159161 A1 | 6/2015 | Krieg et al. |
| 2015/0191722 A1 | 7/2015 | Krieg et al. |
| 2015/0218560 A1 | 8/2015 | Krieg et al. |
| 2015/0225717 A1 | 8/2015 | Lee et al. |
| 2015/0252364 A1 | 9/2015 | Krieg et al. |
| 2016/0122760 A1 | 5/2016 | Barsoum et al. |
| 2016/0201063 A1 | 7/2016 | Ozsolak |
| 2016/0201064 A1 | 7/2016 | Ozsolak |
| 2016/0222391 A1 | 8/2016 | Krieg et al. |
| 2017/0037396 A1 | 2/2017 | Lee et al. |

FOREIGN PATENT DOCUMENTS

| | | |
|---|---|---|
| EP | 1 044 987 A2 | 10/2000 |
| EP | 1 752 536 A1 | 5/2005 |
| EP | 1 695 979 A2 | 8/2006 |
| EP | 1 957 648 B1 | 11/2006 |
| EP | 1 967 525 A2 | 9/2008 |
| EP | 2 021 472 B1 | 6/2011 |
| EP | 2 023 940 B1 | 6/2011 |
| EP | 2 431 467 A2 | 3/2012 |
| EP | 2 431 467 A3 | 5/2012 |
| EP | 2 591 797 A1 | 5/2013 |
| EP | 2604690 A1 | 6/2013 |
| JP | 04-320700 | 11/1992 |
| JP | 3420984 B2 | 6/2003 |
| JP | 2006-522597 | 10/2006 |
| JP | 2008-044958 A | 2/2008 |
| JP | 2009-536037 | 10/2009 |
| JP | 2010-507579 A | 3/2010 |
| JP | 2010-516256 | 5/2010 |
| JP | 11-033863 A | 2/2011 |
| JP | 2015-518714 | 7/2015 |
| KR | 10-2011-0050134 A | 5/2011 |
| WO | WO 89/05358 A1 | 6/1989 |
| WO | WO 92/00386 A1 | 1/1992 |
| WO | WO 93/13121 A1 | 7/1993 |
| WO | WO 94/02499 A1 | 2/1994 |
| WO | WO 94/17093 A1 | 8/1994 |
| WO | WO 95/33852 A1 | 12/1995 |
| WO | WO 2000/020645 A1 | 4/2000 |
| WO | WO 2001/007662 A1 | 2/2001 |
| WO | WO 2001/036627 A2 | 5/2001 |
| WO | WO 2001/066129 A1 | 9/2001 |
| WO | WO 2001/072765 A1 | 10/2001 |
| WO | WO 2001/090341 A1 | 11/2001 |
| WO | WO 2002/022635 A1 | 3/2002 |
| WO | WO 2002/038738 A2 | 5/2002 |
| WO | WO 2002/103015 A2 | 12/2002 |
| WO | WO 2004/011613 A2 | 2/2004 |
| WO | WO 2004/092356 A2 | 10/2004 |
| WO | WO 2004/099382 A2 | 11/2004 |
| WO | WO 2004/113867 A2 | 12/2004 |
| WO | WO 2005/013901 A2 | 2/2005 |
| WO | WO 2005/042018 A2 | 5/2005 |
| WO | WO 2005/044091 A2 | 5/2005 |
| WO | WO 2005/044981 A2 | 5/2005 |
| WO | WO 2005/061710 A1 | 7/2005 |
| WO | WO 2005/089169 A2 | 9/2005 |
| WO | WO 2005/094370 A2 | 10/2005 |
| WO | WO 2006/063356 A1 | 6/2006 |
| WO | WO 2006/069584 A2 | 7/2006 |
| WO | WO 2006/130201 A1 | 12/2006 |
| WO | WO 2007/002390 A2 | 1/2007 |
| WO | WO 2007/004977 A1 | 1/2007 |
| WO | WO 2007/031091 A2 | 3/2007 |
| WO | WO 2007/076328 A2 | 7/2007 |
| WO | WO 2007/086990 A2 | 8/2007 |
| WO | WO 2007/086990 A3 | 8/2007 |
| WO | WO 2007/112753 A2 | 10/2007 |
| WO | WO 2007/112754 A2 | 10/2007 |
| WO | WO 2007/115578 A1 | 10/2007 |
| WO | WO 2007/131237 A2 | 11/2007 |
| WO | WO 2007/133812 A2 | 11/2007 |
| WO | WO 2008/024499 A2 | 2/2008 |
| WO | WO 2008/025069 A1 | 3/2008 |
| WO | WO 2008/029619 A1 | 3/2008 |
| WO | WO 2008/061537 A2 | 5/2008 |
| WO | WO 2008/103761 A2 | 8/2008 |
| WO | WO 2008/103763 A2 | 8/2008 |
| WO | WO 2008/113832 A2 | 9/2008 |
| WO | WO 2008/132234 A2 | 11/2008 |
| WO | WO 2008/138904 A2 | 11/2008 |
| WO | WO 2008/141282 A2 | 11/2008 |
| WO | WO 2009/043353 A2 | 4/2009 |
| WO | WO 2009/044383 A1 | 4/2009 |
| WO | WO 2009/046397 A2 | 4/2009 |
| WO | WO 2009/061851 A2 | 5/2009 |
| WO | WO 2009/064920 A2 | 5/2009 |
| WO | WO 2009/090182 A1 | 7/2009 |
| WO | WO 2009/124341 A1 | 10/2009 |
| WO | WO 2009/127680 A1 | 10/2009 |
| WO | WO 2009/134710 A2 | 11/2009 |
| WO | WO 2009/149182 A1 | 12/2009 |
| WO | WO 2009/151546 A2 | 12/2009 |
| WO | WO 2010/000665 A1 | 1/2010 |
| WO | WO 2010/007522 A1 | 1/2010 |
| WO | WO 2010/014592 A1 | 2/2010 |
| WO | WO 2010/040112 A2 | 4/2010 |
| WO | WO 2010/065671 A2 | 6/2010 |
| WO | WO 2010/065787 A2 | 6/2010 |
| WO | WO 2010/076248 A1 | 7/2010 |
| WO | WO 2010/083615 A1 | 7/2010 |
| WO | WO 2010/093860 A2 | 8/2010 |
| WO | WO 2010/093904 A2 | 8/2010 |
| WO | WO 2010/102058 A2 | 9/2010 |
| WO | WO 2010/107733 A2 | 9/2010 |
| WO | WO 2010/122538 A1 | 10/2010 |
| WO | WO 2010/124231 A2 | 10/2010 |
| WO | WO 2010/129746 A2 | 11/2010 |
| WO | WO 2010/129799 A2 | 11/2010 |
| WO | WO 2010/129861 A2 | 11/2010 |
| WO | WO 2010/135329 A2 | 11/2010 |
| WO | WO 2010/135695 A2 | 11/2010 |
| WO | WO 2010/138806 A2 | 12/2010 |
| WO | WO 2010/148050 A2 | 12/2010 |
| WO | WO 2010/148065 A2 | 12/2010 |
| WO | WO 2010/151671 A2 | 12/2010 |
| WO | WO 2010/151674 A2 | 12/2010 |
| WO | WO 2011/005786 A2 | 1/2011 |
| WO | WO 2011/009624 A1 | 1/2011 |
| WO | WO 2011/010706 A1 | 1/2011 |
| WO | WO 2011/017516 A2 | 2/2011 |
| WO | WO 2011/019815 A2 | 2/2011 |
| WO | WO 2011/022606 A2 | 2/2011 |
| WO | WO 2011/025862 A2 | 3/2011 |
| WO | WO 2011/031482 A2 | 3/2011 |
| WO | WO 2011/032109 A1 | 3/2011 |
| WO | WO 2011/038205 A2 | 3/2011 |
| WO | WO 2011/038210 A2 | 3/2011 |
| WO | WO 2011/048125 A1 | 4/2011 |
| WO | WO 2011/079261 A2 | 6/2011 |
| WO | WO 2011/079263 A2 | 6/2011 |
| WO | WO 2011/082409 A2 | 7/2011 |
| WO | WO 2011/084455 A2 | 7/2011 |
| WO | WO 2011/085066 A2 | 7/2011 |
| WO | WO 2011/097388 A1 | 8/2011 |
| WO | WO 2011/097582 A2 | 8/2011 |
| WO | WO 2011/097641 A1 | 8/2011 |
| WO | WO 2011/123745 A2 | 10/2011 |
| WO | WO 2011/139387 A1 | 11/2011 |
| WO | WO 2011/139917 A1 | 11/2011 |
| WO | WO 2011/146674 A2 | 11/2011 |
| WO | WO 2011/146675 A2 | 11/2011 |
| WO | WO 2011/150005 A2 | 12/2011 |
| WO | WO 2011/159836 A2 | 12/2011 |
| WO | WO 2011/161460 A2 | 12/2011 |
| WO | WO 2011/163499 A2 | 12/2011 |
| WO | WO 2012/009347 A2 | 1/2012 |
| WO | WO 2012/009402 A2 | 1/2012 |
| WO | WO 2012/012467 A2 | 1/2012 |
| WO | WO 2012/018881 A2 | 2/2012 |
| WO | WO 2012/024478 A2 | 2/2012 |
| WO | WO 2012/027033 A1 | 3/2012 |

(56) References Cited

FOREIGN PATENT DOCUMENTS

| | | |
|---|---|---|
| WO | WO 2012/036433 A2 | 3/2012 |
| WO | WO 2012/047956 A2 | 4/2012 |
| WO | WO 2012/054723 A2 | 4/2012 |
| WO | WO 2012/058268 A2 | 5/2012 |
| WO | WO 2012/064806 A2 | 5/2012 |
| WO | WO 2012/065143 A1 | 5/2012 |
| WO | WO 2012/068340 A2 | 5/2012 |
| WO | WO 2012/071238 A2 | 5/2012 |
| WO | WO 2012/087983 A1 | 6/2012 |
| WO | WO 2012/109476 A2 | 8/2012 |
| WO | WO 2012/144220 A1 | 10/2012 |
| WO | WO 2012/170771 A1 | 12/2012 |
| WO | WO 2012/174610 A1 | 12/2012 |
| WO | WO 2013/006619 A1 | 1/2013 |
| WO | WO 2013/036403 A1 | 3/2013 |
| WO | WO 2013/040429 A1 | 3/2013 |
| WO | WO 2013/124807 A2 | 8/2013 |
| WO | WO 2013/138374 A2 | 9/2013 |
| WO | WO 2013/173598 A1 | 11/2013 |
| WO | WO 2013/173599 A1 | 11/2013 |
| WO | WO 2013/173601 A1 | 11/2013 |
| WO | WO 2013/173605 A1 | 11/2013 |
| WO | WO 2013/173608 A1 | 11/2013 |
| WO | WO 2013/173635 A1 | 11/2013 |
| WO | WO 2013/173637 A1 | 11/2013 |
| WO | WO 2013/173638 A1 | 11/2013 |
| WO | WO 2013/173645 A1 | 11/2013 |
| WO | WO 2013/173647 A1 | 11/2013 |
| WO | WO 2013/173652 A1 | 11/2013 |
| WO | WO 2014/043544 A1 | 3/2014 |
| WO | WO 2014/076195 A1 | 5/2014 |
| WO | WO 2014/172698 A1 | 10/2014 |
| WO | WO 2014/197826 A1 | 12/2014 |
| WO | WO 2014/203518 A1 | 12/2014 |
| WO | WO 2014/205551 A1 | 12/2014 |
| WO | WO 2015/035476 A1 | 3/2015 |
| WO | WO 2016/077837 A1 | 5/2016 |

OTHER PUBLICATIONS

[No Author Listed] Locked Nucleic Acid. Exiqon. 2009. Retrieved from http://www.exiqon.com/Is/documents/scientific/lna_folder.pdf on Jun. 6, 2016.

[No Author Listed] ncRNA. 2011;29(11):1716-1721.

[No Author Listed] UCSC Genome Browser on Human Feb. 2009 (GRCh37/hg19) Assembly. Retrieved from http://genome.ucsc.edu/cgi-bin/hgTracks?db=hgl9&position=chr5%3A 702 11 956-7027 1 955&hgsid=452570083 _sxavccFldzrwhzM3tcNOyMcxbye 7 on Nov. 9, 2015.

[No Author Listed], Geneimprint. 2012. http://www.geneimprint.com/site/about-this-site [last accessed May 22, 2015]. 1 page.

[No Author Listed], Imprinted gene. Mosby's Dictionary of Medicine, Nursing and Health Professions. 8th ed. 2009;949.

[No Author Listed], New England BioLabs 1998/99 Catalog. 121, 284.

Aartsma-Rus et al., Antisense-induced multiexon skipping for Duchenne muscular dystrophy makes more sense. Am J Hum Genet. Jan. 2004;74(1):83-92.

Ahn et al., Retinoic acid accelerates downregulation of the Xist repressor, Oct4, and increases the likelihood of Xist activation when Tsix is deficient. BMC Develop Biol. 2010;10:90. 14 pages.

Alvarez-Salas, Nucleic acids as therapeutic agents. Curr Top Med Chem. 2008;8(15):1379-404.

Anderson et al., Post-transcriptional regulons coordinate the initiation and resolution of inflammation. Nat Rev Immunol. Jan. 2010;10(1):24-35. doi: 10.1038/nri2685.

Astuti et al., Epigenetic alteration at the DLK1-GTL2 imprinted domain in human neoplasia: analysis of neuroblastoma, phaeochromocytoma and Wilms' tumour. Br J Cancer. Apr. 25, 2005;92(8):1574-80.

Bauer et al., The quest for mammalian Polycomb response elements: are we there yet? Chromosoma. Jun. 2016;125(3):471-96. doi:10.1007/s00412-015-0539-4.

Behlke et al., Designing antisense oligonucleotides. Integrated DNA Technologies. 2005. 1-17.

Beletskii et al., PNA interference mapping demonstrates functional domains in the noncoding RNA Xist. Proc Natl Acad Sci U S A. Jul. 31, 2001;98(16):9215-20.

Beltran et al., The interaction of PRC2 with RNA or chromatin is mutually antagonistic. Genome Res. Jul. 2016;26(7):896-907. doi:10.1101/gr.197632.115. Epub May 9, 2016.

Bernardi et al., Structure, dynamics and functions of promyelocytic leukaemia nuclear bodies. Nat Rev Mol Cell Biol. Dec. 2007;8(12):1006-16. Review.

Bernstein et al., Mouse polycomb proteins bind differentially to methylated histone H3 and RNA and are enriched in facultative heterochromatin. Mol Cell Biol. Apr. 2006;26(7):2560-9.

Bernstein et al., RNA meets chromatin. Genes Dev. Jul. 15, 2005;19(14):1635-55. Review.

Blauw et al., SMN1 gene duplications are associated with sporadic ALS. Neurology. Mar. 13, 2012;78(11):776-80. doi: 10.1212/WNL.0b013e318249f697. Epub Feb. 8, 2012.

Boyer et al., Polycomb complexes repress developmental regulators in murine embryonic stem cells. Nature. May 18, 2006;441(7091):349-53. Epub Apr. 19, 2006.

Brockdorff et al., The product of the mouse Xist gene is a 15 kb inactive X-specific transcript containing no conserved ORF and located in the nucleus. Cell. Oct. 30, 1992;71(3):515-26.

Broderick et al., MicroRNA therapeutics. Gene Ther. Dec. 2011;18(12):1104-10. doi: 10.1038/gt.2011.50. Epub Apr. 28, 2011.

Brown et al., A gene from the region of the human X inactivation centre is expressed exclusively from the inactive X chromosome. Nature. Jan. 3, 1991;349:38-44.

Brown et al., The Human XIST Gene: Analysis of a 17 kb Inactive X-Specific RNA That Contains Conserved Repeats and Is Highly Localized within the Nucleus. Cell. Oct. 30, 1992;71:527-42.

Buck et al., Design strategies and performance of custom DNA sequencing primers. Biotechniques. Sep. 1999;27(3):528-36.

Burghes et al., Antisense oligonucleotides and spinal muscular atrophy: skipping along. Genes Dev. Aug. 1, 2010;24(15):1574-9. doi:10.1101/gad.1961710.

Burglen et al., Structure and organization of the human survival motor neurone (SMN) gene. Genomics. Mar. 15, 1996;32(3):479-82.

Cantàfora et al., Evaluation of RNA messengers involved in lipid trafficking of human intestinal cells by reverse-transcription polymerase chain reaction with competimer technology and microchip electrophoresis. Electrophoresis. Nov. 2003;24(21):3748-54.

Carninci et al., The transcriptional landscape of the mammalian genome. Science. Sep. 2, 2005;309(5740):1559-63.

Chahrour et al., MeCP2, a key contributor to neurological disease, activates and represses transcription. Science. May 30, 2008;320(5880):1224-9.

Chen et al., Decoding the function of nuclear long non-coding RNAs. Curr Opin Cell Biol. Jun. 2010;22(3):357-64. doi: 10.1016/j.ceb.2010.03.003. Epub Mar. 29, 2010 Review.

Chow et al., Inducible XIST-dependent X-chromosome inactivation in human somatic cells is reversible. Proc Natl Acad Sci U S A. Jun. 12, 2007;104(24):10104-9. Epub May 30, 2007.

Clark et al., The Reality of Pervasive Transcription. PLOS Bio. Jul. 2011;9(7):e1000625. 6 pages.

Clemson et al., XIST RNA paints the inactive X chromosome at interphase: evidence for a novel RNA involved in nuclear/chromosome structure. J Cell Biol. Feb. 1996;132(3):259-75.

Cohen et al., X-chromosome inactivation and the search for chromosome-wide silencers. Curr Opin Genet Dev. 2002;12:219-24.

Coombes et al., Epigenetic properties and identification of an imprint mark in the Nesp-Gnasxl domain of the mouse Gnas imprinted locus. Mol Cell Biol. Aug. 2003;23(16):5475-88.

Corcia et al., Homozygous SMN2 deletion is a protective factor in the Swedish ALS population. Eur J Hum Genet. May 2012;20(5):588-91. doi: 10.1038/ejhg.2011.255. Epub Jan. 25, 2012.

(56) References Cited

OTHER PUBLICATIONS

Corcia et al., The importance of the SMN genes in the genetics of sporadic ALS. Amyotroph Lateral Scler. Oct.-Dec. 2009;10(5-6):436-40. doi: 10.3109/17482960902759162.

Core et al., Nascent RNA sequencing reveals widespread pausing and divergent initiation at human promoters. Science. Dec. 19, 2008;322(5909):1845-8. doi: 10.1126/science.1162228. Epub Dec. 4, 2008.

Costa, Non-coding RNAs: new players in eukaryotic biology. Gene. Sep. 12, 2005;357(2):83-94. Review.

Crea et al., Pharmacologic disruption of Polycomb Repressive Complex 2 inhibits tumorigenicity and tumor progression in prostate cancer. Mol Cancer. Apr. 18, 2011;10:40. doi: 10.1186/1476-4598-10-40.

Crooke, Antisense drug technology. Principles, strategies, and applications. 2nd edition. CRC Press. 2007. 120-123.

Cuddapah et al., A novel human polycomb binding site acts as a functional polycomb response element in Drosophila. PLoS One. 2012;7(5):e36365. doi: 10.1371/journal.pone.0036365. Epub May 3, 2012.

Cushman et al., Synthesis of the covalent hydrate of the incorrectly assumed structure of aurintricarboxylic acid (ATA). Tetrahedron. 1990;46(5):1491-1498.

Daughters et al., RNA gain-of-function in spinocerebellar ataxia type 8. PLoS Genet. Aug. 2009;5(8):e1000600. doi: 10.1371/journal.pgen.1000600. Epub Aug. 14, 2009.

Davidovich et al., The recruitment of chromatin modifiers by long noncoding RNAs: lessons from PRC2. RNA. Dec. 2015;21(12):2007-22. doi:10.1261/rna.053918.115.

Davidovich et al., Toward a consensus on the binding specificity and promiscuity of PRC2 for RNA. Mol Cell. Feb. 5, 2015;57(3):552-8. doi: 10.1016/j.molcel.2014.12.017. Epub Jan. 15, 2015.

Davidson et al., Singles engage the RNA interference pathway. Cell. Aug. 31, 2012;150(5):873-5. doi: 10.1016/j.cell.2012.08.008.

Denisenko et al., Point mutations in the WD40 domain of Eed block its interaction with Ezh2. Mol Cell Biol. Oct. 1998;18(10):5634-42.

Dheda et al., Validation of housekeeping genes for normalizing RNA expression in real-time PCR. Biotechniques. Jul. 2004;37(1):112-4, 116, 118-9.

Di Certo et al., The artificial gene Jazz, a transcriptional regulator of utrophin, corrects the dystrophic pathology in mdx mice. Hum Mol Genet. Mar. 1, 2010;19(5):752-60. doi: 10.1093/hmg/ddp539. Epub Dec. 4, 2009.

Dias et al., Antisense oligonucleotides: basic concepts and mechanisms. Mol Cancer Ther. Mar. 2002;1(5):347-55.

Dinger et al., NRED: a database of long noncoding RNA expression. Nucleic Acids Res. Jan. 2009;37(Database issue):D122-6. doi: 10.1093/nar/gkn617. Epub Oct. 1, 2008.

Dominski et al., Identification and characterization by antisense oligonucleotides of exon and intron sequences required for splicing. Mol Cell Biol. Nov. 1994; 14(11): 7445-7454.

Dominski et al., Restoration of correct splicing in thalassemic pre-mRNA by antisense oligonucleotides. Proc Natl Acad Sci U S A. Sep. 15, 1993;90(18):8673-7.

Du et al., Progress toward therapy with antisense-mediated splicing modulation. Curr Opin Mol Ther. Apr. 2009;11(2):116-23.

Duthie et al., Xist RNA exhibits a banded localization on the inactive X chromosome and is excluded from autosomal material in cis. Hum Mol Genet. Feb. 1999;8(2):195-204.

Eddy, Non-coding RNA genes and the modern RNA world. Nat Rev Genet. Dec. 2001;2(12):919-29.

Edwards et al., Mechanisms regulating imprinted genes in clusters. Curr Opin Cell Biol. Jun. 2007;19(3):281-9. Review.

Efthymiou, T. et al., Chemical architecture and applications of nucleic acid derivatives containing 1, 2, 3-triazole functionalities synthesized via click chemistry, Molecules, 2012, vol. 17, No. 11, pp. 12665-12703.

Engström et al., Complex Loci in human and mouse genomes. PLoS Genet. Apr. 2006;2(4):e47. Epub Apr. 28, 2006.

Faghihi et al., Expression of a noncoding RNA is elevated in Alzheimer's disease and drives rapid feed-forward regulation of [beta]-secretase. Nat Med. Jul. 2008:14(7):723-30. doi:10.1038/nm1784. Epub Feb. 23, 2010. 19 pages.

Feldkötter et al., Quantitative analyses of SMN1 and SMN2 based on real-time lightCycler PCR: fast and highly reliable carrier testing and prediction of severity of spinal muscular atrophy. Am J Hum Genet. Feb. 2002;70(2):358-68. Epub Dec. 21, 2001.

Fish et al., Hypoxia-inducible expression of a natural cis-antisense transcript inhibits endothelial nitric-oxide synthase. J Biol Chem. May 25, 2007;282(21):15652-66. Epub Apr. 2, 2007.

Francis et al., Reconstitution of a functional core polycomb repressive complex. Mol Cell. Sep. 2001;8(3):545-56.

Frieden et al., Expanding the design horizon of antisense oligonucleotides with alpha-L-LNA. Nucleic Acids Res. Nov. 1, 2003;31(21):6365-72.

Froberg et al., Guided by RNAs: X-inactivation as a model for lncRNA function. J Mol Biol. Oct. 9, 2013;425(19):3698-706. doi: 10.1016/j.jmb.2013.06.031. Epub Jun. 28, 2013. Review. 15 pages.

Fu et al., Mir-144 selectively regulates embryonic alpha-hemoglobin synthesis during primitive erythropoiesis. Blood. Feb. 5, 2009;113(6):1340-9.

Gajera et al., Molecular and biochemical characterization of Trichoderma isolates inhibiting a phytopathogenic fungi Aspergillus niger Van Tieghem. Phys Mol Plant Path. 2010;74:274-282.

Ganguli et al., Antagomirbase—a putative antagomir database. Bioinformation. 2011;7(1):41-3.

Genbank Submission; Accession No. AM750048. Gupta et al. Jul. 12, 2007.

Genbank Submission; NCBI, Accession No. AM773775. Radha et al., Jul. 13, 2007.

Genbank Submission; NCBI, Accession No. AM911724.1; Talwar et al. Nov. 26, 2007.

Genbank Submission; NCBI, Accession No. NG_008691.1 Mar. 2011. 11 pages.

Genbank Submission; NCBI, Accession No. NM_022876.2. Apr. 2010. 5 pages.

Genbank Submission; NIH/NCBI, Accession No. AA106140. Marra et al., Feb. 4, 1997. 1 page.

Genbank Submission; NIH/NCBI, Accession No. ABZ86223. Nyce et al. Oct. 17, 2003.

Genbank Submission; NIH/NCBI, Accession No. AL137002. Holt, Dec. 13, 2012. 29 pages.

Genbank Submission; NIH/NCBI, Accession No. BX383579. Li et al., Dec. 23, 2010. 1 page.

Genbank Submission; NIH/NCBI, Accession No. NM_001079668. Young et al., Jan. 18, 2014. 4 pages.

Genbank Submission; NIH/NCBI, Accession No. NM_003317. Young et al., Jan. 18, 2014. 4 pages.

Genbank Submission; NIH/NCBI, Accession No. NM_028475. Diez-Roux et al., Feb. 3, 2014. 6 pages.

Gerbino et al., Mislocalised FUS mutants stall spliceosomal snRNPs in the cytoplasm. Neurobiol Dis. Jul. 2013;55:120-8. doi:10.1016/j.nbd.2013.03.003. Epub Mar. 21, 2013.

Golding et al., Depletion of Kcnq1ot1 non-coding RNA does not affect imprinting maintenance in stem cells. Development. 2011;138:3667-8. doi:10.1242/dev.057778.

Gontan et al., Long Noncoding RNAs and X Chromosome Inactivation. Prog Mol Subcell Biol. 2011;51:43-64. doi: 10.1007/978-3-642-16502-3_3.

Gooding et al., Oligonucleotide conjugates—Candidates for gene silencing therapeutics. European J Pharmaceutics Biopharmaceutics. 2016;107:321-340. [Epub.]Aug. 10, 2016.

Groen et al., ALS-associated mutations in FUS disrupt the axonal distribution and function of SMN. Hum Mol Genet. Sep. 15, 2013;22(18):3690-704. doi: 10.1093/hmg/ddt222. Epub May 15, 2013.

Guo et al., High resolution genome wide binding event finding and motif discovery reveals transcription factor spatial binding constraints. PLoS Comput Biol. 2012;8(8):e1002638. doi: 10.1371/journal.pcbi.1002638. Epub Aug. 9, 2012.

(56) References Cited

OTHER PUBLICATIONS

Gupta et al., Long non-coding RNA HOTAIR reprograms chromatin state to promote cancer metastasis. Nature. Apr. 15, 2010;464(7291):1071-6. doi: 10.1038/nature08975. E-pub version.

Guttman et al., Chromatin signature reveals over a thousand highly conserved large non-coding RNAs in mammals. Nature. Mar. 12, 2009;458(7235):223-7. doi: 10.1038/nature07672. Epub Sep. 30, 2009. 13 pages.

Guttman et al., Modular regulatory principles of large non-coding RNAs. Nature. Feb. 15, 2012;482(7385):339-46. Review.

Halley et al., Natural antisense transcripts as therapeutic targets. Drug Discov Today Ther Strateg. Fall 2013;10(3):e119-e125.

He et al., Polycomb repressive complex 2 regulates normal development of the mouse heart. Circ Res. Feb. 3, 2012;110(3):406-15. doi: 10.1161/CIRCRESAHA.111.252205. Epub Dec. 8, 2011.

He et al., Conjugation and Evaluation of Triazole-Linked Single Guide RNA for CRISPR-Cas9 Gene Editing, ChemBioChem. 2016;17:1809-1812.

Hendrich et al., Evolutionary conservation of possible functional domains of the human and murine XIST genes. Human Molec Gen. 1993;2(6):663-72.

Hernandez et al., Degradation of nuclease-stabilized RNA oligonucleotides in Mycoplasma-contaminated cell culture media. Nucleic Acid Ther. Feb. 2012;22(1):58-68. doi: 10.1089/nat.2011.0316. Epub Jan. 9, 2012.

Horike et al., Targeted disruption of the human LIT1 locus defines a putative imprinting control element playing an essential role in Beckwith-Wiedemann syndrome. Hum Mol Genet. Sep. 1, 2000;9(14):2075-83.

Houseley et al., RNA-quality control by the exosome. Nat Rev Mol Cell Biol. Jul. 2006;7(7):529-39.

Hua et al., Antisense correction of SMN2 splicing in the CNS rescues necrosis in a type III SMA mouse model. Genes Dev. Aug. 1, 2010;24(15):1634-44. doi: 10.1101/gad.1941310. Epub Jul. 12, 2010.

Hua et al., Antisense Masking of an hnRNP A1/A2 Intronic Splicing Silencer Corrects SMN2 Splicing in Transgenic Mice. Am J Hum Genet. Apr. 11, 2008; 82(4):834-48. Published online Apr. 4, 2008. doi: 10.1016/j.ajhg.2008.01.014.

Hua et al., Enhancement of SMN2 Exon 7 Inclusion by Antisense Oligonucleotides Targeting the Exon. PLoS Biol. Apr. 2007;5(4):e73. Published online Mar. 13, 2007. doi: 10.1371/journal.pbio.0050073.

Hua et al., Peripheral SMN restoration is essential for long-term rescue of a severe spinal muscular atrophy mouse model. Nature. Oct. 5, 2011;478(7367):123-6. doi: 10.1038/nature10485.

Huang, Shoujun et al., Non-encoding RNA and development of animals, Science China Life Science, Dec. 31, 2009; pp. 21-30.

Inesi et al., Studies of Ca2+ ATPase (SERCA) inhibition. J Bioenerg Biomembr. Dec. 2005;37(6):365-8. Review.

Inoue et al., Synthesis and hybridization studies on two complementary nona(2'-O-methyl)ribonucleotides. Nucleic Acids Res. Aug. 11, 1987;15(15):6131-48.

Inouye, Antisense RNA: its functions and applications in gene regulation—a review. Gene. Dec. 10, 1988;72(1-2):25-34.

Jackson et al., Expression profiling reveals off-target gene regulation by RNAi. Nat Biotechnol. Jun. 2003;21(6):635-7. Epub May 18, 2003.

Jayaprakash et al., Non-nucleoside building blocks for copper-assisted and copper-free click chemistry for the efficient synthesis of RNA conjugates. Organic Letters. 2010;12(23):5410-5413.

Jeon et al., YY1 tethers Xist RNA to the inactive X nucleation center. Cell. Jul. 8, 2011;146(1):119-33. doi: 10.1016/j.cell.2011.06.026.

Jepsen et al., Locked nucleic acid: a potent nucleic acid analog in therapeutics and biotechnology. Oligonucleotides. 2004;14(2):130-46. Review.

Jia et al., Genome-wide computational identification and manual annotation of human long noncoding RNA genes. RNA. Aug. 2010;16(8):1478-87. doi: 10.1261/rna.1951310. Epub Jun. 29, 2010.

Johansson et al., Target-specific arrest of mRNA translation by antisense 2'-O-alkyloligoribonucleotides. Nucleic Acids Res. Nov. 11, 1994;22(22):4591-8.

Johnson, Long non-coding RNAs in Huntington's disease neurodegeneration. Neurobiol Dis. 2012;46:245-54.

Kanduri et al., The length of the transcript encoded from the Kcnq1ot1 antisense promoter determines the degree of silencing. EMBO J. 2006;25:2096-106.

Kanhere et al., Short RNAs are transcribed from repressed polycomb target genes and interact with polycomb repressive complex-2. Mol Cell. Jun. 11, 2010;38(5):675-88. doi: 10.1016/j.molcel.2010.03.019.

Kao et al., Tumor necrosis factor-alpha decreases sarcoplasmic reticulum Ca2+-ATPase expressions via the promoter methylation in cardiomyocytes. Crit Care Med. Jan. 2010;38(1):217-22. doi: 10.1097/CCM.0b013e3181b4a854.

Kapranov et al., Genome-wide transcription and the implications for genomic organization. Nat Rev Genet. Jun. 2007;8(6):413-23.

Kapranov et al., RNA maps reveal new RNA classes and a possible function for pervasive transcription. Science. Jun. 8, 2007;316(5830):1484-8.

Kariya et al., Mutant superoxide dismutase 1 (SOD1), a cause of amyotrophic lateral sclerosis, disrupts the recruitment of SMN, the spinal muscular atrophy protein to nuclear Cajal bodies. Hum Mol Genet. Aug. 1, 2012;21(15):3421-34. doi: 10.1093/hmg/dds174. Epub May 11, 2012.

Keil et al., A short antisense oligonucleotide ameliorates symptoms of severe mouse models of spinal muscular atrophy. Mol Ther Nucleic Acids. Jul. 8, 2014;3:e174. doi: 10.1038/mtna.2014.23.

Khalil et al., Many human large intergenic noncoding RNAs associate with chromatin-modifying complexes and affect gene expression. Proc Natl Acad Sci U S A. Jul. 14, 2009;106(28):11667-72.

Kierzek et al., The influence of locked nucleic acid residues on the thermodynamic properties of 2'-O-methyl RNA/RNA heteroduplexes. Nucleic Acids Res. Sep. 9, 2005;33(16):5082-93. Print 2005.

Kim et al., Identification of clustered YY1 binding sites in imprinting control regions. Genome Res. Jul. 2006;16(7):901-11. Epub Jun. 7, 2006.

Kiss, Small nucleolar RNA-guided post-transcriptional modification of cellular RNAs. EMBO J. Jul. 16, 2001;20(14):3617-22.

Klein et al., Homeostatic regulation of MeCP2 expression by a CREB-induced microRNA. Nat Neurosci. Dec. 2007;10(12):1513-4.

Krützfeldt et al., Silencing of microRNAs in vivo with 'antagomirs'. Nature. Dec. 1, 2005;438(7068):685-9. Epub Oct. 30, 2005.

Ku et al., Genomewide analysis of PRC1 and PRC2 occupancy identifies two classes of bivalent domains. PLoS Genet. Oct. 2008;4(10):e1000242. doi: 10.1371/journal.pgen.1000242. Epub Oct. 31, 2008. 14 pages.

Kutyavin et al., Reduced aggregation and improved specificity of G-rich oligodeoxyribonucleotides containing pyrazolo[3,4-d]pyrimidine guanine bases. Nucleic Acids Res. Nov. 15, 2002;30(22):4952-9.

Lapointe et al., Gene expression profiling identifies clinically relevant subtypes of prostate cancer. Proc Natl Acad Sci U S A. Jan. 20, 2004;101(3):811-6. Epub Jan. 7, 2004.

Latorra et al., Design considerations and effects of LNA in PCR primers. Mol Cell Probes. Oct. 2003;17(5):253-9.

Lee et al., A 450 kb Transgene Displays Properties of the Mammalian X-Inactivation Center. Cell. Jul. 12, 1996;86:83-94.

Lee et al., Control of developmental regulators by Polycomb in human embryonic stem cells. Cell. Apr. 21, 2006;125(2):301-13.

Lee et al., Genetic analysis of the mouse X inactivation center defines an 80-kb multifunction domain. Proc Natl Acad Sci U S A. Mar. 30, 1999;96(7):3836-41.

Lee et al., Homozygous SMN2 Deletion is a Major Risk Factor among Twenty-Five Korean Sporadic Amyotrophic Lateral Sclerosis Patients. Yonsei Med J. Jan. 2012;53(1):53-57.

Lee et al., Targeted Mutagenesis of Tsix Leads to Nonrandom X Inactivation. Cell. Oct. 1, 1999;99:47-57.

Lee et al., Tsix, a gene antisense to Xist at the X-inactivation centre. Nat Genet. Apr. 1999;21:400-4.

(56) References Cited

OTHER PUBLICATIONS

Lee, Disruption of Imprinted X Inactivation by Parent-of-Origin Effects at Tsix. Cell. Sep. 29, 2000;103:17-27.
Lee, Epigenetic regulation by long noncoding RNAs. Science. Dec. 14, 2012;338(6113):1435-9. Review.
Lee, Homozygous Tsix mutant mice reveal a sex-ratio distortion and revert to random X-inactivation. Nat Genet. Sep. 2002;32:195-200.
Lee, Lessons from X-chromosome inactivation: long ncRNA as guides and tethers to the epigenome. Genes Dev. Aug. 15, 2009;23(16):1831-42. doi: 10.1101/gad.1811209.
Lee, The X as a Model for RNA's Niche in Epigenomic Regulation. Cold Spring Harb Perspect Biol. 2010;2:A003749. 12 pages.
Lennox et al., Improved Performance of Anti-miRNA Oligonucleotides Using a Novel Non-Nucleotide Modifier. Mol Ther Nucleic Acids. Aug. 27, 2013;2:e117. doi: 10.1038/mtna.2013.46.
Li et al., CTCF regulates allelic expression of Igf2 by orchestrating a promoter-polycomb repressive complex 2 intrachromosomal loop. Mol Cell Biol. Oct. 2008;28(20):6473-82. doi: 10.1128/MCB.00204-08. Epub Jul. 28, 2008.
Li et al., Jarid2 and PRC2, partners in regulating gene expression. Genes Dev. Feb. 15, 2010;24(4):368-80. doi: 10.1101/gad.1886410. Epub Feb. 1, 2010.
Lim et al., Modulation of survival motor neuron pre-mRNA splicing by inhibition of alternative 3' splice site pairing. J Biol Chem. Nov. 30, 2001;276(48):45476-83. Epub Oct. 2, 2001.
Lima et al., Single-stranded siRNAs activate RNAi in animals. Cell. Aug. 31, 2012;150(5):883-94. doi: 10.1016/j.cell.2012.08.014.
Lin et al., An in-depth map of polyadenylation sites in cancer. Nucleic Acids Res. Sep. 1, 2012;40(17):8460-71. Epub Jun. 29, 2012.
Lin et al., Asymmetric regulation of imprinting on the maternal and paternal chromosomes at the Dlk1-Gtl2 imprinted cluster on mouse chromosome 12. Nat Genet. Sep. 2003;35(1):97-102. Epub Aug. 24, 2003.
Lipovich et al., MacroRNA underdogs in a microRNA world: evolutionary, regulatory, and biomedical significance of mammalian long non-protein-coding RNA. Biochim Biophys Acta. Sep. 2010;1799(9):597-615. Review.
Margueron et al., The Polycomb complex PRC2 and its mark in life. Nature. Jan. 20, 2011;469(7330):343-9. Review.
Matsuda et al., siRNA conjugates carrying sequentially assembled trivalent N-acetylgalactosamine linked through nucleosides elicit robust gene silencing in vivo in hepatocytes., ACS Chemical Biology. 2015;10:1181-1187.
Mencía et al., Mutations in the seed region of human miR-96 are responsible for nonsyndromic progressive hearing loss. Nat Genet. May 2009;41(5):609-13. doi: 10.1038/ng.355. Epub Apr. 12, 2009.
Mendenhall et al., GC-rich sequence elements recruit PRC2 in mammalian ES cells. PLoS Genet. Dec. 9, 2010;6(12):e1001244. doi: 10.1371/journal.pgen.1001244.
Mercer et al., Long non-coding RNAs: insights into functions. Nat Rev Genet. Mar. 2009;10(3):155-9. Review.
Mercer et al., Structure and function of long noncoding RNAs in epigenetic regulation. Mar. 5, 2013;20:300-7.
Merienne et al., SCA8 CAG/CTG expansions, a tale of two TOXICities: a unique or common case? PLoS Genet. Aug. 2009;5(8):e1000593. doi: 10.1371/journal.pgen.1000593. Epub Aug. 14, 2009.
Miller et al., A TALE nuclease architecture for efficient genome editing. Nat Biotechnol. Feb. 2011;29(2):143-8. doi: 10.1038/nbt.1755. Epub Dec. 22, 2010.
Miremadi et al., Cancer genetics of epigenetic genes. Hum Mol Genet. Apr. 15, 2007;16 Spec No. 1:R28-49. Review.
Mirguet et al., From ApoA1 upregulation to BET family bromodomain inhibition:discovery of I-BET151. Bioorg Med Chem Lett. Apr. 15, 2012;22(8):2963-7. doi:10.1016/j.bmcl.2012.01.125. Epub Feb. 8, 2012.
Miura et al., Utrophin upregulation for treating Duchenne or Becker muscular dystrophy: how close are we? Trends Mol Med. Mar. 2006;12(3):122-9. Epub Jan. 27, 2006.

Miyajima et al., Identification of a cis-acting element for the regulation of SMN exon 7 splicing. J Biol Chem. Jun. 28, 2002;277(26):23271-7. Epub Apr. 15, 2002.
Modarresi et al., Inhibition of natural antisense transcripts in vivo results in gene-specific transcriptional upregulation. Nat Biotechnol. Mar. 25, 2012;30(5):453-9. doi: 10.1038/nbt.2158. 21 pages.
Montgomery et al., The murine polycomb group protein Eed is required for global histone H3 lysine-27 methylation. Curr Biol. May 24, 2005;15(10):942-7.
Morris et al., Small interfering RNA-induced transcriptional gene silencing in human cells. Science. Aug. 27, 2004;305(5688):1289-92. Epub Aug. 5, 2004.
Morris, RNA-mediated transcriptional gene silencing in human cells. Curr Top Microbiol Immunol. 2008;320:211-24. Review.
Morse et al., Depleting regulatory T cells with arginine-rich, cell-penetrating, peptide-conjugated morpholino oligomer targeting FOXP3 inhibits regulatory T-cell function. Cancer Gene Ther. Jan. 2012;19(1):30-7. doi: 10.1038/cgt.2011.63.
Munroe, Antisense RNA inhibits splicing of pre-mRNA in vitro. EMBO J. Aug. 1988; 7(8):2523-32.
Nagano et al., The Air noncoding RNA epigenetically silences transcription by targeting G9a to chromatin. Science. Dec. 12, 2008;322(5908):1717-20.
Nair et al., Multivalent N-acetylgalactosamine-conjugated siRNA localizes in hepatocytes and elicits robust RNAi-mediated gene silencing, J American Chemical Society.2014;136:16958-16961.
Nakao, Gene Cluster control through epigenetic mechanisms and cytopathology. Uehara memorial life science foundation research report collection. 23;2009:1-4.
Nie et al., Long non-coding RNAs: versatile master regulators of gene expression and crucial players in cancer. Am J Transl Res. 2012;4(2):127-50. Epub Apr. 8, 2012.
Nishida et al., Synthesis, RNA selective hybridization and high nuclease resistance of an oligonucleotide containing novel bridged nucleic acid with cyclic urea structure. Chem Commun (Camb). Aug. 7, 2010;46(29):5283-5. doi: 10.1039/c0cc00154f. Epub Jun. 22, 2010.
Niwano et al., Lentiviral vector-mediated SERCA2 gene transfer protects against heart failure and left ventricular remodeling after myocardial infarction in rats. Mol Ther. Jun. 2008;16(6):1026-32. doi: 10.1038/mt.2008.61. Epub Mar. 25, 2008.
Numata et al., Comparative analysis of cis-encoded antisense RNAs in eukaryotes. Gene. May 1, 2007;392(1-2):134-41.
Numata et al., Identification of novel endogenous antisense transcripts by DNA microarray analysis targeting complementary strand of annotated genes. BMC Genomics. Aug. 22, 2009;10:392. doi: 10.1186/1471-2164-10-392.
Okada et al., Comparative expression analysis uncovers novel features of endogenous antisense transcription. Hum Mol Genet. Jun. 1, 2008;17(11):1631-40. doi: 10.1093/hmg/ddn051. Epub Feb. 18, 2008.
Ørom et al., LNA-modified oligonucleotides mediate specific inhibition of microRNA function. Gene. May 10, 2006;372:137-41. Epub Feb. 24, 2006.
Ozsolak et al., Comprehensive polyadenylation site maps in yeast and human reveal pervasive alternative polyadenylation. Cell. Dec. 10, 2010;143(6):1018-29. doi: 10.1016/j.cell.2010.11.020.
Pandey et al., Kcnq1ot1 antisense noncoding RNA mediates lineage-specific transcriptional silencing through chromatin-level regulation. Mol Cell. Oct. 24, 2008;32(2):232-46. doi: 10.1016/j.molcel.2008.08.022.
Paro et al., Extending the frontiers of epigenetic regulation. Curr Opin Genet Dev. Apr. 2010;20(2):107-9. doi: 10.1016/j.gde.2010.03.011.
Pasini et al., Suz12 is essential for mouse development and for EZH2 histone methyltransferase activity. EMBO J. Oct. 13, 2004;23(20):4061-71. Epub Sep. 23, 2004.
Peng et al., Jarid2/Jumonji coordinates control of PRC2 enzymatic activity and target gene occupancy in pluripotent cells. Cell. Dec. 24, 2009;139(7):1290-302. doi: 10.1016/j.cell.2009.12.002. Epub Jul. 29, 2010. 24 pages.
Penny et al., Requirement for Xist in X chromosome inactivation. Nature. Jan. 11, 1996;379(6561):131-7.

(56) References Cited

OTHER PUBLICATIONS

Pereira et al., Ezh2, the histone methyltransferase of PRC2, regulates the balance between self-renewal and differentiation in the cerebral cortex. Proc Natl Acad Sci U S A. Sep. 7, 2010;107(36):15957-62. doi: 10.1073/pnas.1002530107. Epub Aug. 23, 2010.

Petersen et al., LNA: a versatile tool for therapeutics and genomics. Trends Biotech. Feb. 2003;21(2):74-81. Review.

Pietersen et al., Stem cell regulation by polycomb repressors: postponing commitment. Curr Opin Cell Biol. Apr. 2008;20(2):201-7. doi: 10.1016/j.ceb.2008.01.004. Epub Mar. 4, 2008. Review.

Plath et al., Role of Histone H3 Lysine 27 Methylation in X Inactivation. Science. Apr. 4, 2003;300:131-5. doi: 10.1126/science.1084274.

Ponting et al., Evolution and functions of long noncoding RNAs. Cell. Feb. 20, 2009;136(4):629-41. doi: 10.1016/j.cell.2009.02.006. Review.

Prensner et al., Transcriptome sequencing across a prostate cancer cohort identifies PCAT-1, an unannotated lincRNA implicated in disease progression. Nat Biotechnol. Jul. 31, 2011;29(8):742-9. doi: 10.1038/nbt.1914.

Qi et al., Repurposing CRISPR as an RNA-guided platform for sequence-specific control of gene expression. Cell. Feb. 28, 2013;152(5):1173-83. doi: 10.1016/j.cell.2013.02.022.

Rader, Molecular regulation of HDL metabolism and function: implications for novel therapies. J Clin Invest. Dec. 2006;116(12):3090-100.

Rajasekhar et al., Concise review: roles of polycomb group proteins in development and disease: a stem cell perspective. Stem Cells. Oct. 2007;25(10):2498-510. Epub Jun. 28, 2007. Review.

Redrup et al., The long noncoding RNA Kcnq1ot1 organises a lineage-specific nuclear domain for epigenetic gene silencing. Development. Feb. 2009;136(4):525-30. doi: 10.1242/dev.031328. Epub Jan. 14, 2009. 14 pages.

Reyon et al., Flash assembly of TALENs for high-throughput genome editing. Nat Biotechnol. May 2012;30(5):460-5. doi: 10.1038/nbt.2170.

Ringrose et al., Epigenetic regulation of cellular memory by the Polycomb and Trithorax group proteins. Annu Rev Genet. 2004;38:413-43. Review.

Rinn et al., Functional demarcation of active and silent chromatin domains in human HOX loci by noncoding RNAs. Cell. Jun. 29, 2007;129(7):1311-23.

Rinn et al., Genome Regulation by Long Noncoding RNAs. Annu Rev Biochem. 2012;81:145-66.

Røsok et al., Systematic identification of sense-antisense transcripts in mammalian cells. Nat Biotechnol. Jan. 2004;22(1):104-8. Epub Dec. 14, 2003.

Rozen et al., Primer3 on the WWW for general users and for biologist programmers. Methods Mol Biol. 2000;132:365-86.

Sankaran et al., MicroRNA-15a and -16-1 act via MYB to elevate fetal hemoglobin expression in human trisomy 13. Proc Natl Acad Sci U S A. Jan. 25, 2011;108(4):1519-24.

Sankaran, Targeted therapeutic strategies for fetal hemoglobin induction. Hematol Am Soc Hematol Educ Program. 2011;2011:459-65.

Sarma et al., Locked nucleic acids (LNAs) reveal sequence requirements and kinetics of Xist RNA localization to the X chromosome. Proc Natl Acad Sci U S A. Dec. 21, 2010;107(51):22196-201. doi: 10.1073/pnas.1009785107. Epub Dec. 6, 2010.

Saxena et al., Long non-coding RNA modifies chromatin. Bioessays. 2011;33:830-9. Review.

Schadt et al., An integrative genomics approach to infer causal associations between gene expression and disease. Nat Genet. Jul. 2005;37(7):710-7. Epub Jun. 19, 2005.

Schlesinger et al., Polycomb-mediated methylation on Lys27 of histone H3 pre-marks genes for de novo methylation in cancer. Nat Genet. Feb. 2007;39(2):232-6. Epub Dec. 31, 2006.

Schoeftner et al., Recruitment of PRC1 function at the initiation of X inactivation independent of PRC2 and silencing. EMBO J. Jul. 12, 2006;25(13):3110-22. Epub Jun. 8, 2006.

Schuettengruber et al., Genome regulation by polycomb and trithorax proteins. Cell. Feb. 23, 2007;128(4):735-45.

Schultz et al., Enhancers compete with a long non-coding RNA for regulation of the Kcnq1 domain. Nucl Acids Res. 2015;43(2):745-59.

Schwartz et al., Genome-wide analysis of Polycomb targets in *Drosophila melanogaster*. Nat Genet. Jun. 2006;38(6):700-5.

Schwartz et al., Polycomb complexes and epigenetic states. Curr Opin Cell Biol. 2008;20:266-73. doi: 10.1016/j.ceb.2008.03.002.

Schwartz et al., Polycomb silencing mechanisms and the management of genomic programmes. Nat Rev Genet. Jan. 2007;8(1):9-22.

Sciabola et al., Improved nucleic acid descriptors for siRNA efficacy prediction. Nucleic Acids Res. Feb. 1, 2013;41(3):1383-94. doi: 10.1093/nar/gks1191. Epub Dec. 14, 2012.

Seong et al., Huntingtin facilitates polycomb repressive complex 2. Hum Mol Genet. Feb. 15, 2010;19(4):573-83. doi: 10.1093/hmg/ddp524. Epub Nov. 23, 2009.

Shaver et al., Origin of the polycomb repressive complex 2 and gene silencing by an E(z) homolog in the unicellular alga *Chlamydomonas*. Epigenetics. May 16, 2010;5(4):301-12. Epub May 24, 2010.

Shen et al,. EZH1 mediates methylation on histone H3 lysine 27 and complements EZH2 in maintaining stem cell identity and executing pluripotency. Mol Cell. Nov. 21, 2008;32(4):491-502. doi: 10.1016/j.molcel.2008.10.016.

Shen et al., Jumonji modulates polycomb activity and self-renewal versus differentiation of stem cells. Cell. Dec. 24, 2009;139(7):1303-14. doi: 10.1016/j.cell.2009.12.003. Epub Jun. 24, 2010. 26 pages.

Shiraki et al., Cap analysis gene expression for high-throughput analysis of transcriptional starting point and identification of promoter usage. Proc Natl Acad Sci U S A. Dec. 23, 2003;100(26):15776-81. Epub Dec. 8, 2003.

Shore et al., Pregnancy-induced noncoding RNA (PINC) associates with polycomb repressive complex 2 and regulates mammary epithelial differentiation. PLoS Genet. 2012;8(7):e1002840. doi: 10.1371/journal.pgen.1002840. Epub Jul. 26, 2012.

Simon et al., High-resolution Xist binding maps reveal two-step spreading during X-chromosome inactivation. Nature. Dec. 19, 2013;504(7480):465-9. doi: 10.1038/nature12719. Epub Oct. 27, 2013.

Simon et al., Roles of the EZH2 histone methyltransferase in cancer epigenetics. Mutat Res. Dec. 1, 2008;647(1-2):21-9. Review.

Sing et al., A vertebrate Polycomb response element governs segmentation of the posterior hindbrain. Cell. Sep. 4, 2009;138(5):885-97. doi: 10.1016/j.cell.2009.08.020.

Singh et al., A short antisense oligonucleotide masking a unique intronic motif prevents skipping of a critical exon in spinal muscular atrophy. RNA Biol. Jul.-Aug. 2009;6(3):341-50. Epub Jul. 14, 2009.

Singh et al., Splicing of a Critical Exon of Human Survival Motor Neuron Is Regulated by a Unique Silencer Element Located in the Last Intron. Mol Cell Biol. Feb. 2006;26(4):1333-46. doi: 10.1128/MCB.26.4.1333-1346.2006.

Skordis et al., Antisense oligonucleotides provide a trans-acting splicing enhancer that stimulates SMN2 gene expression in patient fibroblasts. Proc Natl Acad Sci U S A. Apr. 1, 2003;100(7):4114-9. Epub Mar. 17, 2003.

Sparmann et al., Polycomb silencers control cell fate, development and cancer. Nat Rev Cancer. Nov. 2006;6(11):846-56. Review.

Submission. EBI Accession No. EMBL:GC092872. Palma et al. Aug. 31, 2008.

Sun et al., Evidence for a preferential targeting of 3'-UTRs by cis-encoded natural antisense transcripts. Nucleic Acids Res. Oct. 4, 2005;33(17):5533-43. Print 2005.

Sun et al., SNPs in human miRNA genes affect biogenesis and function. RNA. Sep. 2009;15(9):1640-51. doi: 10.1261/rna.1560209. Epub Jul. 17, 2009.

Tae et al., Bromodomain protein 7 interacts with PRMT5 and PRC2, and is involved in transcriptional repression of their target genes. Nucleic Acids Res. Jul. 2011;39(13):5424-38. doi: 10.1093/nar/gkr170.

Taft et al., Non-coding RNAs: regulators of disease. J Pathol. Jan. 2010;220(2):126-39. doi: 10.1002/path.2638. Review.

(56) References Cited

OTHER PUBLICATIONS

Taft et al., Tiny RNAs associated with transcription start sites in animals. Nat Genet. May 2009;41(5):572-8. doi: 10.1038/ng.312. Epub Apr. 19, 2009. Erratum in: Nat Genet. Jul. 2009;41(7):859.
Takagi et al., Role of Sp1 in transcription of human ATP2A2 gene in keratinocytes. J Invest Dermatol. Jan. 2008;128(1):96-103. Epub Jun. 28, 2007.
Takahashi et al., Deletion of Gtl2, imprinted non-coding RNA, with its differentially methylated region induces lethal parent-origin-dependent defects in mice. Hum Mol Genet. May 15, 2009;18(10):1879-88. doi: 10.1093/hmg/ddp108. Epub Mar. 4, 2009.
Tano et al., MALAT-1 enhances cell motility of lung adenocarcinoma cells by influencing the expression of motility-related genes. FEBS Lett. Nov. 19, 2010;584(22):4575-80. doi: 10.1016/j.febslet.2010.10.008. Epub Oct. 13, 2010.
Taylor et al., Antisense oligonucleotides: a systematic high-throughput approach to target validation and gene function determination. Drug Discov Today. Dec. 1999;4(12):562-567.
Thomas et al., Development of apolipoprotein B antisense molecules as a therapy for hyperlipidemia. Curr Atheroscler Rep. Jan. 2010;12(1):58-65. doi: 10.1007/s11883-009-0078-7.
Thorvaldsen et al., A YY1 bridge for X inactivation. Cell. Jul. 8, 2011;146(1):11-3. doi: 10.1016/j.cell.2011.06.029.
Thorvaldsen et al., SnapShot: imprinted gene clusters. Cell. Sep. 7, 2007;130(5):958.
Tian et al., The long noncoding RNA, Jpx, is a molecular switch for X chromosome inactivation. Cell. Oct. 29, 2010;143(3):390-403. doi: 10.1016/j.cell.2010.09.049. 21 pages.
Tsai et al., Higher order chromatin structure at the X-inactivation center via looping DNA. Dev Biol. Jul. 15, 2008;319(2):416-25. doi: 10.1016/j.ydbio.2008.04.010. Epub Apr. 18, 2008. 22 pages.
Tsai et al., Long noncoding RNA as modular scaffold of histone modification complexes. Science. Aug. 6, 2010;329(5992):689-93. doi: 10.1126/science.1192002. Epub Nov. 2, 2010. 9 pages.
Tsuiji et al., Spliceosome integrity is defective in the motor neuron diseases ALS and SMA. EMBO Mol Med. Feb. 2013;5(2):221-34. doi: 10.1002/emmm.201202303. Epub Jan. 25, 2013.
Turner et al., Survival motor neuron deficiency enhances progression in an amyotrophic lateral sclerosis mouse model. Neurobiol Dis. Jun. 2009;34(3):511-7. doi: 10.1016/j.nbd.2009.03.005. Epub Mar. 28, 2009.
Valen et al., Genome-wide detection and analysis of hippocampus core promoters using DeepCAGE. Genome Res. Feb. 2009;19(2):255-65. doi: 10.1101/gr.084541.108. Epub Dec. 11, 2008.
Van Peer et al., MiRBase Tracker: keeping track of microRNA annotation changes. Database (Oxford). Aug. 25, 2014;2014. pii:bau080. doi: 10.1093/database/bau080. Print 2014.
Varela et al., Natural Antisense Makes Sense for Gene-specific Activation in Brain. Mol Ther Nucleic Acids. May 15, 2012;1:e24. doi: 10.1038/mtna.2012.17.
Veldink et al., SMN genotypes producing less SMN protein increase susceptibility to and severity of sporadic ALS. Neurology. Sep. 27, 2005;65(6):820-5. Epub Aug. 10, 2005.
Venter et al., The sequence of the human genome. Science. Feb. 16, 2001;291(5507):1304-51. Erratum in: Science Jun. 5, 2001;292(5523):1838.
Vickers et al., Fully modified 2' MOE oligonucleotides redirect polyadenylation. Nucleic Acids Res. Mar. 15, 2001;29(6):1293-9.
Wahlestedt, Natural antisense and noncoding RNA transcripts as potential drug targets. Drug Discov Today. Jun. 2006;11(11-12):503-8.
Wahlestedt, Targeting long non-coding RNA to therapeutically upregulate gene expression. Nature Rev Drug Disc. Jun. 2013;12:433-46. Review.
Wan et al., Regulation of imprinting in clusters: noncoding RNAs versus insulators. Adv Genet. 2008;61:207-23. Review.
Wang et al., Long non-coding RNA UCA1a(CUDR) promotes proliferation and tumorigenesis of bladder cancer. Int J Oncol. Jul. 2012;41(1):276-84.

Wang et al., Molecular mechanisms of long noncoding RNAs. Cell Press. Sep. 16, 2011; 43(6):904-14.
Whitehead et al., Variation in tissue-specific gene expression among natural populations. Genome Biol. 2005;6(2):R13. Epub Jan. 26, 2005.
Williams et al., Oligonucleotide-mediated survival of motor neuron protein expression in CNS improves phenotype in a mouse model of spinal muscular atrophy. J Neurosci. Jun. 17, 2009;29(24):7633-8. doi: 10.1523/JNEUROSCI.0950-09.2009.
Williamson et al., Identification of an imprinting control region affecting the expression of all transcripts in the Gnas cluster. Nat Genet. Mar. 2006;38(3):350-5.
Wilusz et al., A triple helix stabilizes the 3' ends of long noncoding RNAs that lack poly(A) tails. Genes Dev. Nov. 1, 2012;26(21):2392-407. doi: 10.1101/gad.204438.112. Epub Oct. 16, 2012.
Wilusz et al., Long noncoding RNAs: functional surprises from the RNA world. Genes Dev. Jul. 1, 2009;23(13):1494-504. doi:10.1101/gad.1800909.
Woo et al., A Region of the Human HOXDCluster that Confers Polycomb-Group Responsiveness. Cell. Jan. 8, 2010;140:99-110.
Woo et al., Gene activation of SMN by selective disruption of lncRNA-mediated recruitment of PRC2 for the treatment of spinal muscular atrophy. Proc Natl Acad Sci U S A. Feb. 21, 2017;114(8):E1509-E1518. doi:10.1073/pnas.1616521114. Epub Feb. 13, 2017.
Wu et al., Binding interactions between long noncoding RNA HOTAIR and PRC2 proteins. Biochemistry. Dec. 31, 2013;52(52):9519-27. doi: 10.1021/bi401085h.
Wutz et al., A Shift from Reversible to Irreversible X Inactivation Is Triggered during ES Cell Differentiation. Molec Cell. Apr. 2000;5:695-705.
Xiong et al., Polycomb antagonizes p300/CREB-binding protein associated factor to silence FOXP3 in a Kruppel-like factor-dependent manner. J Biol Chem. Oct. 5, 2012;287(41):34372-85. doi: 10.1074/jbc.M111.325332. Epub Aug. 15, 2012.
Yakali et al., Supramolecular chirality-sensing DNA-mimicry of a norbornane derivative decorated with isoxazoline and methylpyrolidine-2,5-dione ring. J Mol Structure. Jun. 10, 2013;1041:164-174.
Yamazaki et al., FUS-SMN protein interactions link the motor neuron diseases ALS and SMA. Cell Rep. Oct. 25, 2012;2(4):799-806. doi:10.1016/j.celrep.2012.08.025. Epub Sep. 27, 2012.
Yang et al., High fidelity PCR with an off/on switch mediated by proofreading polymerases combining with phosphorothioate-modified primer. Biochem Biophys Res Commun. Mar. 4, 2005;328(1):265-72. Erratum in: Biochem Biophys Res Commun. Jun. 3, 2005;331(2):682. Zhang, Jia [removed]; Li, Kai [removed].
Yang et al., Long noncoding RNAs: fresh perspectives into the RNA world. Trends Biochem Sci. Jan. 2014;39(1):35-43. doi: 10.1016/j.tibs.2013.10.002. Epub Nov. 27, 2013. Review.
Yap et al., Molecular interplay of the noncoding RNA ANRIL and methylated histone H3 lysine 27 by polycomb CBX7 in transcriptional silencing of INK4a. Mol Cell. Jun. 11, 2010;38(5):662-74. doi: 10.1016/j.molcel.2010.03.021. Epub Jun. 11, 2011. 23 pages.
Yatsuki et al., Sequence-based structural features between Kvlqt1 and Tapa1 on mouse chromosome 7F4/F5 corresponding to the Beckwith-Wiedemann syndrome region on human 11p15.5: long-stretches of unusually well conserved intronic sequences of kvlqt1 between mouse and human. DNA Res. Jun. 30, 2000;7(3):195-206.
Yu et al., Single-stranded RNAs use RNAi to potently and allele-selectively inhibit mutant huntingtin expression. Cell. Aug. 31, 2012;150(5):895-908. doi: 10.1016/j.cell.2012.08.002.
Zhang et al., Long noncoding RNA-mediated intrachromosomal interactions promote imprinting at the Kcnq1 locus. J Cell Biol. 2014;204(1):61-75.
Zhang et al., NATsDB: Natural Antisense Transcripts DataBase. Nucleic Acids Res. Jan. 2007;35(Database issue):D156-61. Epub Nov. 1, 2006.
Zhang et al., Perinucleolar Targeting of the Inactive X during S Phase: Evidence for a Role in the Maintenance of Silencing. Cell. May 18, 2007;129:693-706.
Zhao et al., Genome-wide identification of polycomb-associated RNAs by RIP-seq. Mol Cell. Dec. 22, 2010;40(6):939-53.

(56) References Cited

OTHER PUBLICATIONS

Zhao et al., Polycomb proteins targeted by a short repeat RNA to the mouse X-chromosome. Science. 2008; 322(5902):750-756. doi:10.1126/science.1163045. E-pub version.
Zhou et al., Targeting RNA-splicing for SMA treatment. Mol Cells. Mar. 2012;33(3):223-8. doi: 10.1007/s10059-012-0005-6.
Extended European Search Report for Application No. EP 13791546.8 dated Jan. 11, 2016.
International Search Report and Written Opinion for Application No. PCT/US2013/041394 dated Aug. 21, 2013.
International Preliminary Report on Patentability for Application No. PCT/US2013/041394 dated Nov. 27, 2014.
[No Author Listed] Designing Antisense Oligonucleotides. Integrated DNA Technologies. 2011. 1-16.
Arvey et al., Inflammation-induced repression of chromatin bound by the transcription factor Foxp3 in regulatory T cells. Nat Immunol. Jun. 2014;15(6):580-587. doi: 10.1038/ni.2868. Epub Apr. 13, 2014.
Axelson, The Notch signaling cascade in neuroblastoma: role of the basic helix-loop-helix proteins HASH-1 and HES-1. Cancer Lett. Feb. 20, 2004;204(2):171-8. Review.
Braasch et al., Locked nucleic acid (LNA): fine-tuning the recognition of DNA and RNA. Chem Biol. Jan. 2001;8(1):1-7.
Cloonan et al., Stem cell transcriptome profiling via massive-scale mRNA sequencing. Nat Methods. Jul. 2008;5(7):613-9.
EBI Accession No. ADH50651. Baker et al. Mar. 25, 2004.
Ebralidze et al., PU.1 expression is modulated by the balance of functional sense and antisense RNAs regulated by a shared cis-regulatory element. Genes Dev. Aug. 1, 2008;22(15):2085-92. doi:10.1101/gad.1654808. Supplemental Data.
Edwards et al., The evolution of the DLK1-DIO3 imprinted domain in mammals. PLoS Biol. Jun. 3, 2008;6(6):e135. doi: 10.1371/journal.pbio.0060135.
ENCODE Project Consortium. A user's guide to the encyclopedia of DNA elements (ENCODE). PLoS Biol. Apr. 2011;9(4):e1001046. doi: 10.1371/journal.pbio.1001046. Epub Apr. 19, 2011.
Genbank Submission; NCBI, Accession No. NG_009361.1; Salomons et al., Jun. 27, 2016.
Genbank Submission; NCBI,Accession No. NM_007294.3; Orban et al.; May 25, 2016.
Genbank Submission; NCBI,Accession No. NM_199461.3; Miles et al.; Jun. 4, 2016.
Genbank Submission; NIH/NCBI, Accession No. NM_022876.2. Singh et al. Mar. 13, 2011. 11 pages.
Jensen et al., Chapter 6: CLIP—Crosslinking and ImmunoPrecipitation of In Vivo RNA Targets of RNA-Binding Proteins. Methods in Molecular Biology. 2008;488:85-98.
Kim et al., Widespread transcription at neuronal activity-regulated enhancers. Nature. 2010; 465(7295):182-7. Epub Jan. 12, 2011. 15 pages.
Lebedeva et al., Phosphorothioate Oligodeoxynucleotides as inhibitors of gene expression: antisense and non-antisense effects. 1991. 99-118.
Lee et al., Yin Yang 1 positively regulates BRCA1 and inhibits mammary cancer formation. Oncogene. 2012;31:116-27.
Liang et al., B1-induced caspase-independent apoptosis in MCF-7 cells is mediated by down-regulation of Bcl-2 via p53 binding to P2 promoter TATA box. Toxicol Appl Pharmacol. Oct. 1, 2011;256(1):52-61. doi:10.1016/j.taap.2011.07.010. Epub Jul. 23, 2011.
Mikkelsen et al., Genome-wide maps of chromatin state in pluripotent and lineage-committed cells. Nature. Aug. 2, 2007;448(7153):553-60. doi:10.1038/nature06008. Epub Aug. 13, 2010.
Modarresi et al., Natural Antisense Inhibition Results in Transcriptional De-Repression and Gene Upregulation. Nat Biotechnol. Mar. 25, 2012;30(5):453-9. doi: 10.1038/nbt.2158. 21 pages.
Mortazavi et al., Mapping and quantifying mammalian transcriptomes by RNA-Seq. Nat Methods. Jul. 2008;5(7):621-8.
Pedersen et al., Identification and classification of conserved RNA secondary structures in the human genome. PLoS Comput Biol. Apr. 2006;2(4):e33. Epub Apr. 21, 2006.
Seila et al., Divergent transcription from active promoters. Science. Dec. 19, 2008;322(5909):1849-51. doi: 10.1126/science.1162253. Epub Dec. 4, 2008.
Sirchia et al., Misbehaviour of XIST RNA in breast cancer cells. PLoS One. 2009;4(5):e5559. doi: 10.1371/journal.pone.0005559. Epub May 15, 2009.
Summerton, Morpholino antisense oligomers: the case for an Rnase H-independent structural type. Biochim Biophys Acta. Dec. 10, 1999;1489(1):141-58.
Torarinsson et al., Thousands of corresponding human and mouse genomic regions unalignable in primary sequence contain common RNA structure. Genome Res. Jul. 2006;16(7):885-9. Epub Jun. 2, 2006. Erratum in: Genome Res. Nov. 2006;16(11):1439.
Ule et al., CLIP Identifies Nova-Regulated RNA Networks in the Brain. Science. 2003;302:1212-5. doi: 10.1126/science.1090095.
Ule et al., CLIP: A method for identifying protein—RNA interaction sites in living cells. Methods. 2005;37:376-86.
Wang et al., Correlation between Dnase I hypersensitive site distribution and gene expression in HeLa S3 cells. PLoS One. 2012;7(8):e42414. doi: 10.1371/journal.pone.0042414. Epub Aug. 10, 2012.
Wang et al., Multifunctional transcription factor YY1: a therapeutic target in human cancer? Expert Opin Ther Targets. 2006;10(2):253-66.
Yang et al., The histone code regulating expression of the imprinted mouse Igf2r gene. Endocrinology. Dec. 2003;144(12):5658-70.
Zaravinos et al., Yin yang 1 expression in human tumors. Cell Cycle. Feb. 1, 2010;9(3):512-22.

COMPOSITIONS AND METHODS FOR MODULATING SMN GENE FAMILY EXPRESSION

CROSS-REFERENCE TO RELATED APPLICATIONS

This application is a continuation-in-part under 35 U.S.C. 111(a) of U.S. patent application Ser. No. 14/401,194, entitled "COMPOSITIONS AND METHODS FOR MODULATING SMN GENE FAMILY EXPRESSION", filed on Nov. 14, 2014, which is a national stage filing under U.S.C. § 371 of PCT International Application PCT/US2013/041440, with an international filing date of May 16, 2013, which claims the benefit under 35 U.S.C. § 119(e) of U.S. Provisional Application No. 61/785,529, entitled "COMPOSITIONS AND METHODS FOR MODULATING SMN GENE FAMILY EXPRESSION", filed Mar. 14, 2013; U.S. Provisional Application No. 61/719,394, entitled "COMPOSITIONS AND METHODS FOR MODULATING SMN GENE FAMILY EXPRESSION", filed Oct. 27, 2012; and U.S. Provisional Application No. 61/647,858, entitled "COMPOSITIONS AND METHODS FOR MODULATING SMN GENE FAMILY EXPRESSION", filed May 16, 2012, and is a continuation-in part of U.S. patent application Ser. No. 14/401,196, entitled "COMPOSITIONS AND METHODS FOR MODULATING UTRN EXPRESSION", filed on Nov. 14, 2014, which is a national stage filing under U.S.C. § 371 of PCT International Application PCT/US2013/041452, with an international filing date of May 16, 2013, which claims the benefit under 35 U.S.C. § 119(e) of U.S. Provisional Application No. 61/647,886, entitled "COMPOSITIONS AND METHODS FOR MODULATING UTRN EXPRESSION", filed May 16, 2012, and is a continuation-in part of U.S. patent application Ser. No. 14/401,201, entitled "COMPOSITIONS AND METHODS FOR MODULATING HEMOGLOBIN GENE FAMILY EXPRESSION", filed on Nov. 14, 2014, which is a national stage filing under U.S.C. § 371 of PCT International Application PCT/US2013/041382, with an international filing date of May 16, 2013, which claims the benefit under 35 U.S.C. § 119(e) of U.S. Provisional Application No. 61/785,956, entitled "COMPOSITIONS AND METHODS FOR MODULATING HEMOGLOBIN GENE FAMILY EXPRESSION", filed Mar. 14, 2013 and U.S. Provisional Application No. 61/647,901, entitled "COMPOSITIONS AND METHODS FOR MODULATING HEMOGLOBIN GENE FAMILY EXPRESSION", filed May 16, 2012, and is a continuation-in part of U.S. patent application Ser. No. 14/401,214, entitled "COMPOSITIONS AND METHODS FOR MODULATING ATP2A2 EXPRESSION", filed on Nov. 14, 2014, which is a national stage filing under U.S.C. § 371 of PCT International Application PCT/US2013/041381, with an international filing date of May 16, 2013, which claims the benefit under 35 U.S.C. § 119(e) of U.S. Provisional Application No. 61/785,832, entitled "COMPOSITIONS AND METHODS FOR MODULATING ATP2A2 EXPRESSION", filed Mar. 14, 2013 and U.S. Provisional Application No. 61/647,925, entitled "COMPOSITIONS AND METHODS FOR MODULATING ATP2A2 EXPRESSION", filed May 16, 2012, and is a continuation-in part of U.S. patent application Ser. No. 14/401,223, entitled "COMPOSITIONS AND METHODS FOR MODULATING APOA1 AND ABCA1 EXPRESSION", filed on Nov. 14, 2014, which is a national stage filing under U.S.C. § 371 of PCT International Application PCT/US2013/041455, with an international filing date of May 16, 2013, which claims the benefit under 35 U.S.C. § 119(e) of U.S. Provisional Application No. 61/785,778, entitled "COMPOSITIONS AND METHODS FOR MODULATING APOA1 AND ABCA1 EXPRESSION", filed Mar. 14, 2013 and U.S. Provisional Application No. 61/647,949, entitled "COMPOSITIONS AND METHODS FOR MODULATING APOA1 AND ABCA1 EXPRESSION", filed May 16, 2012, and is a continuation-in part of U.S. patent application Ser. No. 14/401,227, entitled "COMPOSITIONS AND METHODS FOR MODULATING PTEN EXPRESSION", filed on Nov. 14, 2014, which is a national stage filing under U.S.C. § 371 of PCT International Application PCT/US2013/041389, with an international filing date of May 16, 2013, which claims the benefit under 35 U.S.C. § 119(e) of U.S. Provisional Application No. 61/785,885, entitled "COMPOSITIONS AND METHODS FOR MODULATING PTEN EXPRESSION", filed Mar. 14, 2013 and U.S. Provisional Application No. 61/648,041, entitled "COMPOSITIONS AND METHODS FOR MODULATING PTEN EXPRESSION", filed May 16, 2012, and is a continuation-in part of U.S. patent application Ser. No. 14/401,234, entitled "COMPOSITIONS AND METHODS FOR MODULATING BDNF EXPRESSION", filed on Nov. 14, 2014, which is a national stage filing under U.S.C. § 371 of PCT International Application PCT/US2013/041385, with an international filing date of May 16, 2013, which claims the benefit under 35 U.S.C. § 119(e) of U.S. Provisional Application No. 61/648,058, entitled "COMPOSITIONS AND METHODS FOR MODULATING BDNF EXPRESSION", filed May 16, 2012, and is a continuation-in part of U.S. patent application Ser. No. 15/787,876, entitled "COMPOSITIONS AND METHODS FOR MODULATING MECP2 EXPRESSION", filed on Oct. 19, 2017, which is a continuation of U.S. patent application Ser. No. 14/401,237, entitled "COMPOSITIONS AND METHODS FOR MODULATING MECP2 EXPRESSION", filed on Nov. 14, 2014, which is a national stage filing under U.S.C. § 371 of PCT International Application PCT/US2013/041394, with an international filing date of May 16, 2013, which claims the benefit under 35 U.S.C. § 119(e) of U.S. Provisional Application No. 61/648,051, entitled "COMPOSITIONS AND METHODS FOR MODULATING MECP2 EXPRESSION", filed May 16, 2012, and is a continuation-in part of U.S. patent application Ser. No. 14/401,240, entitled "COMPOSITIONS AND METHODS FOR MODULATING GENE EXPRESSION", filed on Nov. 14, 2014, which is a national stage filing under U.S.C. § 371 of PCT International Application PCT/US2013/041434, with an international filed date of May 16, 2013, which claims the benefit under 35 U.S.C. § 119(e) of U.S. Provisional Application No. 61/647,915, entitled "COMPOSITIONS AND METHODS FOR MODULATING CFTR EXPRESSION", filed May 16, 2012; U.S. Provisional Application No. 61/647,938, entitled "COMPOSITIONS AND METHODS FOR MODULATING PAH EXPRESSION", filed May 16, 2012; U.S. Provisional Application No. 61/648,030, entitled "COMPOSITIONS AND METHODS FOR MODULATING CEP290 EXPRESSION", filed May 16, 2012; U.S. Provisional Application No. 61/648,045, entitled "COMPOSITIONS AND METHODS FOR MODULATING ADIPOQ EXPRESSION", filed May 16, 2012; U.S. Provisional Application No. 61/648,052, entitled "COMPOSITIONS AND METHODS FOR MODULATING CD274 EXPRESSION", filed May 16, 2012; U.S. Provisional Application No. 61/648,069, entitled "COMPOSITIONS AND METHODS FOR MODULATING GENE EXPRESSION", filed May 16, 2012; U.S. Provisional Application No. 61/786,095, entitled "COMPOSITIONS AND METHODS FOR MODULATING GENE EXPRESSION", filed Mar. 14, 2013, and is a continuation-in part of U.S. patent application Ser. No. 14/401,248, entitled "COMPOSITIONS AND METHODS FOR MODULATING GENE EXPRESSION", filed on Nov. 14, 2014, which is a national stage filing under U.S.C. § 371 of PCT International Application PCT/US2013/041437, with an international filing date of May 16, 2013, which, claims the benefit under 35 U.S.C. § 119(e) of U.S. Provisional Application No. 61/648,077, entitled, "COMPOSITIONS AND METHODS FOR MODULATING GENE EXPRESSION", filed on May 16, 2012, and is a continuation-in part of U.S. patent application Ser. No. 14/691,361 entitled "COMPOSITIONS AND METHODS FOR MODULATING GENE EXPRESSION", filed on Apr. 20, 2015, which is a continuation of U.S. patent application Ser. No. 14/401,252, entitled "COMPOSITIONS AND METHODS FOR MODULATING GENE EXPRESSION", filed on Nov. 14, 2014, which is a national stage filing under U.S.C. § 371 of PCT International Application PCT/US2013/041461, with an international filing date of May 16, 2013, which claims the benefit under 35 U.S.C. § 119(e) of U.S. Provisional Application No. 61/648,016, entitled, "COMPOSITIONS AND METHODS FOR MODULATING GENE EXPRESSION", filed on May 16, 2012, of U.S. Provisional Application No. 61/648,021, entitled, "COMPOSITIONS AND METHODS FOR MODULATING GENE EXPRESSION", filed on May 16, 2012, of U.S. Provisional Application No. 61/786,232, entitled, "COMPOSITIONS AND METHODS FOR MODULATING GENE EXPRESSION", filed on Mar. 14, 2013, of U.S. Provisional Application No. 61/647,858, entitled, "COMPOSITIONS AND METHODS FOR MODULATING SMN GENE FAMILY EXPRESSION", filed on May 16, 2012, of U.S. Provisional Application No. 61/719,394, entitled, "COMPOSITIONS AND METHODS FOR MODULATING SMN GENE FAMILY EXPRESSION", filed on Oct. 27, 2012, of U.S. Provisional Application No. 61/785,529, entitled, "COMPOSITIONS AND METHODS FOR MODULATING SMN GENE FAMILY EXPRESSION", filed on Mar. 14, 2013, of U.S. Provisional Application No. 61/647,886, entitled, "COMPOSITIONS AND METHODS FOR MODULATING UTRN EXPRESSION", filed on May 16, 2012, of U.S. Provisional Application No. 61/647,901, entitled, "COMPOSITIONS AND METHODS FOR MODULATING HEMOGLOBIN GENE FAMILY EXPRESSION", filed on May 16, 2012, of U.S. Provisional Application No. 61/785,956, entitled, "COMPOSITIONS AND METHODS FOR MODULATING HEMOGLOBIN GENE FAMILY EXPRESSION", filed on Mar. 14, 2013, of U.S. Provisional Application No. 61/647,925, entitled, "COMPOSITIONS AND METHODS FOR MODULATING ATP2A2 EXPRESSION", filed on May 16, 2012, of U.S. Provisional Application No. 61/785,832, entitled, "COMPOSITIONS AND METHODS FOR MODULATING ATP2A2 EXPRESSION", filed on Mar. 14, 2013, of U.S. Provisional Application No. 61/647,949, entitled, "COMPOSITIONS AND METHODS FOR MODULATING APOA1 AND ABCA1 EXPRESSION", filed on May 16, 2012, of U.S. Provisional Application No. 61/785,778, entitled, "COMPOSITIONS AND METHODS FOR MODULATING APOA1 AND ABCA1 EXPRESSION", filed on Mar. 14, 2013, of U.S. Provisional Application No. 61/648,041, entitled, "COMPOSITIONS AND METHODS FOR MODULATING PTEN EXPRESSION", filed on May 16, 2012, of U.S. Provisional Application No. 61/785,885, entitled, "COMPOSITIONS AND METHODS FOR MODULATING PTEN EXPRESSION", filed on Mar. 14, 2013, of U.S. Provisional Application No. 61/648,058, entitled, "COMPOSITIONS AND METHODS FOR MODULATING BDNF EXPRESSION", filed on May 16, 2012, and of U.S. Provisional Application No. 61/648,051, entitled, "COMPOSITIONS AND METHODS FOR MODULATING MECP2 EXPRESSION", filed on May 16, 2012, the contents of each of which are incorporated herein by reference in their entireties.

FIELD OF THE INVENTION

The invention relates to oligonucleotide based compositions, as well as methods of using oligonucleotide based compositions for treating disease.

BACKGROUND OF THE INVENTION

Spinal muscular atrophy (SMA) is a group of hereditary diseases that causes muscle damage leading to impaired muscle function, difficulty breathing, frequent respiratory infection, and eventually death. There are four types of SMA that are classified based on the onset and severity of the disease. SMA type I is the most severe form and is one of the most common causes of infant mortality, with symptoms of muscle weakness and difficulty breathing occurring at birth. SMA type II occurs later, with muscle weakness and other symptoms developing from ages 6 month to 2 years. Symptoms appear in SMA type III during childhood and in SMA type IV, the mildest form, during adulthood. All four types of SMA have been found to be associated with mutations in the SMN gene family, particularly SMN1.

Survival of motor neuron (SMN) is a protein involved in transcriptional splicing through its involvement in assembly of small nuclear ribonucleoproteins (snRNPs). snRNPs are protein-RNA complexes that bind with pre-mRNA to form a spliceosome, which then splices the pre-mRNA, most often resulting in removal of introns. Three genes encode SMN or a variant of SMN, including SMN1 (survival of motor neuron 1, telomeric), SMN2 (survival of motor neuron 2, centromeric), and SMNP (survival of motor neuron 1, telomeric pseudogene). SMN1 and SMN2 are a result of a gene duplication at 5q13 in humans. A lack of SMN activity results in widespread splicing defects, especially in spinal motor neurons, and degeneration of the spinal cord lower motor neurons.

SUMMARY OF THE INVENTION

Aspects of the invention disclosed herein provide methods and compositions that are useful for upregulating the expression of certain genes in cells. In some embodiments, single stranded oligonucleotides are provided that target a PRC2-associated region of a gene and thereby cause upregulation of the gene. Also provided herein are methods and related single stranded oligonucleotides that are useful for selectively inducing expression of particular splice variants of genes. In some embodiments, the methods are useful for controlling the levels in a cell of particular protein isoforms encoded by the splice variants. In some cases, the methods are useful for inducing expression of proteins to levels sufficient to treat disease.

In some embodiments, single stranded oligonucleotides are provided that target a PRC2-associated region of a SMN gene (e.g., human SMN1, human SMN2) and thereby cause upregulation of the gene. For example, according to some aspects of the invention methods are provided for increasing expression of full-length SMN protein in a cell for purposes of treating SMA. Accordingly, aspects of the invention disclosed herein provide methods and compositions that are useful for upregulating SMN1 or SMN2 in cells. In some embodiments, single stranded oligonucleotides are provided that target a PRC2-associated region of the gene encoding SMN1 or SMN2. In some embodiments, these single stranded oligonucleotides activate or enhance expression of SMN1 or SMN2 by relieving or preventing PRC2 mediated repression of SMN1 or SMN2.

In some embodiments, the methods comprise delivering to the cell a first single stranded oligonucleotide complementary with a PRC2-associated region of an SMN gene, e.g., a PRC2-associated region of SMN1 or SMN2, and a second single stranded oligonucleotide complementary with a splice control sequence of a precursor mRNA of an SMN gene, e.g., a precursor mRNA of SMN1 or SMN2, in amounts sufficient to increase expression of a mature mRNA of SMN1 or SMN2 that comprises (or includes) exon 7 in the cell.

According to some aspects of the invention single stranded oligonucleotides are provided that have a region of complementarity that is complementary with (e.g., at least 8 consecutive nucleotides of) a PRC2-associated region of an SMN gene, e.g., a PRC2-associated region of the nucleotide sequence set forth as SEQ ID NO: 1, 2, 4, or 5. In some embodiments, the oligonucleotide has at least one of the following features: a) a sequence that is 5'X-Y-Z, in which X is any nucleotide and in which X is at the 5' end of the oligonucleotide, Y is a nucleotide sequence of 6 nucleotides in length that is not a human seed sequence of a microRNA, and Z is a nucleotide sequence of 1 to 23 nucleotides in length; b) a sequence that does not comprise three or more consecutive guanosine nucleotides; c) a sequence that has less than a threshold level of sequence identity with every sequence of nucleotides, of equivalent length to the second nucleotide sequence, that are between 50 kilobases upstream of a 5'-end of an off-target gene and 50 kilobases downstream of a 3'-end of the off-target gene; d) a sequence that is complementary to a PRC2-associated region that encodes an RNA that forms a secondary structure comprising at least two single stranded loops; and e) a sequence that has greater than 60% G-C content. In some embodiments, the single stranded oligonucleotide has at least two of features a), b), c), d), and e), each independently selected. In some embodiments, the single stranded oligonucleotide has at least three of features a), b), c), d), and e), each independently selected. In some embodiments, the single stranded oligonucleotide has at least four of features a), b), c), d), and e), each independently selected. In some embodiments, the single stranded oligonucleotide has each of features a), b), c), d), and e). In certain embodiments, the oligonucleotide has the sequence 5'X-Y-Z, in which the oligonucleotide is 8-50 nucleotides in length.

According to some aspects of the invention, single stranded oligonucleotides are provided that have a sequence X-Y-Z, in which X is any nucleotide, Y is a nucleotide sequence of 6 nucleotides in length that is not a seed sequence of a human microRNA, and Z is a nucleotide sequence of 1 to 23 nucleotides in length, in which the single stranded oligonucleotide is complementary with a PRC2-associated region of an SMN gene, e.g., a PRC2-associated region of the nucleotide sequence set forth as SEQ ID NO: 1, 2, 4, or 5. In some aspects of the invention, single stranded oligonucleotides are provided that have a sequence 5'-X-Y-Z, in which X is any nucleotide, Y is a nucleotide sequence of 6 nucleotides in length that is not a seed sequence of a human microRNA, and Z is a nucleotide sequence of 1 to 23 nucleotides in length, in which the single stranded oligonucleotide is complementary with at least 8 consecutive nucleotides of a PRC2-associated region of an SMN gene, e.g., a PRC2-associated region of the nucleotide sequence set forth as SEQ ID NO: 1, 2, 4, or 5. In some embodiments, Y is a sequence selected from Table 1. In some embodiments, the PRC2-associated region is a sequence listed in any one of SEQ ID NOS: 9 to 18.

In some embodiments, the single stranded oligonucleotide comprises a nucleotide sequence as set forth in any one of SEQ ID NOS: 30 to 13087, or a fragment thereof that is at least 8 nucleotides. In some embodiments, the single stranded oligonucleotide comprises a nucleotide sequence as set forth in any one of SEQ ID NOS: 30 to 13087, in which the 5' end of the nucleotide sequence provided is the 5' end of the oligonucleotide. In some embodiments, the region of complementarity (e.g., the at least 8 consecutive nucleotides) is also present within the nucleotide sequence set forth as SEQ ID NO: 7 or 8.

In some embodiments, a PRC2-associated region is a sequence listed in any one of SEQ ID NOS: 9 to 14. In some embodiments, the single stranded oligonucleotide comprises a nucleotide sequence as set forth in any one of SEQ ID NOS: 30 to 8329 and 13093 to 13094 or a fragment thereof that is at least 8 nucleotides. In some embodiments, the single stranded oligonucleotide comprises a nucleotide sequence as set forth in any one of SEQ ID NOS: 30 to 8329 and 13093 to 13094, wherein the 5' end of the nucleotide sequence provided is the 5' end of the oligonucleotide. In some embodiments, the at least 8 consecutive nucleotides are also present within the nucleotide sequence set forth as SEQ ID NO: 7.

In some embodiments, a PRC2-associated region is a sequence listed in any one of SEQ ID NOS: 15 to 18. In some embodiments, the single stranded oligonucleotide comprises a nucleotide sequence as set forth in any one of SEQ ID NOS: 1158-1159, 1171, 1482-1483, 1485-1486, 2465-2471, 2488-2490, 2542-2546, 2656-2657, 2833-2835, 3439-3440, 3916-3918, 4469-4472, 4821, 5429, 5537, 6061, 7327, 8330-13061, and 13062-13087 or a fragment thereof that is at least 8 nucleotides. In some embodiments, the at least 8 consecutive nucleotides are present within the nucleotide sequence set forth as SEQ ID NO: 8.

In some embodiments, the single stranded oligonucleotide comprises a nucleotide sequence as set forth in any one of SEQ ID NOS: 30 to 13087. In some embodiments, the oligonucleotide is up to 50 nucleotides in length. In some embodiments, the single stranded oligonucleotide comprises a fragment of at least 8 nucleotides of a nucleotide sequence as set forth in any one of SEQ ID NOS: 30 to 13087.

In some embodiments, a single stranded oligonucleotide comprises a nucleotide sequence as set forth in Table 4. In some embodiments, the single stranded oligonucleotide comprises a fragment of at least 8 nucleotides of a nucleotide sequence as set forth in Table 4. In some embodiments, a single stranded oligonucleotide consists of a nucleotide sequence as set forth in Table 4.

According to some aspects of the invention, compounds are provided that comprise the general formula A-B-C, wherein A is a single stranded oligonucleotide complementary with at least 8 consecutive nucleotides of a PRC2-associated region of a gene, B is a linker, and C is a single stranded oligonucleotide complementary to a splice control sequence of a precursor mRNA of the gene. In some embodiments, B comprises an oligonucleotide, peptide, low pH labile bond, or disulfide bond. In some embodiments, the splice control sequence resides in an exon of the gene. In some embodiments, the splice control sequence traverses an intron-exon junction of the gene. In some embodiments, the splice control sequence resides in an intron of the gene. In some embodiments, the splice control sequence comprises at least one hnRNAP binding sequence. In some embodiments, hybridization of an oligonucleotide having the sequence of C with the splice control sequence of the precursor mRNA in a cell results in inclusion of a particular exon in a mature mRNA that arises from processing of the precursor mRNA in the cell. In some embodiments, hybridization of an oligonucleotide having the sequence of C with the splice control sequence of the precursor mRNA in a cell results in exclusion of a particular intron or exon in a mature mRNA that arises from processing of the precursor mRNA in the cell.

In some embodiments, the gene is SMN1 or SMN2. In some embodiments, the splice control sequence resides in intron 6, intron 7, exon 7, exon 8 or at the junction of intron 7 and exon 8 of SMN1 or SMN2. In some embodiments, the splice control sequence comprises the sequence: CAGCAUUAUGAAAG (SEQ ID NO: 13100). In some embodiments, B comprises a sequence selected from: TCACTTTCATAATGCTGG (SEQ ID NO: 13088); TCACTTTCATAATGC (SEQ ID NO: 13089); CACTTTCATAATGCT (SEQ ID NO: 13090); ACTTTCATAATGCTG (SEQ ID NO: 13090); and CTTTCATAATGCTGG (SEQ ID NO: 13092).

In some embodiments, A has a sequence 5'-X-Y-Z, wherein X is any nucleotide, Y is a nucleotide sequence of 6 nucleotides in length that is not a seed sequence of a human microRNA, and Z is a nucleotide sequence of 1-23 nucleotides in length. In some embodiments, the PRC2-associated region of an SMN2 gene is a PRC2-associated region within SEQ ID NO: 1, 2, 4 or 5. In some embodiments, Y is a sequence selected from Table 1. In some embodiments, the PRC2-associated region is a sequence set forth in any one of SEQ ID NOS: 9 to 23. In some embodiments, A comprises a nucleotide sequence as set forth in any one of SEQ ID NOS: 30 to 8329 and 13088 to 13094 or a fragment thereof that is at least 8 nucleotides. In some embodiments, A comprises a nucleotide sequence as set forth in any one of SEQ ID NOS: 30 to 8329 and 13088 to 13094, wherein the 5' end of the nucleotide sequence provided is the 5' end of A. In some embodiments, the at least 8 consecutive nucleotides are also present within the nucleotide sequence set forth as SEQ ID NO: 7. In some embodiments, the PRC2-associated region is a sequence set forth in any one of SEQ ID NOS: 24 to 29.

In some embodiments, A comprises a nucleotide sequence as set forth in any one of SEQ ID NOS: 1158-1159, 1171, 1482-1483, 1485-1486, 2465-2471, 2488-2490, 2542-2546, 2656-2657, 2833-2835, 3439-3440, 3916-3918, 4469-4472, 4821, 5429, 5537, 6061, 7327, 8330-13061, and 13062-13087 or a fragment thereof that is at least 8 nucleotides. In some embodiments, the at least 8 consecutive nucleotides are present within the nucleotide sequence set forth as SEQ ID NO: 8. In some embodiments, A does not comprise three or more consecutive guanosine nucleotides. In some embodiments, A does not comprise four or more consecutive guanosine nucleotides. In some embodiments, A or C is 8 to 30 nucleotides in length. In some embodiments, A is 8 to 10 nucleotides in length and all but 1, 2, or 3 of the nucleotides of the complementary sequence of the PRC2-associated region are cytosine or guanosine nucleotides. In some embodiments, B is an oligonucleotide comprising 1 to 10 thymidines or uridines. In some embodiments, B is more susceptible to cleavage in a mammalian extract than A and C.

In some embodiments, A comprises a nucleotide sequence selected from GCTUTGGGAAGUAUG (SEQ ID NO: 11394), CUTUGGGAAGTATG (SEQ ID NO: 11395) and GGTACATGAGTGGCT (SEQ ID NO: 11419); B comprises the nucleotide sequence TTTT or UUUU; and C comprises the nucleotide sequence TCACTTTCATAATGCTGG (SEQ ID NO: 13088); TCACTTTCATAATGC (SEQ ID NO: 13089); CACTTTCATAATGCT (SEQ ID NO: 13090); ACTTTCATAATGCTG (SEQ ID NO: 13091): or CTTTCATAATGCTGG (SEQ ID NO: 13092), and wherein the 3' end of A is linked to the 5' end of B, and the 3' end of B is linked to 5' end of C.

In some embodiments, the single stranded oligonucleotide does not comprise three or more consecutive guanosine nucleotides. In some embodiments, the single stranded oligonucleotide does not comprise four or more consecutive guanosine nucleotides.

In some embodiments, the single stranded oligonucleotide is 8 to 30 nucleotides in length. In some embodiments, the single stranded oligonucleotide is up to 50 nucleotides in length. In some embodiments, the single stranded oligonucleotide is 8 to 10 nucleotides in length and all but 1, 2, or 3 of the nucleotides of the complementary sequence of the PRC2-associated region are cytosine or guanosine nucleotides.

In some embodiments, the single stranded oligonucleotide is complementary with at least 8 consecutive nucleotides of a PRC2-associated region of an SMN gene, e.g., a PRC2-associated region of a nucleotide sequence set forth as SEQ ID NO: 1, 2, 4, or 5, in which the nucleotide sequence of the single stranded oligonucleotide comprises one or more of a nucleotide sequence selected from the group consisting of (a) (X)Xxxxxx, (X)xXxxxx, (X)xxXxxx, (X)xxxXxx, (X)xxxxXx and (X)xxxxxX, (b) (X)XXxxxx, (X)XxXxxx, (X)XxxXxx, (X)XxxxXx, (X)XxxxxX, (X)xXXxxx, (X)xXxXxx, (X)xXxxXx, (X)xXxxxX, (X)xxXXxx, (X)xxXxXx, (X)xxXxxX, (X)xxxXXx, (X)xxxXxX and (X)xxxxXX, (c) (X)XXXxxx, (X)xXXXxx, (X)xxXXXx, (X)xxxXXX, (X)XXxXxx, (X)XxxXXx, (X)XXxxxX, (X)XXxXxx, (X)xXXxXx, (X)xXXxxX, (X)xxXXxX, (X)XxXXxx, (X)XxxXXx, (X)XxxxXX, (X)XxxXXX (X)XxxxXX, (X)xXxxXX, (X)xXxxXX, (X)xXxxXX, (X)xxXxXX, (X)xXxxXX and (X)XxXxXx, (d) (X)xxXXX, (X)xXxXXX, (X)xXXxXX, (X)xXXXxX, (X)xXXXXx, (X)XxxXXXX, (X)XxXxXXX, (X)XxXXxX, (X)XxXXXx, (X)XXxxXX, (X)XXxXxX, (X)XXxXXx, (X)XXXxXx, (X)XXXxxX, (X)XXXXxx, and (X)XXXXxx, (e) (X)xXXXXX, (X)XxXXXX, (X)XXxXXX, (X)XXXxXX, (X)XXXXxX and (X)XXXXXx, and (f) XXXXXX, XxXXXXX, XXxXXXX, XXXxXXX, XXXXxXX, XXXXXxX and XXXXXXx, wherein "X" denotes a nucleotide analogue, (X) denotes an optional nucleotide analogue, and "x" denotes a DNA or RNA nucleotide unit.

In some embodiments, at least one nucleotide of the oligonucleotide is a nucleotide analogue. In some embodiments, the at least one nucleotide analogue results in an increase in Tm of the oligonucleotide in a range of 1 to 5° C. compared with an oligonucleotide that does not have the at least one nucleotide analogue.

In some embodiments, at least one nucleotide of the oligonucleotide comprises a 2' O-methyl. In some embodiments, each nucleotide of the oligonucleotide comprises a 2'

O-methyl. In some embodiments, the oligonucleotide comprises at least one ribonucleotide, at least one deoxyribonucleotide, or at least one bridged nucleotide. In some embodiments, the bridged nucleotide is a LNA nucleotide, a cEt nucleotide or a ENA modified nucleotide. In some embodiments, each nucleotide of the oligonucleotide is a LNA nucleotide.

In some embodiments, the nucleotides of the oligonucleotide comprise alternating deoxyribonucleotides and 2'-fluoro-deoxyribonucleotides. In some embodiments, the nucleotides of the oligonucleotide comprise alternating deoxyribonucleotides and 2'-O-methyl nucleotides. In some embodiments, the nucleotides of the oligonucleotide comprise alternating deoxyribonucleotides and ENA nucleotide analogues. In some embodiments, the nucleotides of the oligonucleotide comprise alternating deoxyribonucleotides and LNA nucleotides. In some embodiments, the 5' nucleotide of the oligonucleotide is a deoxyribonucleotide. In some embodiments, the nucleotides of the oligonucleotide comprise alternating LNA nucleotides and 2'-O-methyl nucleotides. In some embodiments, the 5' nucleotide of the oligonucleotide is a LNA nucleotide. In some embodiments, the nucleotides of the oligonucleotide comprise deoxyribonucleotides flanked by at least one LNA nucleotide on each of the 5' and 3' ends of the deoxyribonucleotides.

In some embodiments, the single stranded oligonucleotide comprises modified internucleotide linkages (e.g., phosphorothioate internucleotide linkages or other linkages) between at least two, at least three, at least four, at least five or more nucleotides. In some embodiments, the single stranded oligonucleotide comprises modified internucleotide linkages (e.g., phosphorothioate internucleotide linkages or other linkages) between all nucleotides.

In some embodiments, the nucleotide at the 3' position of the oligonucleotide has a 3' hydroxyl group. In some embodiments, the nucleotide at the 3' position of the oligonucleotide has a 3' thiophosphate. In some embodiments, the single stranded oligonucleotide has a biotin moiety or other moiety conjugated to its 5' or 3' nucleotide. In some embodiments, the single stranded oligonucleotide has cholesterol, Vitamin A, folate, sigma receptor ligands, aptamers, peptides, such as CPP, hydrophobic molecules, such as lipids, ASGPR or dynamic polyconjugates and variants thereof at its 5' or 3' end.

According to some aspects of the invention compositions are provided that comprise any of the oligonucleotides disclosed herein, and a carrier. In some embodiments, compositions are provided that comprise any of the oligonucleotides in a buffered solution. In some embodiments, the oligonucleotide is conjugated to the carrier. In some embodiments, the carrier is a peptide. In some embodiments, the carrier is a steroid. According to some aspects of the invention pharmaceutical compositions are provided that comprise any of the oligonucleotides disclosed herein, and a pharmaceutically acceptable carrier.

According to other aspects of the invention, kits are provided that comprise a container housing any of the compositions disclosed herein.

According to some aspects of the invention, methods of increasing expression of SMN1 or SMN2 in a cell are provided. In some embodiments, the methods involve delivering any one or more of the single stranded oligonucleotides disclosed herein into the cell. In some embodiments, delivery of the single stranded oligonucleotide into the cell results in a level of expression of SMN1 or SMN2 that is greater (e.g., at least 50% greater) than a level of expression of SMN1 or SMN2 in a control cell that does not comprise the single stranded oligonucleotide.

According to some aspects of the invention, methods of increasing levels of SMN1 or SMN2 in a subject are provided. According to some aspects of the invention, methods of treating a condition (e.g., Spinal muscular atrophy) associated with decreased levels of SMN1 or SMN2 in a subject are provided. In some embodiments, the methods involve administering any one or more of the single stranded oligonucleotides disclosed herein to the subject.

Aspects of the invention relate to methods of increasing expression of SMN protein in a cell. In some embodiments, the method comprise delivering to the cell a first single stranded oligonucleotide complementary with at least 8 consecutive nucleotides of a PRC2-associated region of SMN2 and a second single stranded oligonucleotide complementary with a splice control sequence of a precursor mRNA of SMN2, in amounts sufficient to increase expression of a mature mRNA of SMN2 that comprises exon 7 in the cell. In some embodiments, the region of complementarity with at least 8 consecutive nucleotides of a PRC2-associated region of SMN2 has at least 1, at least 2, at least 3, at least 4, at least 5, at least 6, at least 7, at least 8, or more mismatches with a corresponding region of SMN1. As used herein the term, "splice control sequence" refers to a nucleotide sequence that when present in a precursor mRNA influences splicing of that precursor mRNA in a cell. In some embodiments, a splice control sequence includes one or more binding sites for a molecule that regulates mRNA splicing, such as a hnRNAP protein. In some embodiments, a splice control sequence comprises the sequence CAG or AAAG. In some embodiments, a splice control sequence resides in an exon (e.g., an exon of SMN1 or SMN2, such as exon 7 or exon 8). In some embodiments, a splice control sequence traverses an intron-exon junction (e.g., an intron-exon junction of SMN1 or SMN2, such as the intron 6/exon 7 junction or the intron 7/exon 8 junction). In some embodiments, a splice control sequence resides in an intron (e.g., an intron of SMN1 or SMN2, such as intron 6 or intron 7). In some embodiments, a splice control sequence comprises the sequence: CAGCAUUAUGAAAG (SEQ ID NO: 13100) or a portion thereof.

In some embodiments, the second single stranded oligonucleotide is splice switching oligonucleotide that comprises a sequence selected from: TCACTTTCATAATGCTGG (SEQ ID NO: 13088); TCACTTTCATAATGC (SEQ ID NO: 13089); CACTTTCATAATGCT (SEQ ID NO: 13090); ACTTTCATAATGCTG (SEQ ID NO: 13091); and CTTTCATAATGCTGG (SEQ ID NO: 13092). In some embodiments, the second single stranded oligonucleotide is 8 to 30 nucleotides in length.

In some embodiments, the first single stranded oligonucleotide has a sequence 5'-X-Y-Z, wherein X is any nucleotide, Y is a nucleotide sequence of 6 nucleotides in length that is not a seed sequence of a human microRNA, and Z is a nucleotide sequence of 1-23 nucleotides in length. In some embodiments, the PRC2-associated region of an SMN2 gene is a PRC2-associated region within SEQ ID NO: 1, 2, 4 or 5. In some embodiments, Y is a sequence selected from Table 1. In some embodiments, the PRC2-associated region is a sequence set forth in any one of SEQ ID NOS: 9 to 23. In some embodiments, the first single stranded oligonucleotide comprises a nucleotide sequence as set forth in any one of SEQ ID NOS: 30 to 8329 and 13088 to 13094 or a fragment thereof that is at least 8 nucleotides. In some embodiments, the first single stranded oligonucleotide comprises a nucleotide sequence as set forth in any one of SEQ ID NOS: 30 to 8329 and 13088 to 13094, wherein the 5' end of the nucleotide sequence provided is the 5' end of the first single stranded oligonucleotide. In some embodiments, the at least 8 consecutive nucleotides are also present within the nucleotide sequence set forth as SEQ ID NO: 7.

In some embodiments, the PRC2-associated region is a sequence set forth in any one of SEQ ID NOS: 24 to 29. In some embodiments, the first single stranded oligonucleotide comprises a nucleotide sequence as set forth in any one of SEQ ID NOS: 1158-1159, 1171, 1482-1483, 1485-1486, 2465-2471, 2488-2490, 2542-2546, 2656-2657, 2833-2835, 3439-3440, 3916-3918, 4469-4472, 4821, 5429, 5537, 6061, 7327, 8330-13061, and 13062-13087 or a fragment thereof that is at least 8 nucleotides. In some embodiments, the at least 8 consecutive nucleotides are present within the nucleotide sequence set forth as SEQ ID NO: 8. In some embodiments, the first single stranded oligonucleotide does not comprise three or more consecutive guanosine nucleotides. In some embodiments, the first single stranded oligonucleotide does not comprise four or more consecutive guanosine nucleotides. In some embodiments, the first single stranded oligonucleotide is 8 to 30 nucleotides in length. In some embodiments, the first single stranded oligonucleotide is 8 to 10 nucleotides in length and all but 1, 2, or 3 of the nucleotides of the complementary sequence of the PRC2-associated region are cytosine or guanosine nucleotides.

In some embodiments, the first single stranded oligonucleotide and the second single stranded oligonucleotide are delivered to the cell simultaneously. In some embodiments, the cell is in a subject and the step of delivering to the cell comprises administering the first single stranded oligonucleotide and the second single stranded oligonucleotide to the subject as a co-formulation. In some embodiments, the first single stranded oligonucleotide is covalently linked to the second single stranded oligonucleotide through a linker. In some embodiments, the linker comprises an oligonucleotide, a peptide, a low pH-labile bond, or a disulfide bond. In some embodiments, the linker comprises an oligonucleotide, optionally wherein the oligonucleotide comprises 1 to 10 thymidines or uridines. In some embodiments, the linker is more susceptible to cleavage in a mammalian extract than the first and second single stranded oligonucleotides. In some embodiments, the first single stranded oligonucleotide is not covalently linked to the second single stranded oligonucleotide. In some embodiments, the first single stranded oligonucleotide and the second single stranded oligonucleotide are delivered to the cell separately.

According to some aspects of the invention, methods are provided for treating spinal muscular atrophy in a subject. The methods, in some embodiments, comprise administering to the subject a first single stranded oligonucleotide complementary with at least 8 consecutive nucleotides of a PRC2-associated region of SMN2 and a second single stranded oligonucleotide complementary with a splice control sequence of a precursor mRNA of SMN2, in amounts sufficient to increase expression of SMN protein in the subject.

According to some aspects of the invention methods are provided for treating spinal muscular atrophy in a subject that involve administering to the subject a first single stranded oligonucleotide complementary with a PRC2-associated region of SMN2 and a second single stranded oligonucleotide complementary with a splice control sequence of a precursor mRNA of SMN2, in amounts sufficient to increase expression of SMN protein in the subject. Related compositions are also provided. In some embodiments, compositions are provided that comprise a first single stranded oligonucleotide complementary with at least 8 consecutive nucleotides of a PRC2-associated region of SMN2, and a second single stranded oligonucleotide complementary to a splice control sequence of a precursor mRNA of SMN2. In some embodiments, compositions are provided that comprise a single stranded oligonucleotide complementary with at least 8 consecutive nucleotides of a PRC2-associated region of a gene, linked via a linker to a single stranded oligonucleotide complementary to a splice control sequence of a precursor mRNA of the gene. Related kits comprising single stranded oligonucleotides that regulate SMN1 or SMN2 expression are also provided.

According to some aspects of the invention compositions are provided that comprise any of the oligonucleotides or compounds disclosed herein, and a carrier. In some embodiments, compositions are provided that comprise any of the oligonucleotides or compounds in a buffered solution. In some embodiments, the oligonucleotide is conjugated to the carrier. In some embodiments, the carrier is a peptide. In some embodiments, the carrier is a steroid. According to some aspects of the invention pharmaceutical compositions are provided that comprise any of the oligonucleotides disclosed herein, and a pharmaceutically acceptable carrier.

According to some aspects of the invention, compositions are provided that comprise a first single stranded oligonucleotide complementary with at least 8 consecutive nucleotides of a PRC2-associated region of SMN2, and a second single stranded oligonucleotide complementary to a splice control sequence of a precursor mRNA of SMN2. In some embodiments, the splice control sequence resides in an exon of SMN2. In some embodiments, the exon is exon 7 or exon 8. In some embodiments, the splice control sequence traverses an intron-exon junction of SMN2. In some embodiments, the intron-exon junction is the intron 6/exon 7 junction or the intron 7/exon 8 junction. In some embodiments, the splice control sequence resides in an intron of SMN2. In some embodiments, the intron is intron 6 or intron 7 (SEQ ID NO: 13101). In some embodiments, the splice control sequence comprises the sequence: CAGCAUUAUGAAAG (SEQ ID NO: 13100) or a portion thereof. In some embodiments, the splice control sequence comprises at least one hnRNAP binding sequence. In some embodiments, the second single stranded oligonucleotide comprises a sequence selected from: TCACTTTCATAATGCTGG (SEQ ID NO: 13088); TCACTTTCATAATGC (SEQ ID NO: 13089); CACTTTCATAATGCT (SEQ ID NO: 13090); ACTTTCATAATGCTG (SEQ ID NO: 13091); and CTTTCATAATGCTGG (SEQ ID NO: 13092). In some embodiments, the first single stranded oligonucleotide has a sequence 5'-X-Y-Z, wherein X is any nucleotide, Y is a nucleotide sequence of 6 nucleotides in length that is not a seed sequence of a human microRNA, and Z is a nucleotide sequence of 1-23 nucleotides in length. In some embodiments, the PRC2-associated region of SMN2 is a PRC2-associated region within SEQ ID NO: 1, 2, 4 or 5. In some embodiments, Y is a sequence selected from Table 1. In some embodiments, the PRC2-associated region is a sequence set forth in any one of SEQ ID NOS: 9 to 23. In some embodiments, the first single stranded oligonucleotide comprises a nucleotide sequence as set forth in any one of SEQ ID NOS: 30 to 8329 and 13093 to 13094 or a fragment thereof that is at least 8 nucleotides. In some embodiments, the first single stranded oligonucleotide comprises a nucleotide sequence as set forth in any one of SEQ ID NOS: 30 to 8329 and 13093 to 13094, wherein the 5' end of the nucleotide sequence provided is the 5' end of the first single stranded oligonucleotide. In some embodiments, the at least 8 consecutive nucleotides are also present within the nucleotide sequence set forth as SEQ ID NO: 7. In some embodiments, the PRC2-associated region is a sequence set forth in any one of SEQ ID NOS: 24 to 29. In some embodiments, the first single stranded oligonucleotide comprises a nucleotide sequence as set forth in any one of SEQ ID NOS: 1158-1159, 1171, 1482-1483, 1485-1486, 2465-2471, 2488-2490, 2542-2546, 2656-2657, 2833-2835, 3439-3440, 3916-3918, 4469-4472, 4821, 5429, 5537, 6061, 7327, 8330-13061, and 13062-13087 or a fragment thereof that is at least 8 nucleotides. In some embodiments, the at least 8 consecutive nucleotides are present within the nucleotide sequence set forth as SEQ ID NO: 8. In some embodiments, the first single stranded oligonucleotide does not comprise three or more consecutive guanosine nucleotides. In some embodiments, the first single stranded oligonucleotide does not comprise four or more consecutive guanosine nucleotides. In some embodiments, the first and/or second single stranded oligonucleotide is 8 to 30 nucleotides in length. In some embodiments, the first single stranded oligonucleotide is 8 to 10 nucleotides in length and all but 1, 2, or 3 of the nucleotides of the complementary sequence of the PRC2-associated region are cytosine or guanosine nucleotides. In some embodiments, the first single stranded oligonucleotide is covalently linked to the second single stranded oligonucleotide through a linker. In some embodiments, the linker comprises an oligonucleotide, a peptide, a low pH-labile bond, or a disulfide bond. In some embodiments, the linker comprises an oligonucleotide, optionally wherein the oligonucleotide comprises 1 to 10 thymidines or uridines. In some embodiments, the linker is more susceptible to cleavage in a mammalian extract than the first and second single stranded oligonucleotides. In some embodiments, the first single stranded oligonucleotide is not covalently linked to the second single stranded oligonucleotide. In some embodiments, the composition further comprises a carrier. In some embodiments, the carrier is a pharmaceutically acceptable carrier.

Further aspects of the invention provide methods for selecting oligonucleotides for activating or enhancing expression of SMN1 or SMN2. In some embodiments, methods are provided for selecting a set of oligonucleotides that is enriched in candidates (e.g., compared with a random selection of oligonucleotides) for activating or enhancing expression of SMN1 or SMN2. Accordingly, the methods may be used to establish sets of clinical candidates that are enriched in oligonucleotides that activate or enhance expression of SMN1 or SMN2. Such libraries may be utilized, for example, to identify lead oligonucleotides for developing therapeutics to treat SMN1 or SMN2. Furthermore, in some embodiments, oligonucleotide chemistries are provided that are useful for controlling the pharmacokinetics, biodistribution, bioavailability and/or efficacy of the single stranded oligonucleotides for activating expression of SMN1 or SMN2.

According to other aspects of the invention, kits are provided that comprise a container housing any of the compositions disclosed herein. According to other aspects of the invention, kits are provided that comprise a first container housing first single stranded oligonucleotide complementary with at least 8 consecutive nucleotides of a PRC2-associated region of a gene; and a second container housing a second single stranded oligonucleotide complementary to a splice control sequence of a precursor mRNA of the gene. In some embodiments, the splice control sequence resides in an exon of the gene. In some embodiments, the splice control sequence traverses an intron-exon junction of the gene. In some embodiments, the splice control sequence resides in an intron of the gene. In some embodiments, the splice control sequence comprises at least one hnRNAP binding sequence. In some embodiments, hybridization of an oligonucleotide having the sequence of C with the splice control sequence of the precursor mRNA in a cell results in inclusion of a particular exon in a mature mRNA that arises from processing of the precursor mRNA in the cell. In some embodiments, hybridization of an oligonucleotide having the sequence of C with the splice control sequence of the precursor mRNA in a cell results in exclusion of a particular intron or exon in a mature mRNA that arises from processing of the precursor mRNA in the cell. In some embodiments, the gene is SMN1 or SMN2. In some embodiments, the splice control sequence resides in intron 6, intron 7, exon 7, exon 8 or at the junction of intron 7 and exon 8. In some embodiments, the splice control sequence comprises the sequence: CAGCAUUAUGAAAG (SEQ ID NO: 13100). In some embodiments, the second single stranded oligonucleotide comprises a sequence selected from: TCACTTTCATAATGCTGG (SEQ ID NO: 13088); TCACTTTCATAATGC (SEQ ID NO: 13089); CACTTTCATAATGCT (SEQ ID NO: 13090); ACTTTCATAATGCTG (SEQ ID NO: XX); and CTTTCATAATGCTGG (SEQ ID NO: 13091). In some embodiments, the first single stranded oligonucleotide has a sequence 5'-X-Y-Z, wherein X is any nucleotide, Y is a nucleotide sequence of 6 nucleotides in length that is not a seed sequence of a human microRNA, and Z is a nucleotide sequence of 1-23 nucleotides in length. In some embodiments, the PRC2-associated region of an SMN2 gene is a PRC2-associated region within SEQ ID NO: 1, 2, 4 or 5. In some embodiments, Y is a sequence selected from Table 1. In some embodiments, the PRC2-associated region is a sequence set forth in any one of SEQ ID NOS: 9 to 23. In some embodiments, the first single stranded oligonucleotide comprises a nucleotide sequence as set forth in any one of SEQ ID NOS: 30 to 8329 and 13093 to 13094 or a fragment thereof that is at least 8 nucleotides. In some embodiments, the first single stranded oligonucleotide comprises a nucleotide sequence as set forth in any one of SEQ ID NOS: 30 to 8329 and 13093 to 13094, wherein the 5' end of the nucleotide sequence provided is the 5' end of the first single stranded oligonucleotide. In some embodiments, the at least 8 consecutive nucleotides are also present within the nucleotide sequence set forth as SEQ ID NO: 7. In some embodiments, the PRC2-associated region is a sequence set forth in any one of SEQ ID NOS: 24 to 29. In some embodiments, the first single stranded oligonucleotide comprises a nucleotide sequence as set forth in any one of SEQ ID NOS: 1158-1159, 1171, 1482-1483, 1485-1486, 2465-2471, 2488-2490, 2542-2546, 2656-2657, 2833-2835, 3439-3440, 3916-3918, 4469-4472, 4821, 5429, 5537, 6061, 7327, 8330-13061, and 13062-13087 or a fragment thereof that is at least 8 nucleotides. In some embodiments, the at least 8 consecutive nucleotides are present within the nucleotide sequence set forth as SEQ ID NO: 8.

BRIEF DESCRIPTION OF TABLES

Figure 1:
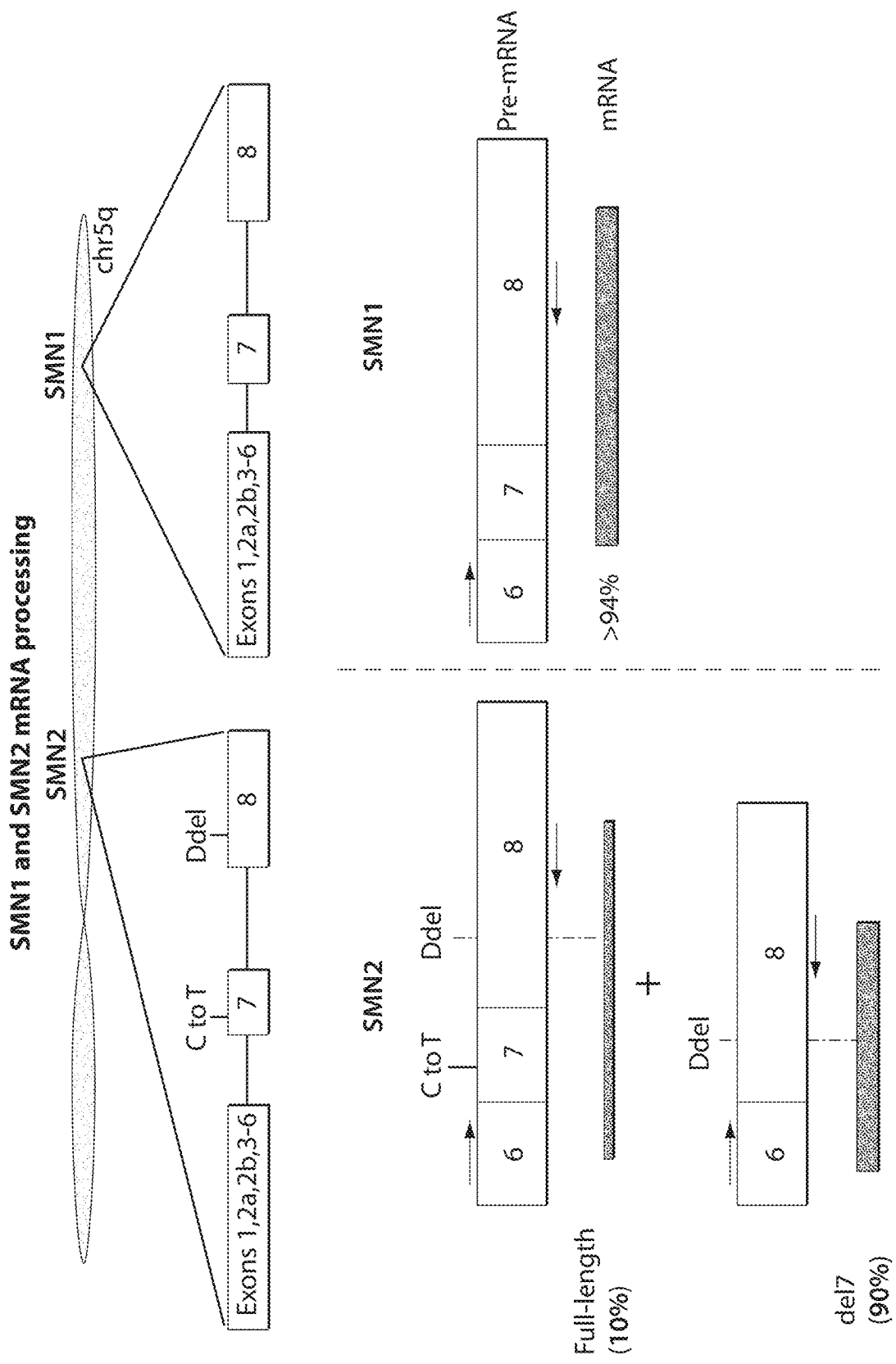
FIG. 1 provides a schematic of SMN1 and SMN2 mRNA processing

Table 1: Hexamers that are not seed sequences of human miRNAs

Table 2: Oligonucleotide sequences made for testing in the lab. RQ (column 2) and RQ SE (column 3) shows the activity of the oligo relative to a control well (usually carrier alone) and the standard error or the triplicate replicates of the experiment. [oligo] is shown in nanomolar for in vitro experiments and in milligrams per kilogram of body weight for in vivo experiments.

Table 3: A listing of oligonucleotide modifications

Table 4: Oligonucleotide sequences made for testing human cells obtained from subjects with Spinal Muscular Atrophy. The table shows the sequence of the modified nucleotides, where lnaX represents an LNA nucleotide with 3' phosphorothioate linkage, omeX is a 2'-O-methyl nucleotide, dX is a deoxy nucleotide. An s at the end of a nucleotide code indicates that the nucleotide had a 3' phosphorothioate linkage. The "-Sup" at the end of the sequence marks the fact that the 3' end lacks either a phosphate or thiophosphate on the 3' linkage. The Formatted Sequence column shows the sequence of the oligonucleotide, including modified nucleotides, for the oligonucleotides tested in Table 2, 5, 6 and 7.

Table 8: Cell lines

BRIEF DESCRIPTION OF THE APPENDICES

Appendix A; Appendix A contains Table 5, which shows RT-PCR data from PGPubs, use the testing of different oligonucleotides. Appendix A can be found on pages 106-287 Gap Bulletin per of WO 2013/173638, which are incorporated by reference herein in their entirety.

Appendix B; Appendix B contains Table 6, which shows RT-PCR data from testing of different combination treatments (e.g., two oligonucleotides, an oligonucleotide and a drug). Appendix B can be found on pages 288-309 of WO 2013/173638, which are incorporated by reference herein in their entirety.

Appendix C; Appendix C contains Table 7, which shows ELISA data from testing of different oligonucleotides. Appendix C can be found on pages 310-399 of WO 2013/173638, which are incorporated by reference herein in their entirety.

Note the following column information for Tables 5-7 in Appendices A-C, respectively. SEQID: sequence identifier of base sequence of oligonucleotide used; Oligo Name: name of oligonucleotide; Avg RQ: average relative quantification of RT-PCR based expression levels of target gene(s); Avg RQ SE: standard error of mean of relative quantification of RT-PCR based expression level; "% SMN over lipo only control" refers to the ratio of SMN protein levels (ng/mg total protein) when compared to Lipofectamine2000 (transfection reagent) treated cells converted into %; "% SMN CVV" refers to coefficient of variation; Exp #: Experiment reference number; Target: target gene; [oligo]: concentration of oligonucleotide used in nM unless otherwise indicated; Cell Line: cell line used; Assay Type: assay used; Time(hr): time of assay following treatment; $2^{nd}$ Drug: name of second oligonucleotide (identified by Oligo Name) or drug used in combination experiment; $[2^{nd}]$: concentration of second oligonucleotide or drug; Units: units of concentration; $3^{rd}$ Drug: name of third oligonucleotide (identified by Oligo Name) or drug used in combination experiment; $[3^{rd}]$: concentration of third oligonucleotide or drug; Notes: comments regarding experiment. Oligo Names correspond to those in Tables 2 and 4.

DETAILED DESCRIPTION OF CERTAIN EMBODIMENTS OF THE INVENTION

Spinal muscular atrophy (SMA), the most common genetic cause of infant mortality, is an autosomal recessive neuromuscular disease characterized by progressive loss of α-motor neurons in the anterior horns of the spinal cord, leading to limb and trunk paralysis and atrophy of voluntary muscles. Based on the severity and age of onset, SMA is clinically subdivided into types I, II, and III (MIMs 253300, 253550, and 253400), with type I generally understood as being the most severe.

Loss of function of the SMN1 gene is responsible for SMA. Humans have an extra SMN gene copy, called SMN2. Both SMN genes reside within a segmental duplication on Chromosome 5q13 as inverted repeats. SMN1 and SMN2 are almost identical. In some cases, SMN1 and SMN2 differ by 11 nucleotide substitutions, including seven in intron 6, two in intron 7, one in coding exon 7, and one in non-coding exon 8. The substitution in exon 7 involves a translationally silent C to T transition compared with SMN1, that results in alternative splicing because the substitution disrupts recognition of the upstream 3' splice site, in which exon 7 is frequently skipped during precursor mRNA splicing. Consequently, SMN2 encodes primarily the exon 7-skipped protein isoform (SMNA7), which is unstable, mislocalized, and only partially functional.

Methods and related single stranded oligonucleotides that are useful for selectively inducing expression of particular splice variants of SMN1 or SMN2 are provided herein. The methods are useful for controlling the levels in a cell of particular SMN protein isoforms encoded by the splice variants. In some cases, the methods are useful for inducing expression of SMN proteins to levels sufficient to treat SMA. For example, according to some aspects of the invention methods are provided for increasing expression of full-length SMN protein in a cell for purposes of treating SMA. In some embodiments, the methods comprise delivering to the cell a first single stranded oligonucleotide complementary with a PRC2-associated region of SMN1 or SMN2 and a second single stranded oligonucleotide complementary with a splice control sequence of a precursor mRNA of SMN1 or SMN2, in amounts sufficient to increase expression of a mature mRNA of SMN1 or SMN2 that comprises (or includes) exon 7 in the cell. Further aspects of the invention are described in detailed herein.

Polycomb Repressive Complex 2 (PRC2)-Interacting RNAs

Aspects of the invention provided herein relate to the discovery of polycomb repressive complex 2 (PRC2)-interacting RNAs. Polycomb repressive complex 2 (PRC2) is a histone methyltransferase and a known epigenetic regulator involved in silencing of genomic regions through methylation of histone H3. Among other functions, PRC2 interacts with long noncoding RNAs (lncRNAs), such as RepA, Xist, and Tsix, to catalyze trimethylation of histone H3-lysine27. PRC2 contains four subunits, Eed, Suz12, RbAp48, and Ezh2. Aspects of the invention relate to the recognition that single stranded oligonucleotides that bind to PRC2-associated regions of RNAs (e.g., lncRNAs) that are expressed from within a genomic region that encompasses or that is in functional proximity to the SMN1 or SMN2 gene can induce or enhance expression of SMN1 or SMN2. In some embodiments, this upregulation is believed to result from inhibition of PRC2 mediated repression of SMN1 or SMN2.

As used herein, the term "PRC2-associated region" refers to a region of a nucleic acid that comprises or encodes a sequence of nucleotides that interact directly or indirectly with a component of PRC2. A PRC2-associated region may be present in a RNA (e.g., a long non-coding RNA (lncRNA)) that interacts with a PRC2. A PRC2-associated region may be present in a DNA that encodes an RNA that interacts with PRC2. In some cases, the PRC2-associated region is equivalently referred to as a PRC2-interacting region.

In some embodiments, a PRC2-associated region is a region of an RNA that crosslinks to a component of PRC2 in response to in situ ultraviolet irradiation of a cell that expresses the RNA, or a region of genomic DNA that encodes that RNA region. In some embodiments, a PRC2-associated region is a region of an RNA that immunoprecipitates with an antibody that targets a component of PRC2, or a region of genomic DNA that encodes that RNA region. In some embodiments, a PRC2-associated region is a region of an RNA that immunoprecipitates with an antibody that binds specifically to SUZ12, EED, EZH2 or RBBP4 (which as noted above are components of PRC2), or a region of genomic DNA that encodes that RNA region.

In some embodiments, a PRC2-associated region is a region of an RNA that is protected from nucleases (e.g., RNases) in an RNA-immunoprecipitation assay that employs an antibody that targets a component of PRC2, or a region of genomic DNA that encodes that protected RNA region. In some embodiments, a PRC2-associated region is a region of an RNA that is protected from nucleases (e.g., RNases) in an RNA-immunoprecipitation assay that employs an antibody that targets SUZ12, EED, EZH2 or RBBP4, or a region of genomic DNA that encodes that protected RNA region.

In some embodiments, a PRC2-associated region is a region of an RNA within which occur a relatively high frequency of sequence reads in a sequencing reaction of products of an RNA-immunoprecipitation assay that employs an antibody that targets a component of PRC2, or a region of genomic DNA that encodes that RNA region. In some embodiments, a PRC2-associated region is a region of an RNA within which occur a relatively high frequency of sequence reads in a sequencing reaction of products of an RNA-immunoprecipitation assay that employs an antibody that binds specifically to SUZ12, EED, EZH2 or RBBP4, or a region of genomic DNA that encodes that protected RNA region. In such embodiments, the PRC2-associated region may be referred to as a "peak."

In some embodiments, a PRC2-associated region comprises a sequence of 40 to 60 nucleotides that interact with PRC2 complex. In some embodiments, a PRC2-associated region comprises a sequence of 40 to 60 nucleotides that encode an RNA that interacts with PRC2. In some embodiments, a PRC2-associated region comprises a sequence of up to 5 kb in length that comprises a sequence (e.g., of 40 to 60 nucleotides) that interacts with PRC2. In some embodiments, a PRC2-associated region comprises a sequence of up to 5 kb in length within which an RNA is encoded that has a sequence (e.g., of 40 to 60 nucleotides) that is known to interact with PRC2. In some embodiments, a PRC2-associated region comprises a sequence of about 4 kb in length that comprise a sequence (e.g., of 40 to 60 nucleotides) that interacts with PRC2. In some embodiments, a PRC2-associated region comprises a sequence of about 4 kb in length within which an RNA is encoded that includes a sequence (e.g., of 40 to 60 nucleotides) that is known to interact with PRC2. In some embodiments, a PRC2-associated region has a sequence as set forth in any one of SEQ ID NOS: 9 to 29. In some embodiments, a PRC2-associated region has a sequence as set forth in any one of SEQ ID NOS: 24 to 29.

In some embodiments, single stranded oligonucleotides are provided that specifically bind to, or are complementary to, a PRC2-associated region in a genomic region that encompasses or that is in proximity to the SMN1 or SMN2 gene. In some embodiments, single stranded oligonucleotides are provided that specifically bind to, or are complementary to, a PRC2-associated region that has a sequence as set forth in any one of SEQ ID NOS: 9 to 29. In some embodiments, single stranded oligonucleotides are provided that specifically bind to, or are complementary to, a PRC2-associated region that has a sequence as set forth in any one of SEQ ID NOS: 9 to 29 combined with up to 2 kb, up to 5 kb, or up to 10 kb of flanking sequences from a corresponding genomic region to which these SEQ IDs map (e.g., in a human genome). In some embodiments, single stranded oligonucleotides have a sequence as set forth in any one of SEQ ID NOS: 30 to 13087. In some embodiments, single stranded oligonucleotides have a sequence as set forth in Table 2. In some embodiments, a PRC2 associated region of SMN1 or SMN2 against which a single stranded oligonucleotide is complementary is selected from SEQ ID NOS: 24-29. In some embodiments, a single stranded oligonucleotide that is complementary with a PRC2 associated region of SMN1 or SMN2 comprises a sequence selected from SEQ ID NOS: 1158-1159, 1171, 1482-1483, 1485-1486, 2465-2471, 2488-2490, 2542-2546, 2656-2657, 2833-2835, 3439-3440, 3916-3918, 4469-4472, 4821, 5429, 5537, 6061, 7327, 8330-13061, and 13062-13087. In some embodiments, a single stranded oligonucleotide that is complementary with a PRC2 associated region of SMN1 or SMN2 comprises a sequence selected from 11395, 11394, 10169, and 10170.

Without being bound by a theory of invention, these oligonucleotides are able to interfere with the binding of and function of PRC2, by preventing recruitment of PRC2 to a specific chromosomal locus. For example, a single administration of single stranded oligonucleotides designed to specifically bind a PRC2-associated region lncRNA can stably displace not only the lncRNA, but also the PRC2 that binds to the lncRNA, from binding chromatin. After displacement, the full complement of PRC2 is not recovered for up to 24 hours. Further, lncRNA can recruit PRC2 in a cis fashion, repressing gene expression at or near the specific chromosomal locus from which the lncRNA was transcribed.

Methods of modulating gene expression are provided, in some embodiments, that may be carried out in vitro, ex vivo, or in vivo. It is understood that any reference to uses of compounds throughout the description contemplates use of the compound in preparation of a pharmaceutical composition or medicament for use in the treatment of condition (e.g., Spinal muscular atrophy) associated with decreased levels or activity of SMN1 or SMN2. Thus, as one nonlimiting example, this aspect of the invention includes use of such single stranded oligonucleotides in the preparation of a medicament for use in the treatment of disease, wherein the treatment involves upregulating expression of SMN1 or SMN2.

In further aspects of the invention, methods are provided for selecting a candidate oligonucleotide for activating expression of SMN1 or SMN2. The methods generally involve selecting as a candidate oligonucleotide, a single stranded oligonucleotide comprising a nucleotide sequence that is complementary to a PRC2-associated region (e.g., a nucleotide sequence as set forth in any one of SEQ ID NOS: 9 to 29). In some embodiments, sets of oligonucleotides may be selected that are enriched (e.g., compared with a random selection of oligonucleotides) in oligonucleotides that activate expression of SMN1 or SMN2.

Single Stranded Oligonucleotides for Modulating Expression of SMN1 or SMN2

In one aspect of the invention, single stranded oligonucleotides complementary to the PRC2-associated regions are provided for modulating expression of SMN1 or SMN2 in a cell. In some embodiments, expression of SMN1 or SMN2 is upregulated or increased. In some embodiments, single stranded oligonucleotides complementary to these PRC2-associated regions inhibit the interaction of PRC2 with long RNA transcripts such that gene expression is upregulated or increased. In some embodiments, single stranded oligonucleotides complementary to these PRC2-associated regions inhibit the interaction of PRC2 with long RNA transcripts, resulting in reduced methylation of histone H3 and reduced gene inactivation, such that gene expression is upregulated or increased. In some embodiments, this interaction may be disrupted or inhibited due to a change in the structure of the long RNA that prevents or reduces binding to PRC2. The oligonucleotide may be selected using any of the methods disclosed herein for selecting a candidate oligonucleotide for activating expression of SMN1 or SMN2.

The single stranded oligonucleotide may comprise a region of complementarity that is complementary with a PRC2-associated region of a nucleotide sequence set forth in any one of SEQ ID NOS: 1 to 8. The region of complementarity of the single stranded oligonucleotide may be complementary with at least 6, e.g., at least 7, at least 8, at least 9, at least 10, at least 15 or more consecutive nucleotides of the PRC2-associated region.

It should be appreciated that due the high homology between SMN1 and SMN2, single stranded oligonucleotides that are complementary with a PRC2-associated region of SMN1 are often also complementary with a corresponding PRC2-associated region of SMN2.

The PRC2-associated region may map to a position in a chromosome between 50 kilobases upstream of a 5'-end of the SMN1 or SMN2 gene and 50 kilobases downstream of a 3'-end of the SMN1 or SMN2 gene. The PRC2-associated region may map to a position in a chromosome between 25 kilobases upstream of a 5'-end of the SMN1 or SMN2 gene and 25 kilobases downstream of a 3'-end of the SMN1 or SMN2 gene. The PRC2-associated region may map to a position in a chromosome between 12 kilobases upstream of a 5'-end of the SMN1 or SMN2 gene and 12 kilobases downstream of a 3'-end of the SMN1 or SMN2 gene. The PRC2-associated region may map to a position in a chromosome between 5 kilobases upstream of a 5'-end of the SMN1 or SMN2 gene and 5 kilobases downstream of a 3'-end of the SMN1 or SMN2 gene.

The genomic position of the selected PRC2-associated region relative to the SMN1 or SMN2 gene may vary. For example, the PRC2-associated region may be upstream of the 5' end of the SMN1 or SMN2 gene. The PRC2-associated region may be downstream of the 3' end of the SMN1 or SMN2 gene. The PRC2-associated region may be within an intron of the SMN1 or SMN2 gene. The PRC2-associated region may be within an exon of the SMN1 or SMN2 gene. The PRC2-associated region may traverse an intron-exon junction, a 5'-UTR-exon junction or a 3'-UTR-exon junction of the SMN1 or SMN2 gene.

The single stranded oligonucleotide may comprise a sequence having the formula X-Y-Z, in which X is any nucleotide, Y is a nucleotide sequence of 6 nucleotides in length that is not a human seed sequence of a microRNA, and Z is a nucleotide sequence of varying length. In some embodiments X is the 5' nucleotide of the oligonucleotide. In some embodiments, when X is anchored at the 5' end of the oligonucleotide, the oligonucleotide does not have any nucleotides or nucleotide analogs linked 5' to X. In some embodiments, other compounds such as peptides or sterols may be linked at the 5' end in this embodiment as long as they are not nucleotides or nucleotide analogs. In some embodiments, the single stranded oligonucleotide has a sequence 5'X-Y-Z and is 8-50 nucleotides in length. Oligonucleotides that have these sequence characteristics are predicted to avoid the miRNA pathway. Therefore, in some embodiments, oligonucleotides having these sequence characteristics are unlikely to have an unintended consequence of functioning in a cell as a miRNA molecule. The Y sequence may be a nucleotide sequence of 6 nucleotides in length set forth in Table 1.

The single stranded oligonucleotide may have a sequence that does not contain guanosine nucleotide stretches (e.g., 3 or more, 4 or more, 5 or more, 6 or more consecutive guanosine nucleotides). In some embodiments, oligonucleotides having guanosine nucleotide stretches have increased non-specific binding and/or off-target effects, compared with oligonucleotides that do not have guanosine nucleotide stretches.

The single stranded oligonucleotide may have a sequence that has less than a threshold level of sequence identity with every sequence of nucleotides, of equivalent length, that map to a genomic position encompassing or in proximity to an off-target gene. For example, an oligonucleotide may be designed to ensure that it does not have a sequence that maps to genomic positions encompassing or in proximity with all known genes (e.g., all known protein coding genes) other than SMN1 or SMN2. In a similar embodiment, an oligonucleotide may be designed to ensure that it does not have a sequence that maps to any other known PRC2-associated region, particularly PRC2-associated regions that are functionally related to any other known gene (e.g., any other known protein coding gene). In either case, the oligonucleotide is expected to have a reduced likelihood of having off-target effects. The threshold level of sequence identity may be 50%, 60%, 70%, 80%, 85%, 90%, 95%, 99% or 100% sequence identity.

The single stranded oligonucleotide may have a sequence that is complementary to a PRC2-associated region that encodes an RNA that forms a secondary structure comprising at least two single stranded loops. In has been discovered that, in some embodiments, oligonucleotides that are complementary to a PRC2-associated region that encodes an RNA that forms a secondary structure comprising one or more single stranded loops (e.g., at least two single stranded loops) have a greater likelihood of being active (e.g., of being capable of activating or enhancing expression of a target gene) than a randomly selected oligonucleotide. In some cases, the secondary structure may comprise a double stranded stem between the at least two single stranded loops. Accordingly, the region of complementarity between the oligonucleotide and the PRC2-associated region may be at a location of the PRC2 associated region that encodes at least a portion of at least one of the loops. In some cases, the region of complementarity between the oligonucleotide and the PRC2-associated region may be at a location of the PRC2-associated region that encodes at least a portion of at least two of the loops. In some cases, the region of complementarity between the oligonucleotide and the PRC2-associated region may be at a location of the PRC2 associated region that encodes at least a portion of the double stranded stem. In some embodiments, a PRC2-associated region (e.g., of an lncRNA) is identified (e.g., using RIP-Seq methodology or information derived therefrom). In some embodiments, the predicted secondary structure RNA (e.g., lncRNA) containing the PRC2-associated region is determined using RNA secondary structure prediction algorithms, e.g., RNAfold, mfold. In some embodiments, oligonucleotides are designed to target a region of the RNA that forms a secondary structure comprising one or more single stranded loop (e.g., at least two single stranded loops) structures which may comprise a double stranded stem between the at least two single stranded loops.

The single stranded oligonucleotide may have a sequence that is has greater than 30% G-C content, greater than 40% G-C content, greater than 50% G-C content, greater than 60% G-C content, greater than 70% G-C content, or greater than 80% G-C content. The single stranded oligonucleotide may have a sequence that has up to 100% G-C content, up to 95% G-C content, up to 90% G-C content, or up to 80% G-C content. In some embodiments in which the oligonucleotide is 8 to 10 nucleotides in length, all but 1, 2, 3, 4, or 5 of the nucleotides of the complementary sequence of the PRC2-associated region are cytosine or guanosine nucleotides. In some embodiments, the sequence of the PRC2-associated region to which the single stranded oligonucleotide is complementary comprises no more than 3 nucleotides selected from adenine and uracil.

The single stranded oligonucleotide may be complementary to a chromosome of a different species (e.g., a mouse, rat, rabbit, goat, monkey, etc.) at a position that encompasses or that is in proximity to that species' homolog of SMN1 or SMN2. The single stranded oligonucleotide may be complementary to a human genomic region encompassing or in proximity to the SMN1 or SMN2 gene and also be complementary to a mouse genomic region encompassing or in proximity to the mouse homolog of SMN1 or SMN2. For example, the single stranded oligonucleotide may be complementary to a sequence as set forth in SEQ ID NO: 1, 2, 4, or 5, which is a human genomic region encompassing or in proximity to the SMN1 or SMN2 gene, and also be complementary to a sequence as set forth in SEQ ID NO:7 or 8, which is a mouse genomic region encompassing or in proximity to the mouse homolog of the SMN1 or SMN2 gene. Oligonucleotides having these characteristics may be tested in vivo or in vitro for efficacy in multiple species (e.g., human and mouse). This approach also facilitates development of clinical candidates for treating human disease by selecting a species in which an appropriate animal exists for the disease.

In some embodiments, the region of complementarity of the single stranded oligonucleotide is complementary with at least 8 to 15, 8 to 30, 8 to 40, or 10 to 50, or 5 to 50, or 5 to 40 bases, e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive nucleotides of a PRC2-associated region. In some embodiments, the region of complementarity is complementary with at least 8 consecutive nucleotides of a PRC2-associated region. In some embodiments the sequence of the single stranded oligonucleotide is based on an RNA sequence that binds to PRC2, or a portion thereof, said portion having a length of from 5 to 40 contiguous base pairs, or about 8 to 40 bases, or about 5 to 15, or about 5 to 30, or about 5 to 40 bases, or about 5 to 50 bases. Complementary, as the term is used in the art, refers to the capacity for precise pairing between two nucleotides. For example, if a nucleotide at a certain position of an oligonucleotide is capable of hydrogen bonding with a nucleotide at the same position of PRC2-associated region, then the single stranded nucleotide and PRC2-associated region are considered to be complementary to each other at that position. The single stranded nucleotide and PRC2-associated region are complementary to each other when a sufficient number of corresponding positions in each molecule are occupied by nucleotides that can hydrogen bond with each other through their bases. Thus, "complementary" is a term which is used to indicate a sufficient degree of complementarity or precise pairing such that stable and specific binding occurs between the single stranded nucleotide and PRC2-associated region. For example, if a base at one position of a single stranded nucleotide is capable of hydrogen bonding with a base at the corresponding position of a PRC2-associated region, then the bases are considered to be complementary to each other at that position. 100% complementarity is not required.

The single stranded oligonucleotide may be at least 80% complementary to (optionally one of at least 85%, 90%, 91%, 92%, 93%, 94%, 95%, 96%, 97%, 98%, 99% or 100% complementary to) the consecutive nucleotides of a PRC2-associated region. In some embodiments the single stranded oligonucleotide may contain 1, 2 or 3 base mismatches compared to the portion of the consecutive nucleotides of a PRC2-associated region. In some embodiments the single stranded oligonucleotide may have up to 3 mismatches over 15 bases, or up to 2 mismatches over 10 bases.

It is understood in the art that a complementary nucleotide sequence need not be 100% complementary to that of its target to be specifically hybridizable. In some embodiments, a complementary nucleic acid sequence for purposes of the present disclosure is specifically hybridizable when binding of the sequence to the target molecule (e.g., lncRNA) interferes with the normal function of the target (e.g., lncRNA) to cause a loss of activity (e.g., inhibiting PRC2-associated repression with consequent up-regulation of gene expression) and there is a sufficient degree of complementarity to avoid non-specific binding of the sequence to non-target sequences under conditions in which avoidance of non-specific binding is desired, e.g., under physiological conditions in the case of in vivo assays or therapeutic treatment, and in the case of in vitro assays, under conditions in which the assays are performed under suitable conditions of stringency.

In some embodiments, the single stranded oligonucleotide is 7, 8, 9, 10, 11, 12, 13, 14, 15, 16, 17, 18, 19, 20, 21, 22, 23, 24, 25, 26, 27, 28, 29, 30, 35, 40, 45, 50 or more nucleotides in length. In a preferred embodiment, the oligonucleotide is 8 to 30 nucleotides in length.

In some embodiments, the PRC2-associated region occurs on the same DNA strand as a gene sequence (sense). In some embodiments, the PRC2-associated region occurs on the opposite DNA strand as a gene sequence (anti-sense). Oligonucleotides complementary to a PRC2-associated region can bind either sense or anti-sense sequences. Base pairings may include both canonical Watson-Crick base pairing and non-Watson-Crick base pairing (e.g., Wobble base pairing and Hoogsteen base pairing). It is understood that for complementary base pairings, adenosine-type bases (A) are complementary to thymidine-type bases (T) or uracil-type bases (U), that cytosine-type bases (C) are complementary to guanosine-type bases (G), and that universal bases such as 3-nitropyrrole or 5-nitroindole can hybridize to and are considered complementary to any A, C, U, or T. Inosine (I) has also been considered in the art to be a universal base and is considered complementary to any A, C, U or T.

In some embodiments, any one or more thymidine (T) nucleotides (or modified nucleotide thereof) or uridine (U) nucleotides (or a modified nucleotide thereof) in a sequence provided herein, including a sequence provided in the sequence listing, may be replaced with any other nucleotide suitable for base pairing (e.g., via a Watson-Crick base pair) with an adenosine nucleotide. In some embodiments, any one or more thymidine (T) nucleotides (or modified nucleotide thereof) or uridine (U) nucleotides (or a modified nucleotide thereof) in a sequence provided herein, including a sequence provided in the sequence listing, may be suitably replaced with a different pyrimidine nucleotide or vice versa. In some embodiments, any one or more thymidine (T) nucleotides (or modified nucleotide thereof) in a sequence provided herein, including a sequence provided in the sequence listing, may be suitably replaced with a uridine (U) nucleotide (or a modified nucleotide thereof) or vice versa.

In some embodiments, GC content of the single stranded oligonucleotide is preferably between about 30-60%. Contiguous runs of three or more Gs or Cs may not be preferable in some embodiments. Accordingly, in some embodiments, the oligonucleotide does not comprise a stretch of three or more guanosine nucleotides.

In some embodiments, the single stranded oligonucleotide specifically binds to, or is complementary to an RNA that is encoded in a genome (e.g., a human genome) as a single contiguous transcript (e.g., a non-spliced RNA). In some embodiments, the single stranded oligonucleotide specifically binds to, or is complementary to an RNA that is encoded in a genome (e.g., a human genome), in which the distance in the genome between the 5'end of the coding region of the RNA and the 3' end of the coding region of the RNA is less than 1 kb, less than 2 kb, less than 3 kb, less than 4 kb, less than 5 kb, less than 7 kb, less than 8 kb, less than 9 kb, less than 10 kb, or less than 20 kb.

It is to be understood that any oligonucleotide provided herein can be excluded.

In some embodiments, single stranded oligonucleotides disclosed herein may increase expression of mRNA corresponding to the gene by at least about 50% (i.e. 150% of normal or 1.5 fold), or by about 2 fold to about 5 fold. In some embodiments, expression may be increased by at least about 15 fold, 20 fold, 30 fold, 40 fold, 50 fold or 100 fold, or any range between any of the foregoing numbers. It has also been found that increased mRNA expression has been shown to correlate to increased protein expression.

In some or any of the embodiments of the oligonucleotides described herein, or processes for designing or synthesizing them, the oligonucleotides will upregulate gene expression and may specifically bind or specifically hybridize or be complementary to the PRC2 binding RNA that is transcribed from the same strand as a protein coding reference gene. The oligonucleotide may bind to a region of the PRC2 binding RNA that originates within or overlaps an intron, exon, intron exon junction, 5' UTR, 3' UTR, a translation initiation region, or a translation termination region of a protein coding sense strand of a reference gene (refGene).

In some or any of the embodiments of oligonucleotides described herein, or processes for designing or synthesizing them, the oligonucleotides will upregulate gene expression and may specifically bind or specifically hybridize or be complementary to a PRC2 binding RNA that transcribed from the opposite strand (the antisense strand) of a protein coding reference gene. The oligonucleotide may bind to a region of the PRC2 binding RNA that originates within or overlaps an intron, exon, intron exon junction, 5' UTR, 3' UTR, a translation initiation region, or a translation termination region of a protein coding antisense strand of a reference gene.

The oligonucleotides described herein may be modified, e.g., comprise a modified sugar moiety, a modified internucleoside linkage, a modified nucleotide and/or combinations thereof. In addition, the oligonucleotides can exhibit one or more of the following properties: do not induce substantial cleavage or degradation of the target RNA; do not cause substantially complete cleavage or degradation of the target RNA; do not activate the RNAse H pathway; do not activate RISC; do not recruit any Argonaute family protein; are not cleaved by Dicer; do not mediate alternative splicing; are not immune stimulatory; are nuclease resistant; have improved cell uptake compared to unmodified oligonucleotides; are not toxic to cells or mammals; may have improved endosomal exit; do interfere with interaction of lncRNA with PRC2, preferably the Ezh2 subunit but optionally the Suz12, Eed, RbAp46/48 subunits or accessory factors such as Jarid2; do decrease histone H3 lysine27 methylation and/or do upregulate gene expression.

Oligonucleotides that are designed to interact with RNA to modulate gene expression are a distinct subset of base sequences from those that are designed to bind a DNA target (e.g., are complementary to the underlying genomic DNA sequence from which the RNA is transcribed).

Splice Switching Oligonucleotides Aspects of the invention provide strategies for targeting SMN1 or SMN2 precursor mRNA to affect splicing to minimize exon skipping. Accordingly, aspects of the invention provide therapeutic compounds useful for the treatment of SMA. In some embodiments, oligonucleotides, referred to herein as "splice switching oligonucleotides" are provided that modulate SMN2 splicing. Methods and related compositions, compounds, and kits are provided, in some embodiments, that are useful for increasing expression of full-length. SMN protein in a cell. The methods generally involve delivering to a cell a first single stranded oligonucleotide complementary with at least 8 consecutive nucleotides of a PRC2-associated region of SMN2 and a second single stranded oligonucleotide complementary with a splice control sequence of a precursor mRNA of SMN2, in amounts sufficient to increase expression of a mature mRNA of SMN2 that comprises (or includes) exon 7 in the cell. Any of the single stranded oligonucleotides that are complementary with at least 8 consecutive nucleotides of a PRC2-associated region of SMN1 or SMN2 may be used. It should be appreciated that single stranded oligonucleotides that are complementary with a splice control sequence may alternatively be referred herein, as splice switching oligonucleotides.

Splice switching oligonucleotides typically comprise a sequence complementary to a splice control sequence (e.g., a intronic splicing silencer sequence) of a precursor mRNA, and are capable of binding to and affecting processing of the precursor mRNA. Splice switching oligonucleotides may be complementary with a region of an exon, a region of an intron or an intron/exon junction. In some embodiments, the splice control sequence comprises the sequence: CAG-CAUUAUGAAAG (SEQ ID NO: 13100) or a portion thereof. In some embodiments, the splice control sequence comprises at least one hnRNAP binding sequence. In some embodiments, splice switching oligonucleotides that target SMN1 or SMN2 function based on the premise that there is a competition between the 3' splice sites of exons 7 and 8 for pairing with the 5' splice site of exon 6, so impairing the recognition of the 3' splice site of exon 8 favors exon 7 inclusion. In some embodiments, splice switching oligonucleotides are provided that promote SMN2 exon 7 inclusion and full-length SMN protein expression, in which the oligonucleotides are complementary to the intron 7/exon 8 junction. In some embodiments, splice switching oligonucleotide are composed of a segment complementary to an exon of SMN1 or SMN2 (e.g., exon 7). In some embodiments, splice switching oligonucleotides comprise a tail (e.g., a non-complementary tail) consisting of RNA sequences with binding motifs recognized by a serine/arginine-rich (SR) protein. In some embodiments, splice switching oligonucleotides are complementary (at least partially) with an intronic splicing silencer (ISS). In some embodiments, the ISS is in intron 6 or intron 7 of SMN1 or SMN2. In some embodiments, splice switching oligonucleotides comprise an antisense moiety complementary to a target exon or intron (e.g., of SMN1 or SMN2) and a minimal RS domain peptide similar to the splicing activation domain of SR proteins. In some embodiments, the splice switching oligonucleotide is 7, 8, 9, 10, 11, 12, 13, 14, 15, 16, 17, 18, 19, 20, 21, 22, 23, 24, 25, 26, 27, 28, 29, 30, 35, 40, 45, 50 or more nucleotides in length. In one embodiment, the oligonucleotide is 8 to 30 nucleotides in length.

Linkers

Any of the oligonucleotides disclosed herein may be linked to one or more other oligonucleotides disclosed herein by a linker, e.g., a cleavable linker. Accordingly, in some embodiments, compounds are provided that comprise a single stranded oligonucleotide complementary with a PRC2-associated region of a gene that is linked via a linker to a single stranded oligonucleotide complementary to a splice control sequence of a precursor mRNA of the gene. In some embodiments, compounds are provided that have the general formula A-B-C, in which A is a single stranded oligonucleotide complementary with a PRC2-associated region of a gene, B is a linker, and C is a single stranded oligonucleotide complementary to a splice control sequence of a precursor mRNA of the gene. In some embodiments, linker B comprises an oligonucleotide, peptide, low pH labile bond, or disulfide bond. In some embodiments, the compounds is orientated as 5'-A-B-C-3'. In some embodiments, the compound is orientated as 3'-A-B-C-5'. In some embodiments, where B is an oligonucleotide, the 3' end of A is linked to the 5' end of B, and the 3' end of B is linked to 5' end of C. In some embodiments, where B is an oligonucleotide, the 5' end of A is linked to the 3' end of B, and the 5' end of B is linked to 3' end of C. In some embodiments, where B is an oligonucleotide, the 5' end of A is linked to the 5' end of B, and/or the 3' end of B is linked to the 3' end of C. In some embodiments, where B is an oligonucleotide, the 3' end of A is linked to the 3' end of B, and/or the 5' end of B is linked to the 5' end of C.

The term "linker" generally refers to a chemical moiety that is capable of covalently linking two or more oligonucleotides. In some embodiments, at least one bond comprised or contained within the linker is capable of being cleaved (e.g., in a biological context, such as in a mammalian extract, such as an endosomal extract), such that at least two oligonucleotides are no longer covalently linked to one another after bond cleavage. It will be appreciated that, in some embodiments, a provided linker may include a region that is non-cleavable, as long as the linker also comprises at least one bond that is cleavable.

In some embodiments, the linker comprises a polypeptide that is more susceptible to cleavage by an endopeptidase in the mammalian extract than the oligonucleotides. The endopeptidase may be a trypsin, chymotrypsin, elastase, thermolysin, pepsin, or endopeptidase V8. The endopeptidase may be a cathepsin B, cathepsin D, cathepsin L, cathepsin C, papain, cathepsin S or endosomal acidic insulinase. For example, the linker comprise a peptide having an amino acid sequence selected from: ALAL, APISFFELG, FL, GFN, R/KXX, GRWHTVGLRWE, YL, GF, and FF, in which X is any amino acid.

In some embodiments, the linker comprises the formula $-(CH_2)_n S-S(CH_2)_m-$, wherein n and m are independently integers from 0 to 10.

In some embodiments, the linker may comprise an oligonucleotide that is more susceptible to cleavage by an endonuclease in the mammalian extract than the oligonucleotides. The linker may have a nucleotide sequence comprising from 1 to 10 thymidines or uridines. The linker may have a nucleotide sequence comprising deoxyribonucleotides linked through phosphodiester internucleotide linkages. The linker may have a nucleotide sequence comprising from 1 to 10 thymidines or uridines linked through phosphodiester internucleotide linkages. The linker may have a nucleotide sequence comprising from 1 to 10 thymidines or uridines linked through phosphorothioate internucleotide linkages.

In some embodiments, at least one linker is 2-fold, 3-fold, 4-fold, 5-fold, 10-fold or more sensitive to enzymatic cleavage in the presence of a mammalian extract than at least two oligonucleotides. It should be appreciated that different linkers can be designed to be cleaved at different rates and/or by different enzymes in compounds comprising two or more linkers. Similarly different linkers can be designed to be sensitive to cleavage in different tissues, cells or subcellular compartments in compounds comprising two or more linkers. This can advantageously permit compounds to have oligonucleotides that are released from compounds at different rates, by different enzymes, or in different tissues, cells or subcellular compartments thereby controlling release of the monomeric oligonucleotides to a desired in vivo location or at a desired time following administration.

In certain embodiments, linkers are stable (e.g., more stable than the oligonucleotides they link together) in plasma, blood or serum which are richer in exonucleases, and less stable in the intracellular environments which are relatively rich in endonucleases. In some embodiments, a linker is considered "non-cleavable" if the linker's half-life is at least 24, or 28, 32, 36, 48, 72, 96 hours or longer under the conditions described here, such as in liver homogenates. Conversely, in some embodiments, a linker is considered "cleavable" if the half-life of the linker is at most 10, or 8, 6, 5 hours or shorter.

In some embodiments, the linker is a nuclease-cleavable oligonucleotide linker. In some embodiments, the nuclease-cleavable linker contains one or more phosphodiester bonds in the oligonucleotide backbone. For example, the linker may contain a single phosphodiester bridge or 2, 3, 4, 5, 6, 7 or more phosphodiester linkages, for example as a string of 1-10 deoxynucleotides, e.g., dT, or ribonucleotides, e.g., rU, in the case of RNA linkers. In the case of dT or other DNA nucleotides dN in the linker, in certain embodiments the cleavable linker contains one or more phosphodiester linkages. In other embodiments, in the case of rU or other RNA nucleotides rN, the cleavable linker may consist of phosphorothioate linkages only. In contrast to phosphorothioate-linked deoxynucleotides, which in some embodiments are cleaved relatively slowly by nucleases (thus termed "noncleavable"), phosphorothioate-linked rU undergoes relatively rapid cleavage by ribonucleases and therefore is considered cleavable herein in some embodiments. It is also possible to combine dN and rN into the linker region, which are connected by phosphodiester or phosphorothioate linkages. In other embodiments, the linker can also contain chemically modified nucleotides, which are still cleavable by nucleases, such as, e.g., 2'-O-modified analogs. In particular, 2'-O-methyl or 2'-fluoro nucleotides can be combined with each other or with dN or rN nucleotides. Generally, in the case of nucleotide linkers, the linker is a part of the compound that is usually not complementary to a target, although it could be. This is because the linker is generally cleaved prior to action of the oligonucleotides on the target, and therefore, the linker identity with respect to a target is inconsequential. Accordingly, in some embodiments, a linker is an (oligo)nucleotide linker that is not complementary to any of the targets against which the oligonucleotides are designed.

In some embodiments, the cleavable linker is an oligonucleotide linker that contains a continuous stretch of deliberately introduced Rp phosphorothioate stereoisomers (e.g., 4, 5, 6, 7 or longer stretches). The Rp stereoisoform, unlike Sp isoform, is known to be susceptible to nuclease cleavage (Krieg et al., 2003, Oligonucleotides, 13:491-499). Such a linker would not include a racemic mix of PS linked oligonucleotides since the mixed linkages are relatively stable and are not likely to contain long stretches of the Rp stereoisomers, and therefore, considered "non-cleavable" herein. Thus, in some embodiments, a linker comprises a stretch of 4, 5, 6, 7 or more phosphorothioated nucleotides, wherein the stretch does not contain a substantial amount or any of the Sp stereoisoform. The amount could be considered substantial if it exceeds 10% on a per-mole basis.

In some embodiments, the linker is a non-nucleotide linker, for example, a single phosphodiester bridge. Another example of such cleavable linkers is a chemical group comprising a disulfide bond, for example, $-(CH_2)_nS-S-(CH_2)_m-$, wherein n and m are integers from 0 to 10. In illustrative embodiments, n=m=6. Additional examples of non-nucleotide linkers are described below.

The linker can be designed so as to undergo a chemical or enzymatic cleavage reaction. Chemical reactions involve, for example, cleavage in acidic environments (e.g., endosomes), reductive cleavage (e.g., cytosolic cleavage) or oxidative cleavage (e.g., in liver microsomes). The cleavage reaction can also be initiated by a rearrangement reaction. Enzymatic reactions can include reactions mediated by nucleases, peptidases, proteases, phosphatases, oxidases, reductases, etc. For example, a linker can be pH-sensitive, cathepsin-sensitive, or predominantly cleaved in endosomes and/or cytosol.

In some embodiments, the linker comprises a peptide. In certain embodiments, the linker comprises a peptide which includes a sequence that is cleavable by an endopeptidase. In addition to the cleavable peptide sequence, the linker may comprise additional amino acid residues and/or non-peptide chemical moieties, such as an alkyl chain. In certain embodiments, the linker comprises Ala-Leu-Ala-Leu, which is a substrate for cathepsin B. See, for example, the maleimidocaproyl-Arg-Arg-Ala-Leu-Ala-Leu linkers described in Schmid et al, Bioconjugate Chem 2007, 18, 702-716. In certain embodiments, a cathepsin B-cleavable linker is cleaved in tumor cells. In certain embodiments, the linker comprises Ala-Pro-Ile-Ser-Phe-Phe-Glu-Leu-Gly, which is a substrate for cathepsins D, L, and B (see, for example, Fischer et al, Chembiochem 2006, 7, 1428-1434). In certain embodiments, a cathepsin-cleavable linker is cleaved in HeLa cells. In some embodiments, the linker comprises Phe-Lys, which is a substrate for cathepsin B. For example, in certain embodiments, the linker comprises Phe-Lys-p-aminobenzoic acid (PABA). See, e.g., the maleimidocaproyl-Phe-Lys-PABA linker described in Walker et al, Bioorg. Med. Chem. Lett. 2002, 12, 217-219. In certain embodiments, the linker comprises Gly-Phe-2-naphthylamide, which is a substrate for cathepsin C (see, for example, Berg et al. Biochem. J. 1994, 300, 229-235). In certain embodiments, a cathepsin C-cleavable linker is cleaved in hepatocytes. In some embodiments, the linker comprises a cathepsin S cleavage site. For example, in some embodiments, the linker comprises Gly-Arg-Trp-His-Thr-Val-Gly-Leu-Arg-Trp-Glu, Gly-Arg-Trp-Pro-Pro-Met-Gly-Leu-Pro-Trp-Glu, or Gly-Arg-Trp-His-Pro-Met-Gly-Ala-Pro-Trp-Glu, for example, as described in Lutzner et al, J. Biol. Chem. 2008, 283, 36185-36194. In certain embodiments, a cathepsin S-cleavable linker is cleaved in antigen presenting cells. In some embodiments, the linker comprises a papain cleavage site. Papain typically cleaves a peptide having the sequence -R/K-X-X (see Chapman et al, Annu. Rev. Physiol 1997, 59, 63-88). In certain embodiments, a papain-cleavable linker is cleaved in endosomes. In some embodiments, the linker comprises an endosomal acidic insulinase cleavage site. For example, in some embodiments, the linker comprises Tyr-Leu, Gly-Phe, or Phe-Phe (see, e.g., Authier et al, FEBS Lett. 1996, 389, 55-60). In certain embodiments, an endosomal acidic insulinase-cleavable linker is cleaved in hepatic cells.

In some embodiments, the linker is pH sensitive. In certain embodiments, the linker comprises a low pH-labile bond. As used herein, a low-pH labile bond is a bond that is selectively broken under acidic conditions (pH<7). Such bonds may also be termed endosomally labile bonds, because cell endosomes and lysosomes have a pH less than 7. For example, in certain embodiments, the linker comprises an amine, an imine, an ester, a benzoic imine, an amino ester, a diortho ester, a polyphosphoester, a polyphosphazene, an acetal, a vinyl ether, a hydrazone, an azidomethyl-methylmaleic anhydride, a thiopropionate, a masked endosomolytic agent or a citraconyl group.

In certain embodiments, the linker comprises a low pH-labile bond selected from the following: ketals that are labile in acidic environments (e.g., pH less than 7, greater than about 4) to form a diol and a ketone; acetals that are labile in acidic environments (e.g., pH less than 7, greater than about 4) to form a diol and an aldehyde; imines or iminiums that are labile in acidic environments (e.g., pH less than 7, greater than about 4) to form an amine and an aldehyde or a ketone; silicon-oxygen-carbon linkages that are labile under acidic condition; silicon-nitrogne (silazane) linkages; silicon-carbon linkages (e.g., arylsilanes, vinylsilanes, and allylsilanes); maleamates (amide bonds synthesized from maleic anhydride derivatives and amines); ortho esters; hydrazones; activated carboxylic acid derivatives (e.g., esters, amides) designed to undergo acid catalyzed hydrolysis); or vinyl ethers. Further examples may be found in International Patent Appln. Pub. No. WO 2008/022309, entitled POLYCONJUGATES FOR IN VIVO DELIVERY OF POLYNUCLEOTIDES, the contents of which are incorporated herein by reference.

In some embodiments, the linker comprises a masked endosomolytic agent. Endosomolytic polymers are polymers that, in response to a change in pH, are able to cause disruption or lysis of an endosome or provide for escape of a normally membrane-impermeable compound, such as a polynucleotide or protein, from a cellular internal membrane-enclosed vesicle, such as an endosome or lysosome. A subset of endosomolytic compounds is fusogenic compounds, including fusogenic peptides. Fusogenic peptides can facilitate endosomal release of agents such as oligomeric compounds to the cytoplasm. See, for example, US Patent Application Publication Nos. 20040198687, 20080281041, 20080152661, and 20090023890, which are incorporated herein by reference.

The linker can also be designed to undergo an organ/tissue-specific cleavage. For example, for certain targets, which are expressed in multiple tissues, only the knock-down in liver may be desirable, as knock-down in other organs may lead to undesired side effects. Thus, linkers susceptible to liver-specific enzymes, such as pyrrolase (TPO) and glucose-6-phosphatase (G-6-Pase), can be engineered, so as to limit the antisense effect to the liver mainly. Alternatively, linkers not susceptible to liver enzymes but susceptible to kidney-specific enzymes, such as gamma-glutamyltranspeptidase, can be engineered, so that the antisense effect is limited to the kidneys mainly. Analogously, intestine-specific peptidases cleaving Phe-Ala and Leu-Ala could be considered for orally administered multimeric oligonucleotides. Similarly, by placing an enzyme recognition site into the linker, which is recognized by an enzyme over-expressed in tumors, such as plasmin (e.g., PHEA-D-Val-Leu-Lys recognition site), tumor-specific knock-down should be feasible. By selecting the right enzyme recognition site in the linker, specific cleavage and knock-down should be achievable in many organs. In addition, the linker can also contain a targeting signal, such as N-acetyl galactosamine for liver targeting, or folate, vitamin A or RGD-peptide in the case of tumor or activated macrophage targeting. Accordingly, in some embodiments, the cleavable linker is organ- or tissue-specific, for example, liver-specific, kidney-specific, intestine-specific, etc.

The oligonucleotides can be linked through any part of the individual oligonucleotide, e.g., via the phosphate, the sugar (e.g., ribose, deoxyribose), or the nucleobase. In certain embodiments, when linking two oligonucleotides together, the linker can be attached e.g. to the 5'-end of the first oligonucleotide and the 3'-end of the second nucleotide, to the 5'-end of the first oligonucleotide and the 5'end of the second nucleotide, to the 3'-end of the first oligonucleotide and the 3'-end of the second nucleotide. In other embodiments, when linking two oligonucleotides together, the linker can attach internal residues of each oligonucleotides, e.g., via a modified nucleobase. One of ordinary skill in the art will understand that many such permutations are available for multimers. Further examples of appropriate linkers as well as methods for producing compounds having such linkers are disclosed in International Patent Application Number, PCT/US2012/05535, entitled MULTIMERIC OLIGONUCLEOTIDE COMPOUNDS the contents of which relating to linkers and related chemistries are incorporated herein by referenced in its entirety.

Methods for Selecting Candidate Oligonucleotides for Activating Expression of SMN1 or SMN2

Methods are provided herein for selecting a candidate oligonucleotide for activating or enhancing expression of SMN1 or SMN2. The target selection methods may generally involve steps for selecting single stranded oligonucleotides having any of the structural and functional characteristics disclosed herein. Typically, the methods involve one or more steps aimed at identifying oligonucleotides that target a PRC2-associated region that is functionally related to SMN1 or SMN2, for example a PRC2-associated region of a lncRNA that regulates expression of SMN1 or SMN2 by facilitating (e.g., in a cis-regulatory manner) the recruitment of PRC2 to the SMN1 or SMN2 gene. Such oligonucleotides are expected to be candidates for activating expression of SMN1 or SMN2 because of their ability to hybridize with the PRC2-associated region of a nucleic acid (e.g., a lncRNA). In some embodiments, this hybridization event is understood to disrupt interaction of PRC2 with the nucleic acid (e.g., a lncRNA) and as a result disrupt recruitment of PRC2 and its associated co-repressors (e.g., chromatin remodeling factors) to the SMN1 or SMN2 gene locus.

Methods of selecting a candidate oligonucleotide may involve selecting a PRC2-associated region (e.g., a nucleotide sequence as set forth in any one of SEQ ID NOS: 9 to 29) that maps to a chromosomal position encompassing or in proximity to the SMN1 or SMN2 gene (e.g., a chromosomal position having a sequence as set forth in any one of SEQ ID NOS: 1 to 8). The PRC2-associated region may map to the strand of the chromosome comprising the sense strand of the SMN1 or SMN2 gene, in which case the candidate oligonucleotide is complementary to the sense strand of the SMN1 or SMN2 gene (i.e., is antisense to the SMN1 or SMN2 gene). Alternatively, the PRC2-associated region may map to the strand of the first chromosome comprising the antisense strand of the SMN1 or SMN2 gene, in which case the oligonucleotide is complementary to the antisense strand (the template strand) of the SMN1 or SMN2 gene (i.e., is sense to the SMN1 or SMN2 gene).

Methods for selecting a set of candidate oligonucleotides that is enriched in oligonucleotides that activate expression of SMN1 or SMN2 may involve selecting one or more PRC2-associated regions that map to a chromosomal position that encompasses or that is in proximity to the SMN1 or SMN2 gene and selecting a set of oligonucleotides, in which each oligonucleotide in the set comprises a nucleotide sequence that is complementary with the one or more PRC2-associated regions. As used herein, the phrase, "a set of oligonucleotides that is enriched in oligonucleotides that activate expression of" refers to a set of oligonucleotides that has a greater number of oligonucleotides that activate expression of a target gene (e.g., SMN1 or SMN2) compared with a random selection of oligonucleotides of the same physicochemical properties (e.g., the same GC content, $T_m$, length etc.) as the enriched set.

Where the design and/or synthesis of a single stranded oligonucleotide involves design and/or synthesis of a sequence that is complementary to a nucleic acid or PRC2-associated region described by such sequence information, the skilled person is readily able to determine the complementary sequence, e.g., through understanding of Watson Crick base pairing rules which form part of the common general knowledge in the field.

In some embodiments design and/or synthesis of a single stranded oligonucleotide involves manufacture of an oligonucleotide from starting materials by techniques known to those of skill in the art, where the synthesis may be based on a sequence of a PRC2-associated region, or portion thereof.

Methods of design and/or synthesis of a single stranded oligonucleotide may involve one or more of the steps of: Identifying and/or selecting PRC2-associated region; Designing a nucleic acid sequence having a desired degree of sequence identity or complementarity to a PRC2-associated region or a portion thereof;
Synthesizing a single stranded oligonucleotide to the designed sequence;
Purifying the synthesized single stranded oligonucleotide; and
Optionally mixing the synthesized single stranded oligonucleotide with at least one pharmaceutically acceptable diluent, carrier or excipient to form a pharmaceutical composition or medicament.

Single stranded oligonucleotides so designed and/or synthesized may be useful in method of modulating gene expression as described herein.

Preferably, single stranded oligonucleotides of the invention are synthesized chemically. Oligonucleotides used to practice this invention can be synthesized in vitro by well-known chemical synthesis techniques.

Oligonucleotides of the invention can be stabilized against nucleolytic degradation such as by the incorporation of a modification, e.g., a nucleotide modification. For example, nucleic acid sequences of the invention include a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA).

As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom.

It is understood that any of the modified chemistries or formats of single stranded oligonucleotides described herein can be combined with each other, and that one, two, three, four, five, or more different types of modifications can be included within the same molecule.

In some embodiments, the method may further comprise the steps of amplifying the synthesized single stranded oligonucleotide, and/or purifying the single stranded oligonucleotide (or amplified single stranded oligonucleotide), and/or sequencing the single stranded oligonucleotide so obtained.

As such, the process of preparing a single stranded oligonucleotide may be a process that is for use in the manufacture of a pharmaceutical composition or medicament for use in the treatment of disease, optionally wherein the treatment involves modulating expression of a gene associated with a PRC2-associated region.

In the methods described above a PRC2-associated region may be, or have been, identified, or obtained, by a method that involves identifying RNA that binds to PRC2.

Such methods may involve the following steps: providing a sample containing nuclear ribonucleic acids, contacting the sample with an agent that binds specifically to PRC2 or a subunit thereof, allowing complexes to form between the agent and protein in the sample, partitioning the complexes, synthesizing nucleic acid that is complementary to nucleic acid present in the complexes.

Where the single stranded oligonucleotide is based on a PRC2-associated region, or a portion of such a sequence, it may be based on information about that sequence, e.g., sequence information available in written or electronic form, which may include sequence information contained in publicly available scientific publications or sequence databases.

Nucleotide Analogues

In some embodiments, the oligonucleotide may comprise at least one ribonucleotide, at least one deoxyribonucleotide, and/or at least one bridged nucleotide. In some embodiments, the oligonucleotide may comprise a bridged nucleotide, such as a locked nucleic acid (LNA) nucleotide, a constrained ethyl (cEt) nucleotide, or an ethylene bridged nucleic acid (ENA) nucleotide. Examples of such nucleotides are disclosed herein and known in the art. In some embodiments, the oligonucleotide comprises a nucleotide analog disclosed in one of the following United States patent or patent Application Publications: U.S. Pat. Nos. 7,399,845, 7,741,457, 8,022,193, 7,569,686, 7,335,765, 7,314,923, 7,335,765, and 7,816,333, US 20110009471, the entire contents of each of which are incorporated herein by reference for all purposes. The oligonucleotide may have one or more 2' O-methyl nucleotides. The oligonucleotide may consist entirely of 2' O-methyl nucleotides.

Often the single stranded oligonucleotide has one or more nucleotide analogues. For example, the single stranded oligonucleotide may have at least one nucleotide analogue that results in an increase in $T_m$ of the oligonucleotide in a range of P° C., 2° C., 3° C., 4° C., or 5° C. compared with an oligonucleotide that does not have the at least one nucleotide analogue. The single stranded oligonucleotide may have a plurality of nucleotide analogues that results in a total increase in $T_m$, of the oligonucleotide in a range of 2° C., 3° C., 4° C., 5° C., 6° C., 7° C., 8° C., 9° C., 10° C., 15° C., 20° C., 25° C., 30° C., 35° C., 40° C., 45° C. or more compared with an oligonucleotide that does not have the nucleotide analogue.

The oligonucleotide may be of up to 50 nucleotides in length in which 2 to 10, 2 to 15, 2 to 16, 2 to 17, 2 to 18, 2 to 19, 2 to 20, 2 to 25, 2 to 30, 2 to 40, 2 to 45, or more nucleotides of the oligonucleotide are nucleotide analogues. The oligonucleotide may be of 8 to 30 nucleotides in length in which 2 to 10, 2 to 15, 2 to 16, 2 to 17, 2 to 18, 2 to 19, 2 to 20, 2 to 25, 2 to 30 nucleotides of the oligonucleotide are nucleotide analogues.

The oligonucleotide may be of 8 to 15 nucleotides in length in which 2 to 4, 2 to 5, 2 to 6, 2 to 7, 2 to 8, 2 to 9, 2 to 10, 2 to 1, 2 to 12, 2 to 13, 2 to 14 nucleotides of the oligonucleotide are nucleotide analogues. Optionally, the oligonucleotides may have every nucleotide except 1, 2, 3, 4, 5, 6, 7, 8, 9, or 10 nucleotides modified.

The oligonucleotide may consist entirely of bridged nucleotides (e.g., LNA nucleotides, cEt nucleotides, ENA nucleotides). The oligonucleotide may comprise alternating deoxyribonucleotides and 2'-fluoro-deoxyribonucleotides. The oligonucleotide may comprise alternating deoxyribonucleotides and 2'-O-methyl nucleotides. The oligonucleotide may comprise alternating deoxyribonucleotides and ENA nucleotide analogues. The oligonucleotide may comprise alternating deoxyribonucleotides and LNA nucleotides. The oligonucleotide may comprise alternating LNA nucleotides and 2'-O-methyl nucleotides. The oligonucleotide may have a 5' nucleotide that is a bridged nucleotide (e.g., a LNA nucleotide, cEt nucleotide, ENA nucleotide). The oligonucleotide may have a 5' nucleotide that is a deoxyribonucleotide.

The oligonucleotide may comprise deoxyribonucleotides flanked by at least one bridged nucleotide (e.g., a LNA nucleotide, cEt nucleotide, ENA nucleotide) on each of the 5' and 3' ends of the deoxyribonucleotides. The oligonucleotide may comprise deoxyribonucleotides flanked by 1, 2, 3, 4, 5, 6, 7, 8 or more bridged nucleotides (e.g., LNA nucleotides, cEt nucleotides, ENA nucleotides) on each of the 5' and 3' ends of the deoxyribonucleotides. The 3' position of the oligonucleotide may have a 3' hydroxyl group. The 3' position of the oligonucleotide may have a 3' thiophosphate.

The oligonucleotide may be conjugated with a label. For example, the oligonucleotide may be conjugated with a biotin moiety, cholesterol, Vitamin A, folate, sigma receptor ligands, aptamers, peptides, such as CPP, hydrophobic molecules, such as lipids, ASGPR or dynamic polyconjugates and variants thereof at its 5' or 3' end.

Preferably the single stranded oligonucleotide comprises one or more modifications comprising: a modified sugar moiety, and/or a modified internucleoside linkage, and/or a modified nucleotide and/or combinations thereof. It is not necessary for all positions in a given oligonucleotide to be uniformly modified, and in fact more than one of the modifications described herein may be incorporated in a single oligonucleotide or even at within a single nucleoside within an oligonucleotide.

In some embodiments, the single stranded oligonucleotides are chimeric oligonucleotides that contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric single stranded oligonucleotides of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In some embodiments, the single stranded oligonucleotide comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than 2'-deoxyoligonucleotides against a given target.

A number of nucleotide and nucleoside modifications have been shown to make the oligonucleotide into which they are incorporated more resistant to nuclease digestion than the native oligodeoxynucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly $CH_2$—NH—O—$CH_2$, CH, ~N($CH_3$)~O~$CH_2$ (known as a methylene(methylimino) or MMI backbone, $CH_2$—O—N ($CH_3$)—$CH_2$, $CH_2$—N($CH_3$)—N($CH_3$)—$CH_2$ and O—N ($CH_3$)— $CH_2$—$CH_2$ backbones, wherein the native phosphodiester backbone is represented as O—P—O—$CH_,$); amide backbones (see De Mesmaeker et al. Ace. Chem. Res. 1995, 28:366-374); morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863;

4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050.

Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991. In some embodiments, the morpholino-based oligomeric compound is a phosphorodiamidate morpholino oligomer (PMO) (e.g., as described in Iverson, Curr. Opin. Mol. Ther., 3:235-238, 2001; and Wang et al., J. Gene Med., 12:354-364, 2010; the disclosures of which are incorporated herein by reference in their entireties).

Cyclohexenyl nucleic acid oligonucleotide mimetics are described in Wang et al., J. Am. Chem. Soc., 2000, 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

Modified oligonucleotides are also known that include oligonucleotides that are based on or constructed from arabinonucleotide or modified arabinonucleotide residues. Arabinonucleosides are stereoisomers of ribonucleosides, differing only in the configuration at the 2'-position of the sugar ring. In some embodiments, a 2'-arabino modification is 2'-F arabino. In some embodiments, the modified oligonucleotide is 2'-fluoro-D-arabinonucleic acid (FANA) (as described in, for example, Lon et al., Biochem., 41:3457-3467, 2002 and Min et al., Bioorg. Med. Chem. Lett., 12:2651-2654, 2002; the disclosures of which are incorporated herein by reference in their entireties). Similar modifications can also be made at other positions on the sugar, particularly the 3' position of the sugar on a 3' terminal nucleoside or in 2'-5' linked oligonucleotides and the 5' position of 5' terminal nucleotide. PCT Publication No. WO 99/67378 discloses arabinonucleic acids (ANA) oligomers and their analogues for improved sequence specific inhibition of gene expression via association to complementary messenger RNA.

Other preferred modifications include ethylene-bridged nucleic acids (ENAs) (e.g., International Patent Publication No. WO 2005/042777, Morita et al., Nucleic Acid Res., Suppl 1:241-242, 2001; Surono et al., Hum. Gene Ther., 15:749-757, 2004; Koizumi, Curr. Opin. Mol. Ther., 8:144-149, 2006 and Horie et al., Nucleic Acids Symp. Ser (Oxf), 49:171-172, 2005; the disclosures of which are incorporated herein by reference in their entireties). Preferred ENAs include, but are not limited to, 2'-O,4'-C-ethylene-bridged nucleic acids.

Examples of LNAs are described in WO/2008/043753 and include compounds of the following general formula.

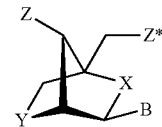

where X and Y are independently selected among the groups —O—,

—S—, —N(H)—, N(R)—, —CH$_2$— or —CH— (if part of a double bond),

—CH$_2$—O—, —CH$_2$—S—, —CH$_2$—N(H)—, —CH$_2$—N(R)—, —CH$_2$—CH$_2$— or —CH$_2$—CH— (if part of a double bond), —CH=CH—, where R is selected from hydrogen and C$_{1-4}$-alkyl; Z and Z* are independently selected among an internucleoside linkage, a terminal group or a protecting group; B constitutes a natural or non-natural nucleotide base moiety; and the asymmetric groups may be found in either orientation.

Preferably, the LNA used in the oligonucleotides described herein comprises at least one LNA unit according any of the formulas

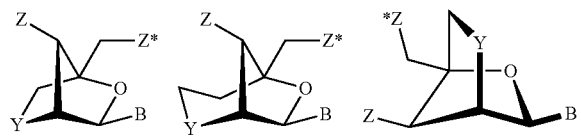

wherein Y is —O—, —S—, —NH—, or N(R$^H$); Z and Z* are independently selected among an internucleoside linkage, a terminal group or a protecting group; B constitutes a natural or non-natural nucleotide base moiety, and RH is selected from hydrogen and C$_{1-4}$-alkyl.

In some embodiments, the Locked Nucleic Acid (LNA) used in the oligonucleotides described herein comprises at least one Locked Nucleic Acid (LNA) unit according any of the formulas shown in Scheme 2 of PCT/DK2006/000512.

In some embodiments, the LNA used in the oligomer of the invention comprises internucleoside linkages selected from —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —S—P(O)$_2$—S—, —O—PO(R$^H$)—O—, O—PO (OCH$_3$)—O—, —O—PO(NR$^H$)—O—, —O—PO (OCH$_2$CH$_2$S—R)—O—, —O—PO(BH$_3$)—O—, —O—PO (NHR$^H$)—O—, —O—P(O)$_2$—NR$^H$—, —NR$^H$—P(O)$_2$—O—, —NR$^H$—CO—O—, where R$^H$ is selected from hydrogen and C$_{1-4}$-alkyl.

Specifically preferred LNA units are shown in scheme 2:

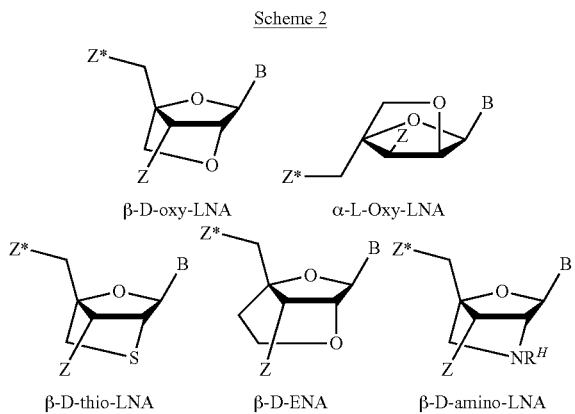

Scheme 2

The term "thio-LNA" comprises a locked nucleotide in which at least one of X or Y in the general formula above is selected from S or —CH$_2$—S—. Thio-LNA can be in both beta-D and alpha-L-configuration.

The term "amino-LNA" comprises a locked nucleotide in which at least one of X or Y in the general formula above is selected from —N(H)—, N(R)—, CH$_2$—N(H)—, and —CH$_2$—N(R)— where R is selected from hydrogen and C$_{1-4}$-alkyl. Amino-LNA can be in both beta-D and alpha-L-configuration.

The term "oxy-LNA" comprises a locked nucleotide in which at least one of X or Y in the general formula above represents —O— or —CH$_2$—O—. Oxy-LNA can be in both beta-D and alpha-L-configuration.

The term "ena-LNA" comprises a locked nucleotide in which Y in the general formula above is —CH$_2$—O— (where the oxygen atom of —CH$_2$—O— is attached to the 2'-position relative to the base B).

LNAs are described in additional detail herein.

One or more substituted sugar moieties can also be included, e.g., one of the following at the 2' position: OH, SH, SCH$_3$, F, OCN, OCH$_3$OCH$_3$, OCH$_3$O(CH$_2$)n CH$_3$, O(CH$_2$)n NH$_2$ or O(CH$_2$)n CH$_3$ where n is from 1 to about 10; C1 to C10 lower alkyl, alkoxyalkoxy, substituted lower alkyl, alkaryl or aralkyl; Cl; Br; CN; CF$_3$; OCF$_3$; O—, S—, or N-alkyl; O—, S—, or N-alkenyl; SOCH$_3$; SO$_2$CH$_3$; ONO$_2$; NO$_2$; N$_3$; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O—CH$_2$CH$_2$OCH$_3$, also known as 2'-O-(2-methoxyethyl)](Martin et al, Helv. Chim. Acta, 1995, 78, 486). Other preferred modifications include 2'-methoxy (2'-0-CH$_3$), 2'-propoxy (2'-OCH$_2$CH$_2$CH$_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Single stranded oligonucleotides can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, isocytosine, pseudoisocytosine, as well as synthetic nucleobases, e.g., 2-aminoadenine, 2-(methylamino)adenine, 2-(imidazolylalkyl)adenine, 2-(aminoalkylamino)adenine or other heterosubstituted alkyladenines, 2-thiouracil, 2-thiothymine, 5-bromouracil, 5-hydroxymethyluracil, 5-propynyluracil, 8-azaguanine, 7-deazaguanine, N6 (6-aminohexyl)adenine, 6-aminopurine, 2-aminopurine, 2-chloro-6-aminopurine and 2,6-diaminopurine or other diaminopurines. See, e.g., Kornberg, "DNA Replication," W. H. Freeman & Co., San Francisco, 1980, pp 75-77; and Gebeyehu, G., et al. Nucl. Acids Res., 15:4513 (1987)). A "universal" base known in the art, e.g., inosine, can also be included. 5-Me-C substitutions have been shown to increase nucleic acid duplex stability by 0.6-1.2° C. (Sanghvi, in Crooke, and Lebleu, eds., Antisense Research and Applications, CRC Press, Boca Raton, 1993, pp. 276-278) and may be used as base substitutions.

It is not necessary for all positions in a given oligonucleotide to be uniformly modified, and in fact more than one of the modifications described herein may be incorporated in a single oligonucleotide or even at within a single nucleoside within an oligonucleotide.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al, Science, 1991, 254, 1497-1500.

Single stranded oligonucleotides can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in "The Concise Encyclopedia of Polymer Science And Engineering", pages 858-859, Kroschwitz, ed. John Wiley & Sons, 1990; those disclosed by Englisch et al., Angewandle Chemie, International Edition, 1991, 30, page 613, and those disclosed by Sanghvi. Chapter 15, Antisense Research and Applications," pages 289-302, Crooke, and Lebleu, eds., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2<0>C (Sanghvi. et al., eds, "Antisense Research and Applications," CRC Press, Boca Raton, 1993, pp. 276-278) and are presently preferred base substitutions, even more particularly when combined with 2'-O-methoxyethyl sugar modifications. Modified to nucleobases are described in U.S. Pat. No. 3,687,808, as well as U.S. Pat. Nos. 4,845,205; 5,130,302; 5,134,066; 5,175, 273; 5, 367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

In some embodiments, the single stranded oligonucleotides are chemically linked to one or more moieties or conjugates that enhance the activity, cellular distribution, or cellular uptake of the oligonucleotide. For example, one or more single stranded oligonucleotides, of the same or different types, can be conjugated to each other; or single stranded oligonucleotides can be conjugated to targeting moieties with enhanced specificity for a cell type or tissue type. Such moieties include, but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al, Ann. N. Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-t oxycholesterol moiety (Crooke et al., J. Pharmacol. Exp. Ther., 1996, 277, 923-937). See also U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

In some embodiments, single stranded oligonucleotide modification include modification of the 5' or 3' end of the oligonucleotide. In some embodiments, the 3' end of the oligonucleotide comprises a hydroxyl group or a thiophosphate. It should be appreciated that additional molecules (e.g. a biotin moiety or a fluorophor) can be conjugated to the 5' or 3' end of the single stranded oligonucleotide. In some embodiments, the single stranded oligonucleotide comprises a biotin moiety conjugated to the 5' nucleotide.

In some embodiments, the single stranded oligonucleotide comprises locked nucleic acids (LNA), ENA modified nucleotides, 2'-O-methyl nucleotides, or 2'-fluoro-deoxyribonucleotides. In some embodiments, the single stranded oligonucleotide comprises alternating deoxyribonucleotides and 2'-fluoro-deoxyribonucleotides. In some embodiments, the single stranded oligonucleotide comprises alternating deoxyribonucleotides and 2'-O-methyl nucleotides. In some embodiments, the single stranded oligonucleotide comprises alternating deoxyribonucleotides and ENA modified nucleotides. In some embodiments, the single stranded oligonucleotide comprises alternating deoxyribonucleotides and locked nucleic acid nucleotides. In some embodiments, the single stranded oligonucleotide comprises alternating locked nucleic acid nucleotides and 2'-O-methyl nucleotides.

In some embodiments, the 5' nucleotide of the oligonucleotide is a deoxyribonucleotide. In some embodiments, the 5' nucleotide of the oligonucleotide is a locked nucleic acid nucleotide. In some embodiments, the nucleotides of the oligonucleotide comprise deoxyribonucleotides flanked by at least one locked nucleic acid nucleotide on each of the 5' and 3' ends of the deoxyribonucleotides. In some embodiments, the nucleotide at the 3' position of the oligonucleotide has a 3' hydroxyl group or a 3' thiophosphate.

In some embodiments, the single stranded oligonucleotide comprises phosphorothioate internucleotide linkages. In some embodiments, the single stranded oligonucleotide comprises phosphorothioate internucleotide linkages between at least two nucleotides. In some embodiments, the single stranded oligonucleotide comprises phosphorothioate internucleotide linkages between all nucleotides.

It should be appreciated that the single stranded oligonucleotide can have any combination of modifications as described herein.

The oligonucleotide may comprise a nucleotide sequence having one or more of the following modification patterns.

(a) (X)Xxxxxx, (X)xXxxxx, (X)xxXxxx, (X)xxxXxx, (X)xxxxXx and (X)xxxxxX, (b) (X)XXxxxx, (X)XxXxxx, (X)XxxXxx, (X)XxxxXx, (X)XxxxxX, (X)xXXxxx, (X)xXxXxx, (X)xXxxXx, (X)xXxxxX, (X)xxXXxx, (X)xxXxXx, (X)xxXxxX, (X)xxxXXx, (X)xxxXxX and (X)xxxxXX, (c) (X)XXXxxx, (X)xXXXxx, (X)xxXXXx, (X)xxxXXX, (X)XXxXxx, (X)XXxxXx, (X)XXxxxX, (X)xXXxXx, (X)xXXxxX, (X)xxXXxX, (X)XxXXxx, (X)XxxXXx, (X)XxxxXX, (X)XxXxXx (X)XxxxXX, (X)xXxXxX, (X)xXxxXX, (X)xxXxXX, (X)xXxXxX and (X)XxXxXx, (d) (X)xxXXX, (X)xXxXXX, (X)xXXxXX, (X)xXXXxX, (X)xXXXXx, (X)XxxXXXX, (X)XxXxXX, (X)XxXXxX, (X)XxXXXx, (X)XXxxXX, (X)XXxXxX, (X)XXxXXx, (X)XXXxxX, (X)XXXxXx, and (X)XXXXxx, (e) (X)xXXXXX, (X)XxXXXX, (X)XXxXXX, (X)XXXxXX, (X)XXXXxX and (X)XXXXXx, and (f) XXXXXX, XxXXXXX, XXxXXXX, XXXxXXX, XXXXxXX, XXXXXxX and XXXXXXx, in which "X" denotes a nucleotide analogue, (X) denotes an optional nucleotide analogue, and "x" denotes a DNA or RNA nucleotide unit. Each of the above listed patterns may appear one or more times within an oligonucleotide, alone or in combination with any of the other disclosed modification patterns.

Methods for Modulating Gene Expression

In some embodiments, methods are provided for increasing expression of SMN protein in a cell. The methods, in some embodiments, involve delivering to the cell a first single stranded oligonucleotide complementary with a PRC2-associated region of SMN1 or SMN2 and a second single stranded oligonucleotide complementary with a splice control sequence of a precursor mRNA of SMN1 or SMN2, in amounts sufficient to increase expression of a mature mRNA of SMN1 or SMN2 that comprises (or includes) exon 7 in the cell. The first and second single stranded oligonucleotides may be delivered together or separately. The first and second single stranded oligonucleotides may be linked together, or unlinked, i.e., separate.

In some embodiments, methods are provided for treating spinal muscular atrophy in a subject. The methods, in some embodiments, involve administering to a subject a first single stranded oligonucleotide complementary with a PRC2-associated region of SMN1 or SMN2 and a second single stranded oligonucleotide complementary with a splice control sequence of a precursor mRNA of SMN1 or SMN2, in amounts sufficient to increase expression of full length SMN protein in the subject to levels sufficient to improve one or more conditions associated with SMA. The first and second single stranded oligonucleotides may be administered together or separately. The first and second single stranded oligonucleotides may be linked together, or unlinked, i.e., separate. The first single stranded oligonucleotide may be administered within 1 hour, 2 hours, 3 hours, 4 hours, 8 hours, 12 hours, 24 hours, 48 hours or more of administration of the second single stranded oligonucleotide. The first single stranded oligonucleotide may be administered before or after the second single stranded oligonucleotide. The oligonucleotides may be administered once or on multiple occasions depending on the needs of the subject and/or judgment of the treating physician. In some cases, the oligonucleotides may be administered in cycles. The administration cycles may vary; for example, the administration cycle may be $2^{nd}$ oligo-$1^{st}$ oligo-$2^{nd}$ oligo-$1^{st}$ oligo and so on; or $1^{st}$ oligo-$2^{nd}$ oligo-$1^{st}$ oligo-$2^{nd}$ oligo, and so on; or $1^{st}$ oligo-$2^{nd}$ oligo-$2^{nd}$ oligo-$1^{st}$ oligo-$1^{st}$ oligo-$2^{nd}$ oligo-$2^{nd}$ oligo-$1^{st}$ oligo, and so on. The skilled artisan will be capable of selecting administration cycles and intervals between each administration that are appropriate for treating a particular subject.

In one aspect, the invention relates to methods for modulating gene expression in a cell (e.g., a cell for which SMN1 or SMN2 levels are reduced) for research purposes (e.g., to study the function of the gene in the cell). In another aspect, the invention relates to methods for modulating gene expression in a cell (e.g., a cell for which SMN1 or SMN2 levels are reduced) for gene or epigenetic therapy. The cells can be in vitro, ex vivo, or in vivo (e.g., in a subject who has a disease resulting from reduced expression or activity of SMN1 or SMN2. In some embodiments, methods for modulating gene expression in a cell comprise delivering a single stranded oligonucleotide as described herein. In some embodiments, delivery of the single stranded oligonucleotide to the cell results in a level of expression of gene that is at least 5%, 10%, 20%, 30%, 40%, 50%, 60%, 70%, 80%, 90%, 100%, 200% or more greater than a level of expression of gene in a control cell to which the single stranded oligonucleotide has not been delivered. In certain embodiments, delivery of the single stranded oligonucleotide to the cell results in a level of expression of gene that is at least 50% greater than a level of expression of gene in a control cell to which the single stranded oligonucleotide has not been delivered.

In another aspect of the invention, methods comprise administering to a subject (e.g. a human) a composition comprising a single stranded oligonucleotide as described herein to increase protein levels in the subject. In some embodiments, the increase in protein levels is at least 5%, 10%, 20%, 30%, 40%, 50%, 60%, 70%, 80%, 90%, 100%, 200%, or more, higher than the amount of a protein in the subject before administering.

As another example, to increase expression of SMN1 or SMN2 in a cell, the methods include introducing into the cell a single stranded oligonucleotide that is sufficiently complementary to a PRC2-associated region (e.g., of a long non-coding RNA) that maps to a genomic position encompassing or in proximity to the SMN1 or SMN2 gene.

In another aspect of the invention provides methods of treating a condition (e.g., Spinal muscular atrophy) associated with decreased levels of expression of SMN1 or SMN2 in a subject, the method comprising administering a single stranded oligonucleotide as described herein.

A subject can include a non-human mammal, e.g. mouse, rat, guinea pig, rabbit, cat, dog, goat, cow, or horse. In preferred embodiments, a subject is a human. Single stranded oligonucleotides have been employed as therapeutic moieties in the treatment of disease states in animals, including humans. Single stranded oligonucleotides can be useful therapeutic modalities that can be configured to be useful in treatment regimes for the treatment of cells, tissues and animals, especially humans.

For therapeutics, an animal, preferably a human, suspected of having Spinal muscular atrophy is treated by administering single stranded oligonucleotide in accordance with this invention. For example, in one non-limiting embodiment, the methods comprise the step of administering to the animal in need of treatment, a therapeutically effective amount of a single stranded oligonucleotide as described herein.

Formulation, Delivery, and Dosing

The oligonucleotides described herein can be formulated for administration to a subject for treating a condition (e.g., Spinal muscular atrophy) associated with decreased levels of SMN protein. It should be understood that the formulations, compositions and methods can be practiced with any of the oligonucleotides disclosed herein. In some embodiments, formulations are provided that comprise a first single stranded oligonucleotide complementary with a PRC2-associated region of a gene and a second single stranded oligonucleotide complementary to a splice control sequence of a precursor mRNA of the gene. In some embodiments, formulations are provided that comprise a first single stranded oligonucleotide complementary with a PRC2-associated region of a gene that is linked via a linker with a second single stranded oligonucleotide complementary to a splice control sequence of a precursor mRNA of the gene. Thus, it should be appreciated that in some embodiments, a first single stranded oligonucleotide complementary with a PRC2-associated region of a gene is linked with a second single stranded oligonucleotide complementary to a splice control sequence of a precursor mRNA of the gene, and in other embodiments, the single stranded oligonucleotides are not linked. Single stranded oligonucleotides that are not linked may be administered to a subject or delivered to a cell simultaneously (e.g., within the same composition) or separately.

The formulations may conveniently be presented in unit dosage form and may be prepared by any methods well known in the art of pharmacy. The amount of active ingredient (e.g., an oligonucleotide or compound of the invention) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect, e.g. tumor regression.

Pharmaceutical formulations of this invention can be prepared according to any method known to the art for the manufacture of pharmaceuticals. Such formulations can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

A formulated single stranded oligonucleotide composition can assume a variety of states. In some examples, the composition is at least partially crystalline, uniformly crystalline, and/or anhydrous (e.g., less than 80, 50, 30, 20, or 10% water). In another example, the single stranded oligonucleotide is in an aqueous phase, e.g., in a solution that includes water. The aqueous phase or the crystalline compositions can, e.g., be incorporated into a delivery vehicle, e.g., a liposome (particularly for the aqueous phase) or a particle (e.g., a microparticle as can be appropriate for a crystalline composition). Generally, the single stranded oligonucleotide composition is formulated in a manner that is compatible with the intended method of administration.

In some embodiments, the composition is prepared by at least one of the following methods: spray drying, lyophilization, vacuum drying, evaporation, fluid bed drying, or a combination of these techniques; or sonication with a lipid, freeze-drying, condensation and other self-assembly.

A single stranded oligonucleotide preparation can be formulated or administered (together or separately) in combination with another agent, e.g., another therapeutic agent or an agent that stabilizes a single stranded oligonucleotide, e.g., a protein that complexes with single stranded oligonucleotide. Still other agents include chelators, e.g., EDTA (e.g., to remove divalent cations such as $Mg^{2+}$), salts, RNAse inhibitors (e.g., a broad specificity RNAse inhibitor such as RNAsin) and so forth. In some embodiments, the other agent used in combination with the single stranded oligonucleotide is an agent that also regulates SMN expression. In some embodiments, the other agent is a growth hormone, a histone deacetylase inhibitor, a hydroxycarbamide (hydroxyurea), a natural polyphenol compound (e.g., resveratrol, curcumin), prolactin, or salbutamol. Examples of histone deacetylase inhibitors that may be used include aliphatic compounds (e.g., butyrates (e.g., sodium butyrate and sodium phenylbutyrate) and valproic acid), benzamides (e.g., M344), and hydroxamic acids (e.g., CBHA, SBHA, Entinostat (MS-275)) Panobinostat (LBH-589), Trichostatin A, Vorinostat (SAHA)), In one embodiment, the single stranded oligonucleotide preparation includes another single stranded oligonucleotide, e.g., a second single stranded oligonucleotide that modulates expression and/or mRNA processing of a second gene or a second single stranded oligonucleotide that modulates expression of the first gene. Still other preparation can include at least 3, 5, ten, twenty, fifty, or a hundred or more different single stranded oligonucleotide species. Such single stranded oligonucleotides can mediated gene expression with respect to a similar number of different genes. In one embodiment, the single stranded oligonucleotide preparation includes at least a second therapeutic agent (e.g., an agent other than an oligonucleotide).

Route of Delivery

A composition that includes a single stranded oligonucleotide can be delivered to a subject by a variety of routes. Exemplary routes include: intravenous, intradermal, topical, rectal, parenteral, anal, intravaginal, intranasal, pulmonary, ocular. The term "therapeutically effective amount" is the amount of oligonucleotide present in the composition that is needed to provide the desired level of SMN1 or SMN2 expression in the subject to be treated to give the anticipated physiological response. The term "physiologically effective amount" is that amount delivered to a subject to give the desired palliative or curative effect. The term "pharmaceutically acceptable carrier" means that the carrier can be administered to a subject with no significant adverse toxicological effects to the subject.

The single stranded oligonucleotide molecules of the invention can be incorporated into pharmaceutical compositions suitable for administration. Such compositions typically include one or more species of single stranded oligonucleotide and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

The route and site of administration may be chosen to enhance targeting. For example, to target muscle cells, intramuscular injection into the muscles of interest would be a logical choice. Lung cells might be targeted by administering the single stranded oligonucleotide in aerosol form. The vascular endothelial cells could be targeted by coating a balloon catheter with the single stranded oligonucleotide and mechanically introducing the oligonucleotide.

Topical administration refers to the delivery to a subject by contacting the formulation directly to a surface of the subject. The most common form of topical delivery is to the skin, but a composition disclosed herein can also be directly applied to other surfaces of the body, e.g., to the eye, a mucous membrane, to surfaces of a body cavity or to an internal surface. As mentioned above, the most common topical delivery is to the skin. The term encompasses several routes of administration including, but not limited to, topical and transdermal. These modes of administration typically include penetration of the skin's permeability barrier and efficient delivery to the target tissue or stratum. Topical administration can be used as a means to penetrate the epidermis and dermis and ultimately achieve systemic delivery of the composition. Topical administration can also be used as a means to selectively deliver oligonucleotides to the epidermis or dermis of a subject, or to specific strata thereof, or to an underlying tissue.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Transdermal delivery is a valuable route for the administration of lipid soluble therapeutics. The dermis is more permeable than the epidermis and therefore absorption is much more rapid through abraded, burned or denuded skin. Inflammation and other physiologic conditions that increase blood flow to the skin also enhance transdermal adsorption. Absorption via this route may be enhanced by the use of an oily vehicle (inunction) or through the use of one or more penetration enhancers. Other effective ways to deliver a composition disclosed herein via the transdermal route include hydration of the skin and the use of controlled release topical patches. The transdermal route provides a potentially effective means to deliver a composition disclosed herein for systemic and/or local therapy. In addition, iontophoresis (transfer of ionic solutes through biological membranes under the influence of an electric field), phonophoresis or sonophoresis (use of ultrasound to enhance the absorption of various therapeutic agents across biological membranes, notably the skin and the cornea), and optimization of vehicle characteristics relative to dose position and retention at the site of administration may be useful methods for enhancing the transport of topically applied compositions across skin and mucosal sites.

Both the oral and nasal membranes offer advantages over other routes of administration. For example, oligonucleotides administered through these membranes may have a rapid onset of action, provide therapeutic plasma levels, avoid first pass effect of hepatic metabolism, and avoid exposure of the oligonucleotides to the hostile gastrointestinal (GI) environment. Additional advantages include easy access to the membrane sites so that the oligonucleotide can be applied, localized and removed easily.

In oral delivery, compositions can be targeted to a surface of the oral cavity, e.g., to sublingual mucosa which includes the membrane of ventral surface of the tongue and the floor of the mouth or the buccal mucosa which constitutes the lining of the cheek. The sublingual mucosa is relatively permeable thus giving rapid absorption and acceptable bioavailability of many agents. Further, the sublingual mucosa is convenient, acceptable and easily accessible.

A pharmaceutical composition of single stranded oligonucleotide may also be administered to the buccal cavity of a human being by spraying into the cavity, without inhalation, from a metered dose spray dispenser, a mixed micellar pharmaceutical formulation as described above and a propellant. In one embodiment, the dispenser is first shaken prior to spraying the pharmaceutical formulation and propellant into the buccal cavity.

Compositions for oral administration include powders or granules, suspensions or solutions in water, syrups, slurries, emulsions, elixirs or non-aqueous media, tablets, capsules, lozenges, or troches. In the case of tablets, carriers that can be used include lactose, sodium citrate and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, the nucleic acid compositions can be combined with emulsifying and suspending agents. If desired, certain sweetening and/or flavoring agents can be added.

Parenteral administration includes intravenous drip, subcutaneous, intraperitoneal or intramuscular injection, intrathecal or intraventricular administration. In some embodiments, parental administration involves administration directly to the site of disease (e.g. injection into a tumor).

Formulations for parenteral administration may include sterile aqueous solutions which may also contain buffers, diluents and other suitable additives. Intraventricular injection may be facilitated by an intraventricular catheter, for example, attached to a reservoir. For intravenous use, the total concentration of solutes should be controlled to render the preparation isotonic.

Any of the single stranded oligonucleotides described herein can be administered to ocular tissue. For example, the compositions can be applied to the surface of the eye or nearby tissue, e.g., the inside of the eyelid. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers. The single stranded oligonucleotide can also be administered to the interior of the eye, and can be introduced by a needle or other delivery device which can introduce it to a selected area or structure.

Pulmonary delivery compositions can be delivered by inhalation by the patient of a dispersion so that the composition, preferably single stranded oligonucleotides, within the dispersion can reach the lung where it can be readily absorbed through the alveolar region directly into blood circulation. Pulmonary delivery can be effective both for systemic delivery and for localized delivery to treat diseases of the lungs.

Pulmonary delivery can be achieved by different approaches, including the use of nebulized, aerosolized, micellular and dry powder-based formulations. Delivery can be achieved with liquid nebulizers, aerosol-based inhalers, and dry powder dispersion devices. Metered-dose devices are preferred. One of the benefits of using an atomizer or inhaler is that the potential for contamination is minimized because the devices are self-contained. Dry powder dispersion devices, for example, deliver agents that may be readily formulated as dry powders. A single stranded oligonucleotide composition may be stably stored as lyophilized or spray-dried powders by itself or in combination with suitable powder carriers. The delivery of a composition for inhalation can be mediated by a dosing timing element which can include a timer, a dose counter, time measuring device, or a time indicator which when incorporated into the device enables dose tracking, compliance monitoring, and/or dose triggering to a patient during administration of the aerosol medicament.

The term "powder" means a composition that consists of finely dispersed solid particles that are free flowing and capable of being readily dispersed in an inhalation device and subsequently inhaled by a subject so that the particles reach the lungs to permit penetration into the alveoli. Thus, the powder is said to be "respirable." Preferably the average particle size is less than about 10 µm in diameter preferably with a relatively uniform spheroidal shape distribution. More preferably the diameter is less than about 7.5 µm and most preferably less than about 5.0 µm. Usually the particle size distribution is between about 0.1 µm and about 5 µm in diameter, particularly about 0.3 µm to about 5 µm.

The term "dry" means that the composition has a moisture content below about 10% by weight (% w) water, usually below about 5% w and preferably less it than about 3% w. A dry composition can be such that the particles are readily dispersible in an inhalation device to form an aerosol.

The types of pharmaceutical excipients that are useful as carrier include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Suitable pH adjusters or buffers include organic salts prepared from organic acids and bases, such as sodium citrate, sodium ascorbate, and the like; sodium citrate is preferred. Pulmonary administration of a micellar single stranded oligonucleotide formulation may be achieved through metered dose spray devices with propellants such as tetrafluoroethane, heptafluoroethane, dimethylfluoropropane, tetrafluoropropane, butane, isobutane, dimethyl ether and other non-CFC and CFC propellants.

Exemplary devices include devices which are introduced into the vasculature, e.g., devices inserted into the lumen of a vascular tissue, or which devices themselves form a part of the vasculature, including stents, catheters, heart valves, and other vascular devices. These devices, e.g., catheters or stents, can be placed in the vasculature of the lung, heart, or leg.

Other devices include non-vascular devices, e.g., devices implanted in the peritoneum, or in organ or glandular tissue, e.g., artificial organs. The device can release a therapeutic substance in addition to a single stranded oligonucleotide, e.g., a device can release insulin.

In one embodiment, unit doses or measured doses of a composition that includes single stranded oligonucleotide are dispensed by an implanted device. The device can include a sensor that monitors a parameter within a subject. For example, the device can include pump, e.g., and, optionally, associated electronics.

Tissue, e.g., cells or organs can be treated with a single stranded oligonucleotide, ex vivo and then administered or implanted in a subject. The tissue can be autologous, allogeneic, or xenogeneic tissue. E.g., tissue can be treated to reduce graft v. host disease. In other embodiments, the tissue is allogeneic and the tissue is treated to treat a disorder characterized by unwanted gene expression in that tissue. E.g., tissue, e.g., hematopoietic cells, e.g., bone marrow hematopoietic cells, can be treated to inhibit unwanted cell proliferation. Introduction of treated tissue, whether autologous or transplant, can be combined with other therapies. In some implementations, the single stranded oligonucleotide treated cells are insulated from other cells, e.g., by a semipermeable porous barrier that prevents the cells from leaving the implant, but enables molecules from the body to reach the cells and molecules produced by the cells to enter the body. In one embodiment, the porous barrier is formed from alginate.

In one embodiment, a contraceptive device is coated with or contains a single stranded oligonucleotide. Exemplary devices include condoms, diaphragms, IUD (implantable uterine devices, sponges, vaginal sheaths, and birth control devices.

Dosage

In one aspect, the invention features a method of administering a single stranded oligonucleotide (e.g., as a compound or as a component of a composition) to a subject (e.g., a human subject). In some embodiments, the methods involve administering a compound (e.g., a compound of the general formula A-B-C, as disclosed herein, or an single stranded oligonucleotide,) in a unit dose to a subject. In one embodiment, the unit dose is between about 10 mg and 25 mg per kg of bodyweight. In one embodiment, the unit dose is between about 1 mg and 100 mg per kg of bodyweight. In one embodiment, the unit dose is between about 0.1 mg and 500 mg per kg of bodyweight. In some embodiments, the unit dose is more than 0.001, 0.005, 0.01, 0.05, 0.1, 0.5, 1, 2, 5, 10, 25, 50 or 100 mg per kg of bodyweight.

The defined amount can be an amount effective to treat or prevent a disease or disorder, e.g., a disease or disorder associated with the SMN1 or SMN2. The unit dose, for example, can be administered by injection (e.g., intravenous or intramuscular), an inhaled dose, or a topical application.

In some embodiments, the unit dose is administered daily. In some embodiments, less frequently than once a day, e.g., less than every 2, 4, 8 or 30 days. In another embodiment, the unit dose is not administered with a frequency (e.g., not a regular frequency). For example, the unit dose may be administered a single time. In some embodiments, the unit dose is administered more than once a day, e.g., once an hour, two hours, four hours, eight hours, twelve hours, etc.

In one embodiment, a subject is administered an initial dose and one or more maintenance doses of a single stranded oligonucleotide. The maintenance dose or doses are generally lower than the initial dose, e.g., one-half less of the initial dose. A maintenance regimen can include treating the subject with a dose or doses ranging from 0.0001 to 100 mg/kg of body weight per day, e.g., 100, 10, 1, 0.1, 0.01, 0.001, or 0.0001 mg per kg of bodyweight per day. The maintenance doses may be administered no more than once every 1, 5, 10, or 30 days. Further, the treatment regimen may last for a period of time which will vary depending upon the nature of the particular disease, its severity and the overall condition of the patient. In some embodiments the dosage may be delivered no more than once per day, e.g., no more than once per 24, 36, 48, or more hours, e.g., no more than once for every 5 or 8 days. Following treatment, the patient can be monitored for changes in his condition and for alleviation of the symptoms of the disease state. The dosage of the oligonucleotide may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable.

In some embodiments, the pharmaceutical composition includes a plurality of single stranded oligonucleotide species. In some embodiments, the pharmaceutical composition comprises a first single stranded oligonucleotide complementary with a PRC2-associated region of a gene (e.g., SMN1 or SMN2), and a second single stranded oligonucleotide complementary to a splice control sequence of a precursor mRNA of a gene (e.g., SMN1 or SMN2). In some embodiments, the pharmaceutical composition includes a compound comprising the general formula A-B-C, in which A is a single stranded oligonucleotide complementary with a PRC2-associated region of a gene, B is a linker, and C is a single stranded oligonucleotide complementary to a splice control sequence of a precursor mRNA of the gene.

In another embodiment, the single stranded oligonucleotide species has sequences that are non-overlapping and non-adjacent to another species with respect to a naturally occurring target sequence (e.g., a PRC2-associated region). In another embodiment, the plurality of single stranded oligonucleotide species is specific for different PRC2-associated regions. In another embodiment, the single stranded oligonucleotide is allele specific. In some cases, a patient is treated with a single stranded oligonucleotide in conjunction with other therapeutic modalities.

Following successful treatment, it may be desirable to have the patient undergo maintenance therapy to prevent the recurrence of the disease state, wherein the compound of the invention is administered in maintenance doses, ranging from 0.0001 mg to 100 mg per kg of body weight.

The concentration of the single stranded oligonucleotide composition is an amount sufficient to be effective in treating or preventing a disorder or to regulate a physiological condition in humans. The concentration or amount of single stranded oligonucleotide administered will depend on the parameters determined for the agent and the method of administration, e.g. nasal, buccal, pulmonary. For example, nasal formulations may tend to require much lower concentrations of some ingredients in order to avoid irritation or burning of the nasal passages. It is sometimes desirable to dilute an oral formulation up to 10-100 times in order to provide a suitable nasal formulation.

Certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a single stranded oligonucleotide can include a single treatment or, preferably, can include a series of treatments. It will also be appreciated that the effective dosage of a single stranded oligonucleotide used for treatment may increase or decrease over the course of a particular treatment. For example, the subject can be monitored after administering a single stranded oligonucleotide composition. Based on information from the monitoring, an additional amount of the single stranded oligonucleotide composition can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of SMN1 or SMN2 expression levels in the body of the patient. Persons of ordinary skill can easily determine optimum dosages, dosing methodologies and repetition rates. Optimum dosages may vary depending on the relative potency of individual compounds, and can generally be estimated based on EC50s found to be effective in in vitro and in vivo animal models. In some embodiments, the animal models include transgenic animals that express a human SMN1 or SMN2. In another embodiment, the composition for testing includes a single stranded oligonucleotide that is complementary, at least in an internal region, to a sequence that is conserved between SMN1 or SMN2 in the animal model and the SMN1 or SMN2 in a human.

In one embodiment, the administration of the single stranded oligonucleotide composition is parenteral, e.g. intravenous (e.g., as a bolus or as a diffusible infusion), intradermal, intraperitoneal, intramuscular, intrathecal, intraventricular, intracranial, subcutaneous, transmucosal, buccal, sublingual, endoscopic, rectal, oral, vaginal, topical, pulmonary, intranasal, urethral or ocular. Administration can be provided by the subject or by another person, e.g., a health care provider. The composition can be provided in measured doses or in a dispenser which delivers a metered dose. Selected modes of delivery are discussed in more detail below.

Kits

In certain aspects of the invention, kits are provided, comprising a container housing a composition comprising a single stranded oligonucleotide. In some embodiments, the kits comprise a container housing a single stranded oligonucleotide complementary with of a PRC2-associated region of a gene; and a second container housing a single stranded oligonucleotide complementary to a splice control sequence of a precursor mRNA of the gene. In some embodiments, the kits comprise a container housing a single stranded oligonucleotide complementary with of a PRC2-associated region of a gene and a single stranded oligonucleotide complementary to a splice control sequence of a precursor mRNA of the gene. In some embodiments, the composition is a pharmaceutical composition comprising a single stranded oligonucleotide and a pharmaceutically acceptable carrier. In some embodiments, the individual components of the pharmaceutical composition may be provided in one container. Alternatively, it may be desirable to provide the components of the pharmaceutical composition separately in two or more containers, e.g., one container for single stranded oligonucleotides, and at least another for a carrier compound. The kit may be packaged in a number of different configurations such as one or more containers in a single box. The different components can be combined, e.g., according to instructions provided with the kit. The components can be combined according to a method described herein, e.g., to prepare and administer a pharmaceutical composition. The kit can also include a delivery device.

INCORPORATION BY REFERENCE

International Patent Appln. Pub. No. WO 2013/173638, entitled COMPOSITIONS AND METHODS FOR MODULATING SMN GENE FAMILY EXPRESSION, International Patent Appln. Pub. No. WO 2013/173645, entitled COMPOSITIONS AND METHODS FOR MODULATING UTRN EXPRESSION, International Patent Appln. Pub. No. WO 2013/173599, entitled COMPOSITIONS AND METHODS FOR MODULATING HEMOGLOBIN GENE FAMILY EXPRESSION, International Patent Appln. Pub. No. WO 2013/173598, entitled COMPOSITIONS AND METHODS FOR MODULATING ATP2A2 EXPRESSION, International Patent Appln. Pub. No. WO 2013/173647, entitled to COMPOSITIONS AND METHODS FOR MODULATING APOA1 AND ABCA1 EXPRESSION, International Patent Appln. Pub. No. WO 2013/173605, entitled COMPOSITIONS AND METHODS FOR MODULATING PTEN EXPRESSION, International Patent Appln. Pub. No. WO 2013/173601, entitled COMPOSITIONS AND METHODS FOR MODULATING BDNF EXPRESSION, International Patent Appln. Pub. No. WO 2013/173608, entitled COMPOSITIONS AND METHODS FOR MODULATING MECP2 EXPRESSION, International Patent Appln. Pub. No. WO 2013/173635, entitled COMPOSITIONS AND METHODS FOR MODULATING GENE EXPRESSION, International Patent Appln. Pub. No. WO 2013/173637, entitled COMPOSITIONS AND METHODS FOR MODULATING GENE EXPRESSION, and International Patent Appln. Pub. No. WO 2013/173652, entitled COMPOSITIONS AND METHODS FOR MODULATING GENE EXPRESSION are incorporated herein by reference in their entirety.

Appendix A contains Table 5. Appendix A can be found on pages 106-287 of WO 2013/173638, which are incorporated by reference herein in their entirety. Appendix B contains Table 6. Appendix B can be found on pages 288-309 of WO 2013/173638, which are incorporated by reference herein in their entirety. Appendix C contains Table 7. Appendix C can be found on pages 310-399 of WO 2013/173638, which are incorporated by reference herein in their entirety.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

The invention is further described in the following examples, which do not limit the scope of the invention described in the claims.

Example 1: Oligonucleotides Targeting PRC2-Associated Regions that Upregulate SMN1

Materials and Methods:
Real Time PCR

RNA was harvested from the cells using Promega SV 96 Total RNA Isolation system or Trizol omitting the DNAse step. In separate pilot experiments, 50 ng of RNA was determined to be sufficient template for the reverse transcriptase reaction. RNA harvested from cells was normalized so that 50 ng of RNA was input to each reverse transcription reaction. For the few samples that were too dilute to reach this limit, the maximum input volume was added. Reverse transcriptase reaction was performed using the Superscript II kit and real time PCR performed on cDNA samples using icycler SYBR green chemistry (Biorad). A baseline level of mRNA expression for each target gene was determined through quantitative PCR as outlined above. Baseline levels were also determined for mRNA of various housekeeping genes which are constitutively expressed. A "control" housekeeping gene with approximately the same level of baseline expression as the target gene was chosen for comparison purposes.

Protein Expression (ELISA)

ELISA to determine SMN protein was carried out per manufacturer's instructions (SMN ELISA kit # ADI-900-209, Enzo Life Sciences).

Cell Culture

Human hepatocyte Hep3B, human hepatocyte HepG2 cells, mouse hepatoma Hepa1-6 cells, and human renal proximal tubule epithelial cells (RPTEC) were cultured using conditions known in the art (see, e.g. Current Protocols in Cell Biology). Other cell lines tested were neuronal cell lines (SK-N-AS, U-87) and SMN patient fibroblasts. Details of the cell lines used in the experiments described herein are provided in Table 8.

TABLE 8

Cell lines

| Cell line | Source | Species | Gender | Cell Type | Tissue | Status | Culture Conditions |
|---|---|---|---|---|---|---|---|
| RPTEC | Lonza | human | N/A | proximal tubule epithelial cells | kidney | primary | Clonetics ™ REGM ™ BulletKit ™ (CC-3190) |
| Hep3B | ATCC | human | M | hepatocytes | liver | immortalized | Eagle's MEM + 10% FBS |
| SK-N-AS | ATCC | human | F | neuroblast | brain | immortalized | DMEM + 10% FBS |
| U-87 | ATCC | human | M | gliobastoma | brain | immortalized | Eagle's MEM + 10% FBS |
| GM03813 | Coriell Institute | human | F | fibroblast | skin | immortalized | MEM + 10% FBS |
| GM03814 | Coriell Institute | human | M | fibroblast | skin | immortalized | MEM + 10% FBS |
| GM09677 | Coriell Institute | human | M | fibroblast | skin | immortalized | MEM + 10% FBS |
| GM00232 | Coriell Institute | human | M | fibroblast | skin | immortalized | MEM + 10% FBS |
| GM03815 | Coriell Institute | human | M | fibroblast | skin | immortalized | MEM + 10% FBS |
| GM22592 | Coriell Institute | human | M | fibroblast | skin | immortalized | MEM + 10% FBS |
| GM10684 | Coriell Institute | human | F | B-lymphocyte | blood | immortalized | MEM + 10% FBS |
| GM00321 (normal) | Coriell Institute | human | F | fibroblast | skin | immortalized | MEM + 10% FBS |

Oligonucleotide Design

Oligonucleotides were designed within PRC2-interacting regions in order to upregulate SMN1. The sequence and structure of each oligonucleotide is shown in Table 2. The following table provides a description of the nucleotide analogs, modifications and intranucleotide linkages used for certain oligonucleotides tested and described in Table 2.

In Vitro Transfection of Cells with Oligonucleotides

Cells were seeded into each well of 24-well plates at a density of 25,000 cells per 500 uL and transfections were performed with Lipofectamine and the single stranded oligonucleotides. Control wells contained Lipofectamine alone. At 48 hours post-transfection, approximately 200 uL of cell culture supernatants were stored at −80 C for ELISA. At 48 hours post-transfection, RNA was harvested from the cells and quantitative PCR was carried out as outlined above. The percent induction of target mRNA expression by each oligonucleotide was determined by normalizing mRNA levels in the presence of the oligonucleotide to the mRNA levels in the presence of control (Lipofectamine alone). This was compared side-by-side with the increase in mRNA expression of the "control" housekeeping gene.

Results:

In Vitro Delivery of Single Stranded Oligonucleotides Upregulated SMN1 Expression Oligonucleotides were designed as candidates for upregulating SMN1 expression. A total of 52 single stranded oligonucleotides were designed to be complementary to a PRC2-interacting region within a sequence as set forth in SEQ ID NO: 1, 2, 4, or 5. Oligonucleotides were tested in at least duplicate. The sequence and structural features of the oligonucleotides are set forth in Table 2. Briefly, cells were transfected in vitro with the oligonucleotides as described above. SMN1 expression in cells following treatment was evaluated by qRT-PCR. Oligonucleotides that upregulated SMN1 expression were identified. Further details are outlined in Table 2.

Table 5 shows further results from experiments in which oligonucleotides were transfected into cells at a particular concentration [oligo] and 48 or 72 h later RNA was prepared and qRTPCR assays carried out to determine mRNA levels of full length (FL) or delta7 SMN. In other cases, oligos were administered gymnotically to cells at 10 μM and RNA harvested 9 days post treatment. The cell lines tested were neuronal cell lines (SK-N-AS, U-87) and SMN patient fibroblasts.

Table 6 shows results from experiments in which oligonucleotides were transfected into cells in combination with either one or two more oligos or small molecule compounds at a particular concentration ([oligo], [2nd], [3rd]) and 48 or 72 h later RNA was prepared and qRTPCR assays carried out to determine mRNA levels of full length (FL) or delta7 SMN. The cell lines tested were SMN patient fibroblasts.

Table 7 shows results from experiments in which oligonucleotides were transfected into cells in combination with either one or two more oligos or as dimers or by gymnotic treatment at a particular concentration ([oligo], [2nd], [3rd]) and 24, 48, 72 or 216 h later cell lysates were prepared and ELISA assays carried out to determine SMN protein levels. The cell lines tested were SMN patient fibroblasts.

TABLES

TABLE 1

Non-Seed hexamer sequences.

AAAAAA, AAAAAG, AAAACA, AAAAGA, AAAAGC, AAAAGG, AAAAUA, AAACAA, AAACAC, AAACAG,

AAACAU, AAACCC, AAACCU, AAACGA, AAACGC, AAACGU, AAACUA, AAACUC, AAACUU, AAAGAU,

AAAGCC, AAAGGA, AAAGGG, AAAGUC, AAAUAC, AAAUAU, AAAUCG, AAAUCU, AAAUGC, AAAUGU,

TABLE 1-continued

Non-Seed hexamer sequences.

AAAUUA, AAAUUG, AACAAC, AACAAG, AACAAU, AACACA, AACACG, AACAGA, AACAGC, AACAGG, AACAUC, AACAUG, AACCAA, AACCAC, AACCAG, AACCAU, AACCCC, AACCCG, AACCGA, AACCGC, AACCGG, AACCUA, AACCUU, AACGAA, AACGAC, AACGAG, AACGAU, AACGCU, AACGGG, AACGGU, AACGUA, AACGUC, AACGUG, AACGUU, AACUAU, AACUCA, AACUCC, AACUCG, AACUGA, AACUGC, AACUGU, AACUUA, AACUUC, AACUUG, AACUUU, AAGAAA, AAGAAG, AAGAAU, AAGACG, AAGAGA, AAGAGC, AAGAGG, AAGAGU, AAGAUU, AAGCAA, AAGCAC, AAGCAG, AAGCAU, AAGCCA, AAGCCC, AAGCCG, AAGCCU, AAGCGA, AAGCGG, AAGCGU, AAGCUA, AAGGAA, AAGGAC, AAGGCU, AAGGGC, AAGGGU, AAGGUU, AAGUAA, AAGUAC, AAGUAU, AAGUCC, AAGUCG, AAGUGA, AAGUGG, AAGUUA, AAGUUU, AAUAAA, AAUAAC, AAUAAG, AAUAAU, AAUACA, AAUACC, AAUACG, AAUAGA, AAUAGC, AAUAGG, AAUAGU, AAUAUC, AAUAUU, AAUCAA, AAUCAU, AAUCCA, AAUCCC, AAUCCG, AAUCGA, AAUCGC, AAUCGU, AAUCUA, AAUCUG, AAUCUU, AAUGAA, AAUGAC, AAUGAG, AAUGAU, AAUGCG, AAUGCU, AAUGGA, AAUGGU, AAUGUA, AAUGUC, AAUGUG, AAUUAA, AAUUAC, AAUUAG, AAUUCC, AAUUCG, AAUUGA, AAUUGG, AAUUGU, AAUUUC, AAUUUG, ACAAAA, ACAAAC, ACAAAG, ACAAAU, ACAACC, ACAACG, ACAACU, ACAAGA, ACAAGC, ACAAGU, ACAAUC, ACAAUG, ACAAUU, ACACAG, ACACCA, ACACCC, ACACCG, ACACCU, ACACGA, ACACGC, ACACGU, ACACUC, ACACUG, ACACUU, ACAGAA, ACAGAC, ACAGCC, ACAGCG, ACAGCU, ACAGGG, ACAGUC, ACAGUG, ACAGUU, ACAUAA, ACAUAC, ACAUCC, ACAUCG, ACAUCU, ACAUGA, ACAUGC, ACAUGU, ACAUUG, ACAUUU, ACCAAA, ACCAAC, ACCAAG, ACCAAU, ACCACC, ACCACG, ACCAGA, ACCAGU, ACCAUA, ACCAUG, ACCAUU, ACCCAA, ACCCAC, ACCCCA, ACCCCG, ACCCGA, ACCCGC, ACCCUA, ACCCUC, ACCCUU, ACCGAA, ACCGAC, ACCGAU, ACCGCA, ACCGCC, ACCGCG, ACCGCU, ACCGGA, ACCGGC, ACCGGU, ACCGUA, ACCGUC, ACCGUG, ACCGUU, ACCUAA, ACCUAC, ACCUAG, ACCUAU, ACCUCA, ACCUCC, ACCUCG, ACCUCU, ACCUGA, ACCUGC, ACCUGU, ACCUUA, ACCUUC, ACCUUU, ACGAAA, ACGAAC, ACGAAG, ACGAAU, ACGACA, ACGACC, ACGACG, ACGACU, ACGAGA, ACGAGC, ACGAGG, ACGAGU, ACGAUA, ACGAUC, ACGAUG, ACGAUU, ACGCAA, ACGCAG, ACGCAU, ACGCCC, ACGCCG, ACGCCU, ACGCGA, ACGCGG, ACGCGU, ACGCUA, ACGCUG, ACGCUU, ACGGAA, ACGGAC, ACGGAG, ACGGAU, ACGGCC, ACGGCG, ACGGCU, ACGGGC, ACGGGG, ACGGGU, ACGGUA, ACGGUC, ACGGUG, ACGGUU, ACGUAA, ACGUAC, ACGUAU, ACGUCC, ACGUCG, ACGUCU, ACGUGA, ACGUGC, ACGUGG, ACGUGU, ACGUUA, ACGUUC, ACGUUG, ACGUUU, ACUAAA, ACUAAG, ACUAAU, ACUACA, ACUACC, ACUACG, ACUACU, ACUAGG, ACUAUC, ACUAUG, ACUAUU, ACUCAU, ACUCCC, ACUCCG, ACUCCU, ACUCGA, ACUCGC, ACUCGG, ACUCUC, ACUCUU, ACUGAG, ACUGAU, ACUGCC, ACUGCG, ACUGCU, ACUGGG, ACUGGU, ACUGUC, ACUUAA, ACUUAC, ACUUAU, ACUUCA, ACUUCC, ACUUCG, ACUUCU, ACUUGA, ACUUGC, ACUUGU, ACUUUA, ACUUUC, ACUUUG, AGAAAA, AGAAAC, AGAAAG, AGAACC, AGAACG, AGAACU, AGAAGC, AGAAGU, AGAAUA, AGAAUC, AGAAUG, AGAAUU, AGACAA, AGACAC, AGACAU, AGACCA, AGACCC, AGACCG, AGACCU, AGACGA, AGACGC, AGACGU, AGACUA, AGACUC, AGACUU, AGAGAC, AGAGAG, AGAGAU, AGAGCC, AGAGCG, AGAGCU, AGAGGC, AGAGGG, AGAGGU, AGAGUA, AGAGUU, AGAUAC, AGAUAG, AGAUAU, AGAUCC, AGAUCG, AGAUCU, AGAUGA, AGAUGC, AGAUGG, AGAUUA, AGAUUC, AGAUUG, AGAUUU, AGCAAC, AGCACA, AGCACG, AGCACU, AGCAGA, AGCAUA, AGCAUC, AGCAUG, AGCCAA, AGCCAU, AGCCCA, AGCCGA, AGCCGC, AGCCGG, AGCCGU, AGCCUA, AGCCUC, AGCGAA, AGCGAG, AGCGAU, AGCGCA, AGCGCC, AGCGCG, AGCGCU, AGCGGA, AGCGGC, AGCGGU,

TABLE 1-continued

Non-Seed hexamer sequences.

AGCGUA, AGCGUC, AGCGUG, AGCGUU, AGCUAA, AGCUAC, AGCUAG, AGCUAU, AGCUCA, AGCUCC,
AGCUCG, AGCUCU, AGCUGA, AGCUGG, AGCUGU, AGCUUC, AGCUUU, AGGAAU, AGGACC, AGGACG,
AGGAGA, AGGAGU, AGGAUA, AGGCAA, AGGCAU, AGGCCG, AGGCGA, AGGCGC, AGGCGG, AGGCUA,
AGGCUC, AGGCUU, AGGGAC, AGGGAU, AGGGGA, AGGGGU, AGGGUA, AGGGUG, AGGUAA,
AGGUAC, AGGUCA, AGGUCC, AGGUCU, AGGUGA, AGGUGC, AGGUGG, AGGUGU, AGGUUC,
AGGUUG, AGUAAA, AGUAAG, AGUAAU, AGUACA, AGUACG, AGUAGC, AGUAGG, AGUAUA, AGUAUC,
AGUAUG, AGUAUU, AGUCAA, AGUCAC, AGUCAG, AGUCAU, AGUCCA, AGUCCG, AGUCCU, AGUCGA,
AGUCGC, AGUCGG, AGUCGU, AGUCUA, AGUCUC, AGUCUG, AGUCUU, AGUGAA, AGUGAC, AGUGCG,
AGUGGG, AGUGUC, AGUUAA, AGUUAC, AGUUAG, AGUUCC, AGUUCG, AGUUGA, AGUUGC,
AGUUGU, AGUUUA, AGUUUC, AGUUUG, AGUUUU, AUAAAC, AUAAAU, AUAACA, AUAACC, AUAACG,
AUAACU, AUAAGA, AUAAGC, AUAAGG, AUAAGU, AUAAUC, AUAAUG, AUAAUU, AUACAC, AUACAG,
AUACAU, AUACCA, AUACCC, AUACCG, AUACGA, AUACGC, AUACGG, AUACGU, AUACUA, AUACUC,
AUACUG, AUACUU, AUAGAA, AUAGAC, AUAGAU, AUAGCA, AUAGCG, AUAGCU, AUAGGA, AUAGGU,
AUAGUA, AUAGUC, AUAGUG, AUAGUU, AUAUAC, AUAUAG, AUAUCC, AUAUCG, AUAUCU, AUAUGA,
AUAUGC, AUAUGG, AUAUGU, AUAUUC, AUAUUG, AUAUUU, AUCAAA, AUCAAC, AUCAAG, AUCAAU,
AUCACA, AUCACC, AUCACG, AUCAGC, AUCAGG, AUCCAA, AUCCAU, AUCCCC, AUCCCG, AUCCGA,
AUCCGC, AUCCGG, AUCCUA, AUCCUC, AUCCUG, AUCGAA, AUCGAC, AUCGAG, AUCGAU, AUCGCA,
AUCGCC, AUCGCG, AUCGCU, AUCGGC, AUCGGG, AUCGGU, AUCGUC, AUCGUG, AUCGUU, AUCUAA,
AUCUAC, AUCUAG, AUCUAU, AUCUCC, AUCUCG, AUCUGU, AUCUUG, AUCUUU, AUGAAA, AUGAAC,
AUGAAG, AUGAAU, AUGACC, AUGACU, AUGAGG, AUGAGU, AUGAUA, AUGAUC, AUGAUU, AUGCAA,
AUGCAG, AUGCCA, AUGCCC, AUGCCG, AUGCGA, AUGCGG, AUGCGU, AUGCUC, AUGCUU, AUGGAC,
AUGGCC, AUGGGA, AUGGGC, AUGGGU, AUGGUC, AUGGUG, AUGUAC, AUGUAU, AUGUCA,
AUGUCC, AUGUCG, AUGUGU, AUGUUA, AUGUUC, AUUAAA, AUUAAC, AUUAAG, AUUAAU, AUUACA,
AUUACC, AUUACG, AUUACU, AUUAGA, AUUAGC, AUUAGG, AUUAGU, AUUAUA, AUUAUC, AUUAUG,
AUUCAC, AUUCCA, AUUCCG, AUUCCU, AUUCGA, AUUCGC, AUUCGG, AUUCGU, AUUCUA, AUUCUC,
AUUCUU, AUUGAA, AUUGAC, AUUGAU, AUUGCC, AUUGCG, AUUGCU, AUUGGA, AUUGGC,
AUUGGG, AUUGGU, AUUGUA, AUUGUC, AUUGUG, AUUGUU, AUUUAA, AUUUAG, AUUUAU,
AUUUCC, AUUUCG, AUUUCU, AUUUGA, AUUUGC, AUUUGU, AUUUUA, AUUUUC, AUUUUG,
AUUUUU, CAAAAG, CAAACA, CAAACC, CAAACG, CAAACU, CAAAGA, CAAAGG, CAAAUA, CAAAUU,
CAACAC, CAACAU, CAACCA, CAACCC, CAACCG, CAACGA, CAACGC, CAACGG, CAACGU, CAACUA,
CAACUC, CAACUG, CAACUU, CAAGAA, CAAGAC, CAAGAU, CAAGCA, CAAGCC, CAAGCG, CAAGCU,
CAAGGA, CAAGGG, CAAGUC, CAAGUG, CAAGUU, CAAUAA, CAAUAC, CAAUAG, CAAUCC, CAAUCG,
CAAUCU, CAAUGA, CAAUGC, CAAUGG, CAAUGU, CAAUUC, CAAUUG, CAAUUU, CACAAU, CACACA,
CACACG, CACACU, CACAGA, CACAGC, CACAGG, CACAUA, CACAUC, CACAUU, CACCAA, CACCAC,
CACCAU, CACCCA, CACCCC, CACCCG, CACCGA, CACCGC, CACCGG, CACCGU, CACCUA, CACCUU,
CACGAA, CACGAC, CACGAG, CACGAU, CACGCA, CACGCC, CACGCU, CACGGA, CACGGC, CACGGG,
CACGGU, CACGUA, CACGUC, CACGUG, CACGUU, CACUAA, CACUAG, CACUAU, CACUCA, CACUCG,
CACUGA, CACUGC, CACUGG, CACUUA, CACUUC, CACUUU, CAGAAA, CAGAAG, CAGAAU, CAGACC,
CAGACG, CAGAGC, CAGAUA, CAGAUC, CAGCCG, CAGCCU, CAGCGA, CAGCGC, CAGCGG, CAGCGU,

TABLE 1-continued

Non-Seed hexamer sequences.

CAGCUC, CAGCUU, CAGGAU, CAGGGG, CAGGGU, CAGGUA, CAGGUC, CAGGUU, CAGUAC, CAGUCG,
CAGUUG, CAUAAA, CAUAAC, CAUAAG, CAUAAU, CAUACA, CAUACC, CAUACG, CAUACU, CAUAGA,
CAUAGG, CAUAGU, CAUAUA, CAUAUC, CAUAUG, CAUCAA, CAUCAC, CAUCAG, CAUCAU, CAUCCA,
CAUCCC, CAUCCG, CAUCGA, CAUCGC, CAUCGG, CAUCGU, CAUCUA, CAUCUC, CAUCUG, CAUCUU,
CAUGAA, CAUGAC, CAUGAG, CAUGAU, CAUGCA, CAUGCC, CAUGCG, CAUGCU, CAUGGC, CAUGGG,
CAUGGU, CAUGUA, CAUGUC, CAUGUU, CAUUAA, CAUUAC, CAUUAG, CAUUCA, CAUUCC, CAUUCG,
CAUUCU, CAUUGA, CAUUGG, CAUUUC, CAUUUG, CAUUUU, CCAAAA, CCAAAC, CCAAAG, CCAAAU,
CCAACA, CCAACC, CCAACG, CCAACU, CCAAGA, CCAAGC, CCAAGG, CCAAUC, CCAAUG, CCAAUU,
CCACAA, CCACAC, CCACAG, CCACAU, CCACCA, CCACCC, CCACCG, CCACCU, CCACGA, CCACGC,
CCACGG, CCACGU, CCACUA, CCACUC, CCACUU, CCAGAA, CCAGAC, CCAGAG, CCAGCC, CCAGGU,
CCAGUC, CCAGUU, CCAUAA, CCAUAC, CCAUAG, CCAUAU, CCAUCA, CCAUCC, CCAUCU, CCAUGA,
CCAUGC, CCAUGG, CCAUUC, CCAUUG, CCAUUU, CCCAAC, CCCAAG, CCCAAU, CCCACA, CCCAGA,
CCCAGC, CCCAGU, CCCAUA, CCCAUC, CCCAUG, CCCAUU, CCCCAA, CCCCAG, CCCCAU, CCCCCC,
CCCCCG, CCCCCU, CCCCGA, CCCCGC, CCCCGU, CCCCUA, CCCCUC, CCCGAA, CCCGAC, CCCGAU,
CCCGCA, CCCGCU, CCCGGA, CCCGGC, CCCGUA, CCCGUG, CCCGUU, CCCUAA, CCCUAG, CCCUCA,
CCCUCU, CCCUGC, CCCUUA, CCCUUC, CCCUUU, CCGAAA, CCGAAC, CCGAAU, CCGACA, CCGACC,
CCGACG, CCGACU, CCGAGA, CCGAGG, CCGAGU, CCGAUA, CCGAUC, CCGAUG, CCGAUU, CCGCAA,
CCGCAC, CCGCAG, CCGCAU, CCGCCA, CCGCCC, CCGCCG, CCGCCU, CCGCGA, CCGCGC, CCGCGG,
CCGCGU, CCGCUA, CCGCUC, CCGCUG, CCGCUU, CCGGAA, CCGGAU, CCGGCA, CCGGCC, CCGGCG,
CCGGCU, CCGGGA, CCGGGC, CCGGGG, CCGGGU, CCGGUA, CCGGUC, CCGGUG, CCGUAA, CCGUAG,
CCGUAU, CCGUCA, CCGUCC, CCGUCG, CCGUGA, CCGUGU, CCGUUA, CCGUUC, CCGUUG, CCGUUU,
CCUAAC, CCUAAG, CCUAAU, CCUACA, CCUACC, CCUACG, CCUACU, CCUAGA, CCUAGC, CCUAGG,
CCUAGU, CCUAUA, CCUAUC, CCUAUG, CCUAUU, CCUCAA, CCUCAC, CCUCAG, CCUCAU, CCUCCA,
CCUCCC, CCUCCG, CCUCGA, CCUCGC, CCUCGG, CCUCGU, CCUCUA, CCUCUG, CCUGAC, CCUGAU,
CCUGCA, CCUGGG, CCUGGU, CCUGUU, CCUUAA, CCUUAC, CCUUAG, CCUUAU, CCUUCG, CCUUGA,
CCUUGU, CCUUUA, CCUUUC, CCUUUU, CGAAAA, CGAAAC, CGAAAG, CGAAAU, CGAACA, CGAACC,
CGAACG, CGAACU, CGAAGA, CGAAGC, CGAAGG, CGAAGU, CGAAUA, CGAAUC, CGAAUG, CGAAUU,
CGACAA, CGACAC, CGACAU, CGACCA, CGACCU, CGACGA, CGACGC, CGACGG, CGACGU, CGACUA,
CGACUG, CGACUU, CGAGAA, CGAGAC, CGAGAG, CGAGAU, CGAGCA, CGAGCC, CGAGCG, CGAGCU,
CGAGGC, CGAGGG, CGAGGU, CGAGUA, CGAGUC, CGAGUG, CGAGUU, CGAUAA, CGAUAC, CGAUAG,
CGAUAU, CGAUCA, CGAUCC, CGAUCG, CGAUCU, CGAUGA, CGAUGC, CGAUGG, CGAUGU, CGAUUA,
CGAUUC, CGAUUG, CGAUUU, CGCAAA, CGCAAC, CGCAAG, CGCAAU, CGCACA, CGCACC, CGCACG,
CGCAGA, CGCAGC, CGCAGG, CGCAGU, CGCAUA, CGCAUC, CGCAUG, CGCAUU, CGCCAA, CGCCAC,
CGCCAG, CGCCAU, CGCCCA, CGCCCC, CGCCCG, CGCCGA, CGCCGC, CGCCGG, CGCCGU, CGCCUA,
CGCCUG, CGCCUU, CGCGAA, CGCGAC, CGCGAG, CGCGAU, CGCGCA, CGCGCC, CGCGCG, CGCGCU,
CGCGGA, CGCGGC, CGCGGG, CGCGGU, CGCGUA, CGCGUC, CGCGUG, CGCGUU, CGCUAA, CGCUAC,
CGCUAG, CGCUAU, CGCUCA, CGCUCC, CGCUCG, CGCUCU, CGCUGA, CGCUGC, CGCUGG, CGCUGU,
CGCUUA, CGCUUC, CGCUUG, CGGAAA, CGGAAC, CGGAAG, CGGACA, CGGACC, CGGACG, CGGACU,
CGGAGC, CGGAGG, CGGAGU, CGGAUA, CGGAUU, CGGCAA, CGGCAC, CGGCAG, CGGCCA, CGGCCC,

TABLE 1-continued

Non-Seed hexamer sequences.

CGGCCG, CGGCGC, CGGCGG, CGGCGU, CGGCUA, CGGCUC, CGGCUG, CGGCUU, CGGGAA, CGGGAC,

CGGGAG, CGGGAU, CGGGCA, CGGGCC, CGGGCG, CGGGCU, CGGGGU, CGGGUA, CGGGUC, CGGGUG,

CGGUAA, CGGUAC, CGGUAG, CGGUAU, CGGUCA, CGGUCG, CGGUCU, CGGUGA, CGGUGG, CGGUGU,

CGGUUA, CGGUUC, CGGUUG, CGGUUU, CGUAAA, CGUAAC, CGUAAG, CGUAAU, CGUACA, CGUACG,

CGUACU, CGUAGA, CGUAGC, CGUAGG, CGUAGU, CGUAUA, CGUAUC, CGUAUG, CGUAUU, CGUCAA,

CGUCAC, CGUCAG, CGUCAU, CGUCCA, CGUCCC, CGUCCG, CGUCCU, CGUCGA, CGUCGG, CGUCGU,

CGUCUA, CGUCUC, CGUCUG, CGUCUU, CGUGAA, CGUGAC, CGUGAG, CGUGAU, CGUGCC, CGUGCG,

CGUGCU, CGUGGA, CGUGGG, CGUGGU, CGUGUA, CGUGUG, CGUUAA, CGUUAC, CGUUAG,

CGUUAU, CGUUCA, CGUUCC, CGUUCG, CGUUCU, CGUUGA, CGUUGC, CGUUGU, CGUUUA, CGUUUC,

CGUUUU, CUAAAA, CUAAAC, CUAAAU, CUAACA, CUAACC, CUAACG, CUAACU, CUAAGA, CUAAGC,

CUAAGU, CUAAUA, CUAAUC, CUAAUG, CUACAC, CUACAU, CUACCA, CUACCC, CUACCG, CUACCU,

CUACGA, CUACGC, CUACGG, CUACGU, CUACUA, CUACUC, CUACUG, CUAGAA, CUAGAG, CUAGAU,

CUAGCA, CUAGCC, CUAGCG, CUAGCU, CUAGGA, CUAGGG, CUAGGU, CUAGUG, CUAGUU, CUAUAA,

CUAUAG, CUAUAU, CUAUCA, CUAUCC, CUAUCG, CUAUCU, CUAUGA, CUAUGC, CUAUGG, CUAUGU,

CUAUUA, CUAUUG, CUCAAC, CUCAAG, CUCAAU, CUCACC, CUCACG, CUCAGC, CUCAUA, CUCAUC,

CUCAUG, CUCAUU, CUCCAC, CUCCCC, CUCCCG, CUCCGA, CUCCGC, CUCCGG, CUCCUA, CUCCUC,

CUCCUU, CUCGAA, CUCGAC, CUCGAG, CUCGAU, CUCGCA, CUCGCC, CUCGCG, CUCGGG, CUCGGU,

CUCGUA, CUCGUC, CUCGUG, CUCGUU, CUCUAA, CUCUAC, CUCUAU, CUCUCA, CUCUCC, CUCUCU,

CUCUGC, CUCUGU, CUCUUA, CUCUUG, CUGAAG, CUGACC, CUGACG, CUGAGC, CUGAUA, CUGAUC,

CUGCCG, CUGCCU, CUGCGA, CUGCUA, CUGCUU, CUGGAG, CUGGAU, CUGGCG, CUGGGU, CUGUAC,

CUGUCA, CUGUCC, CUGUCG, CUGUGG, CUGUGU, CUGUUA, CUGUUU, CUUAAC, CUUAAG, CUUAAU,

CUUACC, CUUACG, CUUAGA, CUUAGC, CUUAGG, CUUAGU, CUUAUA, CUUAUC, CUUAUG, CUUAUU,

CUUCAG, CUUCAU, CUUCCA, CUUCCC, CUUCCG, CUUCCU, CUUCGA, CUUCGC, CUUCGG, CUUCGU,

CUUCUA, CUUGAC, CUUGAG, CUUGAU, CUUGCA, CUUGCC, CUUGCG, CUUGCU, CUUGGC, CUUGGU,

CUUGUU, CUUUAC, CUUUAG, CUUUAU, CUUUCA, CUUUCG, CUUUCU, CUUUGA, CUUUGC, CUUUGU,

CUUUUA, CUUUUC, CUUUUG, CUUUUU, GAAAAA, GAAAAG, GAAAAU, GAAACC, GAAACG, GAAAGA,

GAAAGC, GAAAGU, GAAAUA, GAAAUC, GAAAUG, GAAAUU, GAACAA, GAACAC, GAACAG, GAACAU,

GAACCA, GAACCC, GAACCG, GAACCU, GAACGA, GAACGC, GAACGG, GAACGU, GAACUA, GAACUG,

GAACUU, GAAGAC, GAAGAG, GAAGCA, GAAGCG, GAAGCU, GAAGUC, GAAUAA, GAAUAC, GAAUAG,

GAAUAU, GAAUCC, GAAUCG, GAAUCU, GAAUGA, GAAUGC, GAAUGU, GAAUUA, GAAUUC, GAAUUU,

GACAAA, GACAAG, GACAAU, GACACC, GACAGA, GACAGG, GACAUA, GACAUG, GACAUU, GACCAA,

GACCAC, GACCAG, GACCCA, GACCCC, GACCCG, GACCGC, GACCGG, GACCGU, GACCUA, GACCUC,

GACCUU, GACGAA, GACGAC, GACGAG, GACGAU, GACGCA, GACGCC, GACGCG, GACGCU, GACGGA,

GACGGC, GACGGG, GACGGU, GACGUA, GACGUC, GACGUG, GACGUU, GACUAA, GACUAC, GACUAG,

GACUAU, GACUCA, GACUCC, GACUCG, GACUGG, GACUGU, GACUUA, GACUUG, GACUUU, GAGAAU,

GAGAGA, GAGAGC, GAGAGG, GAGAUA, GAGAUC, GAGCAA, GAGCAU, GAGCCA, GAGCGA, GAGCGG,

GAGCGU, GAGGGU, GAGGUC, GAGGUG, GAGUAA, GAGUAG, GAGUCC, GAGUUC, GAGUUU,

GAUAAA, GAUAAC, GAUAAG, GAUAAU, GAUACA, GAUACC, GAUACG, GAUACU, GAUAGA, GAUAGC,

GAUAGG, GAUAGU, GAUAUA, GAUCAA, GAUCAC, GAUCAU, GAUCCA, GAUCCC, GAUCCU, GAUCGC,

TABLE 1-continued

Non-Seed hexamer sequences.

GAUCGG, GAUCGU, GAUCUA, GAUCUG, GAUCUU, GAUGAA, GAUGAC, GAUGAG, GAUGCA, GAUGCC,
GAUGCG, GAUGCU, GAUGGC, GAUGGG, GAUGGU, GAUGUG, GAUGUU, GAUUAA, GAUUAC,
GAUUAG, GAUUAU, GAUUCA, GAUUCG, GAUUCU, GAUUGA, GAUUGC, GAUUUA, GAUUUC,
GAUUUG, GAUUUU, GCAAAC, GCAAAG, GCAAAU, GCAACA, GCAACC, GCAAGC, GCAAGU, GCAAUA,
GCAAUC, GCAAUG, GCAAUU, GCACAA, GCACAC, GCACAG, GCACCC, GCACCG, GCACCU, GCACGA,
GCACGC, GCACGU, GCACUA, GCACUC, GCACUG, GCACUU, GCAGAU, GCAGCC, GCAGCG, GCAGGC,
GCAGUA, GCAGUC, GCAGUG, GCAGUU, GCAUAA, GCAUAG, GCAUAU, GCAUCG, GCAUCU, GCAUGA,
GCAUGC, GCAUGG, GCAUGU, GCAUUA, GCAUUC, GCAUUG, GCAUUU, GCCAAA, GCCAAC, GCCAAU,
GCCACA, GCCACC, GCCACG, GCCAGA, GCCAGU, GCCAUA, GCCAUC, GCCAUG, GCCAUU, GCCCAA,
GCCCAC, GCCCAG, GCCCCG, GCCCGA, GCCCGG, GCCCGU, GCCGAA, GCCGAC, GCCGAG, GCCGAU,
GCCGCA, GCCGCU, GCCGGA, GCCGGC, GCCGGG, GCCGGU, GCCGUA, GCCGUC, GCCGUG, GCCGUU,
GCCUAA, GCCUAU, GCCUCA, GCCUCC, GCCUCG, GCCUGA, GCCUUA, GCCUUU, GCGAAA, GCGAAC,
GCGAAG, GCGAAU, GCGACC, GCGACG, GCGACU, GCGAGA, GCGAGC, GCGAGG, GCGAGU, GCGAUA,
GCGAUC, GCGAUG, GCGAUU, GCGCAA, GCGCAC, GCGCAG, GCGCAU, GCGCCA, GCGCCC, GCGCCU,
GCGCGA, GCGCGU, GCGCUA, GCGCUC, GCGCUG, GCGCUU, GCGGAA, GCGGAC, GCGGAU, GCGGCA,
GCGGCC, GCGGCU, GCGGGA, GCGGUA, GCGGUC, GCGGUU, GCGUAA, GCGUAC, GCGUAG, GCGUAU,
GCGUCA, GCGUCC, GCGUCG, GCGUCU, GCGUGA, GCGUGC, GCGUGG, GCGUGU, GCGUUA, GCGUUC,
GCGUUG, GCGUUU, GCUAAA, GCUAAC, GCUAAG, GCUAAU, GCUACC, GCUACG, GCUACU, GCUAGA,
GCUAGG, GCUAGU, GCUAUA, GCUAUC, GCUAUU, GCUCAA, GCUCAC, GCUCAG, GCUCAU, GCUCCA,
GCUCCC, GCUCCG, GCUCGA, GCUCGC, GCUCGU, GCUCUA, GCUCUC, GCUCUU, GCUGAA, GCUGAC,
GCUGAU, GCUGCA, GCUGCC, GCUGCG, GCUGCU, GCUGUG, GCUGUU, GCUUAC, GCUUAG, GCUUAU,
GCUUCA, GCUUCG, GCUUGA, GCUUGG, GCUUGU, GCUUUA, GCUUUG, GGAAAG, GGAACA, GGAACC,
GGAACG, GGAACU, GGAAGU, GGAAUA, GGAAUC, GGAAUU, GGACAA, GGACAC, GGACAG, GGACAU,
GGACCG, GGACGA, GGACGC, GGACGU, GGACUA, GGACUC, GGACUU, GGAGAC, GGAGCA, GGAGCG,
GGAGGG, GGAGUA, GGAUAA, GGAUAC, GGAUCA, GGAUCC, GGAUCG, GGAUCU, GGAUGC, GGAUUA,
GGAUUG, GGCAAU, GGCACA, GGCACU, GGCAGA, GGCAUA, GGCAUC, GGCCAC, GGCCAG, GGCCCC,
GGCCGA, GGCCGC, GGCCGU, GGCCUA, GGCCUG, GGCCUU, GGCGAA, GGCGAG, GGCGAU, GGCGCA,
GGCGCU, GGCGGU, GGCGUA, GGCGUC, GGCGUG, GGCGUU, GGCUAA, GGCUAC, GGCUAG, GGCUAU,
GGCUCC, GGCUCG, GGCUGA, GGCUUA, GGCUUC, GGCUUG, GGGAAU, GGGACA, GGGAGA, GGGAGU,
GGGAUA, GGGAUU, GGGCAA, GGGCAC, GGGCAG, GGGCCG, GGGCGG, GGGGCC, GGGGGG,
GGGGGU, GGGGUA, GGGUAC, GGGUAU, GGGUCA, GGGUCC, GGGUCG, GGGUGA, GGGUGC,
GGGUUA, GGGUUG, GGUAAA, GGUAAC, GGUAAG, GGUAAU, GGUACA, GGUACC, GGUACG,
GGUACU, GGUAGC, GGUAGG, GGUAGU, GGUAUA, GGUAUC, GGUAUG, GGUCAA, GGUCAC,
GGUCAG, GGUCAU, GGUCCA, GGUCCG, GGUCCU, GGUCGA, GGUCGC, GGUCGG, GGUCGU, GGUCUC,
GGUCUU, GGUGAA, GGUGAC, GGUGAU, GGUGCA, GGUGCC, GGUGGC, GGUGUA, GGUGUC,
GGUUAA, GGUUAG, GGUUAU, GGUUCA, GGUUCC, GGUUCG, GGUUGC, GGUUUC, GGUUUU,
GUAAAA, GUAAAG, GUAAAU, GUAACC, GUAACG, GUAACU, GUAAGA, GUAAGC, GUAAGG, GUAAGU,
GUAAUA, GUAAUC, GUAAUG, GUAAUU, GUACAA, GUACAC, GUACAG, GUACAU, GUACCA, GUACCC,
GUACCG, GUACCU, GUACGA, GUACGC, GUACGG, GUACGU, GUACUA, GUACUC, GUACUG, GUACUU,

TABLE 1-continued

Non-Seed hexamer sequences.

GUAGAA, GUAGAC, GUAGCA, GUAGCC, GUAGCG, GUAGCU, GUAGGA, GUAGGC, GUAGGG,
GUAGGU, GUAGUA, GUAGUC, GUAUAA, GUAUAC, GUAUAG, GUAUAU, GUAUCA, GUAUCG,
GUAUCU, GUAUGA, GUAUGC, GUAUGG, GUAUUA, GUAUUG, GUAUUU, GUCAAA, GUCAAG,
GUCAAU, GUCACA, GUCACC, GUCACG, GUCAGA, GUCAGC, GUCAGG, GUCAUA, GUCAUC, GUCAUG,
GUCCAA, GUCCAC, GUCCAU, GUCCCC, GUCCCU, GUCCGA, GUCCGC, GUCCGG, GUCCGU, GUCCUA,
GUCCUG, GUCCUU, GUCGAA, GUCGAC, GUCGAG, GUCGAU, GUCGCA, GUCGCC, GUCGCG, GUCGCU,
GUCGGA, GUCGGC, GUCGGG, GUCGGU, GUCGUA, GUCGUC, GUCGUU, GUCUAA, GUCUAG, GUCUCA,
GUCUCC, GUCUCG, GUCUGA, GUCUGG, GUCUGU, GUCUUC, GUCUUU, GUGAAA, GUGAAC, GUGAAG,
GUGACC, GUGACG, GUGAGA, GUGAGC, GUGAGU, GUGAUC, GUGAUG, GUGAUU, GUGCAC,
GUGCAU, GUGCCC, GUGCCG, GUGCGA, GUGCGG, GUGCGU, GUGCUA, GUGCUC, GUGCUG,
GUGGAG, GUGGCG, GUGGCU, GUGGGU, GUGGUC, GUGGUG, GUGUAA, GUGUAG, GUGUCG,
GUGUGA, GUGUGC, GUGUGU, GUGUUG, GUGUUU, GUUAAA, GUUAAC, GUUAAG, GUUACA,
GUUACC, GUUACG, GUUACU, GUUAGA, GUUAGC, GUUAGU, GUUAUA, GUUAUC, GUUAUG,
GUUAUU, GUUCAA, GUUCAC, GUUCAG, GUUCCA, GUUCCG, GUUCGA, GUUCGC, GUUCGG, GUUCGU,
GUUCUA, GUUCUG, GUUGAA, GUUGAC, GUUGAG, GUUGAU, GUUGCG, GUUGCU, GUUGGA,
GUUGGC, GUUGGU, GUUGUC, GUUGUG, GUUGUU, GUUUAA, GUUUAC, GUUUAG, GUUUAU,
GUUUCA, GUUUCC, GUUUCU, GUUUGA, GUUUGC, GUUUGG, GUUUGU, GUUUUA, GUUUUC,
GUUUUU, UAAAAA, UAAAAC, UAAAAG, UAAAAU, UAAACA, UAAACC, UAAACG, UAAACU, UAAAGA,
UAAAGG, UAAAGU, UAAAUA, UAAAUC, UAAAUG, UAAAUU, UAACAA, UAACAC, UAACAG, UAACCA,
UAACCC, UAACCG, UAACCU, UAACGA, UAACGC, UAACGG, UAACGU, UAACUA, UAACUG, UAACUU,
UAAGAG, UAAGAU, UAAGCA, UAAGCC, UAAGCG, UAAGCU, UAAGGA, UAAGGC, UAAGGG, UAAGGU,
UAAGUA, UAAGUC, UAAGUG, UAAGUU, UAAUAA, UAAUCA, UAAUCC, UAAUCG, UAAUCU, UAAUGA,
UAAUGG, UAAUGU, UAAUUA, UAAUUC, UAAUUG, UACAAC, UACAAG, UACAAU, UACACC, UACACG,
UACACU, UACAGA, UACAGC, UACAUA, UACAUC, UACAUU, UACCAA, UACCAC, UACCAG, UACCAU,
UACCCC, UACCCG, UACCCU, UACCGA, UACCGC, UACCGG, UACCGU, UACCUA, UACCUG, UACGAA,
UACGAC, UACGAG, UACGAU, UACGCA, UACGCC, UACGCG, UACGCU, UACGGC, UACGGG, UACGGU,
UACGUA, UACGUC, UACGUG, UACGUU, UACUAA, UACUAC, UACUAG, UACUAU, UACUCA, UACUCC,
UACUCG, UACUCU, UACUGA, UACUGC, UACUGG, UACUUA, UACUUG, UACUUU, UAGAAA, UAGAAG,
UAGAAU, UAGACA, UAGACG, UAGAGA, UAGAGC, UAGAGU, UAGAUA, UAGAUC, UAGAUG, UAGCAU,
UAGCCC, UAGCCG, UAGCCU, UAGCGA, UAGCGC, UAGCGU, UAGCUA, UAGCUC, UAGCUG, UAGGAA,
UAGGAU, UAGGCG, UAGGCU, UAGGGU, UAGGUC, UAGGUG, UAGGUU, UAGUAA, UAGUAC,
UAGUAG, UAGUAU, UAGUCA, UAGUCG, UAGUGU, UAGUUA, UAGUUC, UAGUUG, UAGUUU,
UAUAAC, UAUAAG, UAUACU, UAUAGA, UAUAGC, UAUAGG, UAUAGU, UAUAUA, UAUAUC, UAUAUG,
UAUAUU, UAUCAA, UAUCAC, UAUCAU, UAUCCA, UAUCCC, UAUCCG, UAUCCU, UAUCGA, UAUCGC,
UAUCGG, UAUCGU, UAUCUA, UAUCUC, UAUCUG, UAUCUU, UAUGAA, UAUGAC, UAUGAG,
UAUGAU, UAUGCA, UAUGCG, UAUGCU, UAUGGA, UAUGGC, UAUGUC, UAUGUG, UAUGUU,
UAUUAG, UAUUCA, UAUUCC, UAUUCG, UAUUCU, UAUUGA, UAUUGG, UAUUUA, UAUUUC,
UAUUUG, UAUUUU, UCAAAA, UCAAAC, UCAAAG, UCAACC, UCAACU, UCAAGA, UCAAGC, UCAAUA,
UCAAUC, UCAAUG, UCAAUU, UCACCC, UCACCG, UCACCU, UCACGA, UCACGC, UCACGG, UCACGU,

TABLE 1-continued

Non-Seed hexamer sequences.

UCACUA, UCACUC, UCACUU, UCAGAA, UCAGAC, UCAGAG, UCAGCG, UCAGCU, UCAGGA, UCAGGC,

UCAGGU, UCAGUC, UCAGUU, UCAUAA, UCAUCA, UCAUCC, UCAUCG, UCAUGC, UCAUGG, UCAUGU,

UCAUUA, UCAUUG, UCCAAA, UCCAAC, UCCAAG, UCCAAU, UCCACA, UCCACC, UCCACG, UCCAGC,

UCCAGG, UCCAUA, UCCAUC, UCCAUU, UCCCAA, UCCCAG, UCCCAU, UCCCCC, UCCCCG, UCCCCU,

UCCCGA, UCCCGC, UCCCGG, UCCCGU, UCCCUA, UCCCUC, UCCGAA, UCCGAC, UCCGAG, UCCGAU,

UCCGCA, UCCGCC, UCCGGA, UCCGGC, UCCGGU, UCCGUA, UCCGUC, UCCGUG, UCCUAA, UCCUCA,

UCCUCG, UCCUCU, UCCUGC, UCCUGU, UCCUUA, UCCUUC, UCCUUU, UCGAAA, UCGAAC, UCGAAG,

UCGAAU, UCGACA, UCGACC, UCGACG, UCGACU, UCGAGA, UCGAGC, UCGAGG, UCGAUA, UCGAUC,

UCGAUG, UCGAUU, UCGCAA, UCGCAC, UCGCAG, UCGCAU, UCGCCA, UCGCCC, UCGCCG, UCGCCU,

UCGCGA, UCGCGC, UCGCGU, UCGCUA, UCGCUC, UCGGAA, UCGGAC, UCGGAG, UCGGAU, UCGGCA,

UCGGCU, UCGGGG, UCGGGU, UCGGUC, UCGGUG, UCGGUU, UCGUAA, UCGUAC, UCGUAG,

UCGUAU, UCGUCA, UCGUCC, UCGUCG, UCGUCU, UCGUGA, UCGUGU, UCGUUA, UCGUUC, UCGUUG,

UCGUUU, UCUAAC, UCUAAG, UCUAAU, UCUACA, UCUACC, UCUACG, UCUACU, UCUAGC, UCUAGG,

UCUAGU, UCUAUA, UCUAUC, UCUAUG, UCUAUU, UCUCAG, UCUCAU, UCUCCG, UCUCGC, UCUCGG,

UCUCGU, UCUCUC, UCUGAA, UCUGAU, UCUGCA, UCUGCG, UCUGCU, UCUGGC, UCUGGU, UCUGUC,

UCUGUG, UCUGUU, UCUUAA, UCUUAC, UCUUAG, UCUUAU, UCUUCA, UCUUCC, UCUUCG, UCUUCU,

UCUUGC, UCUUGG, UCUUGU, UCUUUA, UCUUUC, UCUUUG, UCUUUU, UGAAAA, UGAAAC,

UGAACA, UGAACC, UGAAGG, UGAAUC, UGAAUG, UGACAA, UGACAC, UGACAG, UGACCA, UGACCC,

UGACCG, UGACGA, UGACGC, UGACGG, UGACGU, UGACUA, UGACUC, UGACUU, UGAGAG, UGAGAU,

UGAGCA, UGAGCC, UGAGCU, UGAGGC, UGAGGU, UGAGUA, UGAGUU, UGAUAC, UGAUAG,

UGAUAU, UGAUCA, UGAUCG, UGAUCU, UGAUGA, UGAUGC, UGAUGG, UGAUGU, UGAUUA,

UGAUUC, UGAUUG, UGAUUU, UGCAAC, UGCAAG, UGCACA, UGCACG, UGCAGG, UGCAGU, UGCAUC,

UGCCCA, UGCCCC, UGCCCG, UGCCGA, UGCCGC, UGCCGG, UGCCGU, UGCCUA, UGCCUC, UGCCUG,

UGCCUU, UGCGAA, UGCGAC, UGCGAU, UGCGCC, UGCGCG, UGCGCU, UGCGGC, UGCGGG, UGCGGU,

UGCGUA, UGCGUC, UGCGUG, UGCGUU, UGCUAC, UGCUAU, UGCUCC, UGCUCG, UGCUGC, UGCUGG,

UGCUGU, UGCUUA, UGCUUU, UGGAAC, UGGAAG, UGGAGC, UGGAUC, UGGAUU, UGGCAA,

UGGCAC, UGGCAG, UGGCCG, UGGCCU, UGGCGA, UGGCGC, UGGCGU, UGGCUA, UGGCUC, UGGCUU,

UGGGAA, UGGGCA, UGGGCC, UGGGGC, UGGGUC, UGGUAA, UGGUAG, UGGUAU, UGGUCC,

UGGUCG, UGGUCU, UGGUGA, UGGUGC, UGGUGG, UGGUGU, UGGUUA, UGGUUG, UGUAAA,

UGUAAC, UGUAAG, UGUACC, UGUACG, UGUACU, UGUAGA, UGUAGC, UGUAGU, UGUAUC,

UGUAUU, UGUCAA, UGUCAC, UGUCAG, UGUCAU, UGUCCA, UGUCCC, UGUCCG, UGUCGA, UGUCGC,

UGUCGG, UGUCGU, UGUCUA, UGUCUC, UGUGAC, UGUGAG, UGUGAU, UGUGCA, UGUGGU,

UGUGUA, UGUGUU, UGUUAC, UGUUAG, UGUUAU, UGUUCA, UGUUCC, UGUUCG, UGUUGG,

UGUUGU, UGUUUA, UGUUUC, UGUUUG, UGUUUU, UUAAAA, UUAAAC, UUAAAG, UUAAAU,

UUAACC, UUAACG, UUAACU, UUAAGU, UUAAUA, UUAAUC, UUAAUG, UUAAUU, UUACAA, UUACAC,

UUACAG, UUACAU, UUACCA, UUACCC, UUACCG, UUACCU, UUACGA, UUACGC, UUACGG, UUACGU,

UUACUA, UUACUC, UUACUG, UUACUU, UUAGAA, UUAGAC, UUAGCC, UUAGCG, UUAGCU, UUAGGC,

UUAGGU, UUAGUA, UUAGUC, UUAGUU, UUAUAA, UUAUAC, UUAUAG, UUAUAU, UUAUCC,

UUAUCG, UUAUCU, UUAUGA, UUAUGG, UUAUGU, UUAUUA, UUAUUC, UUAUUG, UUAUUU,

TABLE 1-continued

Non-Seed hexamer sequences.

UUCAAC, UUCAAU, UUCACA, UUCACC, UUCACG, UUCACU, UUCAGC, UUCAGG, UUCAGU, UUCAUA,

UUCAUC, UUCAUG, UUCAUU, UUCCAA, UUCCCA, UUCCCG, UUCCGA, UUCCGU, UUCCUU, UUCGAA,

UUCGAC, UUCGAG, UUCGAU, UUCGCA, UUCGCC, UUCGCG, UUCGCU, UUCGGA, UUCGGC, UUCGGG,

UUCGGU, UUCGUA, UUCGUC, UUCGUG, UUCGUU, UUCUAC, UUCUAG, UUCUCA, UUCUCG,

UUCUGG, UUCUUA, UUCUUU, UUGAAA, UUGAAC, UUGAAG, UUGAAU, UUGACC, UUGACG,

UUGACU, UUGAGA, UUGAGC, UUGAGU, UUGAUA, UUGAUC, UUGAUG, UUGAUU, UUGCAA,

UUGCAC, UUGCAG, UUGCAU, UUGCCC, UUGCCG, UUGCGA, UUGCGC, UUGCGG, UUGCGU, UUGCUA,

UUGCUC, UUGCUG, UUGCUU, UUGGAA, UUGGAG, UUGGCC, UUGGCG, UUGGCU, UUGGGC,

UUGGGU, UUGGUA, UUGGUG, UUGUAA, UUGUAC, UUGUCA, UUGUCG, UUGUCU, UUGUGC,

UUGUGG, UUGUUA, UUGUUG, UUGUUU, UUUAAA, UUUAAC, UUUAAG, UUUAAU, UUUACA,

UUUACC, UUUACG, UUUACU, UUUAGA, UUUAGC, UUUAGG, UUUAGU, UUUAUA, UUUAUC,

UUUAUG, UUUAUU, UUUCAU, UUUCCA, UUUCCG, UUUCCU, UUUCGA, UUUCGC, UUUCGG,

UUUCGU, UUUCUA, UUUCUC, UUUCUG, UUUCUU, UUUGAA, UUUGAC, UUUGAG, UUUGAU,

UUUGCC, UUUGCU, UUUGGA, UUUGGC, UUUGGG, UUUGGU, UUUGUA, UUUGUC, UUUGUU,

UUUUAA, UUUUAG, UUUUAU, UUUUCC, UUUUCG, UUUUCU, UUUUGA, UUUUGC, UUUUGG,

UUUUGU, UUUUUA, UUUUUC, UUUUUU

TABLE 2

Oligonucleotide sequences made for testing

| Oligo Name | RQ | RQ SE | Gene Name | Expt Type | Cell Line/Tissue | [Oligo] | Assay Type | Coordinates_g |
|---|---|---|---|---|---|---|---|---|
| SMN1-01 | 0.812671952 | 0.135251351 | SMN1 | in vitro | RPTEC | 100 | qRTPCR | SMN1:21157U20 |
| SMN1-01 | 0.857032101 | 0.027318737 | SMN1 | in vitro | RPTEC | 50 | qRTPCR | SMN1:21157U20 |
| SMN1-01 | 0.167998915 | 0.167998672 | SMN1 | in vitro | Hep3B | 50 | qRTPCR | SMN1:21157U20 |
| SMN1-01 | 1.048125302 | 0.039302784 | SMN1 | in vitro | Hep3B | 100 | qRTPCR | SMN1:21157U20 |
| SMN1-01 | 1.381704207 | 0.053290565 | SMN1 | in vitro | Hep3B | 10 | qRTPCR | SMN1:21157U20 |
| SMN1-01 | 0.979869247 | 0.020515227 | SMN1 | in vitro | Hep3B | 30 | qRTPCR | SMN1:21157U20 |
| SMN1-02 | 0.760000318 | 0.042993212 | SMN1 | in vitro | RPTEC | 100 | qRTPCR | SMN1:21158U20 |
| SMN1-02 | 0.987138447 | 0.068187998 | SMN1 | in vitro | RPTEC | 50 | qRTPCR | SMN1:21158U20 |
| SMN1-02 | 2.252494526 | 1.803190669 | SMN1 | in vitro | Hep3B | 50 | qRTPCR | SMN1:21158U20 |
| SMN1-02 | 1.114387973 | 0.026733251 | SMN1 | in vitro | Hep3B | 100 | qRTPCR | SMN1:21158U20 |
| SMN1-02 | 1.34641929 | 0.027641281 | SMN1 | in vitro | Hep3B | 10 | qRTPCR | SMN1:21158U20 |
| SMN1-02 | 1.153697083 | 0.024999991 | SMN1 | in vitro | Hep3B | 30 | qRTPCR | SMN1:21158U20 |
| SMN1-03 | 1.90722975 | 0.525939296 | SMN1 | in vitro | RPTEC | 100 | qRTPCR | SMN1:21159U20 |
| SMN1-03 | 1.132758264 | 0.094640177 | SMN1 | in vitro | RPTEC | 50 | qRTPCR | SMN1:21159U20 |
| SMN1-03 | 0.29619174 | 0.173282309 | SMN1 | in vitro | Hep3B | 50 | qRTPCR | SMN1:21159U20 |
| SMN1-03 | 1.48817935 | 0.172719507 | SMN1 | in vitro | Hep3B | 100 | qRTPCR | SMN1:21159U20 |
| SMN1-03 | 1.29932826 | 0.059825228 | SMN1 | in vitro | Hep3B | 10 | qRTPCR | SMN1:21159U20 |

TABLE 2-continued

Oligonucleotide sequences made for testing

| Oligo Name | RQ | RQ SE | Gene Name | Expt Type | Cell Line/Tissue | [Oligo] | Assay Type | Coordinates_g |
|---|---|---|---|---|---|---|---|---|
| SMN1-03 | 1.511567814 | 0.054178175 | SMN1 | in vitro | Hep3B | 30 | qRTPCR | SMN1:21159U20 |
| SMN1-04 | 1.048306517 | 0.243934543 | SMN1 | in vitro | RPTEC | 100 | qRTPCR | SMN1:21160U20 |
| SMN1-04 | 1.322407267 | 0.100022392 | SMN1 | in vitro | RPTEC | 50 | qRTPCR | SMN1:21160U20 |
| SMN1-04 | 0.133170013 | 0.032824391 | SMN1 | in vitro | Hep3B | 50 | qRTPCR | SMN1:21160U20 |
| SMN1-04 | 1.289550163 | 0.330195987 | SMN1 | in vitro | Hep3B | 100 | qRTPCR | SMN1:21160U20 |
| SMN1-04 | 1.280225492 | 0.062577972 | SMN1 | in vitro | Hep3B | 10 | qRTPCR | SMN1:21160U20 |
| SMN1-04 | 1.488482795 | 0.044641287 | SMN1 | in vitro | Hep3B | 30 | qRTPCR | SMN1:21160U20 |
| SMN1-05 | 0.876747527 | 0.087392504 | SMN1 | in vitro | RPTEC | 100 | qRTPCR | SMN1:21161U20 |
| SMN1-05 | 1.167120345 | 0.069814091 | SMN1 | in vitro | RPTEC | 50 | qRTPCR | SMN1:21161U20 |
| SMN1-05 | 0.088317863 | 0.039887014 | SMN1 | in vitro | Hep3B | 50 | qRTPCR | SMN1:21161U20 |
| SMN1-05 | 1.310053256 | 0.234231348 | SMN1 | in vitro | Hep3B | 100 | qRTPCR | SMN1:21161U20 |
| SMN1-05 | 1.038699643 | 0.056421362 | SMN1 | in vitro | Hep3B | 10 | qRTPCR | SMN1:21161U20 |
| SMN1-05 | 0.859144751 | 0.039970015 | SMN1 | in vitro | Hep3B | 30 | qRTPCR | SMN1:21161U20 |
| SMN1-06 | 0.704659891 | 0.087244119 | SMN1 | in vitro | RPTEC | 100 | qRTPCR | SMN1:21162U20 |
| SMN1-06 | 1.11194006 | 0.088571377 | SMN1 | in vitro | RPTEC | 50 | qRTPCR | SMN1:21162U20 |
| SMN1-06 | 0.57685962 | 0.246186541 | SMN1 | in vitro | Hep3B | 50 | qRTPCR | SMN1:21162U20 |
| SMN1-06 | 1.419418884 | 0.432447122 | SMN1 | in vitro | Hep3B | 100 | qRTPCR | SMN1:21162U20 |
| SMN1-06 | 1.146251704 | 0.051891541 | SMN1 | in vitro | Hep3B | 10 | qRTPCR | SMN1:21162U20 |
| SMN1-06 | 1.030682317 | 0.013070835 | SMN1 | in vitro | Hep3B | 30 | qRTPCR | SMN1:21162U20 |
| SMN1-07 | 0.682085732 | 0.084885351 | SMN1 | in vitro | RPTEC | 100 | qRTPCR | SMN1:21163U20 |
| SMN1-07 | 0.975853552 | 0.034178542 | SMN1 | in vitro | RPTEC | 50 | qRTPCR | SMN1:21163U20 |
| SMN1-07 | 1.013252314 | 0.118540759 | SMN1 | in vitro | Hep3B | 50 | qRTPCR | SMN1:21163U20 |
| SMN1-07 | 1.039381902 | 0.059815387 | SMN1 | in vitro | Hep3B | 100 | qRTPCR | SMN1:21163U20 |
| SMN1-07 | 1.156949605 | 0.107385405 | SMN1 | in vitro | Hep3B | 10 | qRTPCR | SMN1:21163U20 |
| SMN1-07 | 1.239503954 | 0.134603844 | SMN1 | in vitro | Hep3B | 30 | qRTPCR | SMN1:21163U20 |
| SMN1-08 | 0.948714888 | 0.142708231 | SMN1 | in vitro | RPTEC | 100 | qRTPCR | SMN1:21164U20 |
| SMN1-08 | 1.312080445 | 0.058464993 | SMN1 | in vitro | RPTEC | 50 | qRTPCR | SMN1:21164U20 |
| SMN1-08 | 0.216530007 | 0.177400555 | SMN1 | in vitro | Hep3B | 50 | qRTPCR | SMN1:21164U20 |
| SMN1-08 | 2.082151781 | 0.815184252 | SMN1 | in vitro | Hep3B | 100 | qRTPCR | SMN1:21164U20 |
| SMN1-08 | 1.010090604 | 0.200588791 | SMN1 | in vitro | Hep3B | 10 | qRTPCR | SMN1:21164U20 |
| SMN1-08 | 1.223947667 | 0.295307243 | SMN1 | in vitro | Hep3B | 30 | qRTPCR | SMN1:21164U20 |
| SMN1-09 | 0.77519063 | 0.098695118 | SMN1 | in vitro | RPTEC | 100 | qRTPCR | SMN1:21165U20 |
| SMN1-09 | 1.685731616 | 0.014884028 | SMN1 | in vitro | RPTEC | 50 | qRTPCR | SMN1:21165U20 |
| SMN1-09 | 0.621406781 | 0.227211261 | SMN1 | in vitro | Hep3B | 50 | qRTPCR | SMN1:21165U20 |
| SMN1-09 | 0.85593922 | 0.256108337 | SMN1 | in vitro | Hep3B | 100 | qRTPCR | SMN1:21165U20 |
| SMN1-09 | 0.940186097 | 0.197008464 | SMN1 | in vitro | Hep3B | 10 | qRTPCR | SMN1:21165U20 |
| SMN1-09 | 0.864481145 | 0.162739271 | SMN1 | in vitro | Hep3B | 30 | qRTPCR | SMN1:21165U20 |

TABLE 2-continued

Oligonucleotide sequences made for testing

| Oligo Name | RQ | RQ SE | Gene Name | Expt Type | Cell Line/Tissue | [Oligo] | Assay Type | Coordinates_g |
|---|---|---|---|---|---|---|---|---|
| SMN1-10 | 0.945730986 | 0.08072952 | SMN1 | in vitro | RPTEC | 100 | qRTPCR | SMN1:21166U20 |
| SMN1-10 | 1.574526902 | 0.123062684 | SMN1 | in vitro | RPTEC | 50 | qRTPCR | SMN1:21166U20 |
| SMN1-10 | 0.482822242 | 0.131557474 | SMN1 | in vitro | Hep3B | 50 | qRTPCR | SMN1:21166U20 |
| SMN1-10 | 1.280629128 | 0.17088425 | SMN1 | in vitro | Hep3B | 100 | qRTPCR | SMN1:21166U20 |
| SMN1-10 | 1.127254654 | 0.152486374 | SMN1 | in vitro | Hep3B | 10 | qRTPCR | SMN1:21166U20 |
| SMN1-10 | 1.069571458 | 0.122106758 | SMN1 | in vitro | Hep3B | 30 | qRTPCR | SMN1:21166U20 |
| SMN1-11 | 0.774436979 | 0.038076182 | SMN1 | in vitro | RPTEC | 100 | qRTPCR | SMN1:21167U20 |
| SMN1-11 | 1.562714254 | 0.158043098 | SMN1 | in vitro | RPTEC | 50 | qRTPCR | SMN1:21167U20 |
| SMN1-11 | 0.463655938 | 0.295513886 | SMN1 | in vitro | Hep3B | 50 | qRTPCR | SMN1:21167U20 |
| SMN1-11 | 0.957611652 | 0.334137541 | SMN1 | in vitro | Hep3B | 100 | qRTPCR | SMN1:21167U20 |
| SMN1-11 | 1.225973818 | 0.223472758 | SMN1 | in vitro | Hep3B | 10 | qRTPCR | SMN1:21167U20 |
| SMN1-11 | 1.089302259 | 0.126414268 | SMN1 | in vitro | Hep3B | 30 | qRTPCR | SMN1:21167U20 |
| SMN1-12 | 0.981429476 | 0.07937384 | SMN1 | in vitro | RPTEC | 100 | qRTPCR | SMN1:21168U20 |
| SMN1-12 | 1.585088128 | 0.05291912 | SMN1 | in vitro | RPTEC | 50 | qRTPCR | SMN1:21168U20 |
| SMN1-12 | 0.208586047 | 0.187017655 | SMN1 | in vitro | Hep3B | 50 | qRTPCR | SMN1:21168U20 |
| SMN1-12 | 3.266965896 | 2.002074369 | SMN1 | in vitro | Hep3B | 100 | qRTPCR | SMN1:21168U20 |
| SMN1-12 | 1.03381379 | 0.204376291 | SMN1 | in vitro | Hep3B | 10 | qRTPCR | SMN1:21168U20 |
| SMN1-12 | 1.137471671 | 0.246791954 | SMN1 | in vitro | Hep3B | 30 | qRTPCR | SMN1:21168U20 |
| SMN1-13 | 0.749636437 | 0.103277003 | SMN1 | in vitro | RPTEC | 100 | qRTPCR | SMN1:21169U20 |
| SMN1-13 | 1.175989263 | 0.122355585 | SMN1 | in vitro | RPTEC | 50 | qRTPCR | SMN1:21169U20 |
| SMN1-13 | 0.161499159 | 0.079356287 | SMN1 | in vitro | Hep3B | 50 | qRTPCR | SMN1:21169U20 |
| SMN1-13 | 1.287763591 | 0.090306717 | SMN1 | in vitro | Hep3B | 100 | qRTPCR | SMN1:21169U20 |
| SMN1-13 | 1.336851675 | 0.1778149 | SMN1 | in vitro | Hep3B | 10 | qRTPCR | SMN1:21169U20 |
| SMN1-13 | 1.037772291 | 0.039404507 | SMN1 | in vitro | Hep3B | 30 | qRTPCR | SMN1:21169O20 |
| SMN1-14 | 0.771635177 | 0.086041959 | SMN1 | in vitro | RPTEC | 100 | qRTPCR | SMN1:21170U20 |
| SMN1-14 | 1.467048548 | 0.073113884 | SMN1 | in vitro | RPTEC | 50 | qRTPCR | SMN1:21170U20 |
| SMN1-14 | 1.978254154 | 1.352951156 | SMN1 | in vitro | Hep3B | 50 | qRTPCR | SMN1:21170U20 |
| SMN1-14 | 1.311990937 | 0.073121634 | SMN1 | in vitro | Hep3B | 100 | qRTPCR | SMN1:21170U20 |
| SMN1-14 | 1.12892777 | 0.147162701 | SMN1 | in vitro | Hep3B | 10 | qRTPCR | SMN1:21170U20 |
| SMN1-14 | 0.855795121 | 0.017797181 | SMN1 | in vitro | Hep3B | 30 | qRTPCR | SMN1:21170U20 |
| SMN1-15 | 0.891491964 | 0.039822032 | SMN1 | in vitro | RPTEC | 100 | qRTPCR | SMN1:21171U20 |
| SMN1-15 | 1.573440342 | 0.117453017 | SMN1 | in vitro | RPTEC | 50 | qRTPCR | SMN1:21171U20 |
| SMN1-15 | 0.366043104 | 0.117162019 | SMN1 | in vitro | Hep3B | 50 | qRTPCR | SMN1:21171U20 |
| SMN1-15 | 1.738217394 | 0.520148155 | SMN1 | in vitro | Hep3B | 100 | qRTPCR | SMN1:21171U20 |
| SMN1-15 | 1.383201337 | 0.101830776 | SMN1 | in vitro | Hep3B | 10 | qRTPCR | SMN1:21171U20 |
| SMN1-15 | 1.619495052 | 0.038364989 | SMN1 | in vitro | Hep3B | 30 | qRTPCR | SMN1:21171U20 |
| SMN1-16 | 0.73721881 | 0.038067583 | SMN1 | in vitro | RPTEC | 100 | qRTPCR | SMN1:21172U20 |

TABLE 2-continued

Oligonucleotide sequences made for testing

| Oligo Name | RQ | RQ SE | Gene Name | Expt Type | Cell Line/Tissue | [Oligo] | Assay Type | Coordinates_g |
|---|---|---|---|---|---|---|---|---|
| SMN1-16 | 1.441616196 | 0.059823944 | SMN1 | in vitro | RPTEC | 50 | qRTPCR | SMN1:21172U20 |
| SMN1-16 | 0.510056605 | 0.286522659 | SMN1 | in vitro | Hep3B | 50 | qRTPCR | SMN1:21172U20 |
| SMN1-16 | 1.381914214 | 0.247880229 | SMN1 | in vitro | Hep3B | 100 | qRTPCR | SMN1:21172U20 |
| SMN1-16 | 1.310073573 | 0.026347093 | SMN1 | in vitro | Hep3B | 10 | qRTPCR | SMN1:21172U20 |
| SMN1-16 | 1.418132646 | 0.082371708 | SMN1 | in vitro | Hep3B | 30 | qRTPCR | SMN1:21172U20 |
| SMN1-17 | 1.219065651 | 0.281987674 | SMN1 | in vitro | RPTEC | 100 | qRTPCR | SMN1:21173U20 |
| SMN1-17 | 1.274819195 | 0.179527293 | SMN1 | in vitro | RPTEC | 50 | qRTPCR | SMN1:21173U20 |
| SMN1-17 | 0.416739222 | 0.066066242 | SMN1 | in vitro | Hep3B | 50 | qRTPCR | SMN1:21173U20 |
| SMN1-17 | 3.331843017 | 0.970174873 | SMN1 | in vitro | Hep3B | 100 | qRTPCR | SMN1:21173U20 |
| SMN1-17 | 1.260856522 | 0.038565799 | SMN1 | in vitro | Hep3B | 10 | qRTPCR | SMN1:21173U20 |
| SMN1-17 | 1.609045311 | 0.10487434 | SMN1 | in vitro | Hep3B | 30 | qRTPCR | SMN1:21173U20 |
| SMN1-18 | 0.868441941 | 0.088184698 | SMN1 | in vitro | RPTEC | 100 | qRTPCR | SMN1:21174U20 |
| SMN1-18 | 1.221663574 | 0.064445539 | SMN1 | in vitro | RPTEC | 50 | qRTPCR | SMN1:21174U20 |
| SMN1-18 | 10.28455167 | 3.929310832 | SMN1 | in vitro | Hep3B | 50 | qRTPCR | SMN1:21174U20 |
| SMN1-18 | 1.800920764 | 0.42559045 | SMN1 | in vitro | Hep3B | 100 | qRTPCR | SMN1:21174U20 |
| SMN1-18 | 1.261752602 | 0.069817143 | SMN1 | in vitro | Hep3B | 10 | qRTPCR | SMN1:21174U20 |
| SMN1-18 | 1.592700796 | 0.199280916 | SMN1 | in vitro | Hep3B | 30 | qRTPCR | SMN1:21174U20 |
| SMN1-19 | 0.705512452 | 0.06496675 | SMN1 | in vitro | RPTEC | 100 | qRTPCR | SMN1:21175U20 |
| SMN1-19 | 1.43433309 | 0.075936965 | SMN1 | in vitro | RPTEC | 50 | qRTPCR | SMN1:21175U20 |
| SMN1-19 | 0.538932156 | 0.309273594 | SMN1 | in vitro | Hep3B | 50 | qRTPCR | SMN1:21175U20 |
| SMN1-19 | 1.17374637 | 0.179415746 | SMN1 | in vitro | Hep3B | 100 | qRTPCR | SMN1:21175U20 |
| SMN1-19 | 1.186141471 | 0.036729063 | SMN1 | in vitro | Hep38 | 10 | qRTPCR | SMN1:21175U20 |
| SMN1-19 | 1.834775368 | 0.155761723 | SMN1 | in vitro | Hep3B | 30 | qRTPCR | SMN1:21175U20 |
| SMN1-20 | 0.826303453 | 0.062998254 | SMN1 | in vitro | RPTEC | 100 | qRTPCR | SMN1:21176U20 |
| SMN1-20 | 1.505786689 | 0.170697984 | SMN1 | in vitro | RPTEC | 50 | qRTPCR | SMN1:21176U20 |
| SMN1-20 | 0.06244992 | 0.049069571 | SMN1 | in vitro | Hep3B | 50 | qRTPCR | SMN1:21176U20 |
| SMN1-20 | 1.541480855 | 0.461158669 | SMN1 | in vitro | Hep3B | 100 | qRTPCR | SMN1:21176U20 |
| SMN1-20 | 1.089985692 | 0.043750568 | SMN1 | in vitro | Hep3B | 10 | qRTPCR | SMN1:21176U20 |
| SMN1-20 | 1.41531375 | 0.146502726 | SMN1 | in vitro | Hep3B | 30 | qRTPCR | SMN1:21176U20 |
| SMN1-21 | 0.865566453 | 0.209455026 | SMN1 | in vitro | RPTEC | 100 | qRTPCR | SMN1:21177U20 |
| SMN1-21 | 1.466688787 | 0.116267764 | SMN1 | in vitro | RPTEC | 50 | qRTPCR | SMN1:21177U20 |
| SMN1-21 | 0.388233514 | 0.139680869 | SMN1 | in vitro | Hep3B | 50 | qRTPCR | SMN1:21177U20 |
| SMN1-21 | 1.366269447 | 0.239420557 | SMN1 | in vitro | Hep3B | 100 | qRTPCR | SMN1:21177U20 |
| SMN1-21 | 1.354554841 | 0.013175463 | SMN1 | in vitro | Hep3B | 10 | qRTPCR | SMN1:21177U20 |
| SMN1-21 | 2.026968382 | 0.27827902 | SMN1 | in vitro | Hep3B | 30 | qRTPCR | SMN1:21177U20 |
| SMN1-22 | 0.639934851 | 0.011679891 | SMN1 | in vitro | RPTEC | 100 | qRTPCR | SMN1:21178U20 |

TABLE 2-continued

Oligonucleotide sequences made for testing

| Oligo Name | RQ | RQ SE | Gene Name | Expt Type | Cell Line/Tissue | [Oligo] | Assay Type | Coordinates_g |
|---|---|---|---|---|---|---|---|---|
| SMN1-22 | 1.242593923 | 0.02840519 | SMN1 | in vitro | RPTEC | 50 | qRTPCR | SMN1:21178U20 |
| SMN1-22 | 0.229857922 | 0.128101282 | SMN1 | in vitro | Hep3B | 50 | qRTPCR | SMN1:21178U20 |
| SMN1-22 | 1.499722255 | 0.568788539 | SMN1 | in vitro | Hep3B | 100 | qRTPCR | SMN1:21178U20 |
| SMN1-22 | 1.234783764 | 0.017119432 | SMN1 | in vitro | Hep3B | 10 | qRTPCR | SMN1:21178U20 |
| SMN1-22 | 1.509695591 | 0.175764156 | SMN1 | in vitro | Hep3B | 30 | qRTPCR | SMN1:21178U20 |
| SMN1-23 | 0.748031845 | 0.083732479 | SMN1 | in vitro | RPTEC | 100 | qRTPCR | SMN1:21179U20 |
| SMN1-23 | 1.33910973 | 0.070877143 | SMN1 | in vitro | RPTEC | 50 | qRTPCR | SMN1:21179U20 |
| SMN1-23 | 0.384143384 | 0.14723735 | SMN1 | in vitro | Hep3B | 50 | qRTPCR | SMN1:21179U20 |
| SMN1-23 | 2.620195611 | 0.342101826 | SMN1 | in vitro | Hep3B | 100 | qRTPCR | SMN1:21179U20 |
| SMN1-23 | 1.473663866 | 0.053762605 | SMN1 | in vitro | Hep3B | 10 | qRTPCR | SMN1:21179U20 |
| SMN1-23 | 1.920800418 | 0.127336842 | SMN1 | in vitro | Hep3B | 30 | qRTPCR | SMN1:21179U20 |
| SMN1-24 | 0.907436601 | 0.24201681 | SMN1 | in vitro | RPTEC | 100 | qRTPCR | SMN1:21180U20 |
| SMN1-24 | 1.28379369 | 0.158661709 | SMN1 | in vitro | RPTEC | 50 | qRTPCR | SMN1:21180U20 |
| SMN1-24 | 0.963100208 | 0.117802422 | SMN1 | in vitro | Hep3B | 50 | qRTPCR | SMN1:21180U20 |
| SMN1-24 | 0.994753299 | 0.268415648 | SMN1 | in vitro | Hep3B | 100 | qRTPCR | SMN1:21180U20 |
| SMN1-24 | 0.965440348 | 0.032646295 | SMN1 | in vitro | Hep3B | 10 | qRTPCR | SMN1:21180U20 |
| SMN1-24 | 1.140566171 | 0.10163121 | SMN1 | in vitro | Hep3B | 30 | qRTPCR | SMN1:21180U20 |
| SMN1-25 | 0.908854808 | 0.076026035 | SMN1 | in vitro | RPTEC | 100 | qRTPCR | SMN1:21181U20 |
| SMN1-25 | 1.226185041 | 0.044422705 | SMN1 | in vitro | RPTEC | 50 | qRTPCR | SMN1:21181U20 |
| SMN1-25 | 1.055082301 | 0.326768036 | SMN1 | in vitro | Hep3B | 50 | qRTPCR | SMN1:21181U20 |
| SMN1-25 | 0.969185038 | 0.226484866 | SMN1 | in vitro | Hep3B | 100 | qRTPCR | SMN1:21181U20 |
| SMN1-25 | 1.00974636 | 0.122120737 | SMN1 | in vitro | Hep38 | 10 | qRTPCR | SMN1:21181U20 |
| SMN1-25 | 1.081303639 | 0.101827303 | SMN1 | in vitro | Hep3B | 30 | qRTPCR | SMN1:21181U20 |
| SMN1-26 | 0.876444072 | 0.070457909 | SMN1 | in vitro | RPTEC | 100 | qRTPCR | SMN1:21182U20 |
| SMN1-26 | 1.632434888 | 0.061512357 | SMN1 | in vitro | RPTEC | 50 | qRTPCR | SMN1:21182U20 |
| SMN1-26 | 0.071593319 | 0.071592884 | SMN1 | in vitro | Hep3B | 50 | qRTPCR | SMN1:21182U20 |
| SMN1-26 | 1.999202516 | 0.420387669 | SMN1 | in vitro | Hep38 | 100 | qRTPCR | SMN1:21182U20 |
| SMN1-26 | 0.974107584 | 0.066863661 | SMN1 | in vitro | Hep3B | 10 | qRTPCR | SMN1:21182U20 |
| SMN1-26 | 1.030227891 | 0.096105098 | SMN1 | in vitro | Hep3B | 30 | qRTPCR | SMN1:21182U20 |
| SMN1-27 | 0.834365703 | 0.108102871 | SMN1 | in vitro | RPTEC | 100 | qRTPCR | SMN1:21157U15 |
| SMN1-27 | 1.589954219 | 0.093101653 | SMN1 | in vitro | RPTEC | 50 | qRTPCR | SMN1:21157U15 |
| SMN1-27 | 0.747186714 | 0.007807701 | SMN1 | in vitro | RPTEC | 30 | qRTPCR | SMN1:21157U15 |
| SMN1-27 | 1.049068744 | 0.092645193 | SMN1 | in vitro | RPTEC | 10 | qRTPCR | SMN1:21157U15 |
| SMN1-28 | 1.058343694 | 0.208931576 | SMN1 | in vitro | RPTEC | 100 | qRTPCR | SMN1:21158U15 |
| SMN1-28 | 1.402348414 | 0.101950771 | SMN1 | in vitro | RPTEC | 50 | qRTPCR | SMN1:21158U15 |
| SMN1-28 | 1.150224316 | 0.080077707 | SMN1 | in vitro | Hep3B | 30 | qRTPCR | SMN1:21158U15 |
| SMN1-28 | 1.219828396 | 0.031782762 | SMN1 | in vitro | Hep3B | 10 | qRTPCR | SMN1:21158U15 |

TABLE 2-continued

Oligonucleotide sequences made for testing

| Oligo Name | RQ | RQ SE | Gene Name | Expt Type | Cell Line/Tissue | [Oligo] | Assay Type | Coordinates_g |
|---|---|---|---|---|---|---|---|---|
| SMN1-29 | 0.712268587 | 0.077572838 | SMN1 | in vitro | RPTEC | 100 | qRTPCR | SMN1:21159U15 |
| SMN1-29 | 1.145305552 | 0.044575389 | SMN1 | in vitro | RPTEC | 50 | qRTPCR | SMN1:21159U15 |
| SMN1-29 | 0.937393865 | 0.015700783 | SMN1 | in vitro | Hep3B | 30 | qRTPCR | SMN1:21159U15 |
| SMN1-29 | 1.208521962 | 0.084021899 | SMN1 | in vitro | Hep3B | 10 | qRTPCR | SMN1:21159U15 |
| SMN1-30 | 0.869504109 | 0.147682779 | SMN1 | in vitro | RPTEC | 100 | qRTPCR | SMN1:21160U15 |
| SMN1-30 | 1.166995709 | 0.128900531 | SMN1 | in vitro | RPTEC | 50 | qRTPCR | SMN1:21160U15 |
| SMN1-30 | 1.069533423 | 0.042258392 | SMN1 | in vitro | Hep3B | 30 | qRTPCR | SMN1:21160U15 |
| SMN1-30 | 1.004618999 | 0.068245537 | SMN1 | in vitro | Hep3B | 10 | qRTPCR | SMN1:21160U15 |
| SMN1-31 | 1.223685297 | 0.155258366 | SMN1 | in vitro | Hep3B | 30 | qRTPCR | SMN1:21161U15 |
| SMN1-31 | 0.936569575 | 0.083367899 | SMN1 | in vitro | Hep3B | 10 | qRTPCR | SMN1:21161U15 |
| SMN1-32 | 1.032978469 | 0.02312057 | SMN1 | in vitro | Hep3B | 30 | qRTPCR | SMN1:21162U15 |
| SMN1-32 | 1.053045821 | 0.030158389 | SMN1 | in vitro | Hep3B | 10 | qRTPCR | SMN1:21162U15 |
| SMN1-33 | 1.046361407 | 0.038971809 | SMN1 | in vitro | Hep3B | 30 | qRTPCR | SMN1:21163U15 |
| SMN1-33 | 1.233302232 | 0.063255341 | SMN1 | in vitro | Hep3B | 10 | qRTPCR | SMN1:21163U15 |
| SMN1-34 | 1.079876751 | 0.09859402 | SMN1 | in vitro | Hep3B | 30 | qRTPCR | SMN1:21164U15 |
| SMN1-34 | 1.271026183 | 0.067019476 | SMN1 | in vitro | Hep3B | 10 | qRTPCR | SMN1:21164U15 |
| SMN1-35 | 0.861464008 | 0.024095912 | SMN1 | in vitro | Hep3B | 30 | qRTPCR | SMN1:21165U15 |
| SMN1-35 | 0.836966392 | 0.054159619 | SMN1 | in vitro | Hep3B | 10 | qRTPCR | SMN1:21165U15 |
| SMN1-36 | 1.26636324 | 0.046963681 | SMN1 | in vitro | Hep3B | 30 | qRTPCR | SMN1:21166U15 |
| SMN1-36 | 1.326257117 | 0.039674649 | SMN1 | in vitro | Hep3B | 10 | qRTPCR | SMN1:21166U15 |
| SMN1-37 | 1.232690086 | 0.043476252 | SMN1 | in vitro | Hep3B | 30 | qRTPCR | SMN1:21167U15 |
| SMN1 37 | 1.144632987 | 0.058433353 | SMN1 | in vitro | Hep3B | 10 | qRTPCR | SMN1:21167U15 |
| SMN1-38 | 0.843241863 | 0.033808043 | SMN1 | in vitro | Hep3B | 30 | qRTPCR | SMN1:21168U15 |
| SMN1-38 | 0.93818033 | 0.011376217 | SMN1 | in vitro | Hep3B | 10 | qRTPCR | SMN1:21168U15 |
| SMN1-39 | 0.663746249 | 0.045527014 | SMN1 | in vitro | Hep3B | 30 | qRTPCR | SMN1:21169U15 |
| SMN1-39 | 0.891764551 | 0.019395327 | SMN1 | in vitro | Hep3B | 10 | qRTPCR | SMN1:21169U15 |
| SMN1-40 | 0.888138653 | 0.081401804 | SMN1 | in vitro | Hep3B | 30 | qRTPCR | SMN1:21170U15 |
| SMN1-40 | 0.871602899 | 0.065372936 | SMN1 | in vitro | Hep3B | 10 | qRTPCR | SMN1:21170U15 |
| SMN1-41 | 0.882466148 | 0.031016749 | SMN1 | in vitro | Hep3B | 30 | qRTPCR | SMN1:21171U15 |
| SMN1-41 | 1.093694765 | 0.025996502 | SMN1 | in vitro | Hep3B | 10 | qRTPCR | SMN1:21171U15 |
| SMN1-42 | 0.956860836 | 0.043558382 | SMN1 | in vitro | Hep3B | 30 | qRTPCR | SMN1:21172U15 |
| SMN1-42 | 1.151755999 | 0.067662107 | SMN1 | in vitro | Hep3B | 10 | qRTPCR | SMN1:21172U15 |
| SMN1-43 | 1.341919782 | 0.08080776 | SMN1 | in vitro | Hep3B | 30 | qRTPCR | SMN1:21173U15 |
| SMN1-43 | 1.692919815 | 0.084669198 | SMN1 | in vitro | Hep3B | 10 | qRTPCR | SMN1:21173U15 |
| SMN1-44 | 0 | 0 | SMN1 | NA | NA | 0 | NA | SMN1:21174U15 |
| SMN1-45 | 1.807236897 | 0.11410948 | SMN1 | in vitro | Hep3B | 30 | qRTPCR | SMN1:21175U15 |
| SMN1-45 | 1.377773703 | 0.108540058 | SMN1 | in vitro | Hep3B | 10 | qRTPCR | SMN1:21175U15 |

TABLE 2-continued

Oligonucleotide sequences made for testing

| Oligo Name | RQ | RQ SE | Gene Name | Expt Type | Cell Line/Tissue | [Oligo] | Assay Type | Coordinates_g |
|---|---|---|---|---|---|---|---|---|
| SMN1-46 | 1.545649538 | 0.064006814 | SMN1 | in vitro | Hep3B | 30 | qRTPCR | SMN1:21176U15 |
| SMN1-46 | 1.354291504 | 0.038498944 | SMN1 | in vitro | Hep3B | 10 | qRTPCR | SMN1:21176U15 |
| SMN1-47 | 2.711598361 | 0.260043446 | SMN1 | in vitro | Hep3B | 30 | qRTPCR | SMN1:21177U15 |
| SMN1-47 | 1.986674786 | 0.119436675 | SMN1 | in vitro | Hep3B | 10 | qRTPCR | SMN1:21177U15 |
| SMN1-48 | 1.482342195 | 0.063036343 | SMN1 | in vitro | Hep3B | 30 | qRTPCR | SMN1:21178U15 |
| SMN1-48 | 2.597350628 | 0.145439801 | SMN1 | in vitro | Hep3B | 10 | qRTPCR | SMN1:21178U15 |
| SMN1-49 | 1.534493905 | 0.110688365 | SMN1 | in vitro | Hep3B | 30 | qRTPCR | SMN1:21179U15 |
| SMN1-49 | 2.223340784 | 0.148702992 | SMN1 | in vitro | Hep3B | 10 | qRTPCR | SMN1:21179U15 |
| SMN1-50 | 0.897421396 | 0.034254931 | SMN1 | in vitro | Hep3B | 30 | qRTPCR | SMN1:21180U15 |
| SMN1-50 | 1.132362781 | 0.078523003 | SMN1 | in vitro | Hep3B | 10 | qRTPCR | SMN1:21180U15 |
| SMN1-51 | 1.157921368 | 0.044256319 | SMN1 | in vitro | Hep3B | 30 | qRTPCR | SMN1:21181U15 |
| SMN1-51 | 1.177604665 | 0.038060353 | SMN1 | in vitro | Hep3B | 10 | qRTPCR | SMN1:21181U15 |
| SMN1-52 | 0.973548353 | 0.051461583 | SMN1 | in vitro | Hep3B | 30 | qRTPCR | SMN1:21182U15 |
| SMN1-52 | 1.068355642 | 0.060851146 | SMN1 | in vitro | Hep3B | 10 | qRTPCR | SMN1:21182U15 |

TABLE 3

Oligonucleotide Modifications

| Symbol | Feature Description |
|---|---|
| bio | 5' biotin |
| dAs | DNA w/3' thiophosphate |
| dCs | DNA w/3' thiophosphate |
| dGs | DNA w/3' thiophosphate |
| dTs | DNA w/3' thiophosphate |
| dG | DNA |
| enaAs | ENA w/3' thiophosphate |
| enaCs | ENA w/3' thiophosphate |
| enaGs | ENA w/3' thiophosphate |
| enaTs | ENA w/3' thiophosphate |
| fluAs | 2'-fluoro w/3' thiophosphate |
| fluCs | 2'-fluoro w/3' thiophosphate |
| fluGs | 2'-fluoro w/3' thiophosphate |
| fluUs | 2'-fluoro w/3' thiophosphate |
| lnaAs | LNA w/3' thiophosphate |
| lnaCs | LNA w/3' thiophosphate |
| lnaGs | LNA w/3' thiophosphate |
| lnaTs | LNA w/3' thiophosphate |
| omeAs | 2'-OMe w/3' thiophosphate |
| omeCs | 2'-OMe w/3' thiophosphate |
| omeGs | 2'-OMe w/3' thiophosphate |
| omeTs | 2'-OMe w/3' thiophosphate |
| lnaAs-Sup | LNA w/3' thiophosphate at 3' terminus |
| lnaCs-Sup | LNA w/3' thiophosphate at 3' terminus |
| lnaGs-Sup | LNA w/3' thiophosphate at 3' terminus |
| lnaTs-Sup | LNA w/3' thiophosphate at 3' terminus |
| lnaA-Sup | LNA w/3' OH at 3' terminus |
| lnaC-Sup | LNA w/3' OH at 3' terminus |
| lnaG-Sup | LNA w/3' OH at 3' terminus |
| lnaT-Sup | LNA w/3' OH at 3' terminus |
| omeA-Sup | 2'-OMe w/3' OH at 3' terminus |
| omeC-Sup | 2'-OMe w/3' OH at 3' terminus |
| omeG-Sup | 2'-OMe w/3' OH at 3' terminus |
| omeU-Sup | 2'-OMe w/3' OH at 3' terminus |
| dAs-Sup | DNA w/3' thiophosphate at 3' terminus |
| dCs-Sup | DNA w/3' thiophosphate at 3' terminus |
| dGs-Sup | DNA w/3' thiophosphate at 3' terminus |
| dTs-Sup | DNA w/3' thiophosphate at 3' terminus |
| dA-Sup | DNA w/3' OH at 3' terminus |
| dC-Sup | DNA w/3' OH at 3' terminus |
| dG-Sup | DNA w/3' OH at 3' terminus |
| dT-Sup | DNA w/3' OH at 3' terminus |

BRIEF DESCRIPTION OF SEQUENCE LISTING

| SeqID | Chrom | Gene | Chrom Start | Chrom End | Strand | Name |
|---|---|---|---|---|---|---|
| 1 | chr5 | SMN1 | 70208768 | 70260838 | + | human SMN1 |
| 2 | chr5 | SMN2 | 69333350 | 69385422 | + | human SMN2 |
| 3 | chr9 | SMNP | 20319406 | 20344375 | + | human SMNP |
| 4 | chr5 | SMN1 | 70208768 | 70260838 | − | human SMN1_revComp |
| 5 | chr5 | SMN2 | 69333350 | 69385422 | − | human SMN2_revComp |
| 6 | chr9 | SMNP | 20319406 | 20344375 | − | human SMNP_revComp |
| 7 | chr13 | Smn1 | 100881160 | 100919653 | + | mouse Smn1 |
| 8 | chr13 | Smn1 | 100881160 | 100919653 | − | mouse Smn1_revComp |
| 9 | chr5 | SMN1 | 70240095 | 70240127 | − | S48-193240 |
| 9 | chr5 | SMN2 | 69364672 | 69364704 | + | S48-193240 |

-continued

| SeqID | Chrom | Gene | Chrom Start | Chrom End | Strand | Name |
|---|---|---|---|---|---|---|
| 10 | chr5 | SMN1 | 70214393 | 70214822 | + | S48-441814 |
| 10 | chr5 | SMN2 | 69338976 | 69339405 | + | S48-441814 |
| 11 | chr5 | SMN1 | 70214064 | 70214108 | + | S48-441815 |
| 11 | chr5 | SMN2 | 69338647 | 69338691 | + | S48-441815 |
| 12 | chr5 | SMN1 | 70214276 | 70214317 | + | S48-473289 |
| 12 | chr5 | SMN2 | 69338859 | 69338900 | + | S48-473289 |
| 13 | chr5 | SMN1 | 70214445 | 70214472 | + | S48-473290 |
| 13 | chr5 | SMN2 | 69339028 | 69339055 | + | S48-473290 |
| 14 | chr5 | SMN1 | 70238095 | 70242127 | + | S48-193240 + 2K |
| 15 | chr5 | SMN2 | 69362672 | 69366704 | + | S48-193240 + 2K |
| 16 | chr5 | SMN1 | 70212393 | 70216822 | + | S48-441814 + 2K |
| 17 | chr5 | SMN2 | 69336976 | 69341405 | + | S48-441814 + 2K |
| 18 | chr5 | SMN1 | 70212064 | 70216108 | + | S48-441815 + 2K |
| 19 | chr5 | SMN2 | 69336647 | 69340691 | + | S48-441815 + 2K |
| 20 | chr5 | SMN1 | 70212276 | 70216317 | + | S48-473289 + 2K |
| 21 | chr5 | SMN2 | 69336859 | 69340900 | + | S48-473289 + 2K |
| 22 | chr5 | SMN1 | 70212445 | 70216472 | + | S48-473290 + 2K |
| 23 | chr5 | SMN2 | 69337028 | 69341055 | + | S48-473290 + 2K |
| 24 | chr5 | SMN1 | 70240510 | 70240551 | − | S48-193241 |
| 24 | chr5 | SMN2 | 69365087 | 69365128 | − | S48-193241 |
| 25 | chr5 | SMN1 | 70241924 | 70241968 | − | S48-193242 |
| 25 | chr5 | SMN2 | 69366499 | 69366543 | − | S48-193242 |
| 26 | chr5 | SMN1 | 70238510 | 70242551 | − | S48-193241 + 2K |
| 27 | chr5 | SMN2 | 69363087 | 69367128 | − | S48-193241 + 2K |
| 28 | chr5 | SMN1 | 70239924 | 70243968 | − | S48-193242 + 2K |
| 29 | chr5 | SMN2 | 69364499 | 69368543 | − | S48-193242 + 2K |
| 13100 | chr5 | SMN1 | 70247831 | 70247845 | + | Splice control sequence |
| 13100 | chr5 | SMN2 | 69372411 | 69372425 | + | Splice control sequence |
| 13101 | chr5 | SMN2 | 69372402 | 69372845 | + | Intron 7 |

Single Strand Oligonucleotides (Antisense Strand of Target Gene)
SeqID range: 30 to 8329, 13088-13094
SeqIDs w/o G Runs:
30-142, 156-560, 575-780, 794-912, 926-1013, 1027-1078, 1092-1286, 1300-1335, 1349-1385, 1399-1453, 1460-1527, 1548-1555, 1571-1653, 1675-1691, 1706-1802, 1816-1883, 1897-2009, 2023-2141, 2165-2289, 2303-2320, 2334-2447, 2461-2494, 2508-2526, 2540-2545, 2571-2635, 2651-2670, 2689-2763, 2772-2814, 2828-2854, 2868-3030, 3044-3256, 3270-3360, 3374-3400, 3414-3722, 3737, 3759-3783, 3797-3970, 3986-4059, 4073-4153, 4175-4240, 4255-4415, 4438-4441, 4456-4472, 4484-4505, 4513-4516, 4531-4546, 4560-4650, 4664-4751, 4766-4918, 4932-5035, 5049-5064, 5091-5189, 5203-5448, 5459-5503, 5508-5520, 5535-5654, 5668-5863, 5877-6016, 6025-6029, 6054-6063, 6078-6215, 6229-6701, 6715-6729, 6744-6869, 6883-6945, 6959-6968, 6982-7085, 7099-7173, 7195-7247, 7255-7268, 7273-7309, 7320-7335, 7349-7442, 7456-7465, 7479-7727, 7740-7951, 7977-8208, 8223-8255, 8257-8296, 8304-8312, 8319-8329, 13093-13094
SeqIDs w/o miR Seeds:
30-32, 34-39, 45-62, 64-72, 77-142, 145-151, 153, 157-184, 186-202, 205-246, 249, 251-260, 263, 266-320, 322, 326-328, 331, 333-341, 343-344, 346-394, 396-445, 447-541, 543-562, 564-596, 599-605, 607-646, 648-673, 677-701, 703-735, 737-772, 774-781, 785, 787-793, 795-809, 812, 814-815, 819-820, 822-827, 833-834, 836, 838-850, 852-876, 879, 883-886, 889-890, 892, 894, 897, 899, 901-906, 909, 911, 919, 921-935, 940, 942-1012, 1016-1063, 1065-1067, 1069-1095, 1097-1147, 1149-1166, 1168-1190, 1193-1214, 1217, 1227-1237, 1240, 1244, 1246-1251, 1258-1281, 1283-1312, 1314-1333, 1335, 1337-1356, 1358-1364, 1367, 1369-1381, 1384, 1388-1389, 1392-1404, 1406-1417, 1421-1441, 1443, 1445, 1447-1460, 1462-1492, 1494-1500, 1502, 1506-1512, 1514-1531, 1533, 1535-1539, 1543-1558, 1561-1562, 1564-1601, 1603-1614, 1616-1633, 1635-1646, 1648-1656, 1658, 1661-1675, 1678-1716, 1718-1740, 1742-1750, 1752-1785, 1788-1795, 1798, 1804-1871, 1873-1884, 1892-1973, 1976-1992, 1998-2032, 2034-2053, 2055-2077, 2079-2116, 2118-2135, 2138, 2142, 2149, 2151-2153, 2155-2162, 2165-2174, 2178, 2181-2254, 2256-2268, 2271-2293, 2296-2298, 2301-2312, 2314-2323, 2325-2427, 2429-2438, 2441, 2445, 2450-2476, 2478-2489, 2492-2494, 2497-2513, 2515, 2521-2526, 2529-2545, 2547-2571, 2573-2610, 2613-2620, 2622-2639, 2641, 2644, 2651-2743, 2745, 2747-2755, 2760-2775, 2777-2825, 2828-2841, 2844-2861, 2864-2888, 2894-2954, 2956-2988, 2991-3006, 3008-3043, 3046, 3048-3239, 3241-3253, 3256-3268, 3270-3273, 3276-3320, 3322-3355, 3357-3404, 3406-3428, 3430-3488, 3490-3491, 3493-3522, 3524-3552, 3554-3569, 3571-3650, 3653-3670, 3672-3688, 3690-3717, 3719-3724, 3727-3736, 3743, 3746, 3749, 3751-3821, 3823-3842, 3844, 3846, 3848, 3851, 3855, 3858, 3861-3863, 3866-3881, 3883, 3887-3907, 3909-3917, 3919-3924, 3926-3942, 3944-3952, 3956-3970, 3976-3988, 3991-3998, 4001-4008, 4010-4022, 4026, 4028-4039, 4041-4048, 4051-4059, 4063-4070, 4072-4073, 4075, 4078, 4080-4104, 4106-4124, 4126, 4129-4140, 4143-4153, 4156-4162, 4166-4171, 4174-4196, 4201-4241, 4244-4252, 4254-4285, 4289-4318, 4320-4324, 4327, 4330-4331, 4333-4335, 4337-4351, 4353-4414, 4417, 4419-4425, 4427-4433, 4435, 4438-4446, 4449-4450, 4452-4462, 4470-4472, 4474-4510, 4512-4517, 4520-4546, 4548, 4551-4590, 4592-4619, 4623-4696, 4699, 4701, 4703-4752, 4755-4877, 4879-4949, 4951-5007, 5010, 5013-5046, 5049-5059, 5061-5063, 5066, 5069-5078, 5080-5119, 5121-5131, 5134-5168, 5171-5189, 5191-5228, 5230-5341, 5343-5405, 5407-5426, 5429-5437, 5439-5476, 5478-5491, 5494-5516, 5518-5556, 5558-5572, 5574-5647, 5649, 5652-5653, 5657-5729, 5731-5742, 5744-5769, 5771-5780, 5782-5866, 5868, 5870-5876, 5879-5881, 5884-5899, 5902-5951, 5954-5993, 6000-6006, 6009-6016, 6019-6033, 6035-6065, 6067-6073, 6080-6165, 6168-6249, 6252-6257, 6261-6282, 6284-6289, 6291-6301, 6305-6367, 6369-6378, 6380-6398, 6401-6412, 6415, 6417-6447, 6449-

6456, 6458-6500, 6502-6563, 6565-6589, 6591-6612, 6616-6660, 6663-6702, 6704-6748, 6753, 6758-6763, 6765, 6768-6807, 6810, 6812-6872, 6874-6877, 6879-6913, 6915-6916, 6919, 6922, 6924-6926, 6928, 6930-6936, 6940-6959, 6962, 6964-6990, 6992, 6996, 6998-6999, 7004-7038, 7042-7085, 7087, 7089, 7092-7134, 7136-7140, 7142-7143, 7146-7150, 7152-7157, 7159-7171, 7175, 7177-7178, 7180-7196, 7198-7220, 7223, 7231-7237, 7239, 7242-7246, 7250-7273, 7275-7308, 7310-7312, 7314-7317, 7319-7330, 7332-7400, 7402-7437, 7439, 7441-7466, 7470-7491, 7493, 7495, 7497, 7499, 7502-7614, 7622-7628, 7631-7646, 7649-7651, 7655-7657, 7661-7672, 7676, 7679-7721, 7723-7800, 7802-7803, 7805-7906, 7908, 7910-7939, 7943-7953, 7956-7964, 7966-7981, 7983, 7985-7999, 8002, 8004-8034, 8036-8046, 8048-8080, 8084-8094, 8096-8112, 8114-8115, 8117-8139, 8141-8143, 8146-8148, 8150-8187, 8190-8216, 8218-8229, 8232-8238, 8240-8250, 8253-8255, 8257-8275, 8278-8296, 8299-8304, 8306-8329, 13093-13094
Single Strand Oligonucleotides (Sense Strand of Target Gene)
SeqID range: 1158-1159, 1171, 1482-1483, 1485-1486, 2465-2471, 2488-2490, 2542-2546, 2656-2657, 2833-2835, 3439-3440, 3916-3918, 4469-4472, 4821, 5429, 5537, 6061, 7327, 8330-13061, 13062-13087
SeqIDs w/o G Runs:
1158-1159, 1171, 1482-1483, 1485-1486, 2465-2471, 2488-2490, 2542-2545, 2656-2657, 2833-2835, 3439-3440, 3916-3918, 4469-4472, 4821, 5429, 5537, 6061, 7327, 8330-8495, 8520-8560, 8574-8837, 8857-8882, 8907-8964, 8978-9298, 9312-9382, 9394-9640, 9656-9753, 9767-9974, 9988-10261, 10275-10276, 10290-10301, 10315-10434, 10448-10613, 10623-10641, 10644-10676, 10678-10704, 10714-10802, 10822-11161, 11175-11192, 11207-11386, 11400-11730, 11744-11745, 11759-11852, 11857-11900, 11914-11984, 11999-12011, 12026-12153, 12163-12175, 12178-12195, 12198-12212, 12216-12536, 12547-12564, 12575-12664, 12674-12758, 12772-12797, 12800-12840, 12854-13061, 13062-13069
SeqIDs w/o miR Seeds:
1158-1159, 1171, 1482-1483, 1485-1486, 2465-2471, 2488-2489, 2542-2545, 2656-2657, 2833-2835, 3439-3440, 3916-3917, 4470-4472, 4821, 5429, 5537, 6061, 7327, 8330-8334, 8336-8345, 8347, 8351-8373, 8375-8390, 8392-8399, 8401-8413, 8415-8455, 8457-8493, 8495, 8497-8502, 8510-8517, 8520, 8525, 8527-8634, 8637-8653, 8655-8671, 8673-8718, 8721-8822, 8824-8825, 8827-8842, 8849-8879, 8881-8892, 8894-8902, 8905-8906, 8914-8927, 8929, 8931, 8935, 8937-8975, 8980-8992, 8994, 8996-8997, 8999-9001, 9003, 9005-9086, 9089-9124, 9126-9286, 9288-9307, 9310-9359, 9362-9420, 9425-9427, 9429-9432, 9434, 9436-9437, 9439-9461, 9464-9483, 9486, 9488-9498, 9500-9511, 9513, 9515-9650, 9653-9667, 9669, 9671-9723, 9725-9869, 9871-9872, 9874-9879, 9881-9889, 9891-9973, 9975-10077, 10080-10097, 10099, 10101-10127, 10129-10166, 10168-10170, 10172-10184, 10186-10230, 10232-10237, 10239-10260, 10262-10272, 10274-10342, 10344-10400, 10402-10423, 10426-10441, 10445-10556, 10560, 10562-10580, 10582-10606, 10609-10647, 10650, 10652-10704, 10706, 10710-10713, 10716-10731, 10733-10824, 10826-10842, 10844-10903, 10906-10907, 10909-11101, 11104, 11106-11134, 11137-11138, 11145-11161, 11164-11173, 11175-11181, 11184, 11186-11203, 11207-11212, 11214-11239, 11243-11259, 11261-11347, 11351-11397, 11399-11740, 11742-11747, 11749-11790, 11792-11817, 11821-11852, 11854-11904, 11908-11944, 11946-11959, 11961, 11964-11984, 11986-12007, 12009-12022, 12024-12092, 12095-12119, 12121-12133, 12135-12144, 12146-12157, 12159-12225, 12227-12231, 12233-12300, 12302-12329, 12332-12333, 12335-12382, 12385-12411, 12414-12416, 12418-12444, 12446-12455, 12457-12461, 12465, 12468-12474, 12476-12499, 12501-12536, 12538-12544, 12547-12553, 12559-12610, 12612-12626, 12628-12631, 12633-12637, 12640-12645, 12648-12657, 12659-12671, 12673-12679, 12683-12710, 12712, 12714-12747, 12750, 12752-12766, 12769, 12771-12806, 12808-12826, 12828-12829, 12831, 12833-12846, 12848-12849, 12854-12931, 12933-12946, 12948-13061, 13064, 13066-13068, 13071-13072, 13075, 13077-13081, 13083, 13085, 13087

Figure 2:
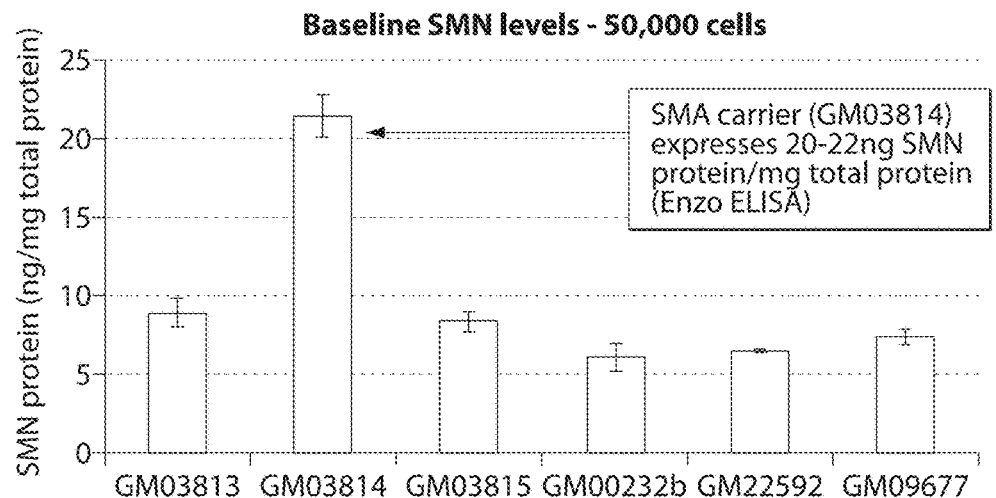
FIG. 2 provides a table outlining genotypes and patent information, including SMA classification, of cell lines tested in Example 2. Baseline SMN protein levels in the cell lines are also depicted.

Example 2: Selective Upregulation of Exon 7 Containing SMN2 Transcripts Using Oligonucleotides Targeting PRC2-Interacting Regions that Upregulate SMN2 and Splice-Switching Oligonucleotides Oligo Design:
Oligonucleotides targeting PRC2-interacting regions (lncRNA peaks) in the SMN1/2 gene loci were designed. These oligos were synthesized with various DNA base modifications, modification placements, inter-nucleoside bonds and inter-oligo linkers (oligos 1-52 and 59-101) as outlined in Table 4.
Splice switching oligos (SSO) were designed based on sequences of SMN2. Various modifications of such SSOs in length and chemistry were prepared (oligos 53-58).
Universal negative control oligos (oligo 232 and 293) were also designed using on bioinformatic analysis.
Methods:
Cell Culture:
Six SMA fibroblast cell lines and one lymphoblast cell line were obtained from the Coriell Institute (FIG. 2). The cells were either transfected with the oligos using Lipofectamine 2000 (Fibroblasts) or by electroporation or unassisted delivery (lymphoblast) to ascertain effects of the oligonucleotides on SMN1/2 mRNA and protein expression. All experiments were carried out as biological triplicates.
mRNA and Protein Expression:
mRNA Expression—
1. On day 1, SMA fibroblasts were seeded into each well of 96-well plates at a density of 5,000 cells per 100 uL.
2. On day 2, transfections were performed using Lipofectamie2000 per manufacturer's instructions with oligos at either 10 nM or 30 nM.
3. 48 hours post-transfection, Ambion Cells-to-CT kit was used to directly obtain qRT-PCR results from the cells per manufacturer's instructions.
4. Quantitative PCR evaluation was completed using Taqman FAST qPCR on StepOne Plus, and change in mRNA expression was quantified using the delta delta Ct method by normalizing SMN expression to a housekeeper gene (B2M).
Protein Expression (ELISA)—
ELISA to determine SMN protein was carried out per manufacturer's instructions (SMN ELISA kit # ADI-900-209, Enzo Life Sciences). Briefly, SMN fibroblasts were cultures at 40,000 cells/well of a 24-well tissue culture coated plate on day 1. Cells were transfected with the oligos using Lipofectamine2000 on day 2 and cell lysates prepared at 24 and 48 hours post-treatment. ELISA was carried out per manufacturer's instructions. Subsequently fold induction of SMN protein was determined by normalizing SMN protein levels induced by oligonucleotides to the SMN protein levels induced by Lipofectamine treatment alone.

Splice Switching Assay (DdeI Assay)—

Figure 5:
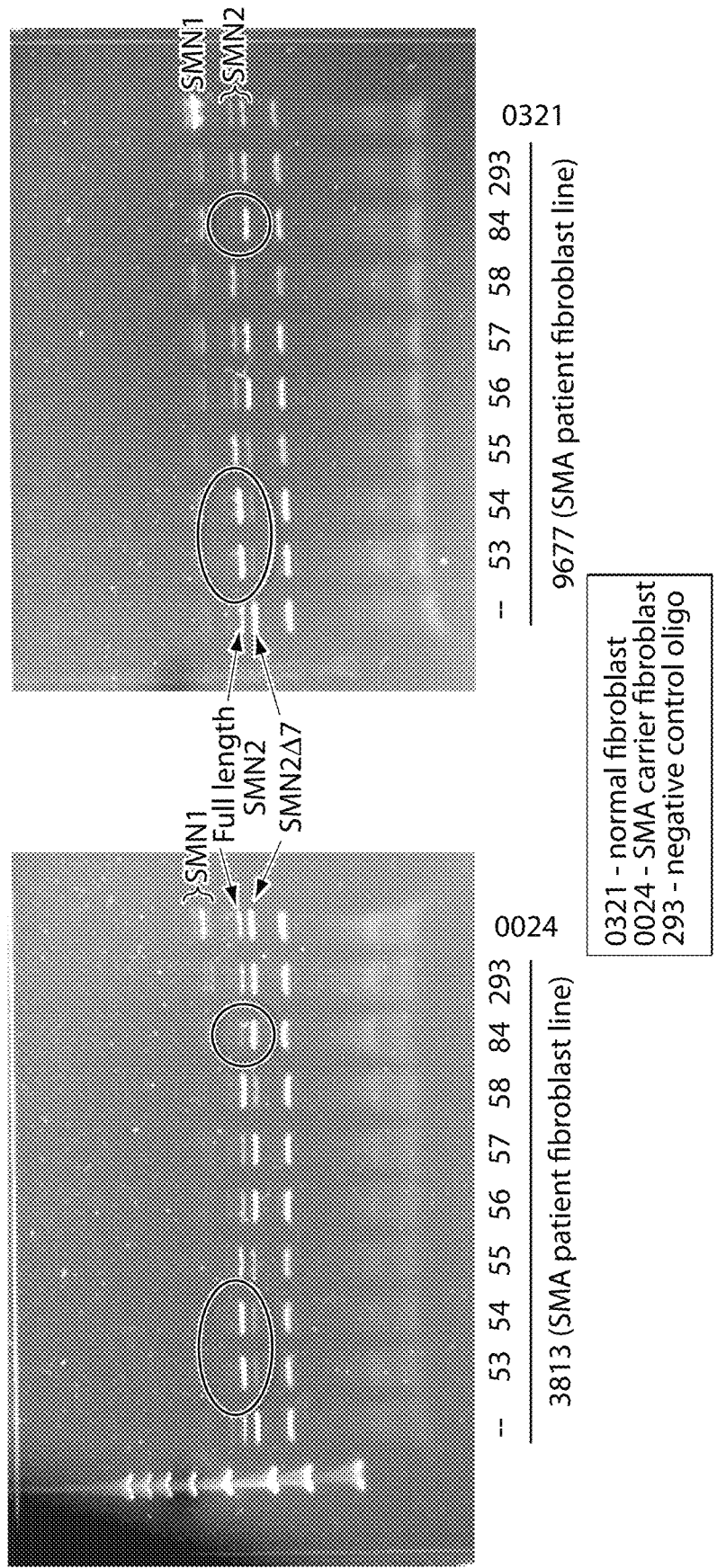
FIG. 5 shows that splice switching oligonucleotides (oligos 53-58) increase expression of full length SMN2. Results are based on a gel separation analysis of PCR products obtained following a DdeI restriction digest. Two cell lines were tested, 3813 and 9677. Oligo 84, which targets a PRC2-associated region of SMN2, did not exhibit an increase in full length SMN2 expression when delivered alone to cells.

SMN2-derived transcripts contain a unique DdeI restriction element introduced because of a nucleotide polymorphism not present in SMN1 and are differentiated from SMN1-derived transcripts because of the faster migration of the SMN2 products. Briefly, SMA fibroblasts were treated with oligonucleotides targeting PRC2-interacting regions with or without SSO at 30 nM each as described before. RT-PCR was carried out with an SMN exon 5 forward primer and an exon 8 reverse primer to generate cDNAs that were then digested with DdeI. The SMN1 transcript, if present, migrates at a slower rate than the DdeI-digested SMN2 transcript and is seen as the first band from the top of the gel. The second band from the top indicates full length SMN2 (accurately spliced form) and the third band indicates the incorrectly spliced SMN2delta7. (FIG. 5)

Results

In Spinal Muscular Atrophy patients, the SMN1 gene is often mutated in such a way that it is unable to correctly code the SMN protein—due to either a deletion encompassing at least a portion of exon 7 or to other mutations. SMA patients, however, generally retain at least one copy of the SMN2 gene (with many having 2 or more copies) that still expresses small amounts of SMN protein. The SMN2 gene has a C to T mutation (compared with SMN1) in exon 7 that alters splicing of its precursor mRNA such that exon 7 is spliced out at a high frequency. Consequently, only about 10% of the normal levels of full length SMN protein are produced from SMN2. (See FIG. 1)

Figure 3:
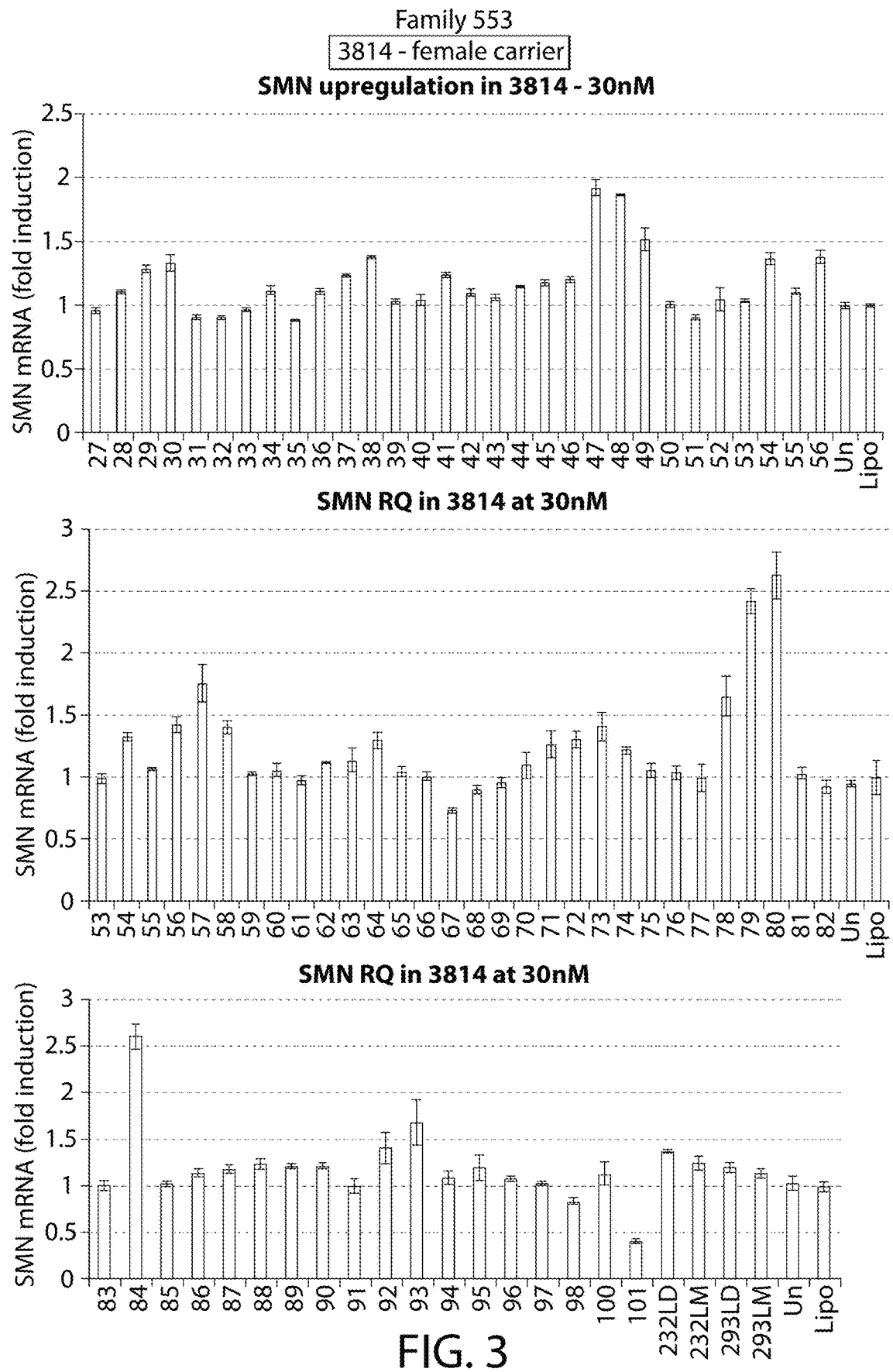
FIG. 3 depicts results of RT-PCR assays showing effects on SMN mRNA expression of oligonucleotides directed against a PRC2-associated region of SMN2 (oligos 1-52 and 59-101) and splice switching oligonucleotides (oligos 53-58) (PCR primers directed against exon 1 of SMN1/2.) in cell line 3814.
Figure 4:
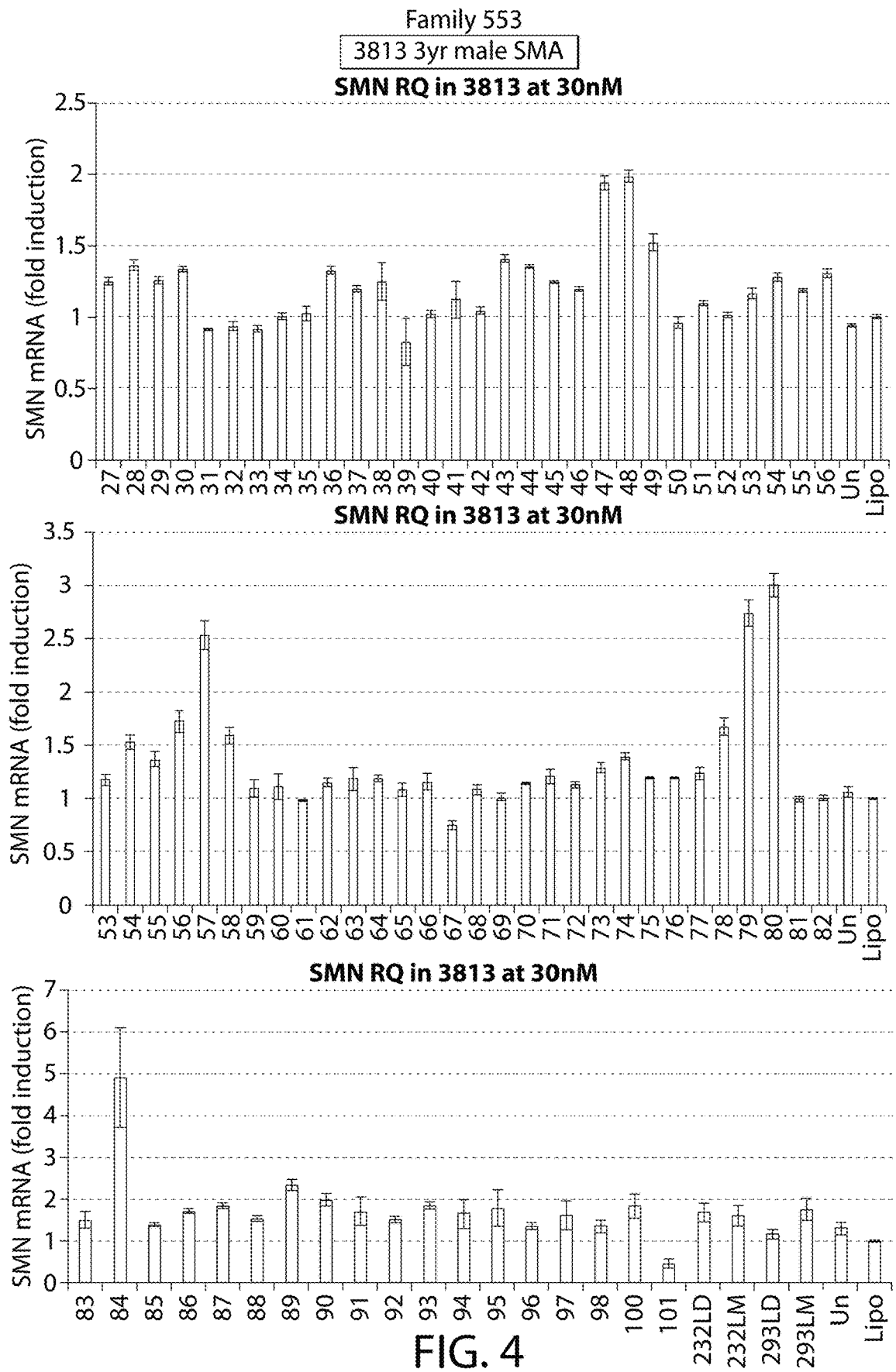
FIG. 4 depicts results of RT-PCR assays showing effects on SMN mRNA expression of oligonucleotides directed against a PRC2-associated region of SMN2 (oligos 1-52 and 59-101) and splice switching oligonucleotides (oligos 53-58) (PCR primers directed against exon 1 of SMN1/2.) in cell line 3813.

Six SMA fibroblast cell lines and one lymphoblast cell line were obtained from the Coriell Institute (FIG. 2). Cells were transfected with oligonucleotides (oligos 1-52 and 59-101) directed against a PRC2-associated region of SMN2 and RT-PCR assays were conducted to evaluate effects on SMN mRNA expression. (See FIGS. 3 and 4 for results in cell lines 3814 and 3813). In separate experiments, cells were transfected with oligonucleotides (oligos 53-58) directed at a splice control sequence in intron 7 of SMN2 and RT-PCR assays were conducted to evaluate effects on SMN mRNA expression (See FIGS. 3 and 4 for results in cell lines 3814 and 3813). Splice switching oligonucleotides (oligos 53-58) were found to increase expression of full length SMN2 based on a gel separation analysis of PCR products obtained following a DdeI restriction digest; whereas certain oligonucleotides directed against a PRC2-associated region of SMN2 did not. (FIG. 5)

Figure 6A:
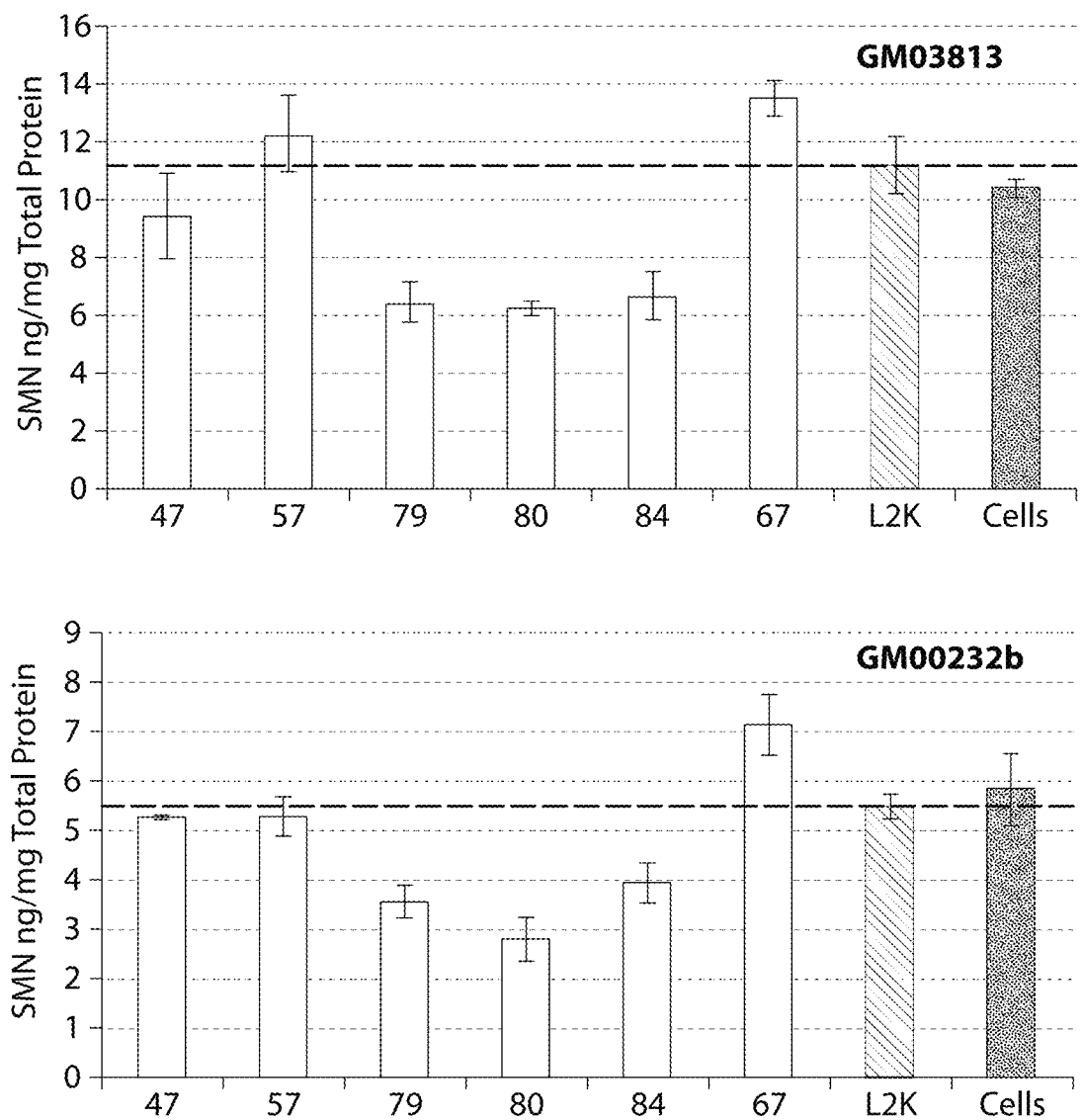
FIGS. 6A-6B provide the results of an SMN ELISA (Enzo) showing that certain oligonucleotides directed against a PRC2-associated region of SMN2 alone do not significantly increase SMN2 protein 24 h post-transfection in certain SMA patient fibroblasts (compared to Lipofectamine treated cells—dashed line).
Figure 6B:
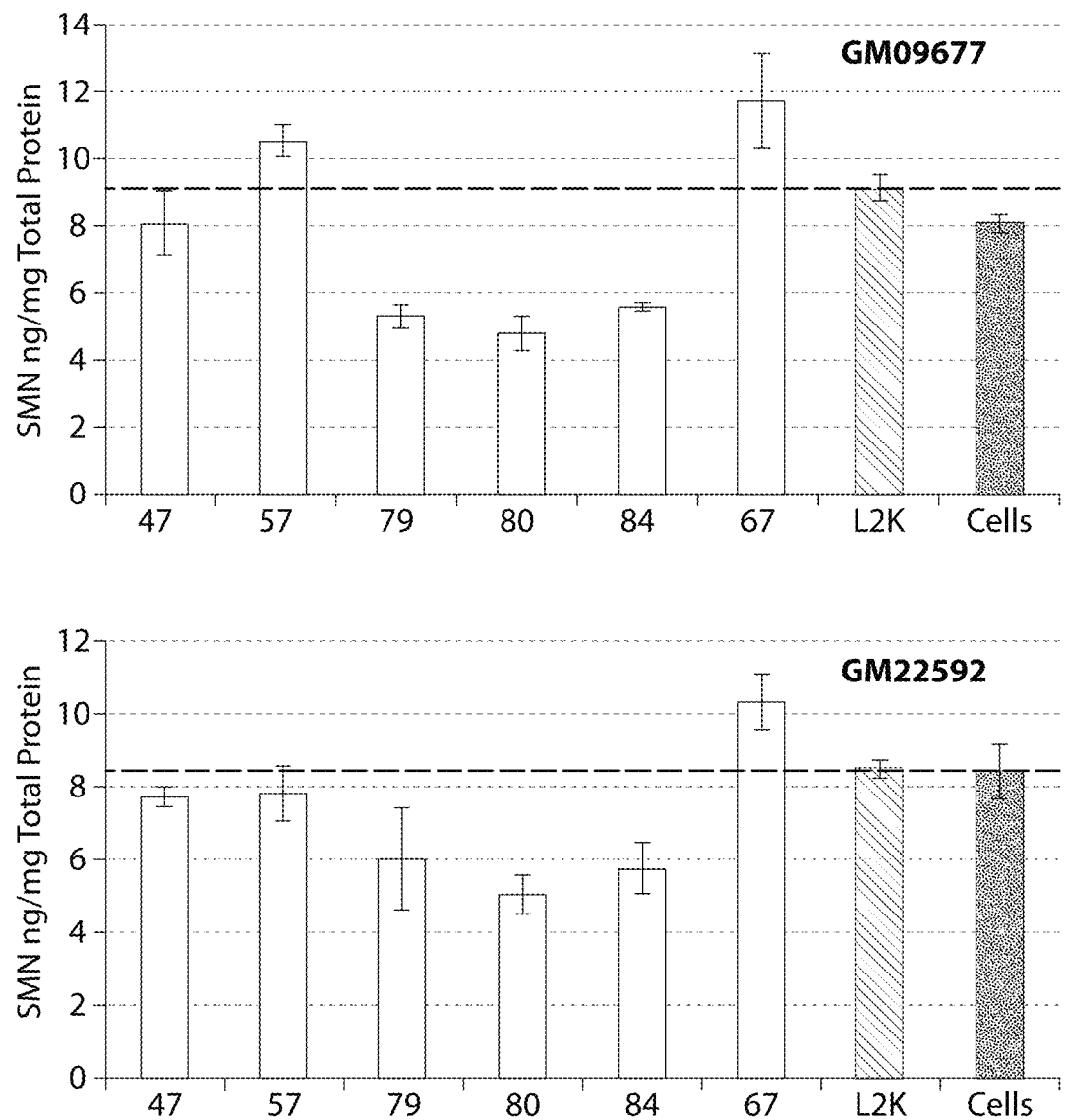
Figure 7A:
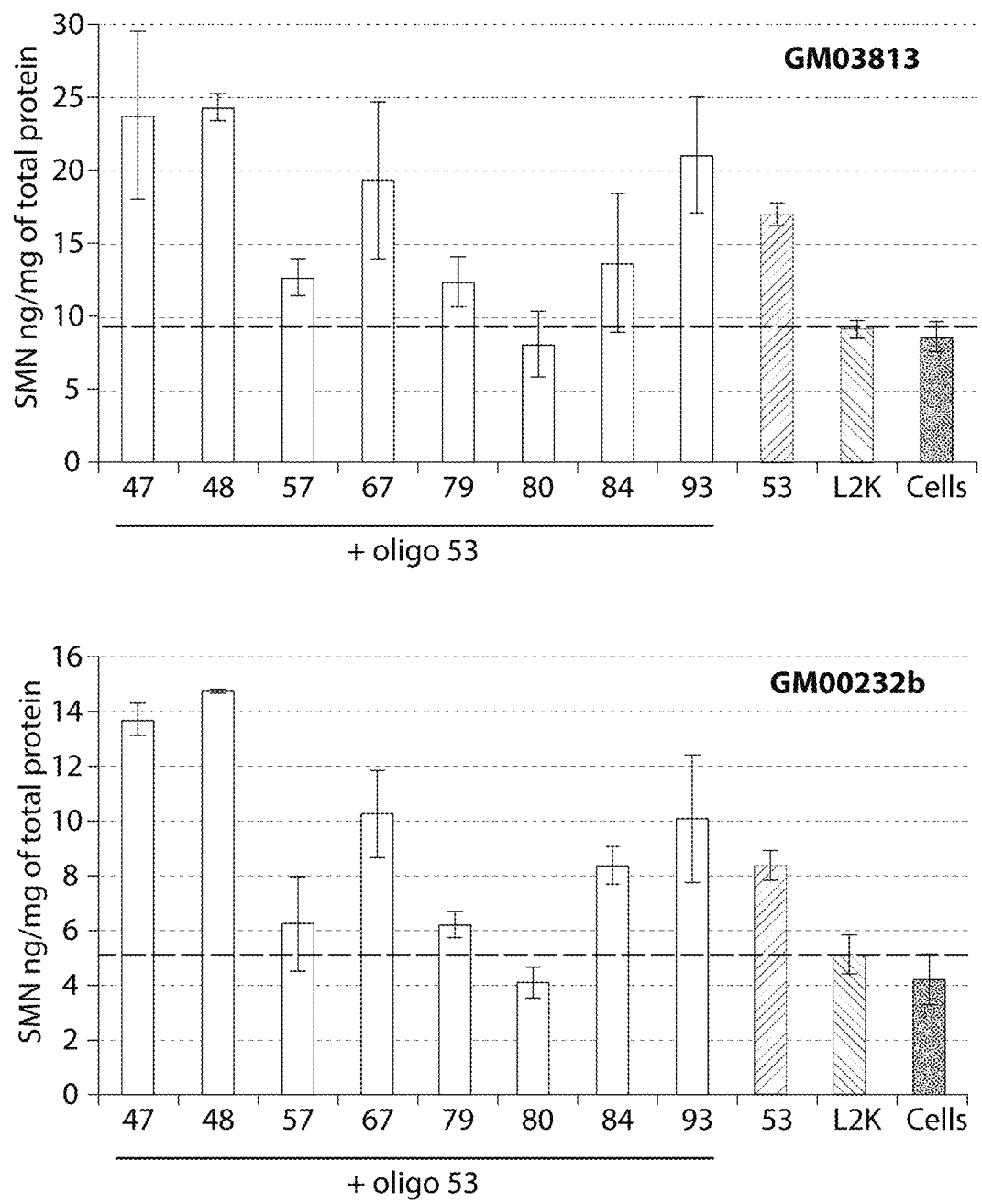
FIGS. 7A-7B provide the results of an SMN ELISA showing that oligonucleotides directed against a PRC2-associated region of SMN2 in combination with a splice switching oligonucleotide (oligo 53) significantly increase SMN2 protein 24 h post-transfection in SMA patient fibroblasts (compared to Lipofectamine treated cells—dashed line).
Figure 7B:
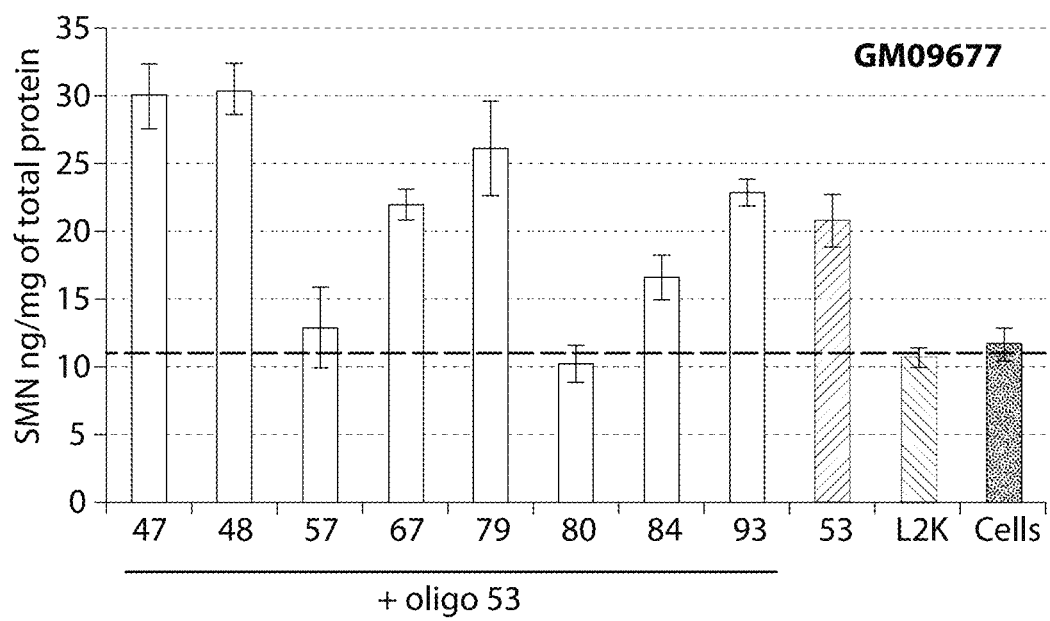
Figure 7B:
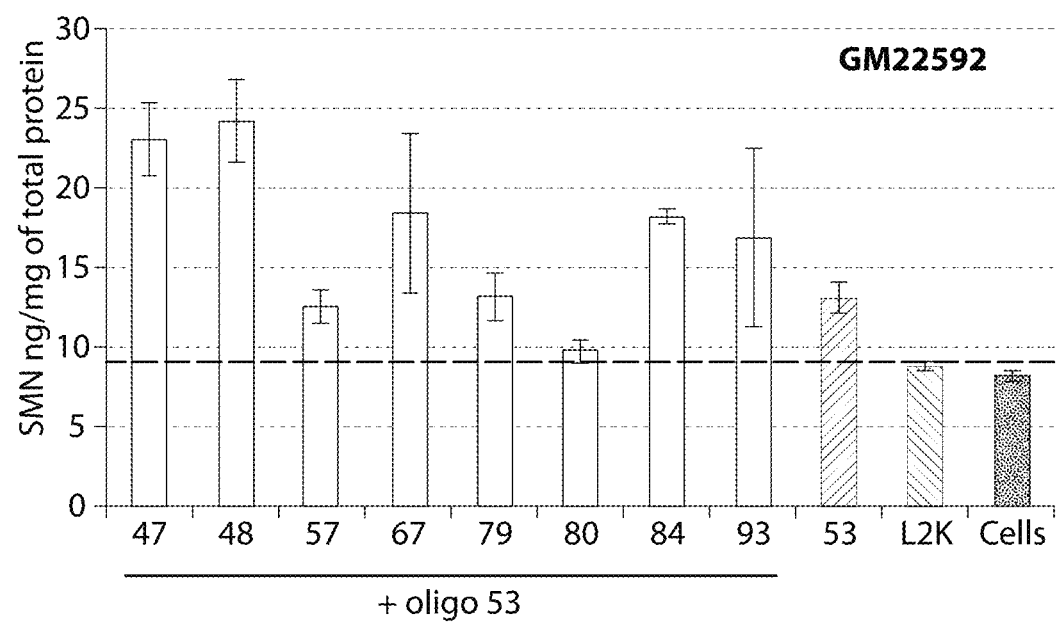
Figure 8A:
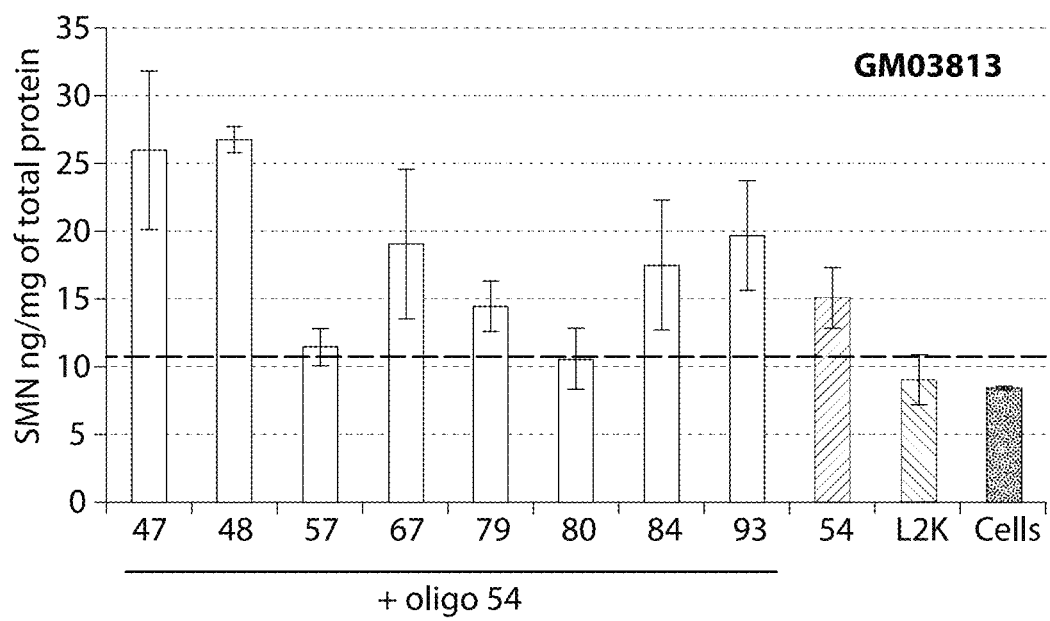
FIGS. 8A-8B provide the results of an SMN ELISA showing that oligonucleotides directed against a PRC2-associated region of SMN2 in combination with a splice switching oligonucleotide (oligo 54) significantly increase SMN2 protein 24 h post-transfection in SMA patient fibroblasts (compared to Lipofectamine treated cells—dashed line).
Figure 8A:
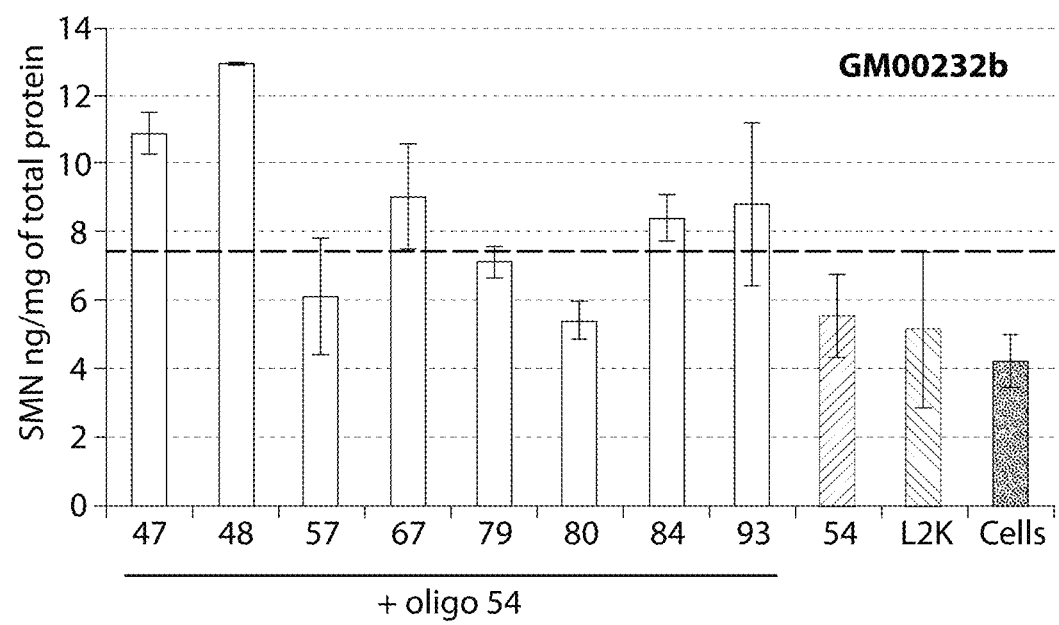
Figure 8B:
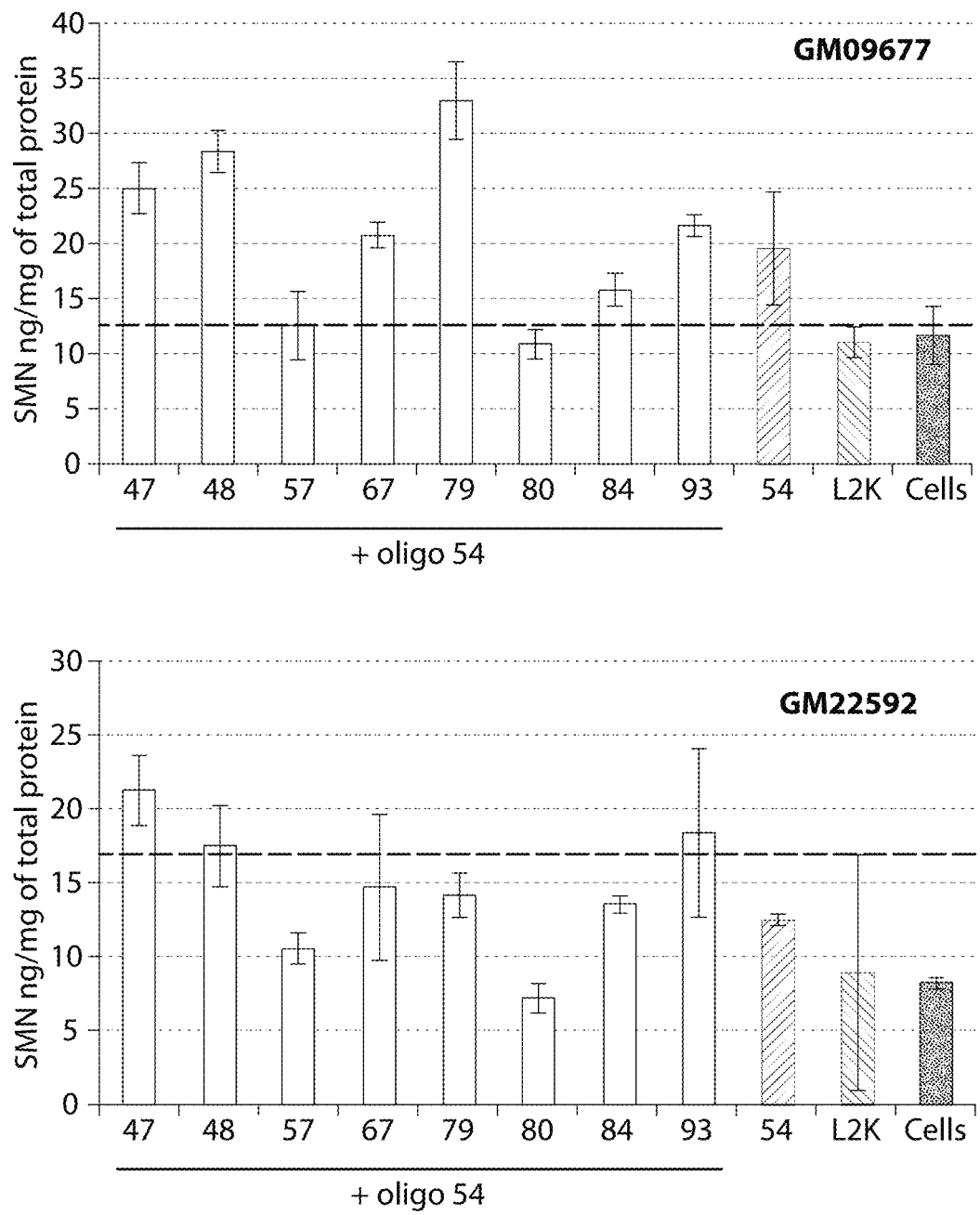
Figure 9:
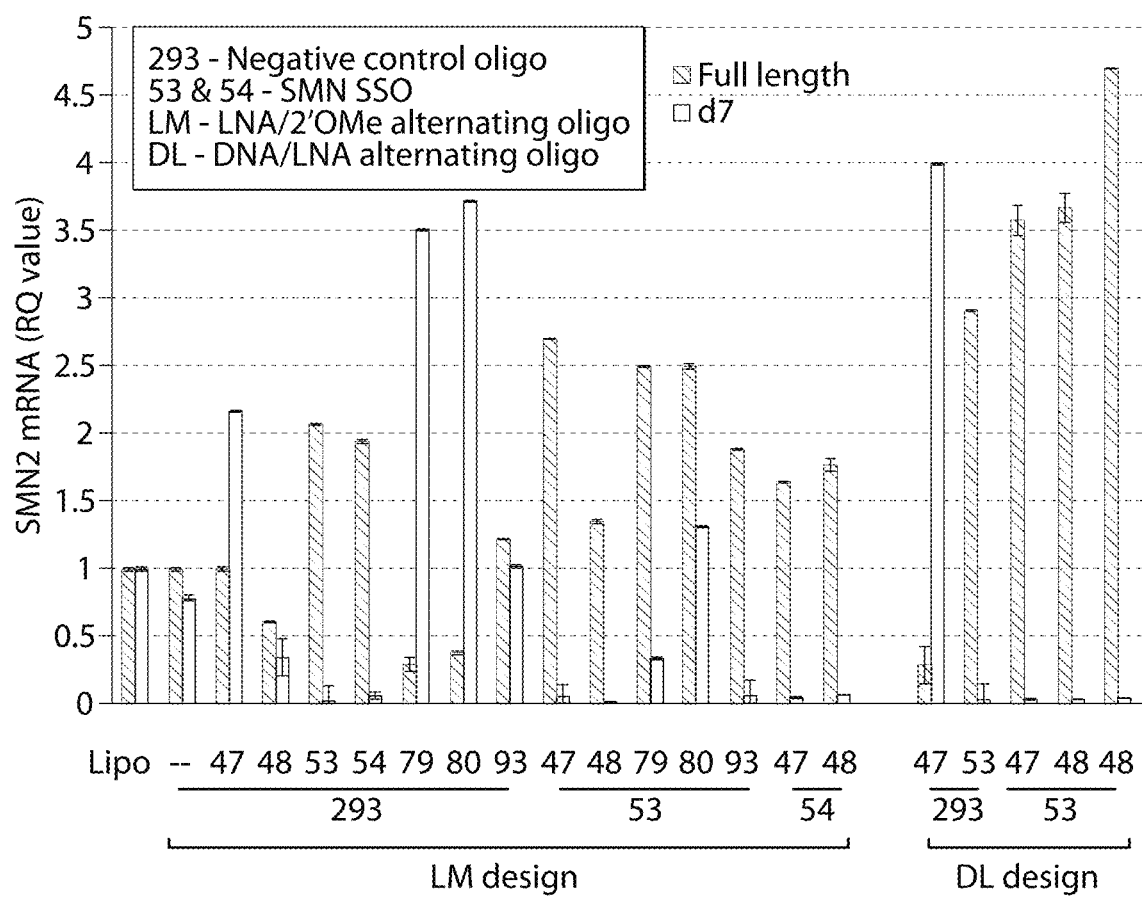
FIG. 9 provides results of an RT-PCR assay showing that oligonucleotides directed against a PRC2-associated region of SMN2 in combination with a splice switching oligonucleotide (oligo 53 or 54) significantly increase SMN2 protein 24 h post-transfection in SMA patient fibroblasts (compared to negative control oligo and Lipofectamine treated cells). LNA/2'OMe alternating oligonucleotide (LM design) and DNA/LNA alternating oligonucleotides (DL design) were tested.

SMN ELISA (Enzo) assays were conducted and revealed that certain oligonucleotides directed against a PRC2-associated region of SMN2 alone did not significantly increase full length SMN protein 24 h post-transfection in certain SMA patient fibroblasts. (FIGS. 6A-6B) However, the same SMN ELISA assays showed that oligonucleotides directed against a PRC2-associated region of SMN2 in combination with a splice switching oligonucleotide (oligo 53 or 54) significantly increase full length SMN protein 24 h post-transfection in SMA patient fibroblasts above that observed with splice switching oligonucleotides alone. (FIGS. 7A-B and 8A-8B). RT-PCR assays were conducted and showed that oligonucleotides directed against a PRC2-associated region of SMN2 in combination with a splice switching oligonucleotide (oligo 53 or 54) significantly increased SMN2 protein 24 h post-transfection in SMA patient fibroblasts. (FIG. 9.) These experiments were conducted modified oligonucleotides with either alternating LNA and 2'OMe nucleotides or alternating DNA and LNA nucleotides.

In summary, the results of Example 2 show that certain oligos targeting PRC2 associated regions of SMN2 induce SMN RNA expression (e.g., of the SMNA7 transcript) SMA patient-derived fibroblasts. The results also show that, in some embodiments, splice-switching oligos may not induce SMN RNA expression, but rather shift SMN RNA splicing to the full-length transcript. Finally, the results show that combination of splice switching oligos with PRC2-associated region targeting oligos substantially increases full length SMN protein in cells from SMA patients.

TABLE 4

Oligonucleotide sequences made for testing human cells obtained from subjects with Spinal Muscular Atrophy (See Table 3 for structural features of formatted sequence).

| Oligo Name | Base Sequence | Formatted Sequence | SeqID |
|---|---|---|---|
| SMN1-01 m03 | ATTCTCTTGA TGATGCTGAT | omeAs;omeUs;omeUs;omeCs;omeUs;omeCs;omeUs;omeUs;omeGs; omeAs;omeUs;omeGs;omeAs;omeUs;omeGs;omeCs;omeUs;omeGs; omeAs;omeU-Sup | 13062 |
| SMN1-02 m03 | TTCTCTTGAT GATGCTGATG | omeUs;omeUs;omeCs;omeUs;omeCs;omeUs;omeUs;omeGs;omeAs; omeUs;omeGs;omeAs;omeUs;omeGs;omeCs;omeUs;omeGs;omeAs; omeUs;omeG-Sup | 13063 |
| SMN1-03 m03 | TCTCTTGATG ATGCTGATGC | omeUs;omeCs;omeUs;omeCs;omeUs;omeUs;omeGs;omeAs;omeUs; omeGs;omeAs;omeUs;omeGs;omeCs;omeUs;omeGs;omeAs;omeUs; omeGs;omeC-Sup | 13064 |
| SMN1-04 m03 | CTCTTGATGA TGCTGATGCT | omeCs;omeUs;omeCs;omeUs;omeUs;omeGs;omeAs;omeUs;omeGs; omeAs;omeUs;omeGs;omeCs;omeUs;omeGs;omeAs;omeUs;omeGs; omeCs;omeU-Sup | 13065 |
| SMN1-05 m03 | TCTTGATGAT GCTGATGCTT | omeUs;omeCs;omeUs;omeUs;omeGs;omeAs;omeUs;omeGs;omeAs; omeUs;omeGs;omeCs;omeUs;omeGs;omeAs;omeUs;omeGs;omeCs; omeUs;omeU-Sup | 13066 |
| SMN1-06 m03 | CTTGATGATG CTGATGCTTT | omeCs;omeUs;omeUs;omeGs;omeAs;omeUs;omeGs;omeAs;omeUs; omeGs;omeCs;omeUs;omeGs;omeAs;omeUs;omeGs;omeCs;omeUs; omeUs;omeU-Sup | 13067 |

TABLE 4-continued

Oligonucleotide sequences made for testing human cells
obtained from subjects with Spinal Muscular Atrophy
(See Table 3 for structural features of formatted sequence).

| Oligo Name | Base Sequence | Formatted Sequence | SeqID |
|---|---|---|---|
| SMN1-07 m03 | TTGATGATGC TGATGCTTTG | omeUs;omeUs;omeGs;omeAs;omeUs;omeGs;omeAs;omeUs;omeGs; omeCs;omeUs;omeGs;omeAs;omeUs;omeGs;omeCs;omeUs;omeUs; omeUs;omeG-Sup | 13068 |
| SMN1-08 m03 | TGATGATGCT GATGCTTTGG | omeUs;omeGs;omeAs;omeUs;omeGs;omeAs;omeUs;omeGs;omeCs; omeUs;omeGs;omeAs;omeUs;omeGs;omeCs;omeUs;omeUs;omeUs; omeGs;omeG-Sup | 13069 |
| SMN1-09 m03 | GATGATGCTG ATGCTTTGGG | omeGs;omeAs;omeUs;omeGs;omeAs;omeUs;omeGs;omeCs;omeUs; omeGs;omeAs;omeUs;omeGs;omeCs;omeUs;omeUs;omeUs;omeGs; omeGs;omeG-Sup | 13070 |
| SMN1-10 m03 | ATGATGCTGA TGCTTTGGGA | omeAs;omeUs;omeGs;omeAs;omeUs;omeGs;omeCs;omeUs;omeGs; omeAs;omeUs;omeGs;omeCs;omeUs;omeUs;omeUs;omeGs;omeGs; omeGs;omeA-Sup | 13071 |
| SMN1-11 m03 | TGATGCTGAT GCTTTGGGAA | omeUs;omeGs;omeAs;omeUs;omeGs;omeCs;omeUs;omeGs;omeAs; omeUs;omeGs;omeCs;omeUs;omeUs;omeUs;omeGs;omeGs;omeGs; omeAs;omeA-Sup | 13072 |
| SMN1-12 m03 | GATGCTGATG CTTTGGGAAG | omeGs;omeAs;omeUs;omeGs;omeCs;omeUs;omeGs;omeAs;omeUs; omeGs;omeCs;omeUs;omeUs;omeUs;omeGs;omeGs;omeGs;omeAs; omeAs;omeG-Sup | 13073 |
| SMN1-13 m03 | ATGCTGATGC TTTGGGAAGT | omeAs;omeUs;omeGs;omeCs;omeUs;omeGs;omeAs;omeUs;omeGs; omeCs;omeUs;omeUs;omeUs;omeGs;omeGs;omeGs;omeAs;omeAs; omeGs;omeU-Sup | 13074 |
| SMN1-14 m03 | TGCTGATGCT TTGGGAAGTA | omeUs;omeGs;omeCs;omeUs;omeGs;omeAs;omeUs;omeGs;omeCs; omeUs;omeUs;omeUs;omeGs;omeGs;omeGs;omeAs;omeAs;omeGs; omeUs;omeA-Sup | 13075 |
| SMN1-15 m03 | GCTGATGCTT TGGGAAGTAT | omeGs;omeCs;omeUs;omeGs;omeAs;omeUs;omeGs;omeCs;omeUs; omeUs;omeUs;omeGs;omeGs;omeGs;omeAs;omeAs;omeGs;omeUs; omeAs;omeU-Sup | 13076 |
| SMN1-16 m03 | CTGATGCTTT GGGAAGTATG | omeCs;omeUs;omeGs;omeAs;omeUs;omeGs;omeCs;omeUs;omeUs; omeUs;omeGs;omeGs;omeGs;omeAs;omeAs;omeGs;omeUs;omeAs; omeUs;omeG-Sup | 13077 |
| SMN1-17 m03 | TGATGCTTTG GGAAGTATGT | omeUs;omeGs;omeAs;omeUs;omeGs;omeCs;omeUs;omeUs;omeUs; omeGs;omeGs;omeGs;omeAs;omeAs;omeGs;omeUs;omeAs;omeUs; omeGs;omeU-Sup | 13078 |
| SMN1-18 m03 | GATGCTTTGG GAAGTATGTT | omeGs;omeAs;omeUs;omeGs;omeCs;omeUs;omeUs;omeUs;omeGs; omeGs;omeGs;omeAs;omeAs;omeGs;omeUs;omeAs;omeUs;omeGs; omeUs;omeU-Sup | 13079 |
| SMN1-19 m03 | ATGCTTTGGG AAGTATGTTA | omeAs;omeUs;omeGs;omeCs;omeUs;omeUs;omeUs;omeGs;omeGs; omeGs;omeAs;omeAs;omeGs;omeUs;omeAs;omeUs;omeGs;omeUs; omeUs;omeA-Sup | 13080 |
| SMN1-20 m03 | TGCTTTGGGA AGTATGTTAA | omeUs;omeGs;omeCs;omeUs;omeUs;omeUs;omeGs;omeGs;omeGs; omeAs;omeAs;omeGs;omeUs;omeAs;omeUs;omeGs;omeUs;omeUs; omeAs;omeA-Sup | 13081 |
| SMN1-21 m03 | GCTTTGGGAA GTATGTTAAT | omeGs;omeCs;omeUs;omeUs;omeUs;omeGs;omeGs;omeGs;omeAs; omeAs;omeGs;omeUs;omeAs;omeUs;omeGs;omeUs;omeUs;omeAs; omeAs;omeU-Sup | 13082 |
| SMN1-22 m03 | CTTTGGGAAG TATGTTAATT | omeCs;omeUs;omeUs;omeUs;omeGs;omeGs;omeGs;omeAs;omeAs; omeGs;omeUs;omeAs;omeUs;omeGs;omeUs;omeUs;omeAs;omeAs; omeUs;omeU-Sup | 13083 |
| SMN1-23 m03 | TTTGGGAAGT ATGTTAATTT | omeUs;omeUs;omeUs;omeGs;omeGs;omeGs;omeAs;omeAs;omeGs; omeUs;omeAs;omeUs;omeGs;omeUs;omeUs;omeAs;omeAs;omeUs; omeUs;omeU-Sup | 13084 |
| SMN1-24 m03 | TTGGGAAGTA TGTTAATTTC | omeUs;omeUs;omeGs;omeGs;omeGs;omeAs;omeAs;omeGs;omeUs; omeAs;omeUs;omeGs;omeUs;omeUs;omeAs;omeAs;omeUs;omeUs; omeUs;omeC-Sup | 13085 |

TABLE 4-continued

Oligonucleotide sequences made for testing human cells
obtained from subjects with Spinal Muscular Atrophy
(See Table 3 for structural features of formatted sequence).

| Oligo Name | Base Sequence | Formatted Sequence | SeqID |
|---|---|---|---|
| SMN1-25 m03 | TGGGAAGTAT GTTAATTTCA | omeUs;omeGs;omeGs;omeGs;omeAs;omeAs;omeGs;omeUs;omeAs; omeUs;omeGs;omeUs;omeUs;omeAs;omeAs;omeUs;omeUs;omeUs; omeCs;omeA-Sup | 13086 |
| SMN1-26 m03 | GGGAAGTATG TTAATTTCAT | omeGs;omeGs;omeGs;omeAs;omeAs;omeGs;omeUs;omeAs;omeUs; omeGs;omeUs;omeUs;omeAs;omeAs;omeUs;omeUs;omeUs;omeCs; omeAs;omeU-Sup | 13087 |
| SMN1-27 m01 | ATTCTCTTGA TGATG | InaAs;omeUs;InaTs;omeCs;InaTs;omeCs;InaTs;omeUs;InaGs; omeAs;InaTs;omeGs;InaAs;omeUs;InaG-Sup | 11374 |
| SMN1-28 m01 | TTCTCTTGAT GATGC | InaTs;omeUs;InaCs;omeUs;InaCs;omeUs;InaTs;omeGs;InaAs; omeUs;InaGs;omeAs;InaTs;omeGs;InaC-Sup | 11375 |
| SMN1-29 m01 | TCTCTTGATG ATGCT | InaTs;omeCs;InaTs;omeCs;InaTs;omeUs;InaGs;omeAs;InaTs; omeGs;InaAs;omeUs;InaGs;omeCs;InaT-Sup | 11376 |
| SMN1-30 m01 | CTCTTGATGA TGCTG | InaCs;omeUs;InaCs;omeUs;InaTs;omeAs;InaTs;omeGs;InaGs; omeAs;InaTs;omeGs;InaCs;omeUs;InaG-Sup | 11377 |
| SMN1-31 m01 | TCTTGATGAT GCTGA | InaTs;omeCs;InaTs;omeUs;InaGs;omeAs;InaTs;omeGs;InaAs; omeUs;InaGs;omeCs;InaTs;omeGs;InaA-Sup | 11378 |
| SMN1-32 m01 | CTTGATGATG CTGAT | InaCs;omeUs;InaTs;omeGs;InaAs;omeUs;InaGs;omeAs;InaTs; omeGs;InaCs;omeUs;InaGs;omeAs;InaT-Sup | 11379 |
| SMN1-33 m01 | TTGATGATGC TGATG | InaTs;omeUs;InaGs;omeAs;InaTs;omeGs;InaAs;omeUs;InaGs; omeCs;InaTs;omeGs;InaAs;omeUs;InaG-Sup | 11380 |
| SMN1-34 m01 | TGATGATGCT GATGC | InaTs;omeGs;InaAs;omeUs;InaGs;omeAs;InaTs;omeGs;InaCs; omeUs;InaGs;omeAs;InaTs;omeGs;InaC-Sup | 11381 |
| SMN1-35 m01 | GATGATGCTG ATGCT | InaGs;omeAs;InaTs;omeGs;InaAs;omeUs;InaGs;omeCs;InaTs; omeGs;InaAs;omeUs;InaGs;omeCs;InaT-Sup | 11382 |
| SMN1-36 m01 | ATGATGCTGA TGCTT | InaAs;omeUs;InaGs;omeAs;InaTs;omeGs;InaCs;omeUs;InaGs; omeAs;InaTs;omeGs;InaCs;omeUs;InaT-Sup | 11383 |
| SMN1-37 m01 | TGATGCTGAT GCTTT | InaTs;omeGs;InaAs;omeUs;InaGs;omeCs;InaTs;omeGs;InaAs; omeUs;InaGs;omeCs;InaTs;omeUs;InaT-Sup | 11384 |
| SMN1-38 m01 | GATGCTGATG CTTTG | InaGs;omeAs;InaTs;omeGs;InaCs;omeUs;InaGs;omeAs;InaTs; omeGs;InaCs;omeUs;InaTs;omeUs;InaG-Sup | 11385 |
| SMN1-39 m01 | ATGCTGATGC TTTGG | InaAs;omeUs;InaGs;omeCs;InaTs;omeGs;InaAs;omeUs;InaGs; omeCs;InaTs;omeUs;InaTs;omeGs;InaG-Sup | 11386 |
| SMN1-40 m01 | TGCTGATGCT TTGGG | InaTs;omeGs;InaCs;omeUs;InaGs;omeAs;InaTs;omeGs;InaCs; omeUs;InaTs;omeUs;InaGs;omeGs;InaG-Sup | 11387 |
| SMN1-41 m01 | GCTGATGCTT TGGGA | InaGs;omeCs;InaTs;omeGs;InaAs;omeUs;InaGs;omeCs;InaTs; omeUs;InaTs;omeGs;InaGs;omeGs;InaA-Sup | 11388 |
| SMN1-42 m01 | CTGATGCTTT GGGAA | InaCs;omeUs;InaGs;omeAs;InaTs;omeGs;InaCs;omeUs;InaTs; omeUs;InaTs;omeGs;InaGs;omeGs;InaA-Sup | 11389 |
| SMN1-43 m01 | TGATGCTTTG GGAAG | InaTs;omeGs;InaAs;omeUs;InaGs;omeCs;InaTs;omeUs;InaTs; omeGs;InaGs;omeGs;InaAs;omeAs;InaG-Sup | 11390 |
| SMN1-44 m01 | GATGCTTTGG GAAGT | InaGs;omeAs;InaTs;omeGs;InaCs;omeUs;InaTs;omeUs;InaGs; omeGs;InaGs;omeAs;InaAs;omeGs;InaT-Sup | 11391 |
| SMN1-45 m01 | ATGCTTTGGG AAGTA | InaAs;omeUs;InaGs;omeCs;InaTs;omeUs;InaTs;omeGs;InaGs; omeGs;InaAs;omeAs;InaGs;omeUs;InaA-Sup | 11392 |
| SMN1-46 m01 | TGCTTTGGGA AGTAT | InaTs;omeGs;InaCs;omeUs;InaTs;omeUs;InaGs;omeGs;InaGs; omeAs;InaAs;omeGs;InaTs;omeAs;InaT-Sup | 11393 |
| SMN1-47 m02 | GCTTTGGGAA GTATG | dGs;InaCs;dTs;InaTs;dTs;InaGs;dGs;InaGs;dAs;InaAs;dGs; InaTs;dAs;InaTs;dG-Sup | 11394 |
| SMN1-47 m01 | GCTTTGGGAA GTATG | InaGs;omeCs;InaTs;omeUs;InaTs;omeGs;InaGs;omeGs;InaAs; omeAs;InaGs;omeUs;InaAs;omeUs;InaG-Sup | 11394 |

TABLE 4-continued

Oligonucleotide sequences made for testing human cells
obtained from subjects with Spinal Muscular Atrophy
(See Table 3 for structural features of formatted sequence).

| Oligo Name | Base Sequence | Formatted Sequence | SeqID |
|---|---|---|---|
| SMN1-48 m05 | CTTTGGGAAG TATGT | dCs;InaTs;dTs;InaTs;dGs;InaGs;dGs;InaAs;dAs;InaGs;dTs; InaAs;dTs;InaGs;dT-Sup | 11395 |
| SMN1-48 m01 | CTTTGGGAAG TATGT | InaCs;omeUs;InaTs;omeUs;omeGs;InaGs;omeAs;InaAs; omeGs;InaTs;omeAs;InaTs;omeGs;InaT-Sup | 11395 |
| SMN1-49 m01 | TTTGGGAAGT ATGTT | InaTs;omeUs;InaTs;omeGs;omeGs;InaAs;omeAs;InaGs; omeUs;InaAs;omeUs;InaGs;omeUs;InaT-Sup | 11396 |
| SMN1-50 m01 | TTGGGAAGTA TGTTA | InaTs;omeUs;InaGs;omeGs;omeAs;InaAs;omeGs;InaTs; omeAs;InaTs;omeGs;InaTs;omeUs;InaA-Sup | 11397 |
| SMN1-51 m01 | TGGGAAGTAT GTTAA | InaTs;omeGs;InaGs;omeGs;InaAs;omeAs;InaGs;omeUs;InaAs; omeUs;InaGs;omeUs;InaTs;omeAs;InaA-Sup | 11398 |
| SMN1-52 m01 | GGGAAGTATG TTAAT | InaGs;omeGs;InaAs;omeAs;omeGs;InaTs;omeAs;InaTs; omeGs;InaTs;omeUs;InaAs;omeAs;InaT-Sup | 11399 |
| SMN1-53 m02 | TCACTTTCAT AATGCTGG | dTs;InaCs;dAs;InaCs;dTs;InaTs;dTs;InaCs;dAs;InaTs;dAs; InaAs;dTs;InaGs;dCs;InaTs;dGs;InaG-Sup | 13088 |
| SMN1-53 m12 | TCACTTTCAT AATGCTGG | InaTs;dCs;InaAs;dCs;InaTs;dTs;InaTs;dCs;InaAs;dTs; InaAs;dAs;InaTs;dGs;InaCs;dTs;InaGs;dG-Sup | 13088 |
| SMN1-54 m01 | TCACTTTCAT AATGCTGG | InaTs;omeCs;InaAs;omeCs;InaTs;omeUs;InaTs;omeCs;InaAs; omeUs;InaAs;omeAs;InaTs;omeGs;InaCs;omeUs;InaGs;omeG-Sup | 13088 |
| SMN1-53 m03 | TCACTTTCAT AATGCTGG | omeUs;omeCs;omeAs;omeCs;omeUs;omeUs;omeUs;omeCs;omeAs; omeUs;omeAs;omeAs;omeUs;omeGs;omeCs;omeUs;omeGs;omeG-Sup | 13088 |
| SMN1-55 m01 | TCACTTTCAT AATGC | InaTs;omeCs;InaAs;omeCs;InaTs;omeUs;InaTs;omeCs;InaAs; omeUs;InaAs;omeAs;InaTs;omeGs;InaC-Sup | 13089 |
| SMN1-56 m01 | CACTTTCATA ATGCT | InaCs;omeAs;InaCs;omeUs;InaTs;omeUs;InaCs;omeAs;InaTs; omeAs;InaAs;omeUs;InaGs;omeCs;InaT-Sup | 13090 |
| SMN1-57 m02 | ACTTTCATAA TGCTG | dAs;InaCs;dTs;InaTs;dTs;InaCs;dAs;InaTs;dAs;InaAs;dTs; InaGs;dCs;InaTs;dG-Sup | 13091 |
| SMN1-57 m01 | ACTTTCATAA TGCTG | InaAs;omeCs;InaTs;omeUs;InaTs;omeCs;InaAs;omeUs;InaAs; omeAs;InaTs;omeGs;InaCs;omeUs;InaG-Sup | 13091 |
| SMN1-58 m01 | CTTTCATAAT GCTGG | InaCs;omeUs;InaTs;omeUs;InaCs;omeAs;InaTs;omeAs;InaAs; omeUs;InaGs;omeCs;InaTs;omeGs;InaG-Sup | 13092 |
| SMN1-59 m01 | AGACCAGTTT TACCT | InaAs;omeGs;InaAs;omeCs;omeAs;InaGs;omeUs;InaTs; omeUs;InaTs;omeAs;InaCs;omeCs;InaT-Sup | 3650 |
| SMN1-60 m01 | CCTAGCTACT TTGAA | InaCs;omeCs;InaTs;omeAs;InaGs;omeCs;InaTs;omeAs;InaCs; omeUs;InaTs;omeUs;InaGs;omeAs;InaA-Sup | 13093 |
| SMN1-61 m01 | TCCTAGCTAC TTTGA | InaTs;omeCs;InaCs;omeUs;InaAs;omeGs;InaCs;omeUs;InaAs; omeCs;InaTs;omeUs;InaTs;omeGs;InaA-Sup | 13094 |
| SMN1-62 m01 | GAAATATTCC TTATA | InaGs;omeAs;InaAs;omeAs;InaTs;omeAs;InaTs;omeUs;InaCs; omeCs;InaTs;omeUs;InaAs;omeUs;InaA-Sup | 10065 |
| SMN1-63 m01 | AAATATTCCT TATAG | InaAs;omeAs;InaAs;omeUs;InaAs;omeUs;InaTs;omeCs;InaCs; omeUs;InaTs;omeAs;InaTs;omeAs;InaG-Sup | 10066 |
| SMN1-64 m01 | AATATTCCTT ATAGC | InaAs;omeAs;InaTsiomeAs;InaTs;omeUs;InaCs;omeCs;InaTs; omeUs;InaAs;omeUs;InaAs;omeUs;InaC-Sup | 10067 |
| SMN1-65 m01 | ATATTCCTTA TAGCC | InaAs;omeUs;InaAs;omeUs;InaTs;omeCs;InaCs;omeUs;InaTs; omeAs;InaTs;omeAs;InaGs;omeCs;InaC-Sup | 10068 |
| SMN1-66 m01 | TATTCCTTAT AGCCA | InaTs;omeAs;InaTs;omeUs;InaCs;omeCs;InaTs;omeUs;InaAs; omeUs;InaAs;omeGs;InaCs;omeCs;InaA-Sup | 10069 |

TABLE 4-continued

Oligonucleotide sequences made for testing human cells
obtained from subjects with Spinal Muscular Atrophy
(See Table 3 for structural features of formatted sequence).

| Oligo Name | Base Sequence | Formatted Sequence | SeqID |
|---|---|---|---|
| SMN1-67 m01 | ATTCCTTATAGCCAG | InaAs;omeUs;InaTs;omeCs;InaCs;omeUs;InaTs;omeAs;InaTs;omeAs;InaGs;omeCs;InaCs;omeAs;InaG-Sup | 10070 |
| SMN1-68 m01 | TTCCTTATAGCCAGG | InaTs;omeUs;InaCs;omeCs;InaTs;omeUs;InaAs;omeUs;InaAs;omeGs;InaCs;omeCs;InaAs;omeGs;InaG-Sup | 10071 |
| SMN1-69 m01 | TCCTTATAGCCAGGT | InaTs;omeCs;InaCs;omeUs;InaTs;omeAs;InaTs;omeAs;InaGs;omeCs;InaCs;omeAs;InaGs;omeGs;InaT-Sup | 10072 |
| SMN1-70 m01 | CCTTATAGCCAGGTC | InaCs;omeCs;InaTs;omeUs;InaAs;omeUs;InaAs;omeGs;InaCs;omeCs;InaAs;omeGs;InaGs;omeUs;InaC-Sup | 10073 |
| SMN1-71 m01 | CTTATAGCCAGGTCT | InaCs;omeUs;InaTs;omeAs;InaTs;omeAs;InaGs;omeCs;InaCs;omeAs;InaGs;omeGs;InaTs;omeCs;InaT-Sup | 10074 |
| SMN1-72 m01 | TTATAGCCAGGTCTA | InaTs;omeUs;InaAs;omeUs;InaAs;omeGs;InaCs;omeCs;InaAs;omeGs;InaGs;omeUs;InaCs;omeUs;InaA-Sup | 10075 |
| SMN1-73 m01 | GCCAGGTCTAAAATT | InaGs;omeCs;InaCs;omeAs;InaGs;omeGs;InaTs;omeCs;InaTs;omeAs;InaAs;omeAs;InaAs;omeUs;InaT-Sup | 10080 |
| SMN1-74 m01 | CCAGGTCTAAAATTC | InaCs;omeCs;InaAs;omeGs;InaGs;omeUs;InaCs;omeUs;InaAs;omeAs;InaAs;omeAs;InaTs;omeUs;InaC-Sup | 10081 |
| SMN1-75 m01 | CAGGTCTAAAATTCA | InaCs;omeAs;InaGs;omeGs;InaTs;omeCs;InaTs;omeAs;InaAs;omeAs;InaAs;omeUs;InaTs;omeCs;InaA-Sup | 10082 |
| SMN1-76 m01 | GGTCTAAAATTCAAT | InaGs;omeGs;InaTs;omeCs;InaTs;omeAs;InaAs;omeAs;InaAs;omeUs;InaTs;omeCs;InaAs;omeAs;InaT-Sup | 10084 |
| SMN1-77 m01 | CTAAAATTCAATGGC | InaCs;omeUs;InaAs;omeAs;InaAs;omeAs;InaTs;omeUs;InaCs;omeAs;InaAs;omeUs;InaGs;omeGs;InaC-Sup | 10087 |
| SMN1-77 m03 | CTAAAATTCAATGGC | omeCs;omeUs;omeAs;omeAs;omeAs;omeAs;omeUs;omeUs;omeCs;omeAs;omeAs;omeUs;omeGs;omeGs;omeC-Sup | 10087 |
| SMN1-78 m01 | GGACCACCAGTAAGT | InaGs;omeGs;InaAs;omeCs;InaCs;omeAs;InaCs;omeCs;InaAs;omeGs;InaTs;omeAs;InaAs;omeGs;InaT-Sup | 10168 |
| SMN1-79 m02 | GACCACCAGTAAGTA | dGs;InaAs;dCs;InaCs;dAs;InaCs;dCs;InaAs;dGs;InaTs;dAs;InaAs;dGs;InaTs;dA-Sup | 10169 |
| SMN1-79 m01 | GACCACCAGTAAGTA | InaGs;omeAs;InaCs;omeCs;InaAs;omeCs;InaCs;omeAs;InaGs;omeUs;InaAs;omeAs;InaGs;omeUs;InaA-Sup | 10169 |
| SMN1-80 m02 | ACCACCAGTAAGTAA | dAs;InaCs;dCs;InaAs;dCs;dAs;InaCs;dTs;InaAs;dAs;InaGs;dTs;InaAs;dA-Sup | 10170 |
| SMN1-80 m01 | ACCACCAGTAAGTAA | InaAs;omeCs;InaCs;omeAs;InaCs;omeCs;InaAs;omeGs;InaTs;omeAs;InaAs;omeGs;InaTs;omeAs;InaA-Sup | 10170 |
| SMN1-81 m01 | TTCTGTTACCCAGAT | InaTs;omeUs;InaCs;omeUs;InaGs;omeUs;InaTs;omeAs;InaCs;omeCs;InaCs;omeAs;InaGs;omeAs;InaT-Sup | 10337 |
| SMN1-82 m01 | TCTGTTACCCAGATG | InaTs;omeCs;InaTs;omeGs;InaTs;omeUs;InaAs;omeCs;InaCs;omeCs;InaAs;omeGs;InaAs;omeUs;InaG-Sup | 10338 |
| SMN1-83 m01 | CTGTTACCCAGATGC | InaCs;omeUs;InaGs;omeUs;InaTs;omeAs;InaCs;omeCs;InaCs;omeAs;InaGs;omeAs;InaTs;omeGs;InaC-Sup | 10339 |
| SMN1-84 m02 | TTTTTAGGTATTAAC | dTs;InaTs;dTs;InaTs;dTs;InaAs;dGs;InaGs;dTs;InaAs;dTs;InaTs;dAs;InaAs;dC-Sup | 10763 |
| SMN1-84 m01 | TTTTTAGGTATTAAC | InaTs;omeUs;InaTs;omeUs;InaTs;omeAs;InaGs;omeGs;InaTs;omeAs;InaTs;omeUs;InaAs;omeAs;InaC-Sup | 10763 |
| SMN1-85 m01 | TTTTAGGTATTAACA | InaTs;omeUs;InaTs;omeUs;InaAs;omeGs;InaGs;omeUs;InaAs;omeUs;InaTs;omeAs;InaAs;omeCs;InaA-Sup | 10764 |
| SMN1-86 m01 | CATAGCTTCATAGTG | InaCs;omeAs;InaTs;omeAs;InaGs;omeCs;InaTs;omeUs;InaCs;omeAs;InaTs;omeAs;InaGs;omeUs;InaG-Sup | 10949 |

TABLE 4-continued

Oligonucleotide sequences made for testing human cells
obtained from subjects with Spinal Muscular Atrophy
(See Table 3 for structural features of formatted sequence).

| Oligo Name | Base Sequence | Formatted Sequence | SeqID |
|---|---|---|---|
| SMN1-87 m01 | TAGCTTCATA GTGGA | InaTs;omeAs;InaGs;omeCs;InaTs;omeUs;InaCs;omeAs;InaTs; omeAs;InaGs;omeUs;InaGs;omeGs;InaA-Sup | 10951 |
| SMN1-88 m01 | AGCTTCATAG TGGAA | InaAs;omeGs;InaCs;omeUs;InaTs;omeCs;InaAs;omeUs;InaAs; omeGs;InaTs;omeGs;InaGs;omeAs;InaA-Sup | 10952 |
| SMN1-89 m01 | GCTTCATAGT GGAAC | InaGs;omeCs;InaTs;omeUs;InaCs;omeAs;InaTs;omeAs;InaGs; omeUs;InaGs;omeGs;InaAs;omeAs;InaC-Sup | 10953 |
| SMN1-90 m01 | CTTCATAGTG GAACA | InaCs;omeUs;InaTs;omeCs;InaAs;omeUs;InaAs;omeGs;InaTs; omeGs;InaGs;omeAs;InaAs;omeCs;InaA-Sup | 10954 |
| SMN1-91 m01 | TCATGGTACA TGAGT | InaTs;omeCs;InaAs;omeUs;InaGs;omeGs;InaTs;omeAs;InaCs; omeAs;InaTs;omeGs;InaAs;omeGs;InaT-Sup | 11415 |
| SMN1-92 m01 | TGGTACATGA GTGGC | InaTs;omeGs;InaGs;omeUs;InaAs;omeCs;InaAs;omeUs;InaGs; omeAs;InaGs;omeUs;InaGs;omeGs;InaC-Sup | 11418 |
| SMN1-93 m02 | GGTACATGAG TGGCT | dGs;InaGs;dTs;InaAs;dCs;InaAs;dTs;InaGs;dAs;InaGs;dTs; InaGs;dGs;InaCs;dT-Sup | 11419 |
| SMN1-93 m01 | GGTACATGAG TGGCT | InaGs;omeGs;InaTs;omeAs;InaCs;omeAs;InaTs;omeGs;InaAs; omeGs;InaTs;omeGs;InaGs;omeCs;InaT-Sup | 11419 |
| SMN1-94 m01 | TACATGAGTG GCTAT | InaTs;omeAs;InaCs;omeAs;InaTs;omeGs;InaAs;omeGs;InaTs; omeGs;InaGs;omeCs;InaTs;omeAs;InaT-Sup | 11421 |
| SMN1-95 m01 | ACATGAGTGG CTATC | InaAs;omeCs;InaAs;omeUs;InaGs;omeAs;InaGs;omeUs;InaGs; omeGs;InaCs;omeUs;InaAs;omeUs;InaC-Sup | 11422 |
| SMN1-96 m01 | CATGAGTGGC TATCA | InaCs;omeAs;InaTs;omeGs;InaAs;omeGs;InaTs;omeGs;InaGs; omeCs;InaTs;omeAs;InaTs;omeCs;InaA-Sup | 11423 |
| SMN1-97 m01 | CTGGCTATTA TATGG | InaCs;omeUs;InaGs;omeGs;InaCs;omeUs;InaAs;omeUs;InaTs; omeAs;InaTs;omeAs;InaTs;omeGs;InaG-Sup | 11440 |
| SMN1-98 m01 | TGGCTATTAT ATGGT | InaTs;omeGs;InaGs;omeCs;InaTs;omeAs;InaTs;omeUs;InaAs; omeUs;InaAs;omeUs;InaGs;omeGs;InaT-Sup | 11441 |
| SMN1-99 m01 | GGCTATTATA TGGTA | InaGs;omeGs;InaCs;omeUs;InaAs;omeUs;InaTs;omeAs;InaTs; omeAs;InaTs;omeGs;InaGs;omeUs;InaA-Sup | 11442 |
| SMN1-100 m01 | GCTATTATAT GGTAA | InaGs;omeCs;InaTs;omeAs;InaTs;omeUs;InaAs;omeUs;InaAs; omeUs;InaGs;omeGs;InaTs;omeAs;InaA-Sup | 11443 |
| SMN1-101 m01 | GTATCATCTG TGTGT | InaGs;omeUs;InaAs;omeUs;InaCs;omeAs;InaTs;omeCs;InaTs; omeGs;InaTs;omeGs;InaTs;omeGs;InaT-Sup | 12369 |
| SMN1-102 m01 | GCTTTGGGAA GTATGTTTTT CACTTTCATA ATGCTGG | InaGs;omeCs;InaTs;omeUs;InaTs;omeGs;InaGs;omeGs;InaAs; omeAs;InaGs;omeUs;InaAs;omeUs;InaG;dT;dT;dT;dT;InaTs; omeCs;InaAs;omeCs;InaTs;omeUs;InaTs;omeCs;InaAs;omeUs; InaAs;omeAs;InaTs;omeGs;InaCs;omeUs;InaGs;omeG-Sup | 13097 |
| SMN1-103 m01 | CTTTGGGAAG TATGTTTTTT CACTTTCATA ATGCTGG | InaCs;omeUs;InaTs;omeUs;InaTs;omeGs;InaGs;omeGs;InaAs; omeAs;InaGs;omeUs;InaAs;omeUs;InaT;dT;dT;dT;dT;InaTs; omeCs;InaAs;omeCs;InaTs;omeUs;InaTs;omeCs;InaAs;omeUs; InaAs;omeAs;InaTs;omeGs;InaCs;omeUs;InaGs;omeG-Sup | 13102 |
| SMN1-104 m01 | GGTACATGAG TGGCTTTTTT CACTTTCATA ATGCTGG | InaGs;omeGs;InaTs;omeAs;InaCs;omeAs;InaTs;omeGs;InaAs; omeGs;InaTs;omeGs;InaGs;omeCs;InaT;dT;dT;dT;dT;InaTs; omeCs;InaAs;omeCs;InaTs;omeUs;InaTs;omeCs;InaAs;omeUs; InaAs;omeAs;InaTs;omeGs;InaCs;omeUs;InaGs;omeG-Sup | 13099 |
| SMN1-105 m01 | TGATGCTGAT GCTTTTTTTC TAAAATTCAA TGGC | InaTs;omeGs;InaAs;omeUs;InaGs;omeCs;InaTs;omeGs;InaAs; omeUs;InaGs;omeCs;InaTs;omeUs;InaT;dT;dT;dT;dT;InaCs; omeUs;InaAs;omeAs;InaAs;omeAs;InaTs;omeUs;InaCs;omeAs; InaAs;omeUs;InaGs;omeGs;InaC-Sup | 13103 |
| SMN1-106 m01 | CTAAAATTCA ATGGCTTTTC TAAAATTCAA TGGC | InaCs;omeUs;InaAs;omeAs;InaAs;omeAs;InaTs;omeUs;InaCs; omeAs;InaUs;InaGs;omeGs;InaC;dT;dT;dT;dT;InaCs; omeUs;InaAs;omeAs;InaAs;omeAs;InaTs;omeUs;InaCs;omeAs; InaAs;omeUs;InaGs;omeGs;InaC-Sup | 13104 |

TABLE 4-continued

Oligonucleotide sequences made for testing human cells
obtained from subjects with Spinal Muscular Atrophy
(See Table 3 for structural features of formatted sequence).

| Oligo Name | Base Sequence | Formatted Sequence | SeqID |
|---|---|---|---|
| SMN1-107 m01 | CTGTTACCCA GATGCTTTTC TAAAATTCAA TGGC | InaCs;omeUs;InaGs;omeUs;InaTs;omeAs;InaCs;omeCs;InaCs; omeAs;InaGs;omeAs;InaTs;omeGs;InaC;dT;dT;dT;dT;InaCs; omeUs;InaAs;omeAs;InaAs;omeAs;InaTs;omeUs;InaCs;omeAs; InaAs;omeUs;InaGs;omeGs;InaC-Sup | 13105 |
| SMN1-108 m01 | CTTCATAGTG GAACATTTTC TAAAATTCAA TGGC | InaCs;omeUs;InaTs;omeCs;InaAs;omeUs;InaAs;omeGs;InaTs; omeGs;InaGs;omeAs;InaAs;omeCs;InaA;dT;dT;dT;dT;InaCs; omeUs;InaAs;omeAs;InaAs;omeAs;InaTs;omeUs;InaCs;omeAs; InaAs;omeUs;InaGs;omeGs;InaC-Sup | 13106 |
| SMN1-109 m01 | TCACTTTCAT AATGCTGGTT TTTCACTTTC ATAATGCTGG | InaTs;omeCs;InaAs;omeCs;InaTs;omeUs;InaTs;omeCs;InaAs; omeUs;InaAs;omeAs;InaTs;omeGs;InaCs;omeUs;InaGs;omeG; dT;dT;dT;dT;InaTs;omeCs;InaAs;omeCs;InaTs;omeUs;InaTs; omeCs;InaAs;omeUs;InaAs;omeAs;InaTs;omeGs;InaCs;omeUs; InaGs;omeG-Sup | 13107 |
| SMN1-110 m01 | AAATTCAATG GCCCA | InaAs;omeAs;InaAs;omeUs;InaTs;omeCs;InaAs;omeAs;InaTs; omeGs;InaGs;omeCs;InaCs;omeCs;InaA-Sup | 10090 |
| SMN1-111 m01 | AATTCAATGG CCCAC | InaAs;omeAs;InaTs;omeUs;InaCs;omeAs;InaAs;omeUs;InaGs; omeGs;InaCs;omeCs;InaCs;omeAs;InaC-Sup | 10091 |
| SMN1-112 m01 | ATTCAATGGC CCACC | InaAs;omeUs;InaTs;omeCs;InaAs;omeAs;InaTs;omeGs;InaGs; omeCs;InaCs;omeCs;InaAs;omeCs;InaC-Sup | 10092 |
| SMN1-113 m01 | TTCAATGGCC CACCA | InaTs;omeUs;InaCs;omeAs;InaAs;omeUs;InaGs;omeGs;InaCs; omeCs;InaCs;omeAs;InaCs;omeCs;InaA-Sup | 10093 |
| SMN1-114 m01 | TCAATGGCCC ACCAC | InaTs;omeCs;InaAs;omeAs;InaUs;omeGs;InaGs;omeCs;InaCs; omeCs;InaAs;omeCs;InaCs;omeAs;InaC-Sup | 10094 |
| SMN1-115 m01 | CAATGGCCCA CCACC | InaCs;omeAs;InaAs;omeUs;InaGs;omeGs;InaCs;omeCs;InaCs; omeAs;InaCs;omeCs;InaAs;omeCs;InaC-Sup | 10095 |
| SMN1-116 m01 | AATGGCCCAC CACCG | InaAs;omeAs;InaTs;omeGs;InaGs;omeCs;InaCs;omeCs;InaAs; omeCs;InaCs;omeAs;InaCs;omeCs;InaG-Sup | 10096 |
| SMN1-117 m01 | ATGGCCCACC ACCGC | InaAs;omeUs;InaGs;omeGs;InaCs;omeCs;InaCs;omeAs;InaCs; omeCs;InaAs;omeCs;InaCs;omeGs;InaC-Sup | 10097 |
| SMN1-118 m01 | AATGCCTTTC TGTTA | InaAs;omeAs;InaTs;omeGs;InaCs;omeCs;InaTs;omeUs;InaTs; omeCs;InaTs;omeGs;InaTs;omeUs;InaA-Sup | 10330 |
| SMN1-119 m01 | ATGCCTTTCT GTTAC | InaAs;omeUs;InaGs;omeCs;InaCs;omeUs;InaTs;omeUs;InaCs; omeUs;InaGs;omeUs;InaTs;omeAs;InaC-Sup | 10331 |
| SMN1-120 m01 | TGCCTTTCTG TTACC | InaTs;omeGs;InaCs;omeCs;InaTs;omeUs;InaTs;omeCs;InaTs; omeGs;InaTs;omeUs;InaAs;omeCs;InaC-Sup | 10332 |
| SMN1-121 m01 | GCCTTTCTGT TACCC | InaGs;omeCs;InaCs;omeUs;InaTs;omeUs;InaCs;omeUs;InaGs; omeUs;InaTs;omeAs;InaCs;omeCs;InaC-Sup | 10333 |
| SMN1-122 m01 | CCTTTCTGTT ACCCA | InaCs;omeCs;InaTs;omeUs;InaTs;omeCs;InaTs;omeGs;InaTs; omeUs;InaAs;omeCs;InaCs;omeCs;InaA-Sup | 10334 |
| SMN1-123 m01 | CTTTCTGTTA CCCAG | InaCs;omeUs;InaTs;omeUs;InaCs;omeUs;InaGs;omeUs;InaTs; omeAs;InaCs;omeCs;InaCs;omeAs;InaG-Sup | 10335 |
| SMN1-124 m01 | TTTCTGTTAC CCAGA | InaTs;omeUs;InaTs;omeCs;InaUs;omeGs;InaTs;omeUs;InaAs; omeCs;InaCs;omeCs;InaAs;omeGs;InaA-Sup | 10336 |
| SMN1-125 m01 | TGTTACCCAG ATGCA | InaTs;omeGs;InaTs;omeUs;InaAs;omeCs;InaCs;omeCs;InaAs; omeGs;InaAs;omeUs;InaGs;omeCs;InaA-Sup | 10340 |
| SMN1-126 m01 | GTTACCCAGA TGCAG | InaGs;omeUs;InaTs;omeAs;InaCs;omeCs;InaCs;omeAs;InaGs; omeAs;InaTs;omeGs;InaCs;omeAs;InaG-Sup | 10341 |
| SMN1-127 m01 | TTACCCAGAT GCAGT | InaTs;omeUs;InaAs;omeCs;InaCs;omeCs;InaAs;omeGs;InaAs; omeUs;InaGs;omeCs;InaAs;omeGs;InaT-Sup | 10342 |
| SMN1-128 m01 | ACCCAGATGC AGTGC | InaAs;omeCs;InaCs;omeCs;InaAs;omeGs;InaAs;omeUs;InaGs; omeCs;InaAs;omeGs;InaTs;omeGs;InaC-Sup | 10344 |

TABLE 4-continued

Oligonucleotide sequences made for testing human cells
obtained from subjects with Spinal Muscular Atrophy
(See Table 3 for structural features of formatted sequence).

| Oligo Name | Base Sequence | Formatted Sequence | SeqID |
|---|---|---|---|
| SMN1-129 m01 | CCCAGATGCAGTGCT | InaCs;omeCs;InaCs;omeAs;InaGs;omeAs;InaTs;omeGs;InaCs;omeAs;InaGs;omeUs;InaGs;omeCs;InaT-Sup | 10345 |
| SMN1-130 m01 | CCAGATGCAGTGCTC | InaCs;omeCs;InaAs;omeGs;InaAs;omeUs;InaGs;omeCs;InaAs;omeGs;InaTs;omeGs;InaCs;omeUs;InaC-Sup | 10346 |
| SMN1-131 m01 | CAGATGCAGTGCTCT | InaCs;omeAs;InaGs;omeAs;InaTs;omeGs;InaCs;omeAs;InaGs;omeUs;InaGs;omeCs;InaTs;omeCs;InaT-Sup | 10347 |
| SMN1-132 m01 | AGATGCAGTGCTCTT | InaAs;omeGs;InaAs;omeUs;InaGs;omeCs;InaAs;omeGs;InaTs;omeGs;InaCs;omeUs;InaCs;omeUs;InaT-Sup | 10348 |
| SMN1-133 m01 | TTTTACTCATAGCTT | InaTs;omeUs;InaTs;omeUs;InaTs;omeCs;InaTs;omeCs;InaAs;omeUs;InaGs;omeCs;InaT-Sup | 10942 |
| SMN1-134 m01 | TTTACTCATAGCTTC | InaTs;omeUs;InaTs;omeAs;InaCs;omeUs;InaCs;omeAs;InaTs;omeAs;InaGs;omeCs;InaTs;omeUs;InaC-Sup | 10943 |
| SMN1-135 m01 | TTACTCATAGCTTCA | InaTs;omeUs;InaAs;omeCs;InaTs;omeCs;InaAs;omeUs;InaAs;omeGs;InaCs;omeUs;InaTs;omeCs;InaA-Sup | 10944 |
| SMN1-136 m01 | TACTCATAGCTTCAT | InaTs;omeAs;InaCs;omeUs;InaCs;omeAs;InaTs;omeAs;InaGs;omeCs;InaTs;omeUs;InaCs;omeAs;InaT-Sup | 10945 |
| SMN1-137 m01 | ACTCATAGCTTCATA | InaAs;omeCs;InaTs;omeCs;InaAs;omeUs;InaAs;omeGs;InaCs;omeUs;InaTs;omeCs;InaAs;omeUs;InaA-Sup | 10946 |
| SMN1-138 m01 | CTCATAGCTTCATAG | InaCs;omeUs;InaCs;omeAs;InaTs;omeAs;InaGs;omeCs;InaTs;omeUs;InaCs;omeAs;InaTs;omeAs;InaG-Sup | 10947 |
| SMN1-139 m01 | TCATAGCTTCATAGT | InaTs;omeCs;InaAs;omeUs;InaAs;omeGs;InaCs;omeUs;InaTs;omeCs;InaAs;omeUs;InaAs;omeGs;InaT-Sup | 10948 |
| SMN1-140 m01 | ATAGCTTCATAGTGG | InaAs;omeUs;InaAs;omeGs;InaCs;omeUs;InaTs;omeCs;InaAs;omeUs;InaAs;omeGs;InaTs;omeGs;InaG-Sup | 10950 |
| SMN1-141 m01 | TTCATAGTGGAACAG | InaTs;omeUs;InaCs;omeAs;InaTs;omeAs;InaGs;omeUs;InaGs;omeGs;InaAs;omeAs;InaCs;omeAs;InaG-Sup | 10955 |
| SMN1-142 m01 | TCATAGTGGAACAGA | InaTs;omeCs;InaAs;omeUs;InaAs;omeGs;InaTs;omeGs;InaGs;omeAs;InaAs;omeCs;InaAs;omeGs;InaA-Sup | 10956 |
| SMN1-143 m01 | CATAGTGGAACAGAT | InaCs;omeAs;InaTs;omeAs;InaGs;omeUs;InaGs;omeGs;InaAs;omeAs;InaCs;omeAs;InaGs;omeAs;InaT-Sup | 10957 |
| SMN1-144 m01 | ATAGTGGAACAGATA | InaAs;omeUs;InaAs;omeGs;InaTs;omeGs;InaGs;omeAs;InaAs;omeCs;InaAs;omeGs;InaAs;omeUs;InaA-Sup | 10958 |
| SMN1-145 m01 | TAGTGGAACAGATAC | InaTs;omeAs;InaGs;omeUs;InaGs;omeGs;InaAs;omeAs;InaCs;omeAs;InaGs;omeAs;InaTs;omeAs;InaC-Sup | 10959 |
| SMN1-146 m01 | AGTGGAACAGATACA | InaAs;omeGs;InaTs;omeGs;InaGs;omeAs;InaAs;omeCs;InaAs;omeGs;InaAs;omeUs;InaAs;omeCs;InaA-Sup | 10960 |
| SMN1-147 m01 | GTGGAACAGATACAT | InaGs;omeUs;InaGs;omeGs;InaAs;omeAs;InaCs;omeAs;InaGs;omeAs;InaTs;omeAs;InaCs;omeAs;InaT-Sup | 10961 |
| SMN1-148 m01 | TGGAACAGATACATA | InaTs;omeGs;InaGs;omeAs;InaAs;omeCs;InaAs;omeGs;InaAs;omeUs;InaAs;omeCs;InaAs;omeUs;InaA-Sup | 10962 |
| SMN1-149 m01 | TGTCCAGATTCTCTT | InaTs;omeGs;InaTs;omeCs;InaCs;omeAs;InaGs;omeAs;InaTs;omeUs;InaCs;omeUs;InaCs;omeUs;InaT-Sup | 11367 |
| SMN1-150 m01 | GTCCAGATTCTCTTG | InaGs;omeUs;InaCs;omeCs;InaAs;omeGs;InaAs;omeUs;InaTs;omeCs;InaTs;omeCs;InaTs;omeUs;InaG-Sup | 11368 |
| SMN1-151 m01 | TCCAGATTCTCTTGA | InaTs;omeCs;InaCs;omeAs;InaGs;omeAs;InaTs;omeUs;InaCs;omeUs;InaCs;omeUs;InaGs;omeAs;InaA-Sup | 11369 |
| SMN1-152 m01 | CCAGATTCTCTTGAT | InaCs;omeCs;InaAs;omeGs;InaAs;omeUs;InaTs;omeCs;InaTs;omeCs;InaTs;omeUs;InaGs;omeAs;InaT-Sup | 11370 |

TABLE 4-continued

Oligonucleotide sequences made for testing human cells
obtained from subjects with Spinal Muscular Atrophy
(See Table 3 for structural features of formatted sequence).

| Oligo Name | Base Sequence | Formatted Sequence | SeqID |
|---|---|---|---|
| SMN1-153 m01 | CAGATTCTCTTGATG | InaCs;omeAs;InaGs;omeAs;InaTs;omeUs;InaCs;omeUs;InaCs;omeUs;InaTs;omeGs;InaAs;omeUs;InaG-Sup | 11371 |
| SMN1-154 m01 | AGATTCTCTTGATGA | InaAs;omeGs;InaAs;omeUs;InaTs;omeCs;InaTs;omeCs;InaTs;omeUs;InaGs;omeAs;InaTs;omeGs;InaA-Sup | 11372 |
| SMN1-155 m01 | GATTCTCTTGATGAT | InaGs;omeAs;InaTs;omeUs;InaCs;omeUs;InaCs;omeUs;InaTs;omeGs;InaAs;omeUs;InaGs;omeAs;InaT-Sup | 11373 |
| SMN1-156 m01 | GGAAGTATGTTAATT | InaGs;omeAs;InaAs;omeAs;InaGs;omeUs;InaAs;omeUs;InaGs;omeUs;InaTs;omeAs;InaAs;omeUs;InaT-Sup | 11400 |
| SMN1-157 m01 | GAAGTATGTTAATTT | InaGs;omeAs;InaAs;omeGs;InaTs;omeAs;InaTs;omeGs;InaTs;omeUs;InaAs;omeAs;InaTs;omeUs;InaT-Sup | 11401 |
| SMN1-158 m01 | AAGTATGTTAATTTC | InaAs;omeAs;InaGs;omeUs;InaAs;omeUs;InaGs;omeUs;InaTs;omeAs;InaAs;omeUs;InaTs;omeUs;InaC-Sup | 11402 |
| SMN1-159 m01 | AGTATGTTAATTTCA | InaAs;omeGs;InaTs;omeAs;InaTs;omeGs;InaTs;omeUs;InaAs;omeAs;InaTs;omeUs;InaTs;omeCs;InaA-Sup | 11403 |
| SMN1-160 m01 | GTATGTTAATTTCAT | InaGs;omeUs;InaAs;omeUs;InaGs;omeUs;InaTs;omeAs;InaAs;omeUs;InaTs;omeUs;InaCs;omeAs;InaT-Sup | 11404 |
| SMN1-161 m01 | TATGTTAATTTCATG | InaTs;omeAs;InaTs;omeGs;InaTs;omeUs;InaAs;omeAs;InaTs;omeUs;InaTs;omeCs;InaAs;omeUs;InaG-Sup | 11405 |
| SMN1-162 m01 | ATGTTAATTTCATGG | InaAs;omeUs;InaGs;omeUs;InaTs;omeUs;InaAs;omeAs;InaUs;omeUs;InaTs;omeUs;InaCs;omeAs;InaUs;omeGs;InaG-Sup | 11406 |
| SMN1-163 m01 | TGAAATATTCCTTAT | InaTs;omeGs;InaAs;omeAs;InaAs;omeUs;InaAs;omeUs;InaTs;omeCs;InaCs;omeUs;InaTs;omeAs;InaT-Sup | 10064 |
| SMN1-164 m01 | TATAGCCAGGTCTAA | InaTs;omeAs;InaTs;omeAs;InaGs;omeCs;InaCs;omeAs;InaGs;omeGs;InaTs;omeCs;InaTs;omeAs;InaA-Sup | 10076 |
| SMN1-165 m01 | ATAGCCAGGTCTAAA | InaAs;omeUs;InaAs;omeGs;InaCs;omeCs;InaAs;omeGs;InaGs;omeUs;InaCs;omeUs;InaAs;omeAs;InaA-Sup | 10077 |
| SMN1-166 m01 | AGGTCTAAAATTCAA | InaAs;omeGs;InaGs;omeUs;InaCs;omeUs;InaAs;omeAs;InaAs;omeAs;InaTs;omeUs;InaCs;omeAs;InaA-Sup | 10083 |
| SMN1-167 m01 | GTCTAAAATTCAATG | InaGs;omeUs;InaCs;omeUs;InaAs;omeAs;InaAs;omeAs;InaTs;omeUs;InaCs;omeAs;InaAs;omeUs;InaG-Sup | 10085 |
| SMN1-168 m01 | TCTAAAATTCAATGG | InaTs;omeCs;InaTs;omeAs;InaAs;omeAs;InaAs;omeUs;InaTs;omeCs;InaAs;omeAs;InaTs;omeGs;InaG-Sup | 10086 |
| SMN1-169 m01 | TAAAATTCAATGGCC | InaTs;omeAs;InaAs;omeAs;InaAs;omeUs;InaTs;omeCs;InaAs;omeAs;InaTs;omeGs;InaGs;omeCs;InaC-Sup | 10088 |
| SMN1-170 m01 | AAAATTCAATGGCCC | InaAs;omeAs;InaAs;omeAs;InaTs;omeUs;InaCs;omeAs;InaAs;omeUs;InaGs;omeGs;InaCs;omeCs;InaC-Sup | 10089 |
| unc-232 m12 | CTACGCGTCGACGGT | InaCs;dTs;InaAs;dCs;InaGs;dCs;InaGs;dTs;InaCs;dGs;InaAs;dCs;InaGs;dGs;InaT-Sup | 13095 |
| unc-232 m01 | CTACGCGTCGACGGT | InaCs;omeUs;InaAs;omeCs;InaGs;omeCs;InaGs;omeUs;InaCs;omeGs;InaAs;omeCs;InaGs;omeGs;InaT-Sup | 13095 |
| unc-293 m12 | CCGATTCGCGCGTAA | InaCs;dCs;InaGs;dAs;InaTs;dTs;InaCs;dGs;InaCs;dGs;InaCs;dGs;InaTs;dAs;InaA-Sup | 13096 |
| unc-293 m01 | CCGATTCGCGCGTAA | InaCs;omeCs;InaGs;omeAs;InaTs;omeUs;InaCs;omeGs;InaCs;omeGs;InaCs;orneGs;InaTs;omeAs;InaA-Sup | 13096 |

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US10837014B2). An electronic copy of the "Sequence Listing" will also be available from the USPTO upon request and payment of the fee set forth in 37 CFR 1.19(b)(3).

What is claimed is:

1. A composition comprising a cell and a single stranded oligonucleotide, wherein the single stranded oligonucleotide is produced by a process comprising:
synthesizing a single stranded oligonucleotide that:
(a) has a sequence 5'-X—Y—Z, wherein X is any nucleotide, Y is a nucleotide sequence of 6 nucleotides in length that is not a seed sequence of a human microRNA, and Z is a nucleotide sequence of 1-8 nucleotides in length,
(b) is 100% complementary with a PRC2-associated region of a human SMN gene, wherein the PRC2-associated region is a region of the SMN gene that has a sequence that occurs at a higher frequency in a sequencing reaction of products of an RNA-immunoprecipitation assay that employs an antibody that targets Ezh2 to immunoprecipitate RNA-associated PRC2 complexes from cells comprising the SMN gene compared to a control sequencing reaction of products of a control RNA-immunoprecipitation assay that employs a control antibody, and
(c) is 8 to 15 nucleotides in length,
wherein, during the synthesis, at least one nucleotide incorporated into the oligonucleotide comprises a 2' O-methyl and/or a 2'-fluoro, and a phosphorothioate internucleotide linkage is incorporated between at least two nucleotides.

2. The composition of claim 1, wherein the oligonucleotide does not comprise three or more consecutive guanosine nucleotides.

3. The composition of claim 1, wherein the oligonucleotide does not comprise four or more consecutive guanosine nucleotides.

4. The composition of claim 1, wherein at least one nucleotide of the oligonucleotide comprises a 2' O-methyl.

5. The composition of claim 1, wherein each nucleotide of the oligonucleotide comprises a 2' O-methyl.

6. The composition of claim 1, wherein the oligonucleotide comprises at least one ribonucleotide, at least one deoxyribonucleotide, or at least one bridged nucleotide.

7. The composition of claim 6, wherein the bridged nucleotide is a LNA nucleotide, a cEt nucleotide or a ENA modified nucleotide.

8. The composition of claim 1, wherein the nucleotides of the oligonucleotide comprise alternating deoxyribonucleotides and 2'-fluoro-deoxyribonucleotides.

9. The composition of claim 1, wherein the nucleotides of the oligonucleotide comprise alternating deoxyribonucleotides and 2'-O-methyl nucleotides.

10. The composition of claim 1, wherein the nucleotides of the oligonucleotide comprise alternating deoxyribonucleotides and ENA nucleotide analogues.

11. The composition of claim 1, wherein the nucleotides of the oligonucleotide comprise alternating deoxyribonucleotides and LNA nucleotides.

12. The composition of claim 8, wherein the 5' nucleotide of the oligonucleotide is a deoxyribonucleotide.

13. The composition of claim 1, wherein the nucleotides of the oligonucleotide comprise alternating LNA nucleotides and 2'-O-methyl nucleotides.

14. The composition of claim 13, wherein the 5' nucleotide of the oligonucleotide is a LNA nucleotide.

15. The composition of claim 1, wherein the nucleotides of the oligonucleotide comprise deoxyribonucleotides flanked by at least one LNA nucleotide on each of the 5' and 3' ends of the deoxyribonucleotides.

16. The composition of claim 1, further comprising phosphorothioate internucleotide linkages between all nucleotides.

17. The composition of claim 1, wherein the nucleotide at the 3' position of the oligonucleotide has a 3' hydroxyl group.

18. The composition of claim 1, wherein the nucleotide at the 3' position of the oligonucleotide has a 3' thiophosphate.

19. The composition of claim 1, further comprising a biotin moiety conjugated to the 5' nucleotide.

20. A composition comprising a cell and a single stranded oligonucleotide, wherein the single stranded oligonucleotide is produced by a process comprising:
synthesizing a single stranded oligonucleotide that:
(a) is 100% complementary with a PRC2-associated region of a human SMN gene, wherein the PRC2-associated region is a region of the SMN gene that has a sequence that occurs at a higher frequency in a sequencing reaction of products of an RNA-immunoprecipitation assay that employs an antibody that targets Ezh2 to immunoprecipitate RNA-associated PRC2 complexes from cells comprising the SMN gene compared to a control sequencing reaction of products of a control RNA-immunoprecipitation assay that employs a control antibody,
(b) is 8 to 15 nucleotides in length and has at least one of the following features i)-iv):
i) a sequence that is 5'X—Y—Z, wherein X is any nucleotide and wherein X is anchored at the 5' end of the oligonucleotide, Y is a nucleotide sequence of 6 nucleotides in length that is not a human seed sequence of a microRNA, and Z is a nucleotide sequence of 1-8 nucleotides in length;

ii) a sequence that does not comprise three or more consecutive guanosine nucleotides;
iii) a sequence that is complementary to a PRC2-associated region that encodes an RNA that forms a secondary structure comprising at least two single stranded loops; and/or
iv) a sequence that has greater than 60% G-C content wherein, during the synthesis, at least one nucleotide incorporated into the oligonucleotide comprises a 2' O-methyl and/or a 2'-fluoro, and a phosphorothioate internucleotide linkage is incorporated between at least two nucleotides.

21. The composition of claim 20, wherein the oligonucleotide has the sequence 5'X—Y-Z.

22. A composition comprising a cell and a single stranded oligonucleotide conjugated to a carrier, wherein the single stranded oligonucleotide is produced by a process comprising:
synthesizing a single stranded oligonucleotide that:
(a) has a sequence 5'-X—Y—Z, wherein X is any nucleotide, Y is a nucleotide sequence of 6 nucleotides in length that is not a seed sequence of a human microRNA, and Z is a nucleotide sequence of 1 to 8 nucleotides in length,
(b) is 100% complementary with a PRC2-associated region of a human SMN gene, wherein the PRC2-associated region is a region of the SMN gene that has a sequence that occurs at a higher frequency in a sequencing reaction of products of an RNA-immunoprecipitation assay that employs an antibody that targets Ezh2 to immunoprecipitate RNA-associated PRC2 complexes from cells comprising the SMN gene compared to a control sequencing reaction of products of a control RNA-immunoprecipitation assay that employs a control antibody, and
(c) is 8 to 15 nucleotides in length,
wherein, during the synthesis, at least one nucleotide incorporated into the oligonucleotide comprises a 2' O-methyl and/or a 2'-fluoro, and a phosphorothioate internucleotide linkage is incorporated between at least two nucleotides.

23. The composition of claim 22, wherein the carrier is a peptide.

24. The composition of claim 22, wherein the carrier is a steroid.

25. A pharmaceutical composition comprising a composition of claim 22 and a pharmaceutically acceptable carrier.

26. A kit comprising a container housing the composition of claim 22.

27. A method of increasing expression of SMN1 or SMN2 in a human cell, the method comprising:
delivering a single stranded oligonucleotide into the cell, wherein the oligonucleotide does not induce substantial cleavage or degradation of the SMN1 or SMN2 mRNA in the cell and wherein the single stranded oligonucleotide is produced by a process comprising:
synthesizing a single stranded oligonucleotide that:
(a) has a sequence 5'-X—Y—Z, wherein X is any nucleotide, Y is a nucleotide sequence of 6 nucleotides in length that is not a seed sequence of a human microRNA, and Z is a nucleotide sequence of 1 to 8 nucleotides in length,
(b) is 100% complementary with a PRC2-associated region of a human SMN gene, wherein the PRC2-associated region is a region of the SMN gene that has a sequence that occurs at a higher frequency in a sequencing reaction of products of an RNA-immunoprecipitation assay that employs an antibody that targets Ezh2 to immunoprecipitate RNA-associated PRC2 complexes from cells comprising the SMN gene compared to a control sequencing reaction of products of a control RNA-immunoprecipitation assay that employs a control antibody, and
(c) is 8 to 15 nucleotides in length,
wherein, during the synthesis, at least one nucleotide incorporated into the oligonucleotide comprises a 2' O-methyl and/or a 2'-fluoro, and a phosphorothioate internucleotide linkage is incorporated between at least two nucleotides.

28. The method of claim 27, wherein delivery of the single stranded oligonucleotide into the cell results in a level of expression of SMN1 or SMN2 mRNA that is at least 50% greater than a level of expression of SMN1 or SMN2 mRNA in a control cell that does not comprise the single stranded oligonucleotide.

29. A method of increasing expression of SMN2 messenger RNA (mRNA) in a human cell, the method comprising:
delivering to the cell a first single stranded oligonucleotide complementary with at least 8 consecutive nucleotides of a PRC2-associated region of human SMN2 and a second single stranded oligonucleotide complementary with at least 8 consecutive nucleotides of a splice control sequence of a precursor mRNA of human SMN2, in amounts sufficient to increase expression of a mature mRNA of SMN2 that comprises exon 7 in the cell, wherein the first and second oligonucleotides do not induce substantial cleavage or degradation of SMN2 mRNA in the cell, wherein at least one nucleotide of the first single stranded oligonucleotide comprises a 2' O-methyl and/or a 2'-fluoro, and the first single stranded oligonucleotide comprises a phosphorothioate internucleotide linkage between at least two nucleotides.

30. The method of claim 29, wherein the first single stranded oligonucleotide is covalently linked to the second single stranded oligonucleotide through a linker.

31. A composition comprising:
a first single stranded oligonucleotide produced by a process comprising synthesizing a first single stranded oligonucleotide that is complementary with at least 8 consecutive nucleotides of a PRC2-associated region of a human SMN2 gene, wherein the PRC2-associated region is a region of the SMN2 gene that has a sequence that occurs at a higher frequency in a sequencing reaction of products of an RNA-immunoprecipitation assay that employs an antibody that targets Ezh2 to immunoprecipitate RNA-associated PRC2 complexes from cells comprising the SMN2 gene compared to a control sequencing reaction of products of a control RNA-immunoprecipitation assay that employs a control antibody, and a second single stranded oligonucleotide complementary with at least 9 consecutive nucleotides of a splice control sequence of a precursor mRNA encoded by the SMN2 gene, wherein, during the synthesis, at least one nucleotide incorporated into the first single stranded oligonucleotide comprises a 2' O-methyl and/or a 2'-fluoro, and a phosphorothioate internucleotide linkage is incorporated between at least two nucleotides.

32. The composition of claim 31, wherein the first single stranded oligonucleotide is covalently linked to the second single stranded oligonucleotide through a linker.

* * * * *